(12) United States Patent
Fuchs et al.

(10) Patent No.: US 11,291,705 B2
(45) Date of Patent: Apr. 5, 2022

(54) USE OF CASPASE-3 INHIBITORS AND CASPASE-3 ACTIVATORS IN THE MANUFACTURE OF MEDICAMENT FOR TREATING CANCER AND WOUND HEALING

(71) Applicant: Technion Research & Development Foundation Limited, Haifa (IL)

(72) Inventors: Yaron Fuchs, Haifa (IL); Yahav Yosefzon, Haifa (IL); Despina Soteriou, Haifa (IL)

(73) Assignee: Technion Research & Development Foundation Limited, Haifa (IL)

( * ) Notice: Subject to any disclaimer, the term of this patent is extended or adjusted under 35 U.S.C. 154(b) by 224 days.

(21) Appl. No.: 16/339,732

(22) PCT Filed: Oct. 13, 2017

(86) PCT No.: PCT/IB2017/056364
§ 371 (c)(1),
(2) Date: Apr. 5, 2019

(87) PCT Pub. No.: WO2018/069885
PCT Pub. Date: Apr. 19, 2018

(65) Prior Publication Data
US 2020/0046796 A1   Feb. 13, 2020

(30) Foreign Application Priority Data

Oct. 13, 2016  (IL) .......................................... 248468

(51) Int. Cl.
| | |
|---|---|
| *A61K 38/07* | (2006.01) |
| *G01N 33/68* | (2006.01) |
| *A61K 45/06* | (2006.01) |
| *A61P 35/00* | (2006.01) |
| *A61K 31/495* | (2006.01) |
| *A61K 31/635* | (2006.01) |
| *A61K 31/5377* | (2006.01) |
| *A61K 9/00* | (2006.01) |
| *A61P 17/02* | (2006.01) |

(52) U.S. Cl.
CPC ............ *A61K 38/07* (2013.01); *A61K 9/0014* (2013.01); *A61K 31/495* (2013.01); *A61K 31/5377* (2013.01); *A61K 31/635* (2013.01); *A61K 45/06* (2013.01); *A61P 17/02* (2018.01); *A61P 35/00* (2018.01); *G01N 33/6872* (2013.01); *G01N 2800/52* (2013.01)

(58) Field of Classification Search
None
See application file for complete search history.

(56) References Cited

U.S. PATENT DOCUMENTS

| | | |
|---|---|---|
| 2011/0165143 A1 | 7/2011 | Li et al. |
| 2012/0303057 A1 | 11/2012 | Choy et al. |
| 2015/0056604 A1 | 2/2015 | Sehgal |
| 2015/0190456 A1 | 7/2015 | Li et al. |

FOREIGN PATENT DOCUMENTS

| | | |
|---|---|---|
| RU | 2229475 | 5/2004 |
| WO | WO 2004/078731 | 9/2004 |
| WO | WO 2006/054773 | 5/2006 |
| WO | WO 2012/177684 | 12/2012 |
| WO | WO 2016/057041 | 4/2016 |
| WO | WO 2017/117182 | 7/2017 |
| WO | WO 2018/069885 | 4/2018 |

OTHER PUBLICATIONS

Li, Xiu Juan, Oncology reports, 2013, 30(5): 2419-2426 (Year: 2013).*
Cregan, The Journal of Neuroscience, Sep. 15, 1999, 19(18):7860-7869 (Year: 1999).*
Putt, Nature Chemical Biology vol. 2, pp. 543-550 (2006) (Year: 2006).*
Website: https://www.scbt.com/browse/chemicals-Protein-Interacting-Inhibitors-Activators-Substrates-Protein-Activators-caspase-3-Activators/_/N-cix5v, 13 pages, retrieved on Jun. 9, 2021 (Year: 2021).*
Zheng, Nature Medicine, vol. 6, No. 11, Nov. 2000, pp. 1241-1247 (Year: 2000).*
Huang, Nature Medicine, 17(7): 860-866, Published Online Jul. 3, 2011 (listed on IDS dated Jun. 12, 2019 (Year: 2011).*
International Preliminary Report on Patentability dated Apr. 25, 2019 From the International Bureau of WIPO Re. Application No. PCT/IB2017/056364. (8 Pages).
International Search Report and the Written Opinion dated Jan. 29, 2018 From the International Searching Authority Re. Application No. PCT/IB2017/056364. (12 Pages).
Office Action dated Mar. 21, 2017 From the Israel Patent Office Re. Application No. 248468. (4 Pages).
Abraham et al. "Death Without Caspases, Caspases Without Death", Trends in Cell Biology, 14(4): 184-193, Apr. 2004.
Bergmann et al. "Apoptosis, Stem Cells, and Tissue Regeneration", Science Signaling, 2(145): re8-1-re8-10, Oct. 26, 2010.
Bhola et al. "Mitochondria—Judges and Executioners of Cell Death Sentences", Molecular Cell, 61(5): 695-704, Mar. 3, 2016.
Chen et al. "Homeostatic Control of Hippo Signaling Activity Revealed by an Endogenous Activating Mutation in YAP", Genes & Development, 29(12): 1285-1297, Jun. 15, 2015.

(Continued)

*Primary Examiner* — Satyanarayana R Gudibande

(57) ABSTRACT

Provided are methods of selecting a treatment for a cancer in a subject in need thereof, by analyzing activity of Yes associated protein 1 (YAP) in cancer cells of the subject, and methods of treating cancer using a therapeutically effective amount of an caspase-3 inhibitor. Also provided are methods of improving wound healing by administering a wound healing effective amount of a caspase-3 activator.

Figure 3N:
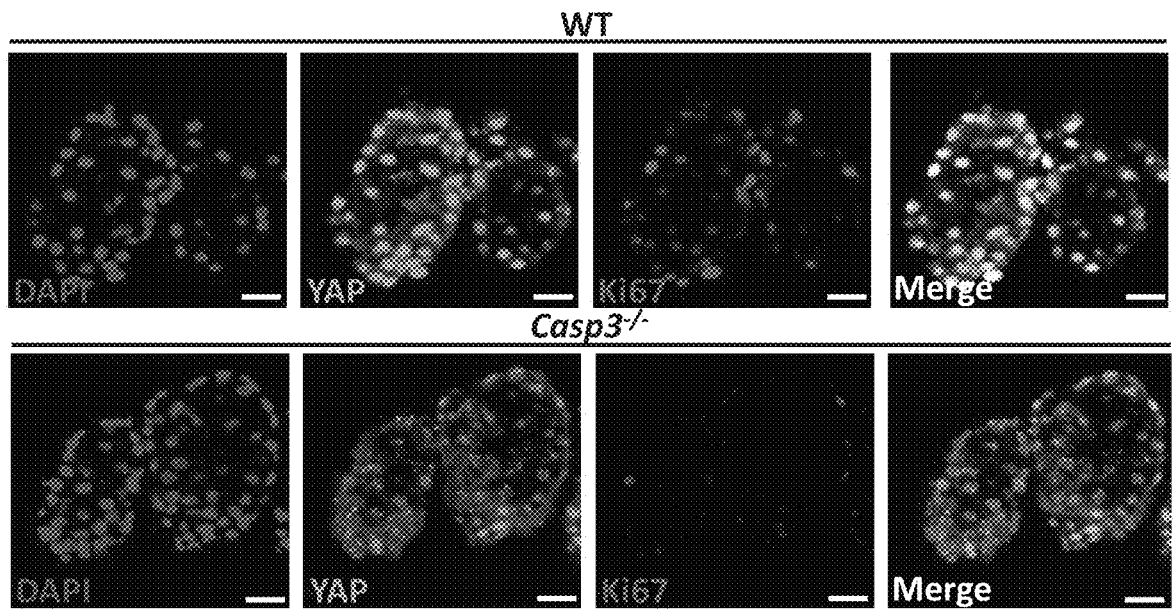

3 Claims, 36 Drawing Sheets
(33 of 36 Drawing Sheet(s) Filed in Color)

Specification includes a Sequence Listing.

(56) References Cited

OTHER PUBLICATIONS

Dvorak "Tumors: Wounds That Do Not Heal", New England Journal of Medicine, 315(26): 1650-1659, Dec. 25, 1986.
Ellis et al. "Genetic Control of Programmed Cell Death in the Nematode C. Elegans", Cell, 44(6): 817-829, Mar. 28, 1986.
Feinstein-Rotkopf et al. "Can't Live Without Them, Can Live With Them: Roles of Caspases During Vital Cellular Processes", Apoptosis, 14(8): 980-995, Published Online Apr. 17, 2009.
Fuchs "Scratching the Surface of Skin Development", Nature, 445(7130): 834-842, Feb. 22, 2007.
Fuchs et al. "Live to Die Another Way: Modes of Programmed Cell Death and Signals Emanating From Dying Cells", Nature Reviews Molecular Cell Biology, 16(6): 329-344, Published Online May 20, 2015.
Fuchs et al. "Programmed Cell Death in Animal Development and Disease", Cell, 147(4): 742-758, Nov. 11, 2011.
Hashimoto et al. "Contribution of Caspase(s) to the Cell Cycle Regulation at Mitotic Phase", PLoS One, 6(3): e18449-1-e18449-9, Mar. 30, 2011.
Hengartner "The Biochemistry of Apoptosis", Nature, 407(6805): 770-776, Oct. 12, 2000.
Huang et al. "Caspase 3-Mediated Stimulation of Tumor Cell Repopulation During Cancer Radiotherapy", Nature Medicine, 17(7): 860-866, Published Online Jul. 3, 2011.
Ichim et al. "A Fate Worse Than Death: Apoptosis as an Oncogenic Process", Nature Reviews Cancer, 16(8): 539-548, Published Online Jul. 1, 2016.
Kravchenko et al. "1,3-Dioxo-4-Methyl-2,3-Dihydro-1H-Pyrrolo[3,4-c]Quinolines as Potent Caspase-3 Inhibitors", Bioorganic & Medinal Chemistry Letters, 15(7): 1841-1845, Apr. 1, 2005.
Kravchenko et al. "Design and Synthesis of New Nonpeptide Caspase-3 Inhibitors", Pharmaceutical Chemistry Journal, 40(3): 127-131, Mar. 2006.
Kravchenko et al. "Pyrrolo[3,4-c]Quinoline-1,3-Diones as Potent Caspase-3 Inhibitors: Synthesis and SAR of 8-Sulfamoyl-1,3-Dioxo-2.3-Dihydro-1H-Pyrrolo[3,4-c]Quinolines", Letters in Drug Design & Discovery, 3(1): 61-70, Feb. 1, 2006.
Kravchenko et al. "Pyrrolo[3,4-c]Quinoline-1.3-Diones as Potent Caspase-3 Inhibitors. Synthesis and SAR of 2-Substituted 4-Methyl-8-(Morpholine-4-Sulfonyl)-Pyrrolo[3,4-c]Quinoline-1,3-Diones", European Journal of Medicinal Chemistry, 40(12): 1377-1383, Available Online Sep. 15, 2005.
Kravchenko et al. "Synthesis and Structure-Activity Relationship of 4-Substituted 2-(2-Acetyloxyethyl)-8-(Morpholine-4-Sulfonyl)Pyrrolo[3,4-c]Quinoline-1,3-Diones as Potent Caspase-2 Inhibitors", Journal of Medicinal Chemistry, 48(11): 3680-3683, Published on Web Apr. 29, 2005.
Kuranaga et al. "Nonapoptotic Functions of Caspases: Caspases as Regulatory Molecules for Immunity and Cell-Fate Determination", Trends in Cell Biology, 17(3): 135-144, Available Online Feb. 1, 2007.
Li et al. "3,3'-Diindolylmethane Suppresses the Growth of Gastric Cancer Cells Via Activation of the Hippo Signaling Pathway", Oncology Reports, 30(5): 2419-2426, Nov. 2013.
Li et al. "3,3'-Diindolylmethane Suppresses the Growth of Gastric Cancer Cells Via Activation of the Hippo Signaling Pathway", Oncology Reports, 30(5): 2419-2426, Published Online Sep. 4, 2013.
Li et al. "AlphaE-Catenin Inhibits A Src-YAP1 Oncogenic Module That Couples Tyrosine Kinases and the Effector of Hippo Signaling Pathway", Genes & Development, 30(7): 798-811, Apr. 2016.
Li et al. "Apoptotic Cells Activate the 'Phoenix Rising' Pathway to Promote Wound Healing and Tissue Regeneration", Science Signaling, 3(110): ra13, 1-11, Feb. 23, 2010.
Li et al. "DIM Inhibits Growth of Human Gastric Cancer Through Modulation of the Hippo Signaling Pathway", Proceedings of the American Association for Cancer Research, AACR 104th Annual Meeting, Washington, DC, USA, Apr. 6-10, 2013, 73(8 Suppl.): # 3243, Apr. 6, 2013. Abstract.
Lin et al. "The Hippo Effector YAP Promotes Resistance to RAF- and MEK-Targeted Cancer Therapies", Nature Genetics, 47(3): 1-9, Published Online Feb. 9, 2015. Fig. 1f.
Liu et al. "Caspase 3 Promotes Genetic Instability and Carcinogenesis", Molecular Cell, 58(2): 284-296, Published Online Apr. 9, 2015.
Liu et al. "YAP Modulates TGF-betal-Induced Simultaneous Apoptosis and EMT Through Upregulation of the EGF Receptor", Scientific Reports, 7: 45523, 1-13, Apr. 20, 2017.
Maillard et al. "A Label-Free LC/MS/MS-Based Enzymatic Activity Assay for the Detection of Genuine Caspase Inhibitors and SAR Development", Journal of Biomolecular Screening, 18(8): 868-878, Published Online Jun. 24, 2013.
Meier et al. "Apoptosis in Development", Nature, 407(6805): 796-801, Oct. 12, 2000.
Miura "Active Participation of Cell Deah in Development and Organismal Homeostasis", Developmen, Growth and Differentiation, 53(2): 125-136, Published Online Feb. 22, 2011.
Nagata "Apoptosis by Death Factor", Cell, 88(3): 355-365, Feb. 7, 1997.
Niemann et al. "Development and Homeostasis of the Sebaceous Gland", Seminars in Cell and Developmental Biology, 23(8): 928-936, Oct. 2012.
Schlegelmilch et al. "Yap1 Acts Downstream of Alpha-Catenin to Control Epidermal Proliferation", Cell, 144(5): 782-795, Mar. 4, 2011. Abstract, p. 785, 1-h col., Last Para to p. 786,1-h col., 1st Para.
Silvis et al. "Alpha-Catenin Is a Tumor Suppressor That Controls Cell Accumulation by Regulating the Localization and Activity of the Transcriptional Coactivator Yap1", Science Signaling, 4(174): ra33-1-ra33-19, May 24, 2011.
Suzanne et al. "Shaping Organisms With Apoptosis", Cell Death and Differentiation, 20(5): 669-675, Published Online Mar. 1, 2013.
Taylor et al. "Apoptosis: Controlled Demolition at the Cellular Level", Nature Reviews Molecular Cell Biology, 9(3): 231-241, Published Online Dec. 12, 2007.
Thornberry et al. "Caspases: Enemies Within", Science, 281(5381): 1312-1316, Aug. 28, 1998.
Tseng et al. "Apoptosis is Required During Early Stages of Tail Regeneration in Xenopus Laevis", Developmental Biology, 301(1): 62-69, Available Online Nov. 6, 2006.
Watt "Mammalian Skin Cell Biology: At the Interface Between Laboratory and Clinic", Science, 346(6212): 937-940, Nov. 21, 2014.
Woo et al. "SnapShot: Hair Follicle Stem Cells", Cell, 146(2): 334-334.e2, Jul. 22, 2011.
Yamaguchi et al. "Programmed Cell Death in Neurodevelopment", Developmental Cell, 32(4): 478-490, Feb. 23, 2015.
Yi et al. "The Jekyll and Hyde Functions of Caspases", Developmental Cell, 16(1): 21-34, Jan. 20, 2009.
Yu et al. "Hippo Pathway in Organ Size Control, Tissue Homeostasis, and Cancer", Cell, 163(4): 811-828, Nov. 5, 2015.
Zanconato et al. "YAP/TAZ at the Roots of Cancer", Cancer Cell, 29(6): 783-803, Jun. 13, 2016.
Supplementary European Search Report and the European Search Opinion dated May 15, 2020 From the European Patent Office Re. Application No. 17860888.1. (10 Pages).

* cited by examiner

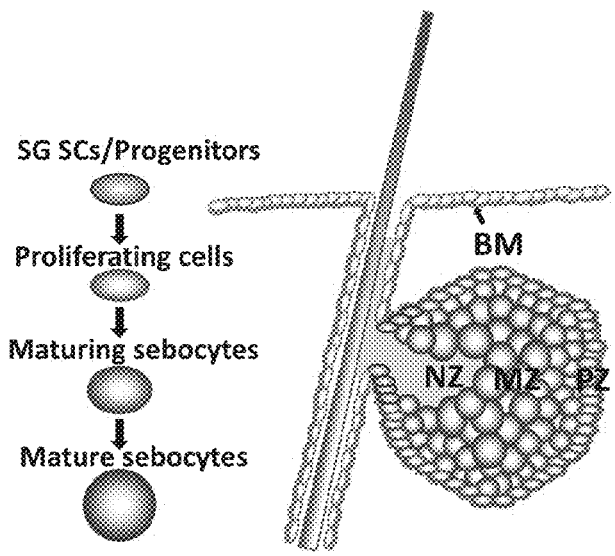
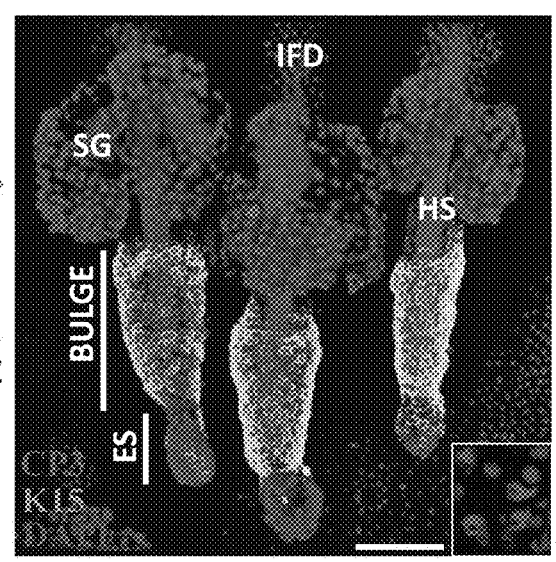
Fig. 1A  Fig. 1B
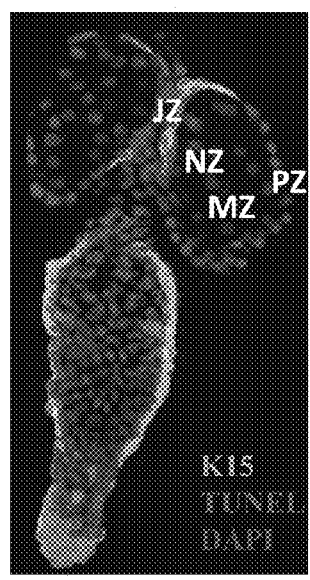
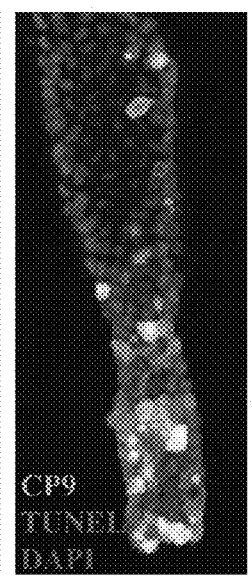
Fig. 1C  Fig. 1D  Fig. 1E  Fig. 1F
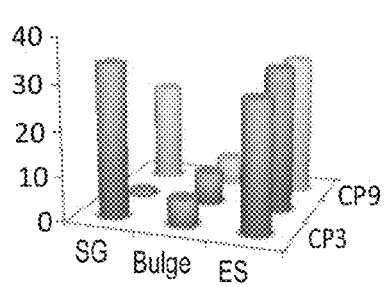
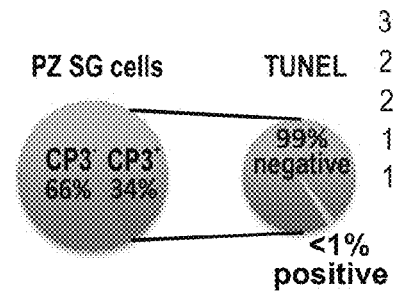
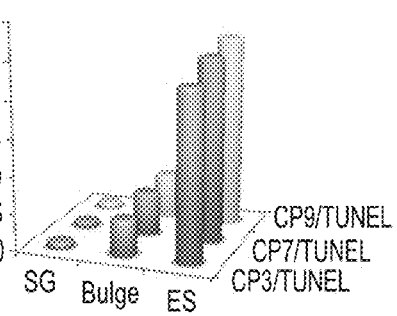
Fig. 1H  Fig. 1G  Fig. 1I

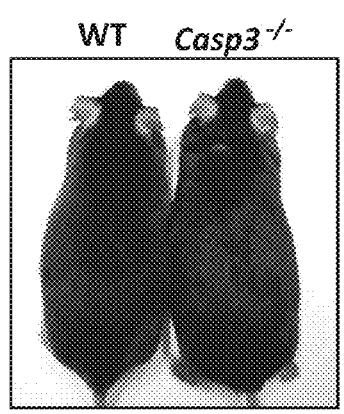
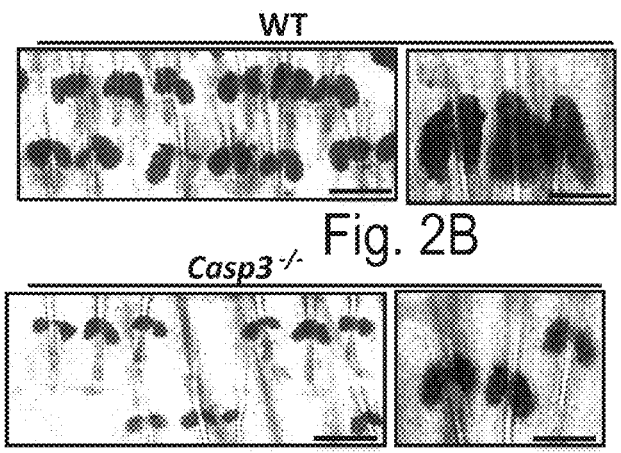
Fig. 2A
Fig. 2B
Fig. 2C
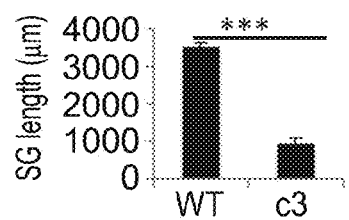
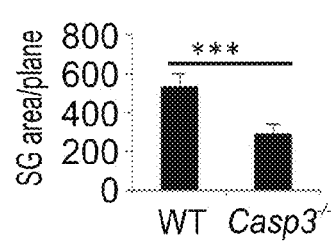
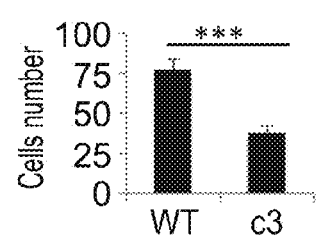
Fig. 2D
Fig. 2E
Fig. 2F
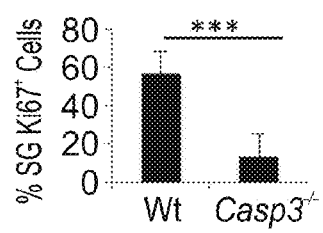
Fig. 2G
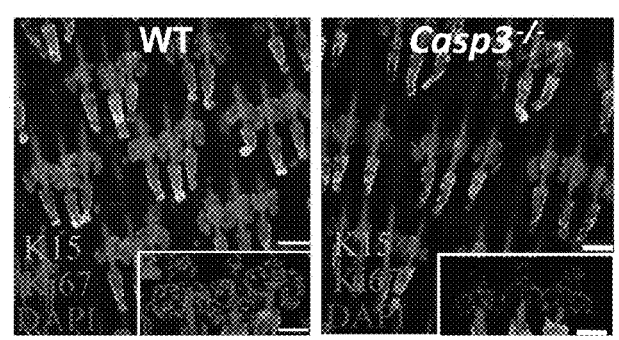
Fig. 2H
Fig. 2I
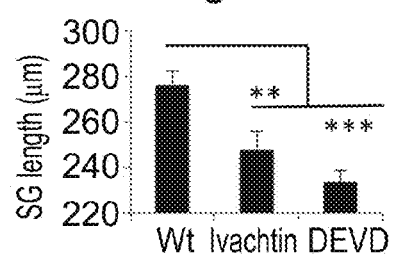
Fig. 2J
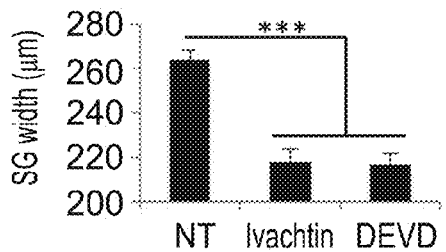
Fig. 2K
Fig. 2L
Fig. 2M

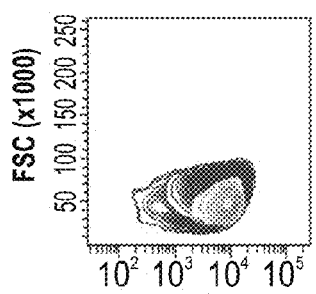
Fig. 2N
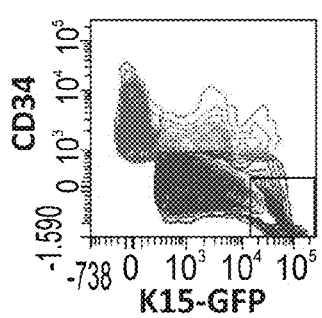
Fig. 2O
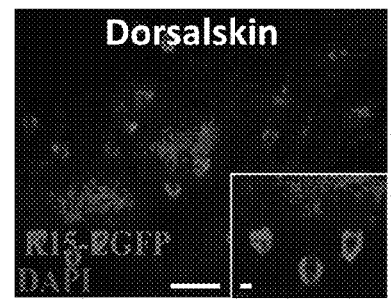
Fig. 2R
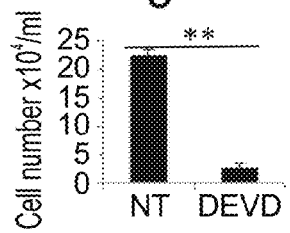
Fig. 2P
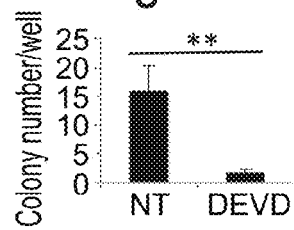
Fig. 2Q
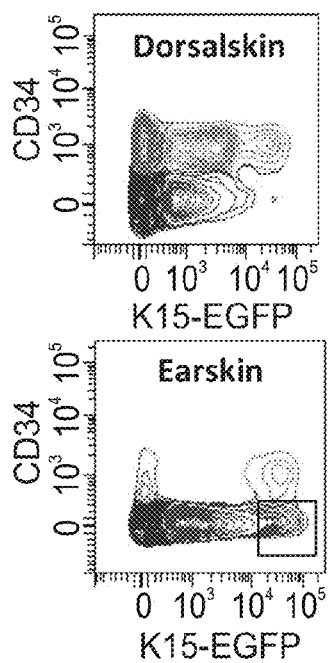
Fig. 2S
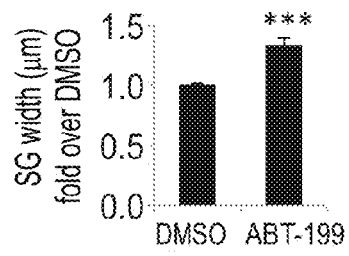
Fig. 2T
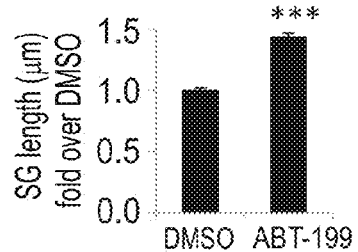
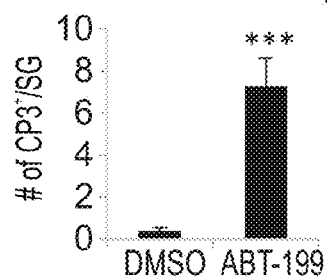
Fig. 2U
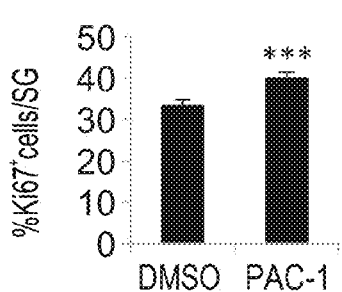
Fig. 2V
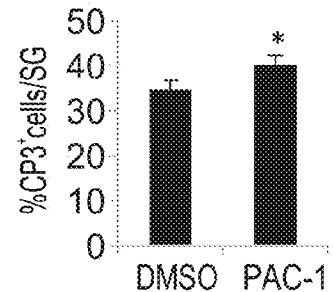
Fig. 2W

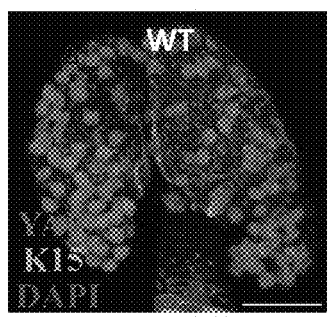
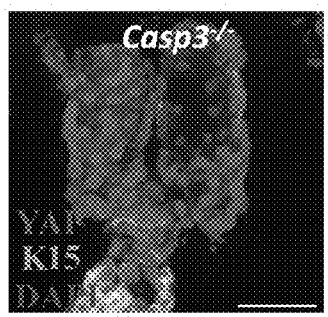
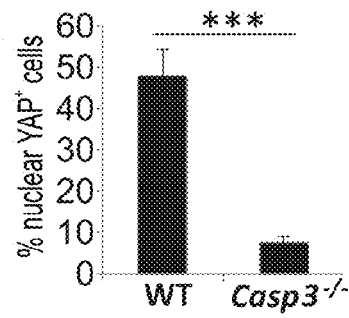
Fig. 3A  Fig. 3B  Fig. 3C
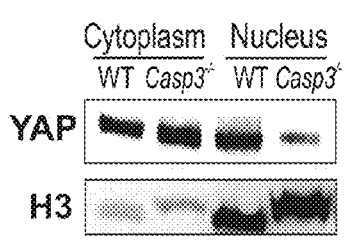
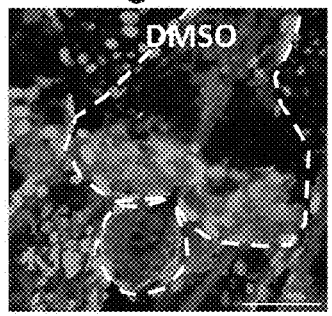
Fig. 3D  Fig. 3E  Fig. 3F
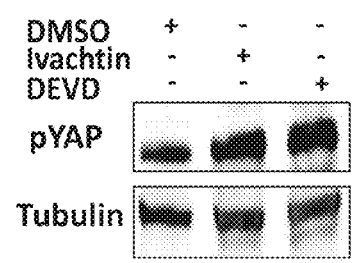
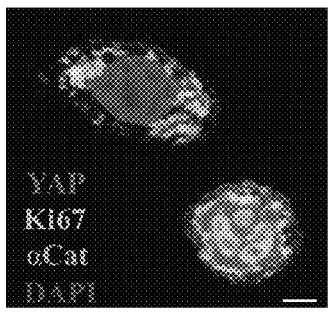
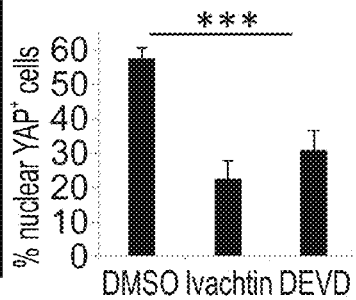
Fig. 3G  Fig. 3H  Fig. 3I
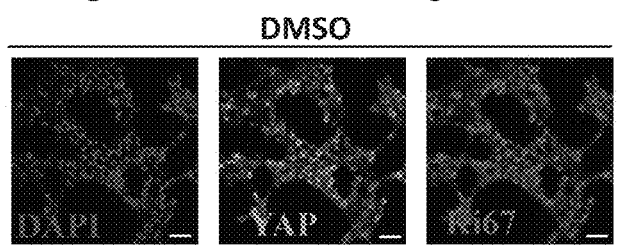
Fig. 3J
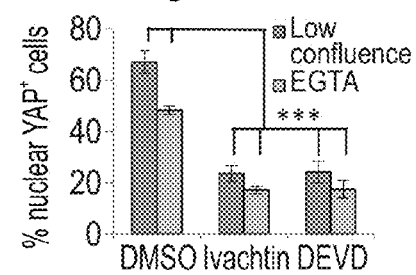
Fig. 3L
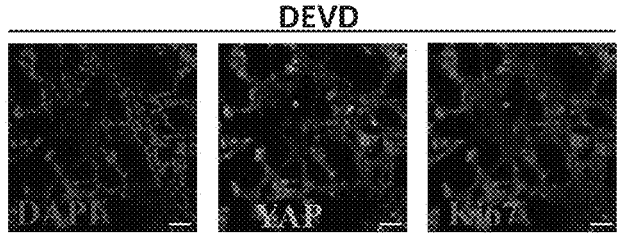
Fig. 3K
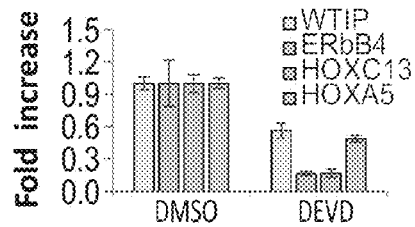
Fig. 3M

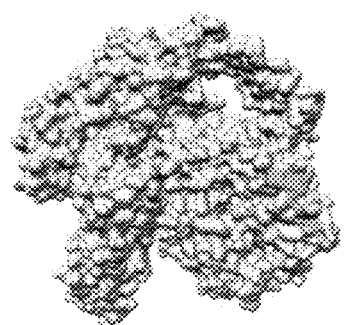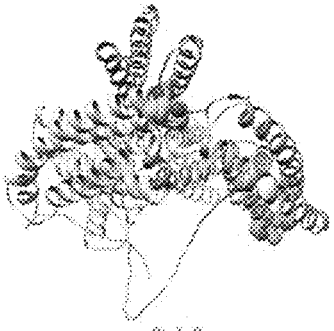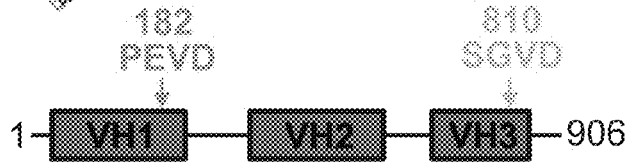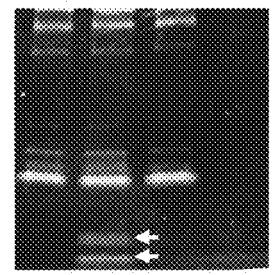
Fig. 4A  Fig. 4B
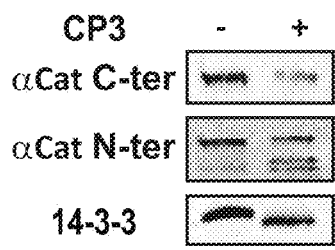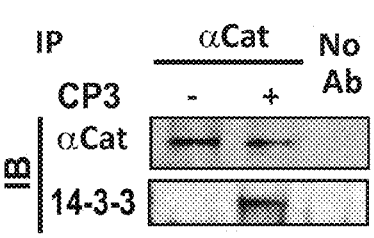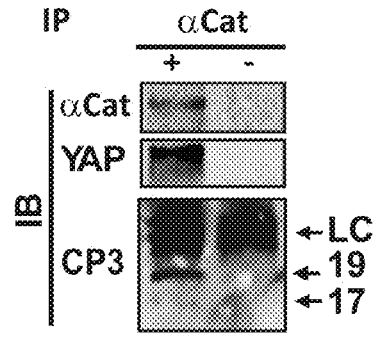
Fig. 4C  Fig. 4D  Fig. 4E
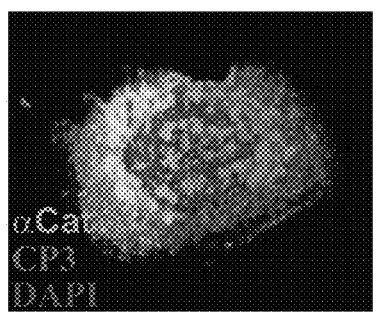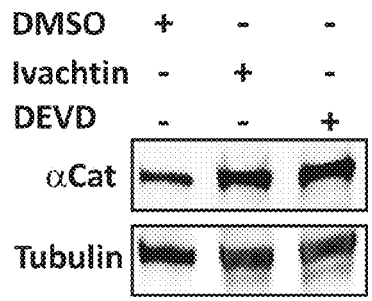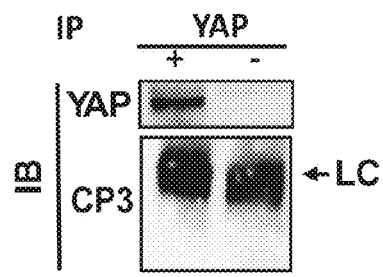
Fig. 4G  Fig. 4H  Fig. 4F
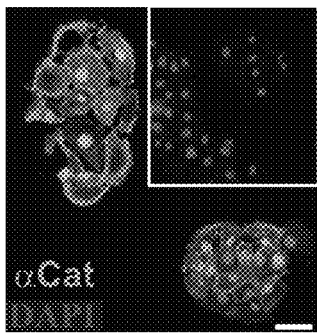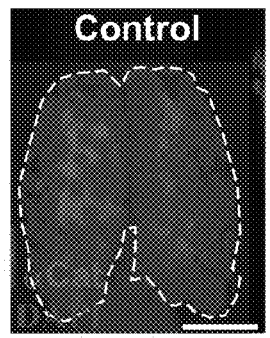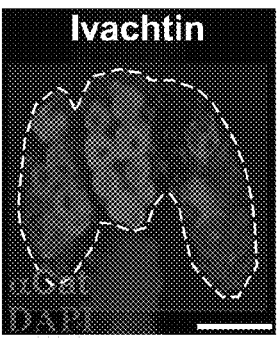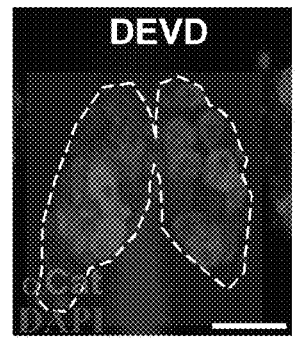
Fig. 4I  Fig. 4J  Fig. 4K  Fig. 4L

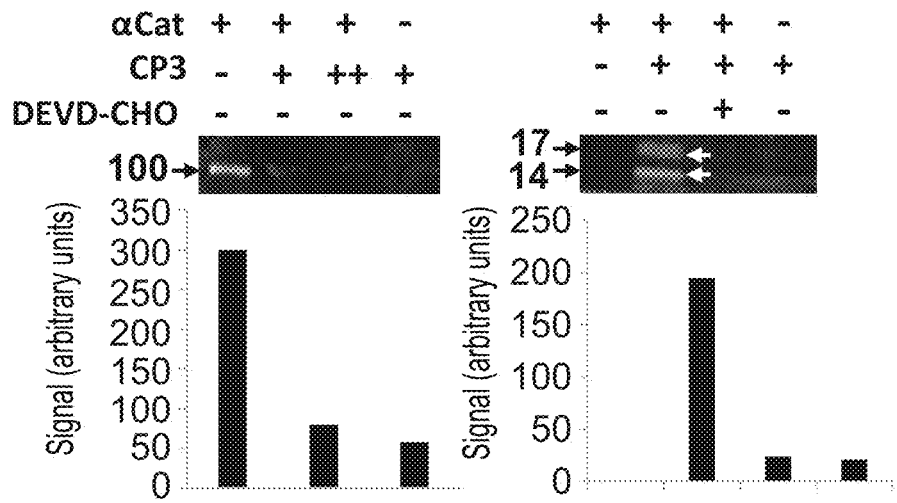
Fig. 4M    Fig. 4N
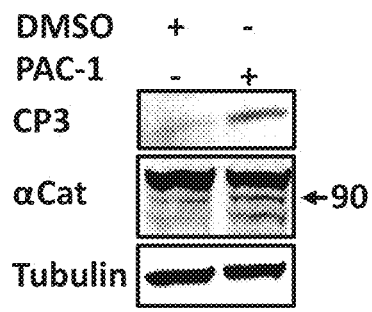 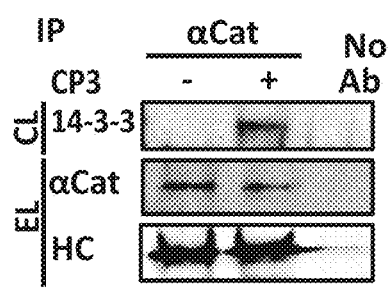 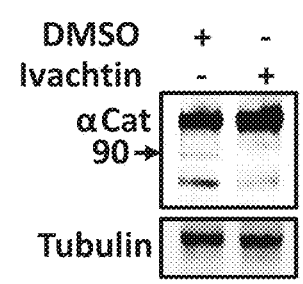
Fig. 4O    Fig. 4P    Fig. 4Q
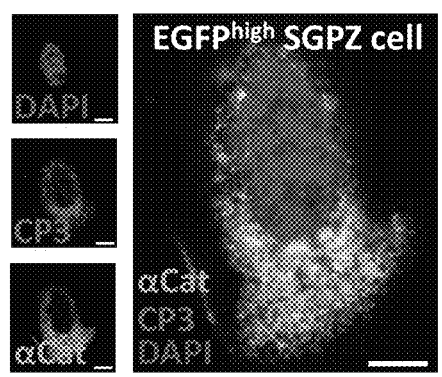 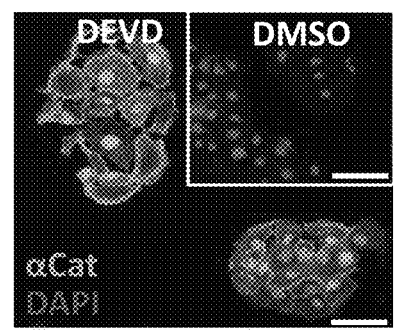
Fig. 4R    Fig. 4S Day 5 PWI Day 7 PWI Day 12 PWI

Fig. 6A
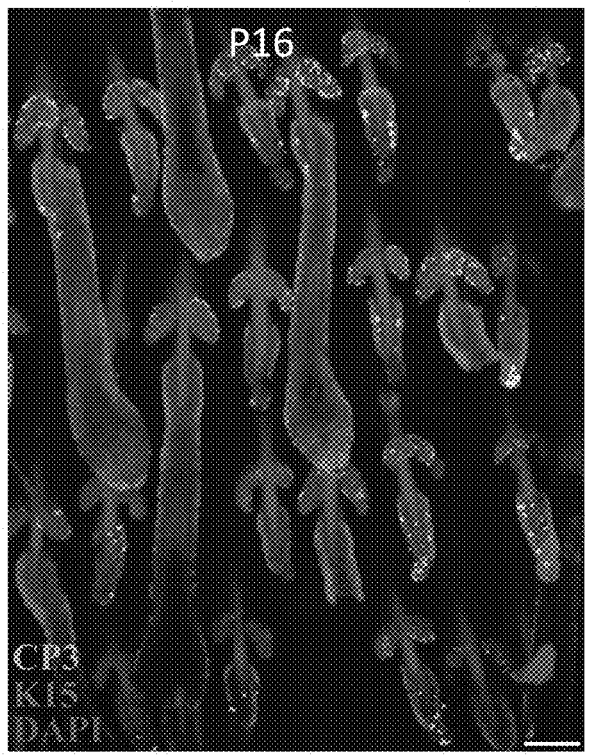
Fig. 6C
Fig. 6B
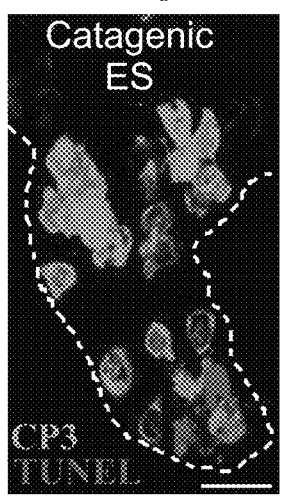
Fig. 6D
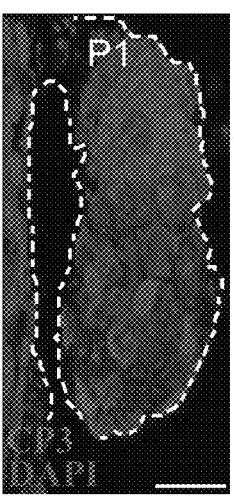
Fig. 6E
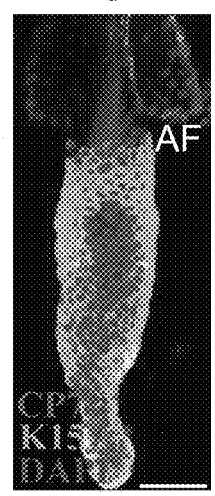
Fig. 6F
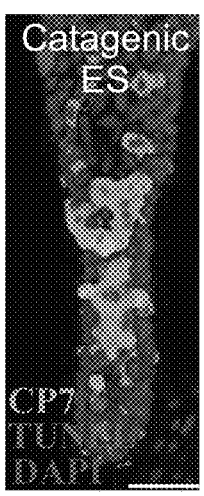
Fig. 6G

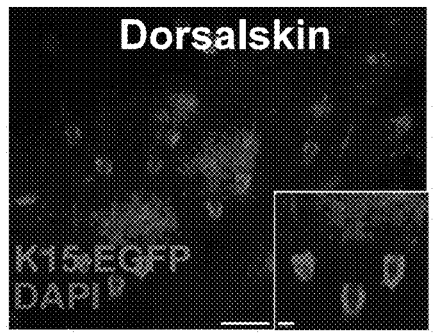
Fig. 9A
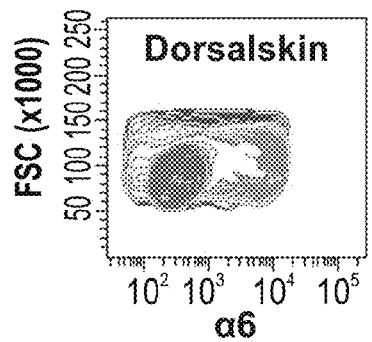
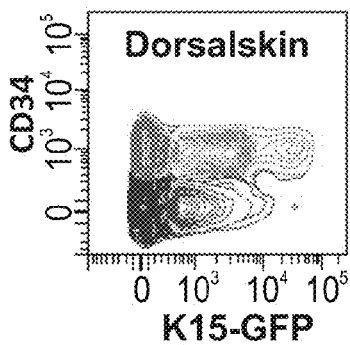
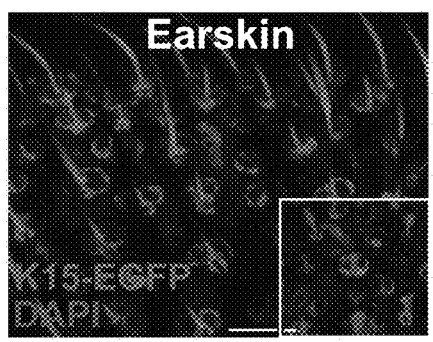
Fig. 9B
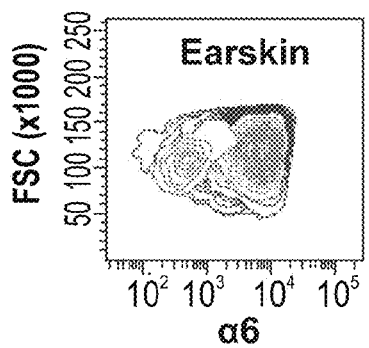
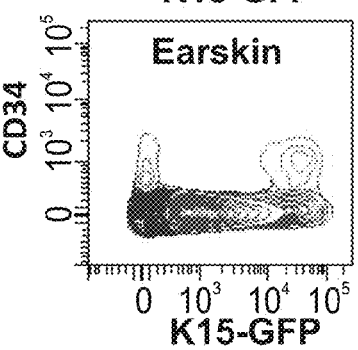
Fig. 9D
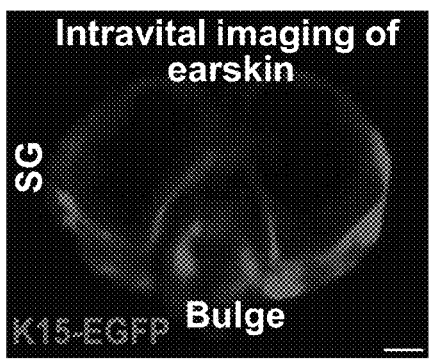
Fig. 9C
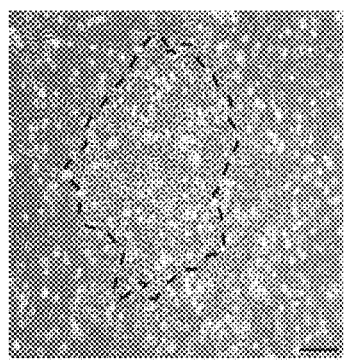
Fig. 9E
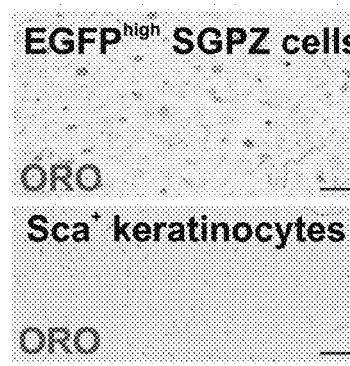
Fig. 9F Fig. 10A  EGFP^high SGPZs
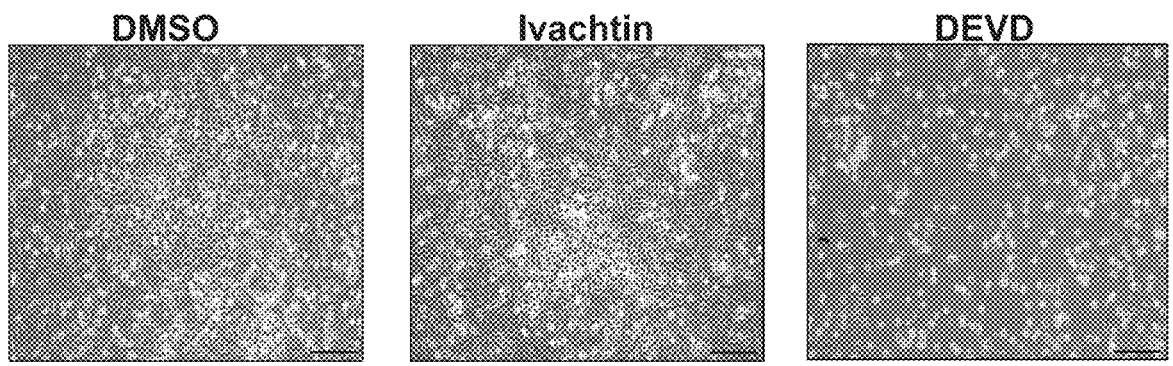
Fig. 10B  CD34+ HFSCs
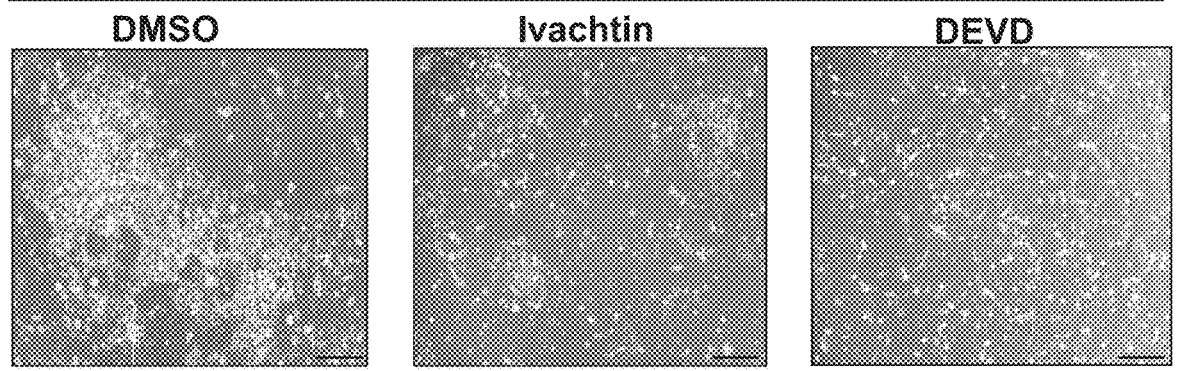
Fig. 10C  HaCaT
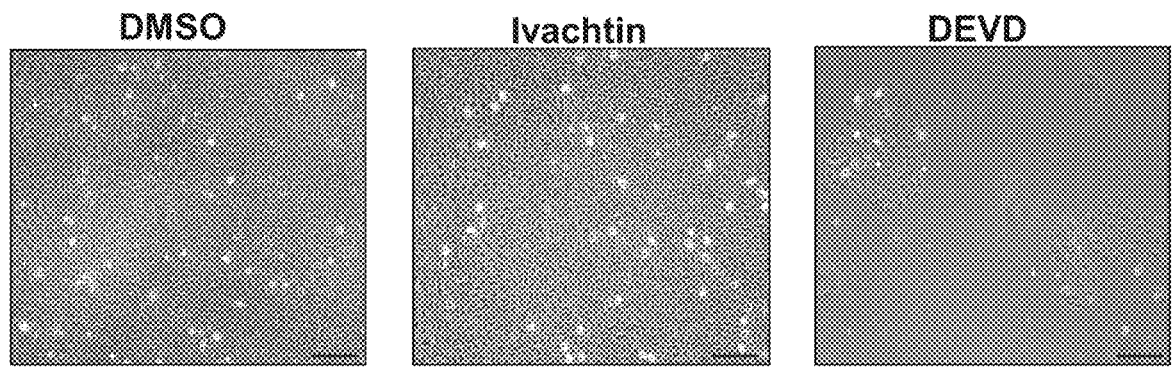
Fig. 10D  HEK293
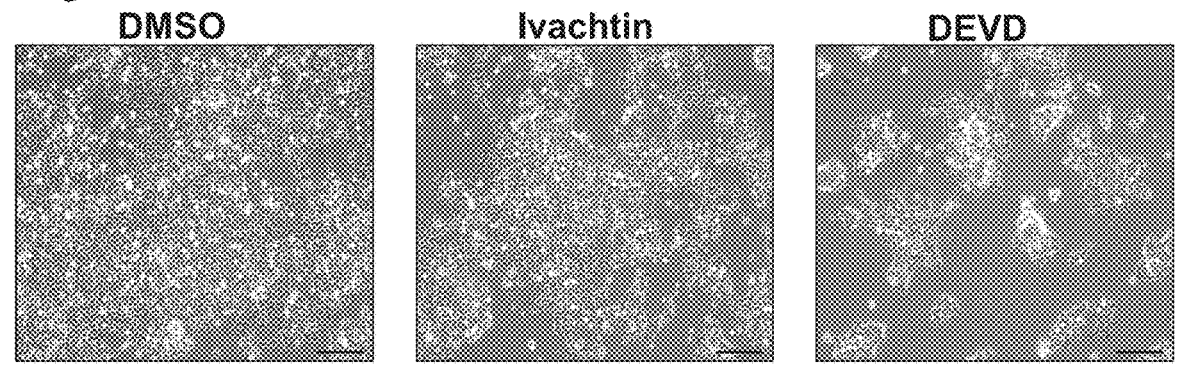

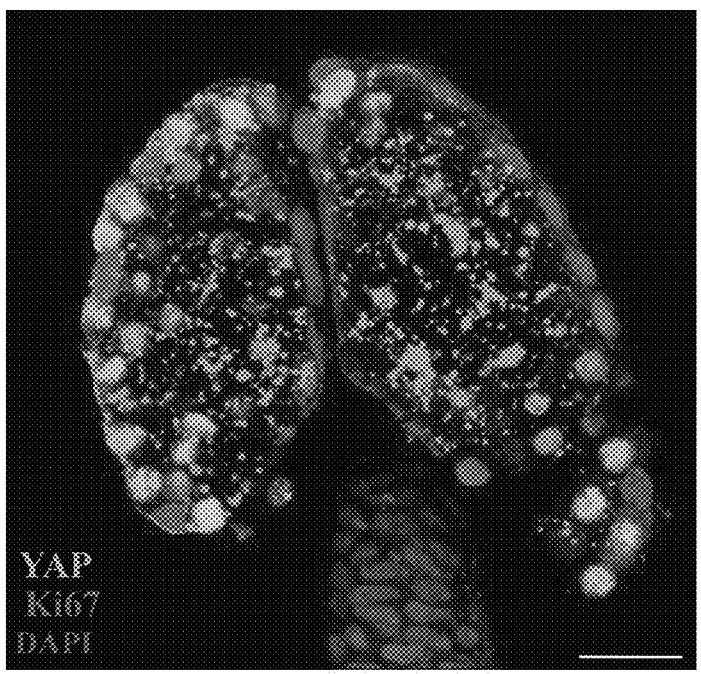
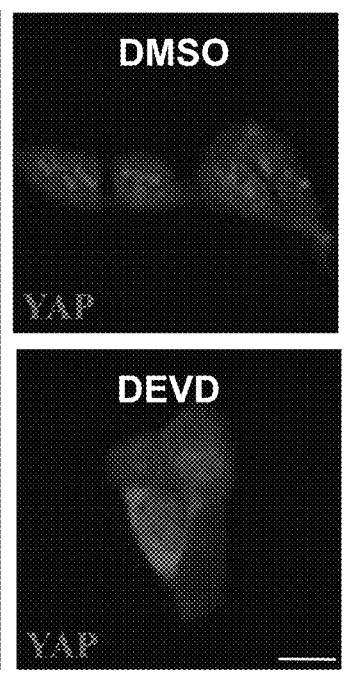
Fig. 11A  Fig. 11B
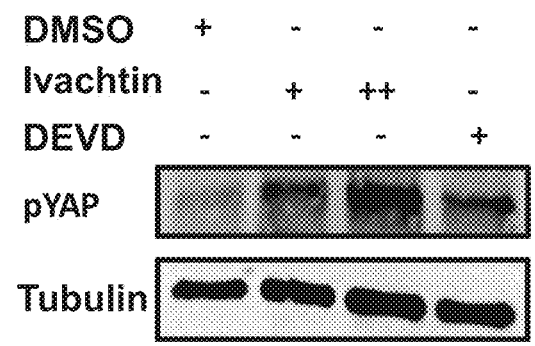
Fig. 11C  Fig. 11D
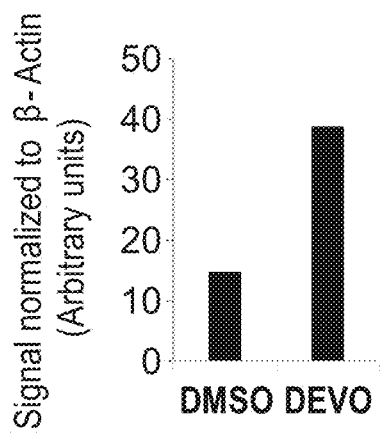
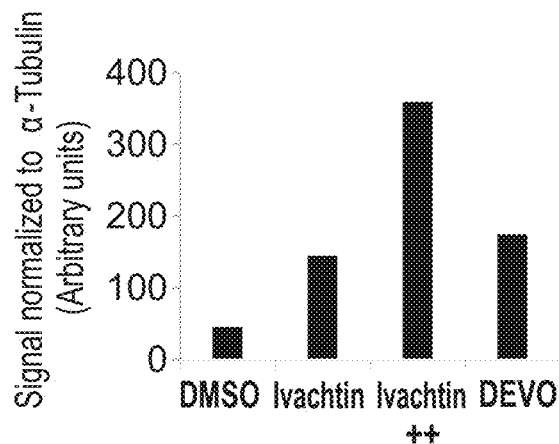
Fig. 11E  Fig. 11F

Fig. 11G

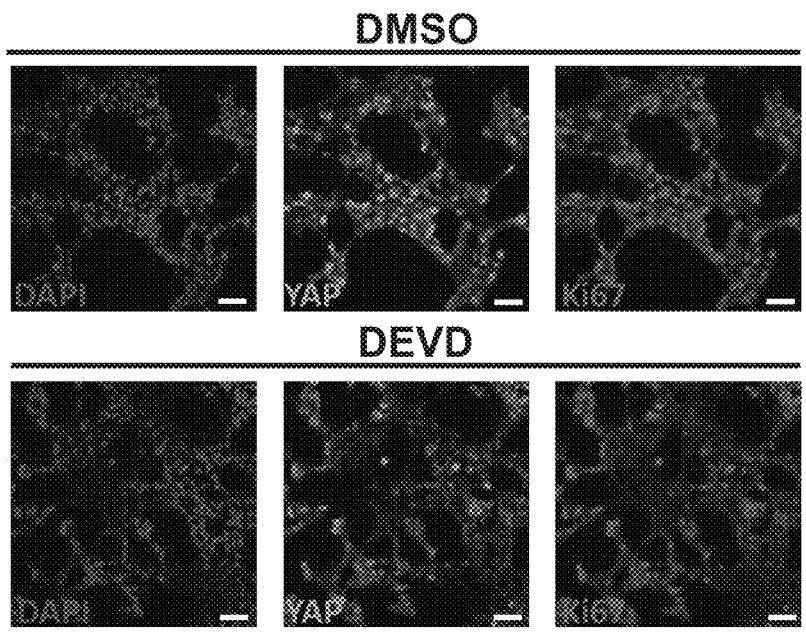

Fig. 11H

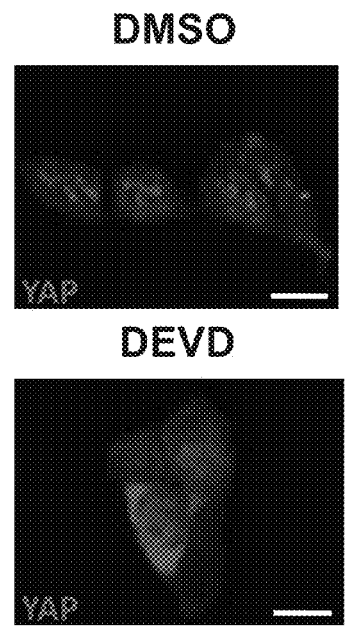

Fig. 12A

|  | 179 | 205 | SEQ ID NO: |
|---|---|---|---|
| Mus musculus | KALKPEVDKLNIMAAKRQQELKDVGNR | | 61 |
| Homo sapiens | KALKPEVDKLNIMAAKRQQELKDVGHR | | 62 |
| Rattus norvegicus | RALKPEVDKLNIMAAKRQQELKDVGHR | | 63 |
| Gallus gallus | KALKPEVDKLNIMAAKRQQELKDVGHR | | 64 |
| Danio reiro | KALKPEVDKLNMMAAKRQQELKDVHHK | | 65 |

|  | 807 | 833 | SEQ ID NO: |
|---|---|---|---|
| Mus musculus | ELVVSGVDSAMSLIQAAKNLMNAVVQT | | 66 |
| Homo sapiens | ELVVSGVDSAMSLIQAAKNLMNAVVQT | | 67 |
| Rattus norvegicus | ELVVSGVDSAMSLIQAAKNLMNAVVQT | | 68 |
| Gallus gallus | ELVVSGVDSAMSLIQAAKNLMNAVVQT | | 69 |
| Danio reiro | ELVVSGLDSAMSLIQAAKNLMNSVVST | | 70 |

```
    1      101      201                                              801    906
```

MTAVHAGNIN FKWDPKSLEI RTLAVERLLE PLVTQVTTLV NTNSKGPSNK
KRGRSKKAHV LAASVEQATE NFLEKGDKIA KESQFLKEEL VAAVEDVRKQ
GDLMK...... ..........  RGNMVRAARA LLSAVTELLI LADMADVYKL
LVQLK..... ....LRNAGNE QDLGIQYKAL KEEVDKLNIM AAKRQQELKD
VGHRDQMAAA RGILQKNVPI LYTASQACLQ RPDVAAYKAN RDLIYKQLQQ
AVTSISNAAQ ATASDDASQH QGKKRELAY ALNNFDKQII VDPLSFSEER
FRPSLEERLE SIISGAALMA DSSCTRDDRR ERIVAECNAV RQALQDLISS
YMGNAGRKER SDALNSAIDK MTKKTRDLRR QLRKAVMDHV SDSFLETNVP
LLVLIEAAKN GNEKEVKEYA QVFREHANKL IEVANLACSI SNNEEGVKLV
RMSASQLEAL CPQVINAALA LAAKPQSKLA QENMDLFKEQ WEKQVRVLTD
AVGDITSIDD FLAVSENHEL KDVNKCVIAL QEKDVDGLDR TAGAIRGRAA
KVIHVVTSEM DNYEPSVYTE KVLEATRLLS NTYMFRTTEQ VEAAVEALSS
DPAQPMDENE FIDASRLVYD GIRDIRKAVL MIRTPSELDD SDFETEDFDY
RSRTSVQTED DQLIAGQSAR AIMAQLPQEQ KAKIAEQVAS FQEEKSKLDA
EVSKWDDSGN DIIVLAKQMC MIMMEMTDFT RGKGPLENTS DVISAAKKIA
EAGSRNDKLG RTIADHCPDS ACKQDLLAYL QRIALYCHQL NICSKVRAEV
QNLDGELVVS GVISAMSLIQ AAKH...... ..........SYVAS TKYQK.....
.......... MKAPEKKFLV KREKQDETQT KIKRASQKKR VNFVQALSEF
KAMDSI
(SEQ ID NO: 60)

Fig. 12B

Fig. 14A  501A Melanoma
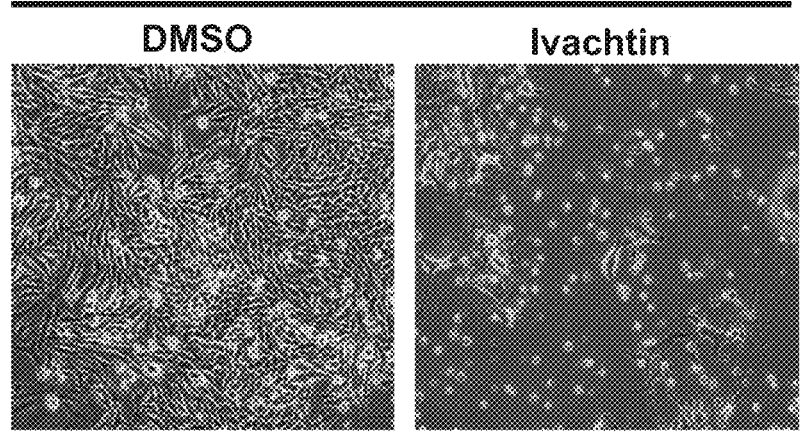
Fig. 14B  624-38 Melanoma
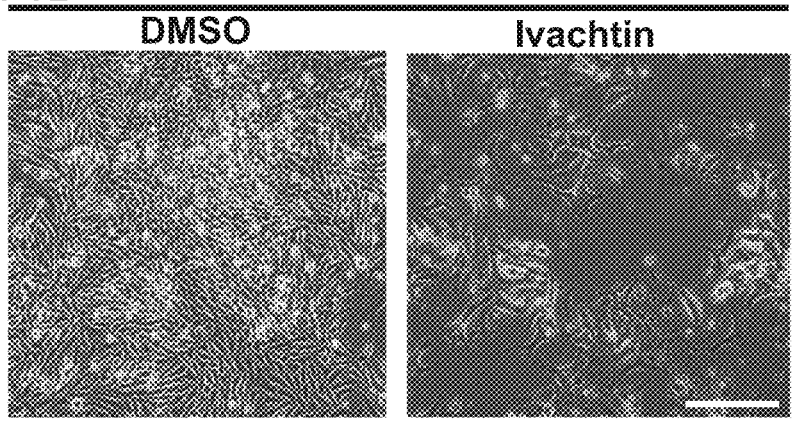
Fig. 14C  624-38 Melanoma
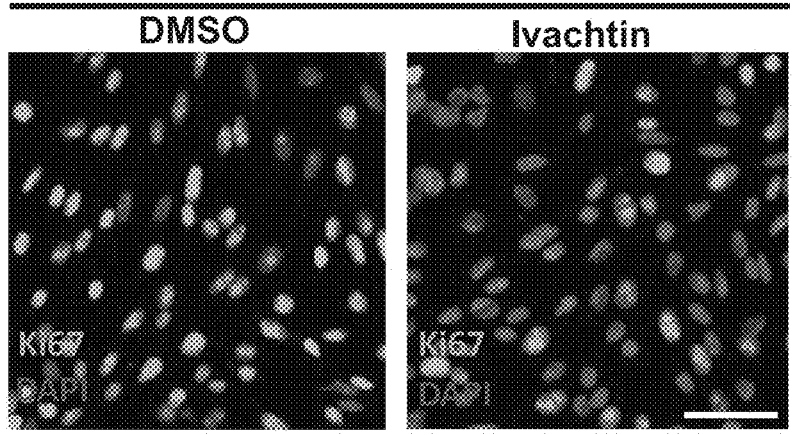

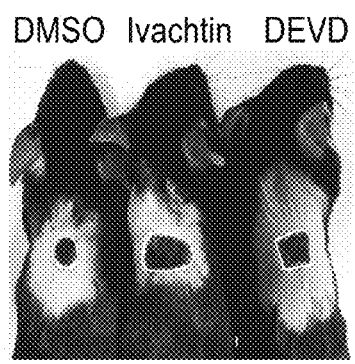
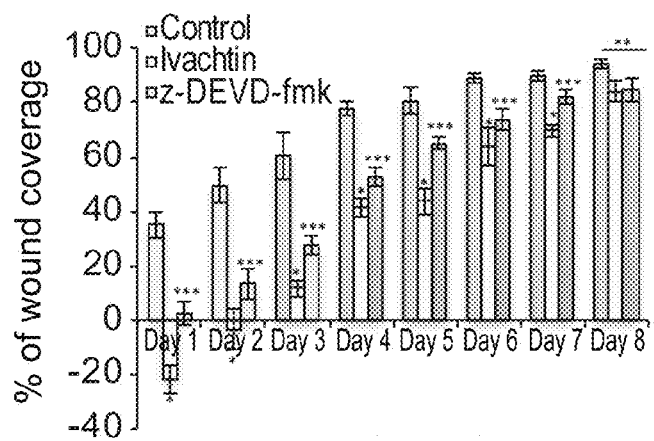
Fig. 19A
Fig. 19B
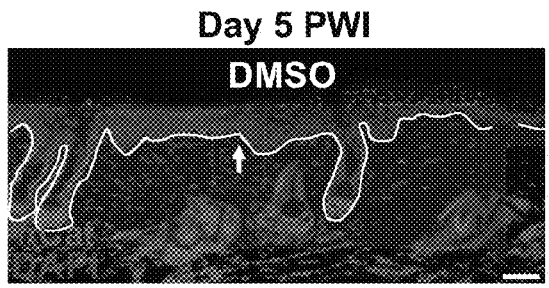
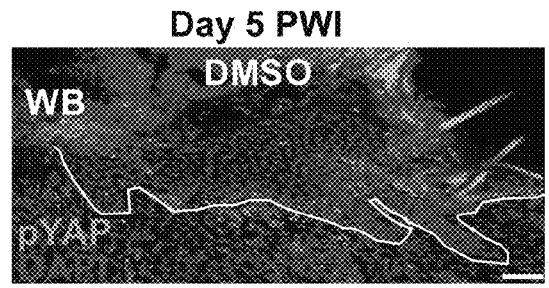
Fig. 19C
Fig. 19D
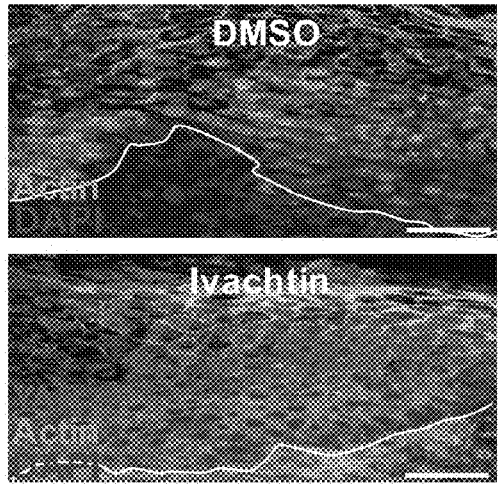
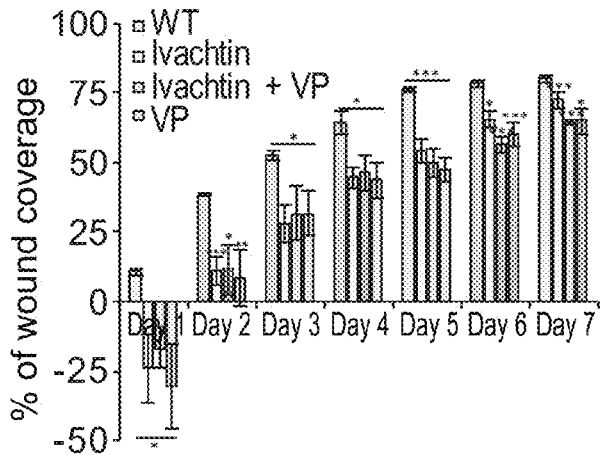
Fig. 19E
Fig. 19F

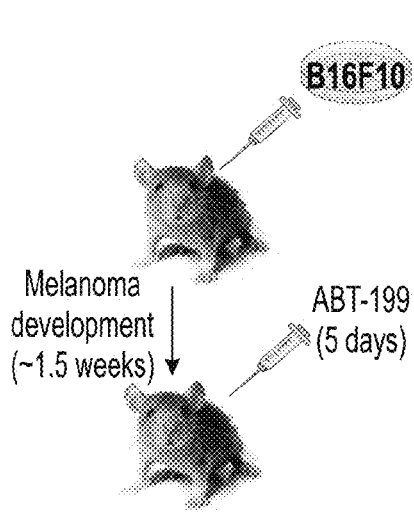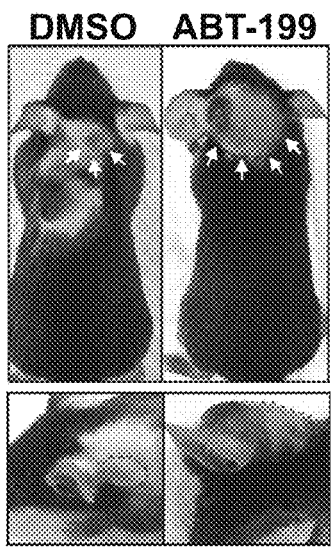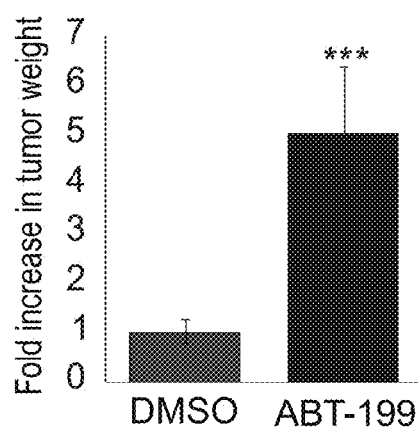
Fig. 21A  Fig. 21B  Fig. 21C
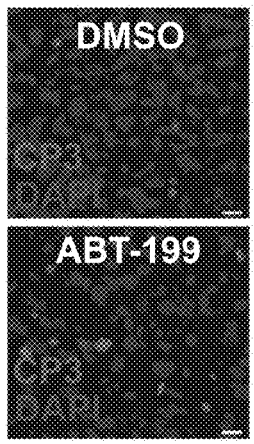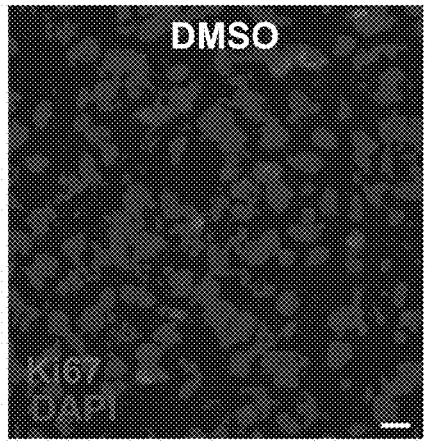
Fig. 21D  Fig. 21E
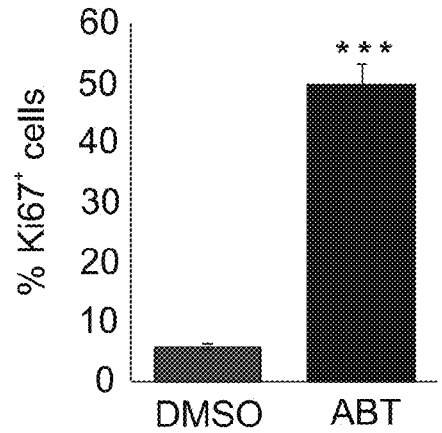
Fig. 21F

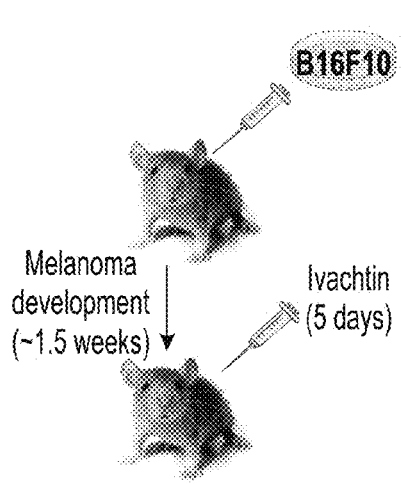
Fig. 22A
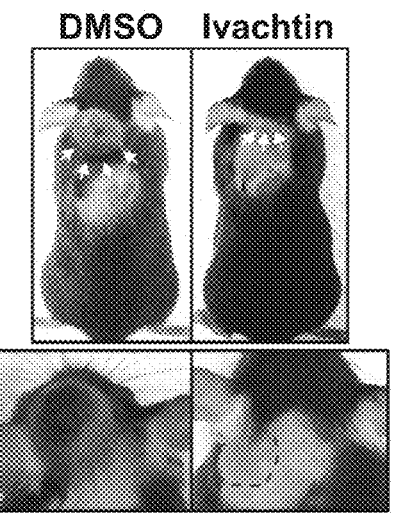
Fig. 22B
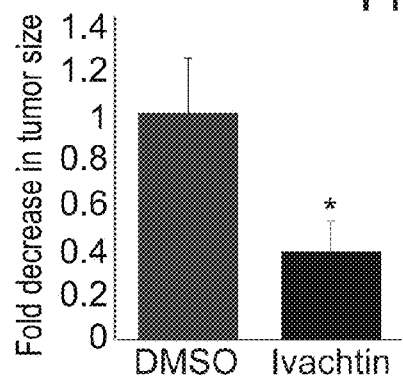
Fig. 22C
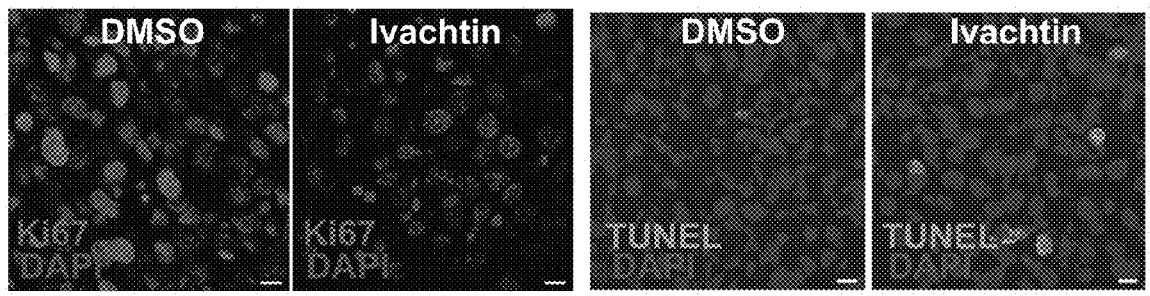
Fig. 22D
Fig. 22F
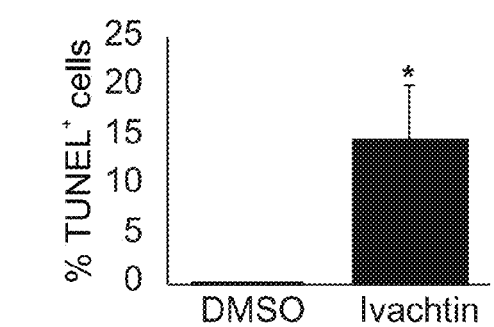
Fig. 22E
Fig. 22G Acridine orange assay

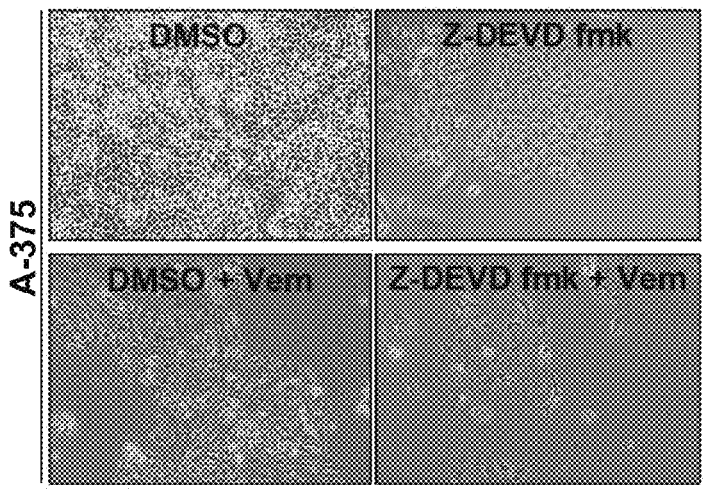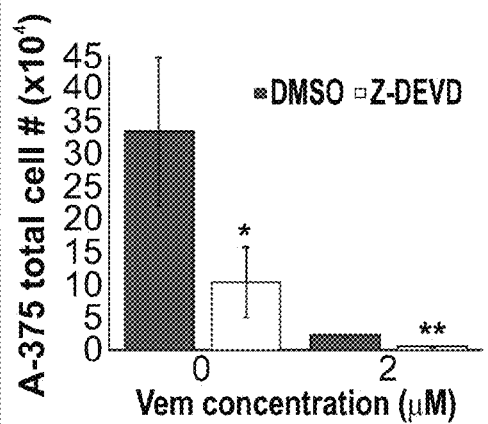
Fig. 26A            Fig. 26B
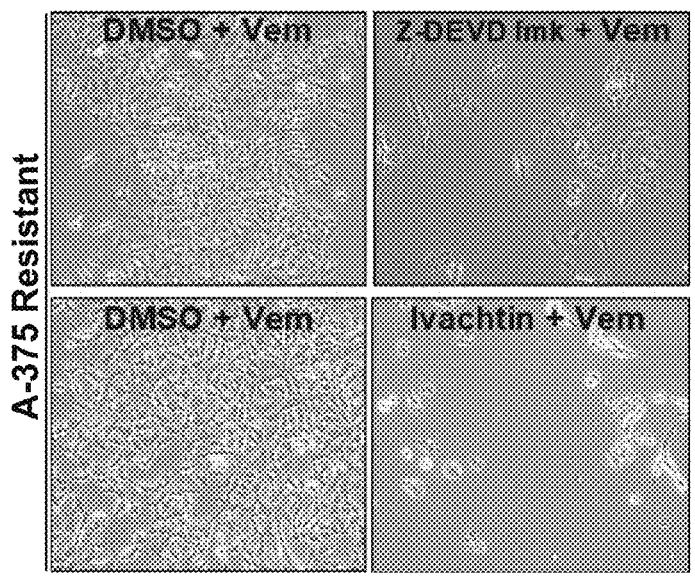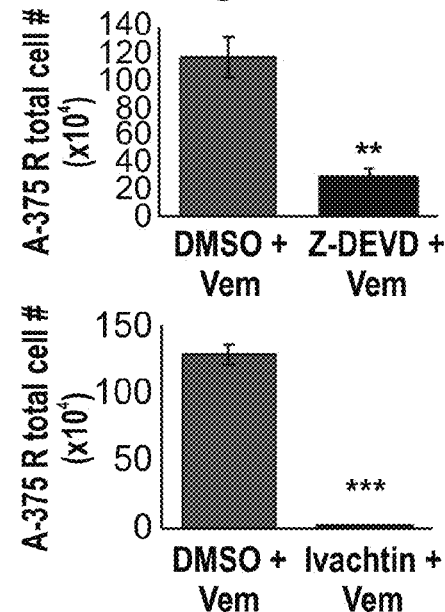
Fig. 26C            Fig. 26D
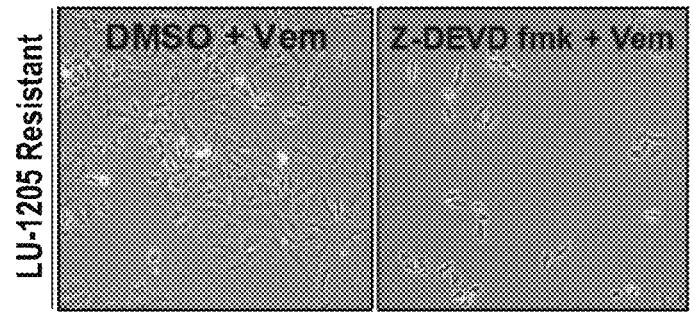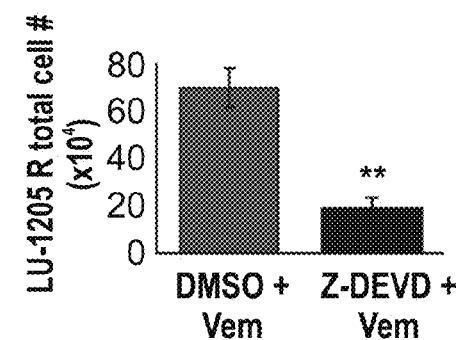
Fig. 26E            Fig. 26F

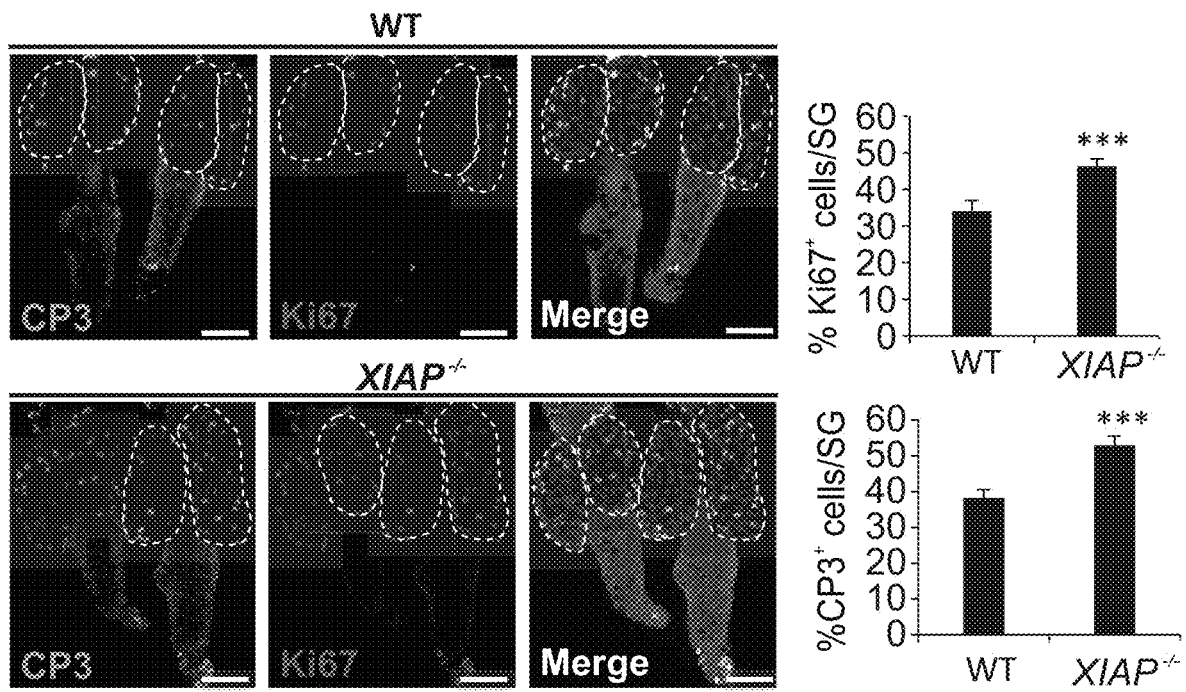
Fig. 29A
Fig. 29B
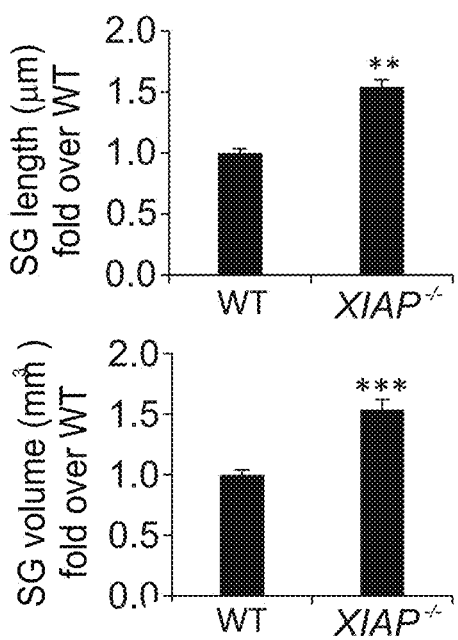
Fig. 29C
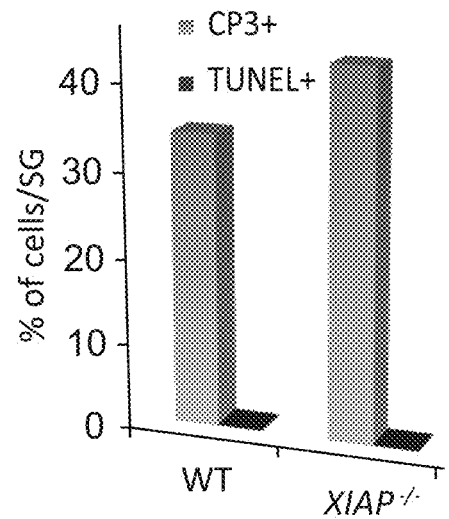
Fig. 29D

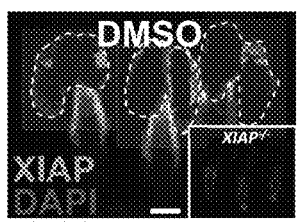 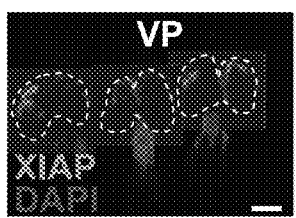 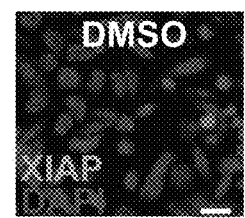
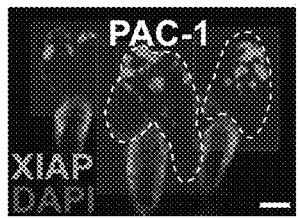 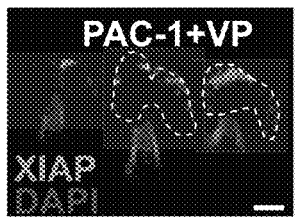 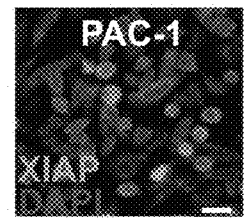
Fig. 29E
Fig. 29F
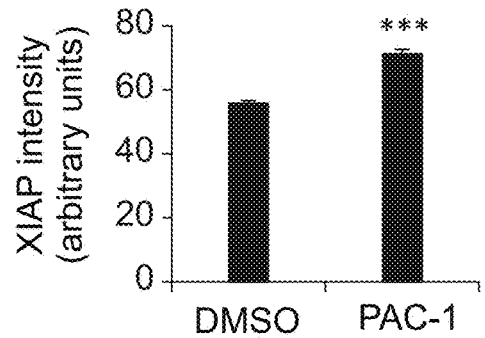
Fig. 29G
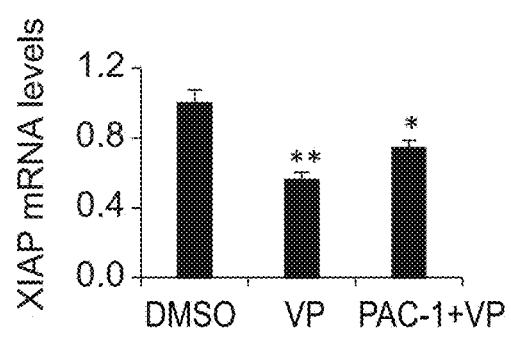
Fig. 29H
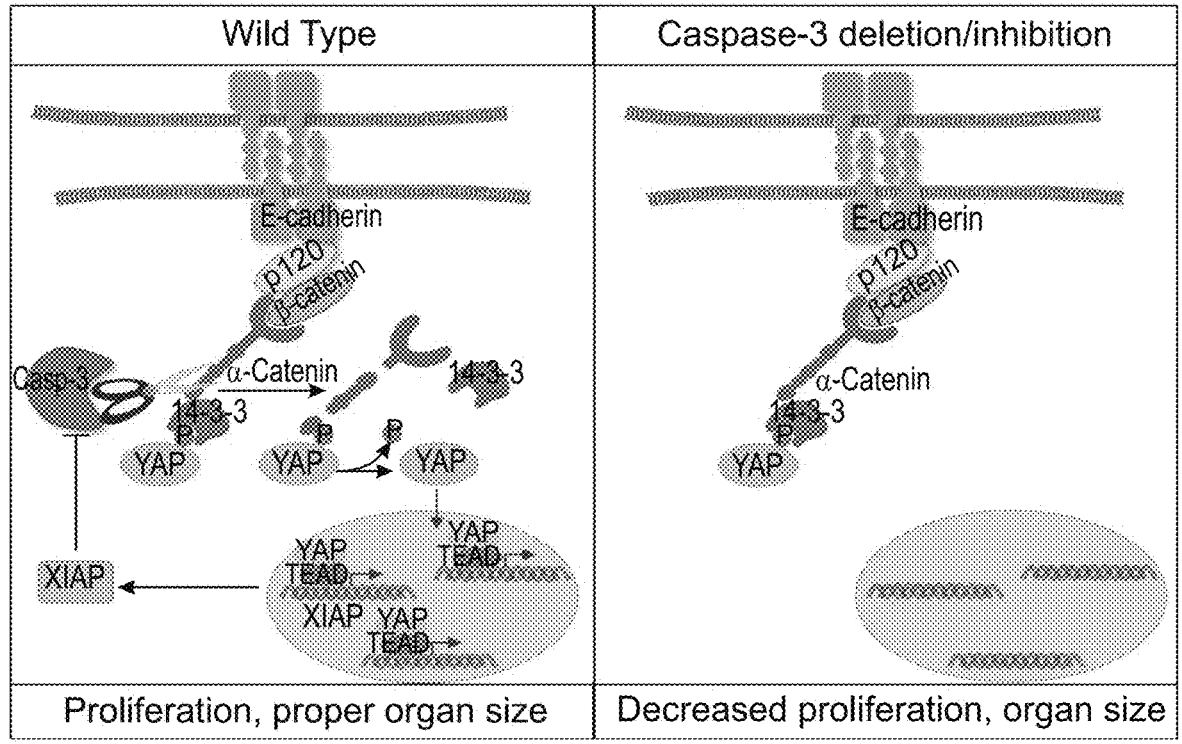
Fig. 29I

SEQUENCE LISTING

```
<160> NUMBER OF SEQ ID NOS: 77

<210> SEQ ID NO 1
<211> LENGTH: 504
<212> TYPE: PRT
<213> ORGANISM: homo sapiens

<400> SEQUENCE: 1

Met Asp Pro Gly Gln Gln Pro Pro Gln Pro Ala Pro Gln Gly Gln
1               5                   10                  15

Gly Gln Pro Pro Ser Gln Pro Pro Gln Gly Gln Gly Pro Pro Ser Gly
                20                  25                  30

Pro Gly Gln Pro Ala Pro Ala Ala Thr Gln Ala Ala Pro Gln Ala Pro
            35                  40                  45

Pro Ala Gly His Gln Ile Val His Val Arg Gly Asp Ser Glu Thr Asp
        50                  55                  60

Leu Glu Ala Leu Phe Asn Ala Val Met Asn Pro Lys Thr Ala Asn Val
65                  70                  75                  80

Pro Gln Thr Val Pro Met Arg Leu Arg Lys Leu Pro Asp Ser Phe Phe
                85                  90                  95

Lys Pro Pro Glu Pro Lys Ser His Ser Arg Gln Ala Ser Thr Asp Ala
                100                 105                 110

Gly Thr Ala Gly Ala Leu Thr Pro Gln His Val Arg Ala His Ser Ser
            115                 120                 125

Pro Ala Ser Leu Gln Leu Gly Ala Val Ser Pro Gly Thr Leu Thr Pro
        130                 135                 140

Thr Gly Val Val Ser Gly Pro Ala Ala Thr Pro Thr Ala Gln His Leu
145                 150                 155                 160

Arg Gln Ser Ser Phe Glu Ile Pro Asp Asp Val Pro Leu Pro Ala Gly
                165                 170                 175

Trp Glu Met Ala Lys Thr Ser Ser Gly Gln Arg Tyr Phe Leu Asn His
                180                 185                 190

Ile Asp Gln Thr Thr Thr Trp Gln Asp Pro Arg Lys Ala Met Leu Ser
            195                 200                 205

Gln Met Asn Val Thr Ala Pro Thr Ser Pro Pro Val Gln Gln Asn Met
        210                 215                 220
```

Met Asn Ser Ala Ser Gly Pro Leu Pro Asp Gly Trp Glu Gln Ala Met
225                 230                 235                 240

Thr Gln Asp Gly Glu Ile Tyr Tyr Ile Asn His Lys Asn Lys Thr Thr
            245                 250                 255

Ser Trp Leu Asp Pro Arg Leu Asp Pro Arg Phe Ala Met Asn Gln Arg
        260                 265                 270

Ile Ser Gln Ser Ala Pro Val Lys Gln Pro Pro Leu Ala Pro Gln
    275                 280                 285

Ser Pro Gln Gly Gly Val Met Gly Gly Ser Asn Ser Asn Gln Gln Gln
290                 295                 300

Gln Met Arg Leu Gln Leu Gln Met Glu Lys Glu Arg Leu Arg Leu
305                 310                 315                 320

Lys Gln Gln Glu Leu Leu Arg Gln Ala Met Arg Asn Ile Asn Pro Ser
                325                 330                 335

Thr Ala Asn Ser Pro Lys Cys Gln Glu Leu Ala Leu Arg Ser Gln Leu
            340                 345                 350

Pro Thr Leu Glu Gln Asp Gly Gly Thr Gln Asn Pro Val Ser Ser Pro
        355                 360                 365

Gly Met Ser Gln Glu Leu Arg Thr Met Thr Thr Asn Ser Ser Asp Pro
370                 375                 380

Phe Leu Asn Ser Gly Thr Tyr His Ser Arg Asp Glu Ser Thr Asp Ser
385                 390                 395                 400

Gly Leu Ser Met Ser Ser Tyr Ser Val Pro Arg Thr Pro Asp Asp Phe
                405                 410                 415

Leu Asn Ser Val Asp Glu Met Asp Thr Gly Asp Thr Ile Asn Gln Ser
            420                 425                 430

Thr Leu Pro Ser Gln Gln Asn Arg Phe Pro Asp Tyr Leu Glu Ala Ile
        435                 440                 445

Pro Gly Thr Asn Val Asp Leu Gly Thr Leu Glu Gly Asp Gly Met Asn
450                 455                 460

Ile Glu Gly Glu Glu Leu Met Pro Ser Leu Gln Glu Ala Leu Ser Ser
465                 470                 475                 480

Asp Ile Leu Asn Asp Met Glu Ser Val Leu Ala Ala Thr Lys Leu Asp
                485                 490                 495

Lys Glu Ser Phe Leu Thr Trp Leu
            500

<210> SEQ ID NO 2
<211> LENGTH: 5396
<212> TYPE: DNA
<213> ORGANISM: homo sapiens

<400> SEQUENCE: 2
gccgccgcca gggaaaagaa agggaggaag gaaggaacaa gaaaaggaaa taagagaaa        60 ggggaggcgg ggaaaggcaa cgagctgtcc ggcctccgtc aagggagttg gagggaaaaa      120
gttctcaggc gccgcaggtc cgagtgcctc gcagcccctc ccgaggcgca gccgccagac      180
cagtggagcc ggggcgcagg gcgggggcgg aggcgccggg gcgggggatg cggggccgcg      240
gcgcagcccc ccgccctga gagcgaggac agcgccgccc ggcccgcagc cgtcgccgct      300
tctccacctc ggcccgtgga gccggggcgt ccgggcgtag ccctcgctcg cctgggtcag      360
ggggtgcgcg tcgggggagg cagaagccat ggatcccggg cagcagccgc gcctcaacc      420 ggcccccag ggccaagggc agccgccttc gcagcccccg caggggcagg gccgccgtc        480

```
cggacccggg caaccggcac ccgcggcgac ccaggcggcg ccgcaggcac ccccgccgg      540 gcatcagatc gtgcacgtcc gcggggactc ggagaccgac ctggaggcgc tcttcaacgc      600
cgtcatgaac cccaagacgg ccaacgtgcc ccagaccgtg cccatgaggc tccggaagct      660
gcccgactcc ttcttcaagc cgccggagcc caaatcccac tcccgacagg ccagtactga      720
tgcaggcact gcaggagccc tgactccaca gcatgttcga gctcattcct ctccagcttc      780
tctgcagttg ggagctgttt ctcctgggac actgaccccc actggagtag tctctggccc      840
agcagctaca cccacagctc agcatcttcg acagtcttct tttgagatac ctgatgatgt      900
acctctgcca gcaggttggg agatggcaaa gacatcttct ggtcagagat acttcttaaa      960
tcacatcgat cagacaacaa catggcagga ccccaggaag gccatgctgt cccagatgaa     1020
cgtcacagcc cccaccagtc caccagtgca gcagaatatg atgaactcgg cttcaggtcc     1080
tcttcctgat ggatgggaac aagccatgac tcaggatgga gaaatttact atataaacca     1140
taagaacaag accacctctt ggctagaccc aaggcttgac cctcgttttg ccatgaacca     1200
gagaatcagt cagagtgctc cagtgaaaca gccaccaccc ctggctcccc agagcccaca     1260
gggaggcgtc atgggtggca gcaactccaa ccagcagcaa cagatgcgac tgcagcaact     1320
gcagatggag aaggagaggc tgcggctgaa acagcaagaa ctgcttcggc aggcaatgcg     1380
gaatatcaat cccagcacag caaattctcc aaaatgtcag gagttagccc tgcgtagcca     1440
gttaccaaca ctggagcagg atggtgggac tcaaaatcca gtgtcttctc ccgggatgtc     1500
tcaggaattg agaacaatga cgaccaatag ctcagatcct ttccttaaca gtggcaccta     1560
tcactctcga gatgagagta cagacagtgg actaagcatg agcagctaca gtgtccctcg     1620
aaccccagat gacttcctga acagtgtgga tgagatggat acaggtgata ctatcaacca     1680
aagcaccctg ccctcacagc agaaccgttt cccagactac cttgaagcca ttcctgggac     1740
aaatgtggac cttggaacac tggaaggaga tggaatgaac atagaaggag aggagctgat     1800
gccaagtctg caggaagctt tgagttctga catccttaat gacatggagt ctgttttggc     1860
tgccaccaag ctagataaag aaagctttct tacatggtta tagagccctc aggcagactg     1920
aattctaaat ctgtgaagga tctaaggaga cacatgcacc ggaaatttcc ataagccagt     1980
tgcagttttc aggctaatac agaaaaagat gaacaaacgt ccagcaagat actttaatcc     2040
tctatttgtg tcttccttgt ccattgctgc tgttaatgta ttgctgacct cttttcacagt     2100 tggctctaaa gaatcaaaag aaaaaaactt tttatttctt ttgctattaa aactactgtt     2160
cattttgggg gctgggggaa gtgagcctgt ttggatgatg gatgccattc cttttgccca     2220
gttaaatgtt caccaatcat tttaactaaa tactcagact tagaagtcag atgcttcatg     2280
tcacagcatt tagtttgttc aacagttgtt tcttcagctt cctttgtcca gtggaaaaac     2340
atgatttact ggtctgacaa gccaaaaatg ttatatctga tattaaatac ttaatgctga     2400
tttgaagaga tagctgaaac caaggctgaa gactgtttta ctttcagtat tttcttttcc     2460
tcctagtgct atcattagtc acataatgac cttgatttta ttttaggagc ttataaggca     2520
tgagacaatt tccatataaa tatattaatt attgccacat actctaatat agattttggt     2580
ggataatttt gtgggtgtgc attttgttct gttttgttgg gttttttgtt ttttttgttt     2640
ttggcagggt cggtgggggg gttggttggt tggttggttt tgtcggaacc taggcaaatg     2700
accatattag tgaatctgtt aatagttgta gcttgggatg gttattgtag ttgttttggt     2760
aaaatcttca tttcctggtt ttttttacca ccctatttaa atctcgatta tctgctctct     2820 ctttttatata catacacaca cccaaacata acatttataa tagtgtggta gtggaatgta     2880
```

```
tccttttttta ggtttccctg ctttccagtt aattttaaa atggtagcgc tttgtatgca    2940
tttagaatac atgactagta gtttatattt cactggtagt ttaaatctgg ttggggcagt    3000
ctgcagatgt ttgaagtagt ttagtgttct agaaagagct attactgtgg atagtgccta    3060
ggggagtgct ccacgccctc tgggcatacg gtagatatta tctgatgaat tggaaaggag    3120
caaaccagaa atggctttat tttctcccctt ggactaattt ttaagtctcg attggaattc    3180
agtgagtagg ttcataatgt gcatgacaga aataagcttt atagtggttt accttcattt    3240
agctttggaa gttttctttg ccttagtttt ggaagtaaat tctagtttgt agttctcatt    3300
tgtaatgaac acattaacga ctagattaaa atattgcctt caagattgtt cttacttaca    3360
agacttgctc ctacttctat gctgaaaatt gaccctggat agaatactat aaggttttga    3420
gttagctgga aaagtgatca gattaataaa tgtatattgg tagttgaatt tagcaaagaa    3480
atagagataa tcatgattat acctttattt ttacaggaag agatgatgta actagagtat    3540
gtgtctacag gagtaataat ggtttccaaa gagtattttt taaaggaaca aaacgagcat    3600
gaattaactc ttcaatataa gctatgaagt aatagttggt tgtgaattaa agtggcacca    3660
gctagcacct ctgtgtttta agggtctttc aatgtttcta gaataagccc ttatttttcaa    3720 gggttcataa caggcataaa atctcttctc ctggcaaaag ctgctatgaa aagcctcagc    3780
ttgggaagat agatttttt ccccccaatt acaaaatcta agtattttgg cccttcaatt    3840
tggaggaggg caaagttgg aagtaagaag ttttatttta agtactttca gtgctcaaaa    3900
aaatgcaatc actgtgttgt atataatagt tcataggttg atcactcata ataattgact    3960
ctaaggcttt tattaagaaa acagcagaaa gattaaatct tgaattaagt ctgggggaa    4020 atggccactg cagatggagt tttagagtag taatgaaatt ctacctagaa tgcaaaattg    4080
ggtatatgaa ttacatagca tgttgttggg attttttta atgtgcagaa gatcaaagct    4140
acttggaagg agtgcctata atttgccagt agccacagat taagattata tcttatatat    4200
cagcagatta gctttagctt agggggaggg tgggaaagtt tgggggggg gttgtgaaga    4260 tttaggggga ccttgataga gaactttata aacttctttc tctttaataa agacttgtct    4320
tacaccgtgc tgccattaaa ggcagctgtt ctagagtttc agtcacctaa gtacacccac    4380
aaaacaatat gaatatggag atcttccttt accccctcaac tttaatttgc ccagttatac    4440
ctcagtgttg tagcagtact gtgatacctg gcacagtgct ttgatcttac gatgccctct    4500
gtactgacct gaaggagacc taagagtcct ttcccttttt gagtttgaat catagccttg    4560
atgtggtctc ttgttttatg tccttgttcc taatgtaaaa gtgcttaact gcttcttggt    4620
tgtattgggt agcattggga taagatttta actgggtatt cttgaattgc ttttacaata    4680
aaccaatttt ataatcttta aatttatcaa cttttttacat ttgtgttatt ttcagtcagg    4740
gcttcttaga tctacttatg gttgatggag cacattgatt tggagtttca gatcttccaa    4800
agcactattt gttgtaataa cttttctaaa tgtagtgcct ttaaaggaaa aatgaacaca    4860
gggaagtgac tttgctacaa ataatgttgc tgtgttaagt attcatatta aatacatgcc    4920
ttctatatgg aacatggcag aaagactgaa aaataacagt aattaattgt gtaattcaga    4980
attcatacca atcagtgttg aaactcaaac attgcaaaag tgggtggcaa tattcagtgc    5040
ttaacacttt tctagcgttg gtacatctga gaaatgagtg ctcaggtgga ttttatcctc    5100
gcaagcatgt tgttataaga attgtgggtg tgcctatcat aacaattgtt ttctgtatct    5160
tgaaaaagta ttctccacat tttaaatgtt ttatattaga gaattcttta atgcacactt    5220
```

```
gtcaaatata tatatatagt accaatgtta cctttttatt ttttgtttta gatgtaagag    5280
catgctcata tgttaggtac ttacataaat tgttacatta ttttttctta tgtaatacct    5340
ttttgtttgt ttatgtggtt caaatatatt ctttccttaa actcttaaaa aaaaaa        5396
```

<210> SEQ ID NO 3
<211> LENGTH: 450
<212> TYPE: PRT
<213> ORGANISM: homo sapiens

<400> SEQUENCE: 3

```
Met Asp Pro Gly Gln Gln Pro Pro Gln Ala Pro Gln Gly Gln
1               5                   10                  15

Gly Gln Pro Pro Ser Gln Pro Gln Gly Gln Gly Pro Pro Ser Gly
            20                  25                  30

Pro Gly Gln Pro Ala Pro Ala Ala Thr Gln Ala Ala Pro Gln Ala Pro
                35                  40                  45

Pro Ala Gly His Gln Ile Val His Val Arg Gly Asp Ser Glu Thr Asp
            50                  55                  60

Leu Glu Ala Leu Phe Asn Ala Val Met Asn Pro Lys Thr Ala Asn Val
65                  70                  75                  80

Pro Gln Thr Val Pro Met Arg Leu Arg Lys Leu Pro Asp Ser Phe Phe
                85                  90                  95

Lys Pro Pro Glu Pro Lys Ser His Ser Arg Gln Ala Ser Thr Asp Ala
                100                 105                 110

Gly Thr Ala Gly Ala Leu Thr Pro Gln His Val Arg Ala His Ser Ser
            115                 120                 125

Pro Ala Ser Leu Gln Leu Gly Ala Val Ser Pro Gly Thr Leu Thr Pro
130                 135                 140

Thr Gly Val Val Ser Gly Pro Ala Ala Thr Pro Thr Ala Gln His Leu
145                 150                 155                 160

Arg Gln Ser Ser Phe Glu Ile Pro Asp Asp Val Pro Leu Pro Ala Gly
                165                 170                 175

Trp Glu Met Ala Lys Thr Ser Ser Gly Gln Arg Tyr Phe Leu Asn His
            180                 185                 190

Ile Asp Gln Thr Thr Thr Trp Gln Asp Pro Arg Lys Ala Met Leu Ser
        195                 200                 205

Gln Met Asn Val Thr Ala Pro Thr Ser Pro Pro Val Gln Gln Asn Met
210                 215                 220

Met Asn Ser Ala Ser Ala Met Asn Gln Arg Ile Ser Gln Ser Ala Pro
225                 230                 235                 240

Val Lys Gln Pro Pro Pro Leu Ala Pro Gln Ser Pro Gln Gly Gly Val
                245                 250                 255

Met Gly Gly Ser Asn Ser Asn Gln Gln Gln Met Arg Leu Gln Gln
            260                 265                 270

Leu Gln Met Glu Lys Glu Arg Leu Arg Leu Lys Gln Gln Glu Leu Leu
            275                 280                 285

Arg Gln Glu Leu Ala Leu Arg Ser Gln Leu Pro Thr Leu Glu Gln Asp
        290                 295                 300

Gly Gly Thr Gln Asn Pro Val Ser Ser Pro Gly Met Ser Gln Glu Leu
305                 310                 315                 320

Arg Thr Met Thr Thr Asn Ser Ser Asp Pro Phe Leu Asn Ser Gly Thr
                325                 330                 335

Tyr His Ser Arg Asp Glu Ser Thr Asp Ser Gly Leu Ser Met Ser Ser
            340                 345                 350
```

```
Tyr Ser Val Pro Arg Thr Pro Asp Asp Phe Leu Asn Ser Val Asp Glu
        355                 360                 365

Met Asp Thr Gly Asp Thr Ile Asn Gln Ser Thr Leu Pro Ser Gln Gln
370                 375                 380

Asn Arg Phe Pro Asp Tyr Leu Glu Ala Ile Pro Gly Thr Asn Val Asp
385                 390                 395                 400

Leu Gly Thr Leu Glu Gly Asp Gly Met Asn Ile Glu Gly Glu Leu
                405                 410                 415

Met Pro Ser Leu Gln Glu Ala Leu Ser Ser Asp Ile Leu Asn Asp Met
            420                 425                 430

Glu Ser Val Leu Ala Ala Thr Lys Leu Asp Lys Glu Ser Phe Leu Thr
        435                 440                 445

Trp Leu
    450

<210> SEQ ID NO 4
<211> LENGTH: 5234
<212> TYPE: DNA
<213> ORGANISM: homo sapiens

<400> SEQUENCE: 4
```

| | | | | | |
|---|---|---|---|---|---|
| gccgccgcca | gggaaaagaa | agggaggaag | gaaggaacaa | gaaaaggaaa | taaagagaaa | 60
| ggggaggcgg | ggaaaggcaa | cgagctgtcc | ggcctccgtc | aagggagttg | gagggaaaaa | 120
| gttctcaggc | gccgcaggtc | cgagtgcctc | gcagcccctc | ccgaggcgca | gccgccagac | 180
| cagtggagcc | ggggcgcagg | gcggggggcgg | aggcgccggg | gcggggggatg | cggggccgcg | 240
| gcgcagcccc | ccggccctga | gagcgaggac | agcgccgccc | ggcccgcagc | cgtcgccgct | 300
| tctccacctc | ggcccgtgga | gccggggcgt | ccgggcgtag | ccctcgctcg | cctgggtcag | 360
| ggggtgcgcg | tcggggggagg | cagaagccat | ggatcccggg | cagcagccgc | cgcctcaacc | 420
| ggccccccag | ggccaagggc | agccgccttc | gcagcccccg | caggggcagg | gcccgccgtc | 480
| cggacccggg | caaccggcac | ccgcggcgac | ccaggcggcg | ccgcaggcac | ccccgccgg | 540
| gcatcagatc | gtgcacgtcc | gcggggactc | ggagaccgac | ctggaggcgc | tcttcaacgc | 600
| cgtcatgaac | cccaagacgg | ccaacgtgcc | ccagaccgtg | cccatgaggc | tccggaagct | 660
| gcccgactcc | ttcttcaagc | cgccggagcc | caaatcccac | tcccgacagg | ccagtactga | 720
| tgcaggcact | gcaggagccc | tgactccaca | gcatgttcga | gctcattcct | ctccagcttc | 780
| tctgcagttg | ggagctgttt | ctcctgggac | actgaccccc | actggagtag | tctctggccc | 840
| agcagctaca | cccacagctc | agcatcttcg | acagtcttct | tttgagatac | ctgatgatgt | 900
| acctctgcca | gcaggttggg | agatggcaaa | gacatcttct | ggtcagagat | acttcttaaa | 960
| tcacatcgat | cagacaacaa | catggcagga | ccccaggaag | gccatgctgt | cccagatgaa | 1020
| cgtcacagcc | cccaccagtc | caccagtgca | gcagaatatg | atgaactcgg | cttcagccat | 1080
| gaaccagaga | atcagtcaga | gtgctccagt | gaaacagcca | ccacccctgg | ctccccagag | 1140
| cccacaggga | ggcgtcatgg | gtggcagcaa | ctccaaccag | cagcaacaga | tgcgactgca | 1200
| gcaactgcag | atggagaagg | agaggctgcg | gctgaaacag | caagaactgc | ttcggcagga | 1260
| gttagccctg | cgtagccagt | accaacact | ggagcaggat | ggtgggactc | aaaatccagt | 1320
| gtcttctccc | gggatgtctc | aggaattgag | aacaatgacg | accaatagct | cagatccttt | 1380
| ccttaacagt | ggcaccctatc | actctcgaga | tgagagtaca | gacagtggac | taagcatgag | 1440
| cagctacagt | gtccctcgaa | ccccagatga | cttcctgaac | agtgtggatg | agatggatac | 1500

```
aggtgatact atcaaccaaa gcaccctgcc ctcacagcag aaccgtttcc cagactacct    1560
tgaagccatt cctgggacaa atgtggacct tggaacactg aaggagatg gaatgaacat     1620 agaaggagag gagctgatgc caagtctgca ggaagctttg agttctgaca tccttaatga    1680
catggagtct gttttggctg ccaccaagct agataaagaa agcttttctta catggttata   1740 gagccctcag gcagactgaa ttctaaatct gtgaaggatc taaggagaca catgcaccgg    1800
aaatttccat aagccagttg cagttttcag gctaatacag aaaaagatga acaaacgtcc    1860
agcaagatac tttaatcctc tattttgctc ttccttgtcc attgctgctg ttaatgtatt    1920
gctgacctct ttcacagttg gctctaaaga atcaaaagaa aaaacttttt tatttctttt    1980
gctattaaaa ctactgttca ttttgggggc tgggggaagt gagcctgttt ggatgatgga    2040
tgccattcct tttgcccagt taaatgttca ccaatcattt taactaaata ctcagactta    2100
gaagtcagat gcttcatgtc acagcattta gtttgttcaa cagttgtttc ttcagcttcc    2160
tttgtccagt ggaaaaacat gatttactgg tctgacaagc caaaaatgtt atatctgata    2220
ttaaatactt aatgctgatt tgaagagata gctgaaacca aggctgaaga ctgttttact    2280
ttcagtattt tcttttcctc ctagtgctat cattagtcac ataatgacct tgattttatt    2340
ttaggagctt ataaggcatg agacaatttc catataaata tattaattat tgccacatac    2400
tctaatatag attttggtgg ataatttttgt gggtgtgcat tttgttctgt tttgttgggt   2460 ttttttgtttt ttttgttttt ggcagggtcg gtgggggggt tggttggttg gttggtttttg  2520 tcggaaccta ggcaaatgac catattagtg aatctgttaa tagttgtagc ttgggatggt    2580
tattgtagtt gttttggtaa aatcttcatt tcctggtttt ttttaccacc ttatttaaat    2640
ctcgattatc tgctctctct tttatataca tacacacacc caaacataac atttataata    2700
gtgtggtagt ggaatgtatc ctttttttagg tttccctgct ttccagttaa tttttaaaat   2760
ggtagcgctt tgtatgcatt tagaatacat gactagtagt ttatatttca ctggtagttt    2820
aaatctggtt ggggcagtct gcagatgttt gaagtagttt agtgttctag aaagagctat    2880
tactgtggat agtgcctagg ggagtgctcc acgccctctg ggcatacggt agatattatc     2940
tgatgaattg gaaaggagca aaccagaaat ggctttattt tctcccttgg actaattttt    3000
aagtctcgat tggaattcag tgagtaggtt cataatgtgc atgacagaaa taagctttat    3060
agtggtttac cttcatttag ctttggaagt tttctttgcc ttagttttgg aagtaaattc    3120
tagtttgtag ttctcatttg taatgaacac attaacgact agattaaaat attgccttca    3180
agattgttct tacttacaag acttgctcct acttctatgc tgaaaattga ccctggatag    3240
aatactataa ggttttgagt tagctggaaa agtgatcaga ttaataaatg tatattggta    3300
gttgaattta gcaaagaaat agagataatc atgattatac ctttatttttt acaggaagag   3360 atgatgtaac tagagtatgt gtctacagga gtaataatgg tttccaaaga gtattttta    3420 aaggaacaaa acgagcatga attaactctt caatataagc tatgaagtaa tagttggttg    3480
tgaattaaag tggcaccagc tagcacctct gtgttttaag ggtctttcaa tgtttctaga   3540
ataagccctt attttcaagg gttcataaca ggcataaaat ctcttctcct ggcaaaagct   3600
gctatgaaaa gcctcagctt gggaagatag atttttttcc ccccaattac aaaatctaag   3660
tattttggcc cttcaatttg gaggagggca aaagttggaa gtaagaagtt ttatttttaag  3720 tactttcagt gctcaaaaaa atgcaatcac tgtgttgtat ataatagttc ataggttgat    3780
cactcataat aattgactct aaggcttttta ttaagaaaac agcagaaaga ttaaatcttg   3840
```

-continued

```
aattaagtct gggggggaaat ggccactgca gatggagttt tagagtagta atgaaattct   3900
acctagaatg caaaattggg tatatgaatt acatagcatg ttgttgggat ttttttttaat   3960 gtgcagaaga tcaaagctac ttggaaggag tgcctataat ttgccagtag ccacagatta   4020
agattatatc ttatatatca gcagattagc tttagcttag ggggagggtg ggaaagtttg   4080 ggggggggggt tgtgaagatt taggggggacc ttgatagaga actttataaa cttctttctc   4140
tttaataaag acttgtctta caccgtgctg ccattaaagg cagctgttct agagtttcag   4200
tcacctaagt acacccacaa aacaatatga atatggagat cttcctttac ccctcaactt   4260
taatttgccc agttatacct cagtgttgta gcagtactgt gatacctggc acagtgcttt   4320
gatcttacga tgccctctgt actgacctga aggagaccta agagtccttt ccctttttga   4380
gtttgaatca tagccttgat gtggtctctt gttttatgtc cttgttccta atgtaaaagt   4440
gcttaactgc ttcttggttg tattgggtag cattgggata agattttaac tgggtattct   4500
tgaattgctt ttacaataaa ccaatttttat aatctttaaa tttatcaact ttttacattt   4560
gtgttatttt cagtcagggc ttcttagatc tacttatggt tgatggagca cattgatttg   4620
gagtttcaga tcttccaaag cactatttgt tgtaataact tttctaaatg tagtgccttt   4680
aaaggaaaaa tgaacacagg gaagtgactt tgctacaaat aatgttgctg tgttaagtat   4740
tcatattaaa tacatgcctt ctatatggaa catggcagaa agactgaaaa ataacagtaa   4800
ttaattgtgt aattcagaat tcataccaat cagtgttgaa actcaaacat tgcaaaagtg   4860
ggtggcaata ttcagtgctt aacactttttc tagcgttggt acatctgaga aatgagtgct   4920
caggtggatt ttatcctcgc aagcatgttg ttataagaat tgtgggtgtg cctatcataa   4980
caattgtttt ctgtatcttg aaaaagtatt ctccacattt taaatgtttt atattagaga   5040 attcttttaat gcacacttgt caaatatata tatatagtac caatgttacc ttttttatttt   5100 ttgtttttaga tgtaagagca tgctcatatg ttaggtactt acataaattg ttacattatt   5160
ttttcttatg taatacccttt ttgtttgttt atgtggttca aatatattct ttccttaaac   5220
tcttaaaaaa aaaa                                                      5234
```

<210> SEQ ID NO 5
<211> LENGTH: 488
<212> TYPE: PRT
<213> ORGANISM: homo sapiens

<400> SEQUENCE: 5

```
Met Asp Pro Gly Gln Gln Pro Pro Gln Pro Ala Pro Gln Gly Gln
1               5                   10                  15

Gly Gln Pro Pro Ser Gln Pro Pro Gln Gly Gln Gly Pro Pro Ser Gly
                20                  25                  30

Pro Gly Gln Pro Ala Pro Ala Thr Gln Ala Ala Pro Gln Ala Pro
            35                  40                  45

Pro Ala Gly His Gln Ile Val His Val Arg Gly Asp Ser Glu Thr Asp
        50                  55                  60

Leu Glu Ala Leu Phe Asn Ala Val Met Asn Pro Lys Thr Ala Asn Val
65                  70                  75                  80

Pro Gln Thr Val Pro Met Arg Leu Arg Lys Leu Pro Asp Ser Phe Phe
                85                  90                  95

Lys Pro Pro Glu Pro Lys Ser His Ser Arg Gln Ala Ser Thr Asp Ala
                100                 105                 110

Gly Thr Ala Gly Ala Leu Thr Pro Gln His Val Arg Ala His Ser Ser
            115                 120                 125
```

Pro Ala Ser Leu Gln Leu Gly Ala Val Ser Pro Gly Thr Leu Thr Pro
130                 135                 140

Thr Gly Val Val Ser Gly Pro Ala Ala Thr Pro Thr Ala Gln His Leu
145                 150                 155                 160

Arg Gln Ser Ser Phe Glu Ile Pro Asp Asp Val Pro Leu Pro Ala Gly
            165                 170                 175

Trp Glu Met Ala Lys Thr Ser Ser Gly Gln Arg Tyr Phe Leu Asn His
            180                 185                 190

Ile Asp Gln Thr Thr Thr Trp Gln Asp Pro Arg Lys Ala Met Leu Ser
            195                 200                 205

Gln Met Asn Val Thr Ala Pro Thr Ser Pro Val Gln Gln Asn Met
210                 215                 220

Met Asn Ser Ala Ser Gly Pro Leu Pro Asp Gly Trp Glu Gln Ala Met
225                 230                 235                 240

Thr Gln Asp Gly Glu Ile Tyr Tyr Ile Asn His Lys Asn Lys Thr Thr
                245                 250                 255

Ser Trp Leu Asp Pro Arg Leu Asp Pro Arg Phe Ala Met Asn Gln Arg
            260                 265                 270

Ile Ser Gln Ser Ala Pro Val Lys Gln Pro Pro Leu Ala Pro Gln
            275                 280                 285

Ser Pro Gln Gly Gly Val Met Gly Gly Ser Asn Ser Asn Gln Gln Gln
            290                 295                 300

Gln Met Arg Leu Gln Gln Leu Gln Met Glu Lys Glu Arg Leu Arg Leu
305                 310                 315                 320

Lys Gln Gln Glu Leu Leu Arg Gln Glu Leu Ala Leu Arg Ser Gln Leu
                325                 330                 335

Pro Thr Leu Glu Gln Asp Gly Gly Thr Gln Asn Pro Val Ser Ser Pro
            340                 345                 350

Gly Met Ser Gln Glu Leu Arg Thr Met Thr Thr Asn Ser Ser Asp Pro
            355                 360                 365

Phe Leu Asn Ser Gly Thr Tyr His Ser Arg Asp Glu Ser Thr Asp Ser
370                 375                 380

Gly Leu Ser Met Ser Ser Tyr Ser Val Pro Arg Thr Pro Asp Asp Phe
385                 390                 395                 400

Leu Asn Ser Val Asp Glu Met Asp Thr Gly Asp Thr Ile Asn Gln Ser
                405                 410                 415

Thr Leu Pro Ser Gln Gln Asn Arg Phe Pro Asp Tyr Leu Glu Ala Ile
            420                 425                 430

Pro Gly Thr Asn Val Asp Leu Gly Thr Leu Glu Gly Asp Gly Met Asn
            435                 440                 445

Ile Glu Gly Glu Glu Leu Met Pro Ser Leu Gln Glu Ala Leu Ser Ser
            450                 455                 460

Asp Ile Leu Asn Asp Met Glu Ser Val Leu Ala Ala Thr Lys Leu Asp
465                 470                 475                 480

Lys Glu Ser Phe Leu Thr Trp Leu
                485

<210> SEQ ID NO 6
<211> LENGTH: 5348
<212> TYPE: DNA
<213> ORGANISM: homo sapiens

<400> SEQUENCE: 6

```
gccgccgcca gggaaaagaa agggaggaag gaaggaacaa gaaaaggaaa taaagagaaa         60
ggggaggcgg ggaaaggcaa cgagctgtcc ggcctccgtc aagggagttg gagggaaaaa        120
gttctcaggc gccgcaggtc cgagtgcctc gcagcccctc ccgaggcgca gccgccagac        180
cagtggagcc ggggcgcagg gcgggggcgg aggcgccggg gcgggggatg cggggccgcg        240
gcgcagcccc ccgccctga gagcgaggac agcgccgccc ggcccgcagc cgtcgccgct        300
tctccacctc ggcccgtgga gccggggcgt ccgggcgtag ccctcgctcg cctgggtcag        360
ggggtgcgcg tcgggggagg cagaagccat ggatcccggg cagcagccgc cgcctcaacc        420
ggccccccag ggccaagggc agccgccttc gcagccccg cagggcagg gcccgccgtc         480
cggacccggg caaccggcac ccgccggcgac ccaggcggcg ccgcaggcac ccccgccgg        540
gcatcagatc gtgcacgtcc gcggggactc ggagaccgac ctggaggcgc tcttcaacgc        600
cgtcatgaac cccaagacgg ccaacgtgcc ccagaccgtg cccatgaggc tccggaagct        660
gcccgactcc ttcttcaagc cgccggagcc caaatcccac tcccgacagg ccagtactga        720
tgcaggcact gcaggagccc tgactccaca gcatgttcga gctcattcct ctccagcttc        780
tctgcagttg ggagctgttt ctcctgggac actgaccccc actggagtag tctctggccc        840
agcagctaca cccacagctc agcatcttcg acagtcttct tttgagatac ctgatgatgt        900
acctctgcca gcaggttggg agatggcaaa gacatcttct ggtcagagat acttcttaaa        960
tcacatcgat cagacaacaa catggcagga ccccaggaag gccatgctgt cccagatgaa       1020
cgtcacagcc cccaccagtc caccagtgca gcagaatatg atgaactcgg cttcaggtcc       1080
tcttcctgat ggatgggaac aagccatgac tcaggatgga gaaatttact atataaacca       1140
taagaacaag accacctctt ggctagaccc aaggcttgac cctcgttttg ccatgaacca       1200
gagaatcagt cagagtgctc cagtgaaaca gccaccaccc ctggctcccc agagcccaca       1260
gggaggcgtc atgggtggca gcaactccaa ccagcagcaa cagatgcgac tgcagcaact       1320
gcagatggag aaggagaggc tgcggctgaa acagcaagaa ctgcttcggc aggagttagc       1380
cctgcgtagc cagttaccaa cactggagca ggatggtggg actcaaaatc cagtgtcttc       1440
tcccgggatg tctcaggaat tgagaacaat gacgaccaat agctcagatc ctttccttaa       1500
cagtggcacc tatcactctc gagatgagag tacagacagt ggactaagca tgagcagcta       1560
cagtgtccct cgaaccccag atgacttcct gaacagtgtg gatgagatgg atacaggtga       1620
tactatcaac caaagcaccc tgccctcaca gcagaaccgt ttcccagact accttgaagc       1680
cattcctggg acaaatgtgg accttggaac actggaagga gatggaatga acatagaagg       1740
agaggagctg atgccaagtc tgcaggaagc tttgagttct gacatcctta atgacatgga       1800
gtctgttttg gctgccacca agctagataa agaaagcttt cttacatggt tatagagccc       1860
tcaggcagac tgaattctaa atctgtgaag gatctaagga gacacatgca ccggaaattt       1920
ccataagcca gttgcagttt tcaggctaat acagaaaaag atgaacaaac gtccagcaag       1980
atactttaat cctctatttt gctcttcctt gtccattgct gctgttaatg tattgctgac       2040
ctctttcaca gttggctcta aagaatcaaa agaaaaaaac ttttatttc ttttgctatt        2100
aaaactactg ttcattttgg gggctggggg aagtgagcct gtttggatga tggatgccat       2160
tccttttgcc cagttaaatg ttcaccaatc attttaacta aatactcaga cttagaagtc       2220
agatgcttca tgtcacagca tttagtttgt tcaacagttg tttcttcagc ttcctttgtc       2280
```

```
cagtggaaaa acatgattta ctggtctgac aagccaaaaa tgttatatct gatattaaat    2340
acttaatgct gatttgaaga gatagctgaa accaaggctg aagactgttt tactttcagt    2400
attttctttt cctcctagtg ctatcattag tcacataatg accttgattt tattttagga    2460
gcttataagg catgagacaa tttccatata aatatattaa ttattgccac atactctaat    2520
atagattttg gtggataatt tgtgggtgt gcattttgtt ctgttttgtt gggttttttg     2580
ttttttttgt ttttggcagg gtcggtgggg gggttggttg gttggttggt tttgtcggaa    2640
cctaggcaaa tgaccatatt agtgaatctg ttaatagttg tagcttggga tggttattgt    2700
agttgttttg gtaaaatctt catttcctgg tttttttttac caccttattt aaatctcgat   2760
tatctgctct ctctttttata tacatacaca cacccaaaca taacatttat aatagtgtgg   2820
tagtggaatg tatcctttt taggtttccc tgctttccag ttaattttta aaatggtagc    2880
gctttgtatg catttagaat acatgactag tagtttatat ttcactggta gtttaaatct   2940
ggttggggca gtctgcagat gttgaagta gtttagtgtt ctagaaagag ctattactgt    3000
ggatagtgcc taggggagtg ctccacgccc tctgggcata cggtagatat tatctgatga   3060
attggaaagg agcaaaccag aaatggcttt attttctccc ttggactaat ttttaagtct   3120
cgattggaat tcagtgagta ggttcataat gtgcatgaca gaaataagct ttatagtggt   3180
ttaccttcat ttagctttgg aagttttctt tgccttagtt ttggaagtaa attctagttt   3240
gtagttctca tttgtaatga acacattaac gactagatta aaatattgcc ttcaagattg   3300
ttcttactta caagacttgc tcctacttct atgctgaaaa ttgaccctgg atagaatact   3360
ataaggtttt gagttagctg gaaaagtgat cagattaata aatgtatatt ggtagttgaa   3420
tttagcaaag aaatagagat aatcatgatt ataccttat ttttacagga agagatgatg    3480
taactagagt atgtgtctac aggagtaata atggtttcca aagagtattt tttaaaggaa   3540
caaaacgagc atgaattaac tcttcaatat aagctatgaa gtaatagttg gttgtgaatt   3600
aaagtggcac cagctagcac ctctgtgttt taagggtctt tcaatgtttc tagaataagc   3660
ccttattttc aagggttcat aacaggcata aaatctcttc tcctggcaaa agctgctatg   3720
aaaagcctca gctgggaag atagattttt ttccccccaa ttacaaaatc taagtatttt    3780
ggcccttcaa tttggaggag ggcaaaagtt ggaagtaaga agttttattt taagtacttt   3840
cagtgctcaa aaaaatgcaa tcactgtgtt gtatataata gttcataggt tgatcactca   3900
taataattga ctcaaggct tttattaaga aaacagcaga aagattaaat cttgaattaa    3960
gtctgggggg aaatggccac tgcagatgga gttttagagt agtaatgaaa ttctacctag   4020
aatgcaaaat tgggtatatg aattacatag catgttgttg ggattttttt taatgtgcag   4080
aagatcaaag ctacttggaa ggagtgccta taatttgcca gtagccacag attaagatta   4140
tatcttatat atcagcagat tagctttagc ttaggggag ggtgggaaag tttgggggg     4200 gggttgtgaa gatttagggg gaccttgata gagaacttta taaacttctt tctctttaat   4260
aaagacttgt cttacaccgt gctgccatta aaggcagctg ttctagagtt tcagtcacct   4320
aagtacaccc acaaaacaat atgaatatgg agatcttcct ttaccctca actttaattt   4380 gcccagttat acctcagtgt tgtagcagta ctgtgatacc tggcacagtg ctttgatctt    4440
acgatgccct ctgtactgac ctgaaggaga cctaagagtc cttccctttt ttgagtttga   4500
atcatagcct tgatgtggtc tcttgttta tgtccttgtt cctaatgtaa aagtgcttaa    4560
ctgcttcttg gttgtattgg gtagcattgg gataagattt taactgggta ttcttgaatt   4620
gcttttacaa taaaccaatt ttataatctt taaatttatc aacttttac atttgtgtta    4680
```

-continued

```
ttttcagtca gggcttctta gatctactta tggttgatgg agcacattga tttggagttt      4740
cagatcttcc aaagcactat ttgttgtaat aacttttcta aatgtagtgc ctttaaagga      4800
aaaatgaaca cagggaagtg actttgctac aaataatgtt gctgtgttaa gtattcatat      4860
taaatacatg ccttctatat ggaacatggc agaaagactg aaaaataaca gtaattaatt      4920
gtgtaattca gaattcatac caatcagtgt tgaaactcaa acattgcaaa agtgggtggc      4980
aatattcagt gcttaacact tttctagcgt tggtacatct gagaaatgag tgctcaggtg      5040
gattttatcc tcgcaagcat gttgttataa gaattgtggg tgtgcctatc ataacaattg      5100
ttttctgtat cttgaaaaag tattctccac attttaaatg ttttatatta gagaattctt      5160
taatgcacac ttgtcaaata tatatatata gtaccaatgt tacctttta tttttgttt       5220 tagatgtaag agcatgctca tatgttaggt acttacataa attgttacat tattttttct      5280
tatgtaatac cttttgttt gtttatgtgg ttcaaatata ttctttcctt aaactcttaa      5340
aaaaaaaa                                                              5348

<210> SEQ ID NO 7
<211> LENGTH: 326
<212> TYPE: PRT
<213> ORGANISM: homo sapiens

<400> SEQUENCE: 7

Met Ala Lys Thr Ser Ser Gly Gln Arg Tyr Phe Leu Asn His Ile Asp
1               5                   10                  15

Gln Thr Thr Thr Trp Gln Asp Pro Arg Lys Ala Met Leu Ser Gln Met
            20                  25                  30

Asn Val Thr Ala Pro Thr Ser Pro Val Gln Gln Asn Met Met Asn
        35                  40                  45

Ser Ala Ser Gly Pro Leu Pro Asp Gly Trp Glu Gln Ala Met Thr Gln
    50                  55                  60

Asp Gly Glu Ile Tyr Tyr Ile Asn His Lys Asn Lys Thr Thr Ser Trp
65                  70                  75                  80

Leu Asp Pro Arg Leu Asp Pro Arg Phe Ala Met Asn Gln Arg Ile Ser
                85                  90                  95

Gln Ser Ala Pro Val Lys Gln Pro Pro Leu Ala Pro Gln Ser Pro
            100                 105                 110

Gln Gly Gly Val Met Gly Gly Ser Asn Ser Asn Gln Gln Gln Gln Met
        115                 120                 125

Arg Leu Gln Gln Leu Gln Met Glu Lys Glu Arg Leu Arg Leu Lys Gln
    130                 135                 140

Gln Glu Leu Leu Arg Gln Ala Met Arg Asn Ile Asn Pro Ser Thr Ala
145                 150                 155                 160

Asn Ser Pro Lys Cys Gln Glu Leu Ala Leu Arg Ser Gln Leu Pro Thr
                165                 170                 175

Leu Glu Gln Asp Gly Gly Thr Gln Asn Pro Val Ser Ser Pro Gly Met
            180                 185                 190

Ser Gln Glu Leu Arg Thr Met Thr Thr Asn Ser Ser Asp Pro Phe Leu
        195                 200                 205

Asn Ser Gly Thr Tyr His Ser Arg Asp Glu Ser Thr Asp Ser Gly Leu
    210                 215                 220

Ser Met Ser Ser Tyr Ser Val Pro Arg Thr Pro Asp Asp Phe Leu Asn
225                 230                 235                 240
```

```
Ser Val Asp Glu Met Asp Thr Gly Asp Thr Ile Asn Gln Ser Thr Leu
            245                 250                 255

Pro Ser Gln Gln Asn Arg Phe Pro Asp Tyr Leu Glu Ala Ile Pro Gly
        260                 265                 270

Thr Asn Val Asp Leu Gly Thr Leu Glu Gly Asp Gly Met Asn Ile Glu
        275                 280                 285

Gly Glu Glu Leu Met Pro Ser Leu Gln Glu Ala Leu Ser Ser Asp Ile
290                 295                 300

Leu Asn Asp Met Glu Ser Val Leu Ala Ala Thr Lys Leu Asp Lys Glu
305                 310                 315                 320

Ser Phe Leu Thr Trp Leu
            325

<210> SEQ ID NO 8
<211> LENGTH: 4993
<212> TYPE: DNA
<213> ORGANISM: homo sapiens

<400> SEQUENCE: 8
tttttttgag aacttgcttc aggctaaact tcagcatagg aactttgccc aaaagttaat      60
aggttttcca atactgcaa tgtagttagc ccactcggga tgtaacttga gtggaaagaa     120
gagttaccgc ccccactccc attccctctc ctatttgcag gcctgttgta tagtctcctg     180
tcggagacca aagggttttg aactcagaa aaaatcactt aacctgatga caaaaacccg     240
ggttaaggag gaggaaagaa ggaaaaacaa tttagctgct tgcctaaaca cttcaatttg     300
tcttaggcca gtactgatgc aggcactgca ggagccctga ctccacagca tgttcgagct     360
cattcctctc cagcttctct gcagttggga gctgtttctc ctgggacact gacccccact     420
ggagtagtct ctggcccagc agctacaccc acagctcagc atcttcgaca gtcttctttt     480
gagatacctg atgatgtacc tctgccagca ggttgggaga tggcaaagac atcttctggt     540
cagagatact tcttaaatca catcgatcag acaacaacat ggcaggaccc caggaaggcc     600
atgctgtccc agatgaacgt cacagccccc accagtccac cagtgcagca gaatatgatg     660
aactcggctt caggtcctct tcctgatgga tgggaacaag ccatgactca ggatggagaa     720
atttactata taaaccataa gaacaagacc acctcttggc tagacccaag gcttgaccct     780
cgttttgcca tgaaccagag aatcagtcag agtgctccag tgaaacagcc accacccctg     840
gctccccaga gcccacaggg aggcgtcatg gtggcagca actccaacca gcagcaacag     900
atgcgactgc agcaactgca gatggagaag gagaggctgc ggctgaaaca gcaagaactg     960
cttcggcagg caatgcggaa tatcaatccc agcacagcaa attctccaaa atgtcaggag    1020
ttagccctgc gtagccagtt accaacactg gagcaggatg tgggactcaa aatccagtg     1080 tcttctcccg ggatgtctca ggaattgaga acaatgacga ccaatagctc agatcctttc    1140
cttaacagtg gcacctatca ctctcgagat gagagtacag acagtggact aagcatgagc    1200
agctacagtg tccctcgaac cccagatgac ttcctgaaca gtgtggatga gatggatata    1260
ggtgatacta tcaaccaaag cacccctgccc tcacagcaga accgtttccc agactacctt    1320
gaagccattc tgggacaaa tgtggacctt ggaacactgg aagagatgg aatgaacata    1380 gaaggagagg agctgatgcc aagtctgcag gaagctttga gttctgacat ccttaatgac    1440
atggagtctg ttttggctgc caccaagcta gataaagaaa gctttcttac atggttatag    1500
agccctcagg cagactgaat tctaaatctg tgaaggatct aaggagacac atgcaccgga    1560
```

| | |
|---|---|
| aatttccata agccagttgc agttttcagg ctaatacaga aaaagatgaa caaacgtcca | 1620 |
| gcaagatact ttaatcctct attttgctct tccttgtcca ttgctgctgt taatgtattg | 1680 |
| ctgacctctt tcacagttgg ctctaaagaa tcaaagaaa aaaactttt atttcttttg | 1740 |
| ctattaaaac tactgttcat tttgggggct gggggaagtg agcctgtttg gatgatggat | 1800 |
| gccattcctt ttgcccagtt aaatgttcac caatcatttt aactaaatac tcagacttag | 1860 |
| aagtcagatg cttcatgtca cagcatttag tttgttcaac agttgtttct tcagcttcct | 1920 |
| ttgtccagtg gaaaaacatg atttactggt ctgacaagcc aaaaatgtta tatctgatat | 1980 |
| taaatactta atgctgattt gaagagatag ctgaaaccaa ggctgaagac tgttttactt | 2040 |
| tcagtatttt cttttcctcc tagtgctatc attagtcaca taatgacctt gatttatt | 2100 |
| taggagctta taaggcatga gacaatttcc atataaatat attaattatt gccacatact | 2160 |
| ctaatataga ttttggtgga taattttgtg ggtgtgcatt ttgttctgtt ttgttgggtt | 2220 |
| ttttgttttt tttgtttttg gcagggtcgg tgggggggtt ggttggttgg ttggttttgt | 2280 |
| cggaacctag gcaaatgacc atattagtga atctgttaat agttgtagct tgggatggtt | 2340 |
| attgtagttg ttttggtaaa atcttcattt cctggttttt tttaccacct tatttaaatc | 2400 |
| tcgattatct gctctctctt ttatatacat acacacaccc aaacataaca tttataatag | 2460 |
| tgtggtagtg gaatgtatcc ttttttaggt ttccctgctt tccagttaat ttttaaaatg | 2520 |
| gtagcgcttt gtatgcattt agaatacatg actagtagtt tatatttcac tggtagttta | 2580 |
| aatctggttg gggcagtctg cagatgtttg aagtagttta gtgttctaga aagagctatt | 2640 |
| actgtggata gtgcctaggg gagtgctcca cgccctctgg gcatacggta gatattatct | 2700 |
| gatgaattgg aaaggagcaa accagaaatg gctttatttt ctcccttgga ctaattttta | 2760 |
| agtctcgatt ggaattcagt gagtaggttc ataatgtgca tgacagaaat aagctttata | 2820 |
| gtggtttacc ttcatttagc tttggaagtt ttctttgcct tagttttgga agtaaattct | 2880 |
| agtttgtagt tctcatttgt aatgaacaca ttaacgacta gattaaaata ttgccttcaa | 2940 |
| gattgttctt acttacaaga cttgctccta cttctatgct gaaaattgac cctggataga | 3000 |
| atactataag gttttgagtt agctggaaaa gtgatcagat taataaatgt atattggtag | 3060 |
| ttgaatttag caaagaaata gagataatca tgattatacc tttattttta caggaagaga | 3120 |
| tgatgtaact agagtatgtg tctacaggag taataatggt ttccaaagag tattttttaa | 3180 |
| aggaacaaaa cgagcatgaa ttaactcttc aatataagct atgaagtaat agttggttgt | 3240 |
| gaattaaagt ggcaccagct agcacctctg tgttttaagg gtctttcaat gtttctagaa | 3300 |
| taagcccctta ttttcaaggg ttcataacag gcataaaatc tcttctcctg gcaaaagctg | 3360 |
| ctatgaaaag cctcagcttg gaagataga ttttttttccc cccaattaca aaatctaagt | 3420 |
| attttggccc ttcaatttgg aggagggcaa aagttggaag taagaagttt tattttaagt | 3480 |
| actttcagtg ctcaaaaaaa tgcaatcact gtgttgtata taagttca taggttgatc | 3540 |
| actcataata attgactcta aggctttat taagaaaaca gcagaaagat taaatcttga | 3600 |
| attaagtctg gggggaaatg gccactgcag atggagtttt agagtagtaa tgaaattcta | 3660 |
| cctagaatgc aaaattgggt atatgaatta catgcatgt tgttgggatt ttttttaatg | 3720 |
| tgcagaagat caaagctact tggaaggagt gcctataatt tgccagtagc cacagattaa | 3780 |
| gattatatct tatatatcag cagattagct ttagcttagg gggagggtgg gaaagtttgg | 3840 |
| gggggggtt gtgaagattt agggggacct tgatagagaa ctttataaac ttcttctctct | 3900 |
| ttaataaaga cttgtcttac accgtgctgc cattaaaggc agctgttcta gagtttcagt | 3960 |

```
cacctaagta cacccacaaa acaatatgaa tatggagatc ttcctttacc cctcaacttt    4020
aatttgccca gttatacctc agtgttgtag cagtactgtg atacctggca cagtgctttg    4080
atcttacgat gccctctgta ctgacctgaa ggagacctaa gagtcctttc ccttttgag     4140 tttgaatcat agccttgatg tggtctcttg ttttatgtcc ttgttcctaa tgtaaaagtg    4200
cttaactgct tcttggttgt attgggtagc attgggataa gatttaact gggtattctt     4260 gaattgcttt tacaataaac caattttata atctttaaat ttatcaactt tttacatttg    4320
tgttattttc agtcagggct tcttagatct acttatggtt gatggagcac attgatttgg    4380
agtttcagat cttccaaagc actatttgtt gtaataactt ttctaaatgt agtgccttta    4440
aaggaaaaat gaacacaggg aagtgacttt gctacaaata atgttgctgt gttaagtatt    4500
catattaaat acatgccttc tatatggaac atggcagaaa gactgaaaaa taacagtaat    4560
taattgtgta attcagaatt cataccaatc agtgttgaaa ctcaaacatt gcaaaagtgg    4620
gtggcaatat tcagtgctta acactttct agcgttggta catctgagaa atgagtgctc     4680
aggtggattt tatcctcgca agcatgttgt tataagaatt gtgggtgtgc ctatcataac    4740
aattgttttc tgtatcttga aaagtattc tccacatttt aaatgtttta tattagagaa     4800
ttctttaatg cacacttgtc aaatatatat atatagtacc aatgttacct ttttattttt    4860
tgttttagat gtaagagcat gctcatatgt taggtactta cataaattgt tacattattt    4920
tttcttatgt aataccttt tgtttgttta tgtggttcaa atatattctt tccttaaact      4980
cttaaaaaaa aaa                                                        4993

<210> SEQ ID NO 9
<211> LENGTH: 454
<212> TYPE: PRT
<213> ORGANISM: homo sapiens

<400> SEQUENCE: 9

Met Asp Pro Gly Gln Gln Pro Pro Gln Pro Ala Pro Gln Gly Gln
1               5                   10                  15

Gly Gln Pro Pro Ser Gln Pro Gln Gly Gln Gly Pro Pro Ser Gly
            20                  25                  30

Pro Gly Gln Pro Ala Pro Ala Thr Gln Ala Ala Pro Gln Ala Pro
        35                  40                  45

Pro Ala Gly His Gln Ile Val His Val Arg Gly Asp Ser Glu Thr Asp
    50                  55                  60

Leu Glu Ala Leu Phe Asn Ala Val Met Asn Pro Lys Thr Ala Asn Val
65                  70                  75                  80

Pro Gln Thr Val Pro Met Arg Leu Arg Lys Leu Pro Asp Ser Phe Phe
                85                  90                  95

Lys Pro Pro Glu Pro Lys Ser His Ser Arg Gln Ala Ser Thr Asp Ala
            100                 105                 110

Gly Thr Ala Gly Ala Leu Thr Pro Gln His Val Arg Ala His Ser Ser
        115                 120                 125

Pro Ala Ser Leu Gln Leu Gly Ala Val Ser Pro Gly Thr Leu Thr Pro
    130                 135                 140

Thr Gly Val Val Ser Gly Pro Ala Ala Thr Pro Thr Ala Gln His Leu
145                 150                 155                 160

Arg Gln Ser Ser Phe Glu Ile Pro Asp Asp Val Pro Leu Pro Ala Gly
                165                 170                 175
```

```
Trp Glu Met Ala Lys Thr Ser Ser Gly Gln Arg Tyr Phe Leu Asn His
            180                 185                 190
Ile Asp Gln Thr Thr Thr Trp Gln Asp Pro Arg Lys Ala Met Leu Ser
            195                 200                 205
Gln Met Asn Val Thr Ala Pro Thr Ser Pro Val Gln Gln Asn Met
210                 215                 220
Met Asn Ser Ala Ser Ala Met Asn Gln Arg Ile Ser Gln Ser Ala Pro
225                 230                 235                 240
Val Lys Gln Pro Pro Pro Leu Ala Pro Gln Ser Pro Gln Gly Gly Val
                245                 250                 255
Met Gly Gly Ser Asn Ser Asn Gln Gln Gln Gln Met Arg Leu Gln Gln
            260                 265                 270
Leu Gln Met Glu Lys Glu Arg Leu Arg Leu Lys Gln Gln Glu Leu Leu
            275                 280                 285
Arg Gln Val Arg Pro Gln Glu Leu Ala Leu Arg Ser Gln Leu Pro Thr
            290                 295                 300
Leu Glu Gln Asp Gly Gly Thr Gln Asn Pro Val Ser Ser Pro Gly Met
305                 310                 315                 320
Ser Gln Glu Leu Arg Thr Met Thr Thr Asn Ser Ser Asp Pro Phe Leu
                325                 330                 335
Asn Ser Gly Thr Tyr His Ser Arg Asp Glu Ser Thr Asp Ser Gly Leu
            340                 345                 350
Ser Met Ser Ser Tyr Ser Val Pro Arg Thr Pro Asp Asp Phe Leu Asn
            355                 360                 365
Ser Val Asp Glu Met Asp Thr Gly Asp Thr Ile Asn Gln Ser Thr Leu
            370                 375                 380
Pro Ser Gln Gln Asn Arg Phe Pro Asp Tyr Leu Glu Ala Ile Pro Gly
385                 390                 395                 400
Thr Asn Val Asp Leu Gly Thr Leu Glu Gly Asp Gly Met Asn Ile Glu
                405                 410                 415
Gly Glu Glu Leu Met Pro Ser Leu Gln Glu Ala Leu Ser Ser Asp Ile
            420                 425                 430
Leu Asn Asp Met Glu Ser Val Leu Ala Ala Thr Lys Leu Asp Lys Glu
            435                 440                 445
Ser Phe Leu Thr Trp Leu
    450

<210> SEQ ID NO 10
<211> LENGTH: 5246
<212> TYPE: DNA
<213> ORGANISM: homo sapiens

<400> SEQUENCE: 10
gccgccgcca gggaaaagaa agggaggaag gaaggaacaa gaaaaggaaa taagagaaa       60 ggggaggcgg ggaaaggcaa cgagctgtcc ggcctccgtc aagggagttg gagggaaaaa      120
gttctcaggc gccgcaggtc cgagtgcctc gcagcccctc ccgaggcgca gccgccagac      180
cagtggagcc ggggcgcagg gcgggggcgg aggcgccggg gcgggggatg cggggccgcg      240
gcgcagcccc ccgccctga gagcgaggac agcgccgccc ggcccgcagc cgtcgccgct      300
tctccacctc ggcccgtgga gccggggcgt ccgggcgtag ccctcgctcg cctgggtcag      360
ggggtgcgcg tcgggggagg cagaagccat ggatcccggg cagcagccgc gcctcaacc      420 ggcccccccag ggccaagggc agccgccttc gcagcccccg caggggcagg gccgccgtc      480
```

```
cggacccggg caaccggcac ccgcggcgac ccaggcggcg ccgcaggcac ccccgccgg    540 gcatcagatc gtgcacgtcc gcggggactc ggagaccgac ctggaggcgc tcttcaacgc    600
cgtcatgaac cccaagacgg ccaacgtgcc ccagaccgtg cccatgaggc tccggaagct    660
gcccgactcc ttcttcaagc cgccggagcc caaatcccac tcccgacagg ccagtactga    720
tgcaggcact gcaggagccc tgactccaca gcatgttcga gctcattcct ctccagcttc    780
tctgcagttg ggagctgttt ctcctgggac actgacccc actggagtag tctctggccc     840
agcagctaca cccacagctc agcatcttcg acagtcttct tttgagatac ctgatgatgt    900
acctctgcca gcaggttggg agatggcaaa gacatcttct ggtcagagat acttcttaaa    960
tcacatcgat cagacaacaa catggcagga ccccaggaag gccatgctgt cccagatgaa    1020
cgtcacagcc cccaccagtc caccagtgca gcagaatatg atgaactcgg cttcagccat    1080
gaaccagaga atcagtcaga gtgctccagt gaaacagcca ccaccctgg ctccccagag     1140 cccacaggga ggcgtcatgg gtggcagcaa ctccaaccag cagcaacaga tgcgactgca    1200
gcaactgcag atggagaagg agaggctgcg gctgaaacag caagaactgc ttcggcaggt    1260
gaggccacag gagttagccc tgcgtagcca gttaccaaca ctggagcagg atggtgggac    1320
tcaaaatcca gtgtcttctc ccgggatgtc tcaggaattg agaacaatga cgaccaatag    1380
ctcagatcct ttccttaaca gtggcaccta tcactctcga gatgagagta cagacagtgg    1440
actaagcatg agcagctaca gtgtccctcg aacccccagat gacttcctga acagtgtgga    1500
tgagatggat acaggtgata ctatcaacca aagcaccctg ccctcacagc agaaccgttt    1560
cccagactac cttgaagcca ttcctgggac aaatgtggac cttggaacac tggaaggaga    1620
tggaatgaac atagaaggag aggagctgat gccaagtctg caggaagctt tgagttctga    1680
catccttaat gacatggagt ctgttttggc tgccaccaag ctagataaag aaagctttct    1740
tacatggtta tagagccctc aggcagactg aattctaaat ctgtgaagga tctaaggaga    1800
cacatgcacc ggaaatttcc ataagccagt tgcagttttc aggctaatac agaaaaagat    1860
gaacaaacgt ccagcaagat actttaatcc tctattttgc tcttccttgt ccattgctgc    1920
tgttaatgta ttgctgacct ctttcacagt tggctctaaa gaatcaaaag aaaaaaactt    1980
tttatttctt ttgctattaa aactactgtt catttgggg gctggggaa gtgagcctgt      2040 ttggatgatg gatgccattc cttttgccca gttaaatgtt caccaatcat tttaactaaa    2100
tactcagact tagaagtcag atgcttcatg tcacagcatt tagtttgttc aacagttgtt    2160
tcttcagctt cctttgtcca gtggaaaaac atgatttact ggtctgacaa gccaaaaatg    2220
ttatatctga tattaaatac ttaatgctga tttgaagaga tagctgaaac caaggctgaa    2280
gactgtttta ctttcagtat tttcttttcc tcctagtgct atcattagtc acataatgac    2340
cttgatttta ttttaggagc ttataaggca tgagacaatt tccatataaa tatattaatt    2400
attgccacat actctaatat agattttggt ggataatttt gtgggtgtgc attttgttct    2460
gttttgttgg gttttttgtt ttttttgttt ttggcagggt cggtgggggg gttggttggt    2520
tggttggttt tgtcggaacc taggcaaatg accatattag tgaatctgtt aatagttgta    2580
gcttgggatg gttattgtag ttgttttggt aaaatcttca tttcctggtt ttttttacca    2640
ccttatttaa atctcgatta tctgctctct cttttatata catacacaca cccaaacata    2700
acatttataa tagtgtggta gtggaatgta tccttttta ggtttccctg ctttccagtt      2760 aattttttaaa atggtagcgc tttgtatgca tttagaatac atgactagta gtttatattt    2820
cactggtagt ttaaatctgg ttggggcagt ctgcagatgt ttgaagtagt ttagtgttct    2880
```

```
agaaagagct attactgtgg atagtgccta ggggagtgct ccacgccctc tgggcatacg    2940
gtagatatta tctgatgaat tggaaaggag caaaccagaa atggctttat tttctcccct    3000
ggactaattt ttaagtctcg attggaattc agtgagtagg ttcataatgt gcatgacaga    3060
aataagcttt atagtggttt accttcattt agctttggaa gttttctttg ccttagtttt    3120
ggaagtaaat tctagtttgt agttctcatt tgtaatgaac acattaacga ctagattaaa    3180
atattgcctt caagattgtt cttacttaca agacttgctc ctacttctat gctgaaaatt    3240
gaccctggat agaatactat aaggttttga gttagctgga aaagtgatca gattaataaa    3300
tgtatattgg tagttgaatt tagcaaagaa atagagataa tcatgattat acctttattt    3360
ttacaggaag agatgatgta actagagtat gtgtctacag gagtaataat ggtttccaaa    3420
gagtattttt taaaggaaca aaacgagcat gaattaactc ttcaatataa gctatgaagt    3480
aatagttggt tgtgaattaa agtggcacca gctagcacct ctgtgtttta agggtctttc    3540
aatgtttcta gaataagccc ttattttcaa gggttcataa caggcataaa atctcttctc    3600
ctggcaaaag ctgctatgaa aagcctcagc ttgggaagat agattttttt cccccccaatt    3660 acaaaatcta agtattttgg cccttcaatt tggaggaggg caaaagttgg aagtaagaag    3720 ttttattta agtactttca gtgctcaaaa aaatgcaatc actgtgttgt atataatagt    3780
tcataggttg atcactcata ataattgact ctaaggcttt tattaagaaa acagcagaaa    3840
gattaaatct tgaattaagt ctgggggaa atggccactg cagatggagt tttagagtag    3900
taatgaaatt ctacctagaa tgcaaaattg ggtatatgaa ttacatagca tgttgttggg    3960 attttttta atgtgcagaa gatcaaagct acttggaagg agtgcctata atttgccagt    4020
agccacagat taagattata tcttatatat cagcagatta gctttagctt agggggaggg    4080
tgggaaagtt tgggggggg gttgtgaaga tttaggggga ccttgataga gaactttata    4140
aacttctttc tctttaataa agacttgtct tacaccgtgc tgccattaaa ggcagctgtt    4200
ctagagtttc agtcacctaa gtacacccac aaaacaatat gaatatggag atcttccttt    4260 accccctcaac tttaatttgc ccagttatac ctcagtgttg tagcagtact gtgatacctg    4320
gcacagtgct ttgatcttac gatgccctct gtactgacct gaaggagacc taagagtcct    4380 ttccctttt gagtttgaat catagccttg atgtggtctc ttgttttatg tccttgttcc    4440
taatgtaaaa gtgcttaact gcttcttggt tgtattgggt agcattggga taagatttta    4500
actgggtatt cttgaattgc ttttacaata aaccaatttt ataatcttta aatttatcaa    4560 cttttacat ttgtgttatt ttcagtcagg gcttcttaga tctacttatg gttgatggag    4620
cacattgatt tggagtttca gatcttccaa agcactattt gttgtaataa cttttctaaa    4680
tgtagtgcct ttaaaggaaa aatgaacaca gggaagtgac tttgctacaa ataatgttgc    4740
tgtgttaagt attcatatta aatacatgcc ttctatatgg aacatggcag aaagactgaa    4800
aaataacagt aattaattgt gtaattcaga attcatacca atcagtgttg aaactcaaac    4860
attgcaaaag tgggtggcaa tattcagtgc ttaaactttt tctagcgttg gtacatctga    4920
gaaatgagtg ctcaggtgga ttttatcctc gcaagcatgt tgttataaga attgtgggtg    4980
tgcctatcat aacaattgtt ttctgtatct tgaaaaagta ttctccacat tttaaatgtt    5040
ttatattaga gaattcttta atgcacactt gtcaaatata tatatatagt accaatgtta    5100 ccttttttatt ttttgttttta gatgtaagag catgctcata tgttaggtac ttacataaat    5160
```

```
tgttacatta tttttctta tgtaataacct ttttgtttgt ttatgtggtt caaatatatt    5220
ctttccttaa actcttaaaa aaaaaa                                         5246
```

<210> SEQ ID NO 11
<211> LENGTH: 466
<212> TYPE: PRT
<213> ORGANISM: homo sapiens

<400> SEQUENCE: 11

```
Met Asp Pro Gly Gln Gln Pro Pro Gln Pro Ala Pro Gln Gly Gln
1               5                   10                  15

Gly Gln Pro Pro Ser Gln Pro Pro Gln Gly Gly Pro Pro Ser Gly
            20                  25                  30

Pro Gly Gln Pro Ala Pro Ala Ala Thr Gln Ala Ala Pro Gln Ala Pro
        35                  40                  45

Pro Ala Gly His Gln Ile Val His Val Arg Gly Asp Ser Glu Thr Asp
    50                  55                  60

Leu Glu Ala Leu Phe Asn Ala Val Met Asn Pro Lys Thr Ala Asn Val
65                  70                  75                  80

Pro Gln Thr Val Pro Met Arg Leu Arg Lys Leu Pro Asp Ser Phe Phe
                85                  90                  95

Lys Pro Pro Glu Pro Lys Ser His Ser Arg Gln Ala Ser Thr Asp Ala
            100                 105                 110

Gly Thr Ala Gly Ala Leu Thr Pro Gln His Val Arg Ala His Ser Ser
        115                 120                 125

Pro Ala Ser Leu Gln Leu Gly Ala Val Ser Pro Gly Thr Leu Thr Pro
    130                 135                 140

Thr Gly Val Val Ser Gly Pro Ala Ala Thr Pro Thr Ala Gln His Leu
145                 150                 155                 160

Arg Gln Ser Ser Phe Glu Ile Pro Asp Asp Val Pro Leu Pro Ala Gly
                165                 170                 175

Trp Glu Met Ala Lys Thr Ser Ser Gly Gln Arg Tyr Phe Leu Asn His
            180                 185                 190

Ile Asp Gln Thr Thr Thr Trp Gln Asp Pro Arg Lys Ala Met Leu Ser
        195                 200                 205

Gln Met Asn Val Thr Ala Pro Thr Ser Pro Pro Val Gln Gln Asn Met
    210                 215                 220

Met Asn Ser Ala Ser Ala Met Asn Gln Arg Ile Ser Gln Ser Ala Pro
225                 230                 235                 240

Val Lys Gln Pro Pro Pro Leu Ala Pro Gln Ser Pro Gln Gly Gly Val
                245                 250                 255

Met Gly Gly Ser Asn Ser Asn Gln Gln Gln Gln Met Arg Leu Gln Gln
            260                 265                 270

Leu Gln Met Glu Lys Glu Arg Leu Arg Leu Lys Gln Gln Glu Leu Leu
        275                 280                 285

Arg Gln Ala Met Arg Asn Ile Asn Pro Ser Thr Ala Asn Ser Pro Lys
    290                 295                 300

Cys Gln Glu Leu Ala Leu Arg Ser Gln Leu Pro Thr Leu Glu Gln Asp
305                 310                 315                 320

Gly Gly Thr Gln Asn Pro Val Ser Ser Pro Gly Met Ser Gln Glu Leu
                325                 330                 335

Arg Thr Met Thr Thr Asn Ser Ser Asp Pro Phe Leu Asn Ser Gly Thr
            340                 345                 350
```

```
Tyr His Ser Arg Asp Glu Ser Thr Asp Ser Gly Leu Ser Met Ser Ser
            355                 360                 365

Tyr Ser Val Pro Arg Thr Pro Asp Asp Phe Leu Asn Ser Val Asp Glu
    370                 375                 380

Met Asp Thr Gly Asp Thr Ile Asn Gln Ser Thr Leu Pro Ser Gln Gln
385                 390                 395                 400

Asn Arg Phe Pro Asp Tyr Leu Glu Ala Ile Pro Gly Thr Asn Val Asp
                405                 410                 415

Leu Gly Thr Leu Glu Gly Asp Gly Met Asn Ile Glu Gly Glu Glu Leu
            420                 425                 430

Met Pro Ser Leu Gln Glu Ala Leu Ser Ser Asp Ile Leu Asn Asp Met
    435                 440                 445

Glu Ser Val Leu Ala Ala Thr Lys Leu Asp Lys Glu Ser Phe Leu Thr
    450                 455                 460

Trp Leu
465

<210> SEQ ID NO 12
<211> LENGTH: 5282
<212> TYPE: DNA
<213> ORGANISM: homo sapiens

<400> SEQUENCE: 12
gccgccgcca gggaaaagaa agggaggaag gaaggaacaa gaaaaggaaa taaagagaaa      60
ggggaggcgg ggaaaggcaa cgagctgtcc ggcctccgtc aagggagttg gagggaaaaa     120
gttctcaggc gccgcaggtc cgagtgcctc gcagcccctc ccgaggcgca gccgccagac     180
cagtggagcc ggggcgcagg gcggggcgg aggcgccggg gcggggatg cggggccgcg      240 gcgcagcccc ccgccctga gagcgaggac agccgccgcc ggcccgcagc cgtcgccgct     300
tctccacctc ggcccgtgga gccggggcgt ccgggcgtag ccctcgctcg cctgggtcag     360
ggggtgcgcg tcgggggagg cagaagccat ggatcccggg cagcagccgc cgcctcaacc     420
ggccccccag ggccaagggc agccgccttc gcagcccccg caggggcagg gcccgccgtc     480
cggacccggg caaccggcac ccgcggcgac ccaggcggcg ccgcaggcac ccccgccgg      540 gcatcagatc gtgcacgtcc gcggggactc ggagaccgac ctggaggcgc tcttcaacgc     600
cgtcatgaac cccaagacgg ccaacgtgcc ccagaccgtg cccatgaggc tccgaaagct     660
gcccgactcc ttcttcaagc cgccggagcc caaatcccac tcccgacagg ccagtactga     720
tgcaggcact gcaggagccc tgactccaca gcatgttcga gctcattcct ctccagcttc     780
tctgcagttg ggagctgttt ctcctgggac actgaccccc actggagtag tctctggccc     840
agcagctaca cccacagctc agcatcttcg acagtcttct tttgagatac ctgatgatgt     900
acctctgcca gcaggttggg agatggcaaa gacatcttct ggtcagagat acttcttaaa     960
tcacatcgat cagacaacaa catggcagga ccccaggaag gccatgctgt cccagatgaa    1020
cgtcacagcc cccaccagtc caccagtgca gcagaatatg atgaactcgg cttcagccat    1080
gaaccagaga atcagtcaga gtgctccagt gaaacagcca ccacccctgg ctctcccagag    1140 cccacaggga ggcgtcatgg gtggcagcaa ctccaaccag cagcaacaga tgcgactgca    1200
gcaactgcag atggagaagg agaggctgcg gctgaaacag caagaactgc ttcggcaggc    1260
aatgcggaat atcaatccca gcacagcaaa ttctccaaaa tgtcaggagt tagccctgcg    1320
tagccagtta ccaacactgg agcaggatgg tgggactcaa aatccagtgt cttctcccgg    1380
gatgtctcag gaattgagaa caatgacgac caatagctca gatccttttcc ttaacagtgg    1440
```

```
cacctatcac tctcgagatg agagtacaga cagtggacta agcatgagca gctacagtgt    1500
ccctcgaacc ccagatgact tcctgaacag tgtggatgag atggatacag gtgatactat    1560
caaccaaagc accctgccct cacagcagaa ccgtttccca gactaccttg aagccattcc    1620
tgggacaaat gtggaccttg aacactgga aggagatgag atgaacatag aaggagagga    1680
gctgatgcca agtctgcagg aagctttgag ttctgacatc cttaatgaca tggagtctgt    1740
tttggctgcc accaagctag ataaagaaag ctttcttaca tggttataga gccctcaggc    1800
agactgaatt ctaaatctgt gaaggatcta aggagacaca tgcaccggaa atttccataa    1860
gccagttgca gttttcaggc taatacagaa aaagatgaac aaacgtccag caagatactt    1920
taatcctcta ttttgctctt ccttgtccat tgctgctgtt aatgtattgc tgacctcttt    1980
cacagttggc tctaaagaat caaagaaaaa aactttta tttcttttgc tattaaaact       2040
actgttcatt ttgggggctg ggggaagtga gcctgtttgg atgatggatg ccattccttt    2100
tgcccagtta aatgttcacc aatcatttta actaaatact cagacttaga agtcagatgc    2160
ttcatgtcac agcatttagt ttgttcaaca gttgtttctt cagcttcctt tgtccagtgg    2220
aaaaacatga tttactggtc tgacaagcca aaaatgttat atctgatatt aaatacttaa    2280
tgctgatttg aagagatagc tgaaaccaag gctgaagact gttttacttt cagtattttc    2340
ttttcctcct agtgctatca ttagtcacat aatgaccttg attttatttt aggagcttat    2400
aaggcatgag acaatttcca tataaatata ttaattattg ccacatactc taatatagat    2460
tttggtggat aattttgtgg gtgtgcattt tgttctgttt tgttgggttt tttgtttttt    2520 ttgttttttgg cagggtcggt gggggggttg gttggttggt tggttttgtc ggaacctagg    2580
caaatgacca tattagtgaa tctgttaata gttgtagctt gggatggtta ttgtagttgt    2640
tttggtaaaa tcttcatttc ctggtttttt ttaccacctt atttaaatct cgattatctg    2700 ctctctctt tatatacata cacacaccca aacataacat ttataatagt gtggtagtgg     2760
aatgtatcct tttttaggtt tccctgcttt ccagttaatt tttaaaatgg tagcgctttg    2820
tatgcattta gaatacatga ctagtagttt atatttcact ggtagtttaa atctggttgg    2880
ggcagtctgc agatgtttga agtagtttag tgttctagaa agagctatta ctgtggatag    2940
tgcctagggg agtgctccac gccctctggg catacggtag atattatctg atgaattgga    3000
aaggagcaaa ccagaaatgg ctttattttc tcccttggac taattttta gtctcgattg     3060 gaattcagtg agtaggttca taatgtgcat gacagaaata agcttatag tggtttacct     3120 tcatttagct ttgaagtttt tctttgcctt agttttggaa gtaaattcta gtttgtagtt    3180
ctcatttgta atgaacacat taacgactag attaaaatat tgccttcaag attgttctta    3240
cttacaagac ttgctcctac ttctatgctg aaaattgacc ctggatagaa tactataagg    3300
ttttgagtta gctggaaaag tgatcagatt aataaatgta tattggtagt tgaatttagc    3360
aaagaaatag agataatcat gattatacct ttattttttac aggaagagat gatgtaacta   3420
gagtatgtgt ctacaggagt aataatggtt tccaaagagt atttttaaa ggaacaaaac     3480 gagcatgaat taactcttca atataagcta tgaagtaata gttggttgtg aattaaagtg    3540
gcaccagcta gcacctctgt gttttaaggg tctttcaatg tttctagaat aagcccttat    3600
tttcaagggt tcataacagg cataaaatct cttctcctgg caaaagctgc tatgaaaagc    3660
ctcagcttgg gaagatagat tttttcccc ccaattacaa aatctaagta ttttggccct     3720
tcaatttgga ggagggcaaa agttggaagt aagaagtttt attttaagta ctttcagtgc    3780
```

```
tcaaaaaaat gcaatcactg tgttgtatat aatagttcat aggttgatca ctcataataa    3840
ttgactctaa ggcttttatt aagaaaacag cagaaagatt aaatcttgaa ttaagtctgg    3900
ggggaaatgg ccactgcaga tggagtttta gagtagtaat gaaattctac ctagaatgca    3960
aaattgggta tatgaattac atagcatgtt gttgggattt tttttaatgt gcagaagatc    4020
aaagctactt ggaaggagtg cctataattt gccagtagcc acagattaag attatatctt    4080
atatatcagc agattagctt tagcttaggg ggagggtggg aaagtttggg gggggggttg    4140
tgaagattta gggggacctt gatagagaac tttataaact tctttctctt taataaagac    4200
ttgtcttaca ccgtgctgcc attaaaggca gctgttctag agtttcagtc acctaagtac    4260
acccacaaaa caatatgaat atggagatct tcctttaccc ctcaacttta atttgcccag    4320
ttatacctca gtgttgtagc agtactgtga tacctggcac agtgctttga tcttacgatg    4380
ccctctgtac tgacctgaag gagacctaag agtcctttcc cttttgagt ttgaatcata    4440
gccttgatgt ggtctcttgt tttatgtcct tgttcctaat gtaaagtgc ttaactgctt    4500
cttggttgta ttgggtagca ttgggataag attttaactg ggtattcttg aattgctttt    4560
acaataaacc aatttataa tctttaaatt tatcaacttt ttacatttgt gttatttca    4620
gtcagggctt cttagatcta cttatggttg atggagcaca ttgatttgga gtttcagatc    4680
ttccaaagca ctatttgttg taataacttt tctaaatgta gtgcctttaa aggaaaaatg    4740
aacacaggga agtgactttg ctacaaataa tgttgctgtg ttaagtattc atattaaata    4800
catgccttct atatggaaca tggcagaaag actgaaaaat aacagtaatt aattgtgtaa    4860
ttcagaattc ataccaatca gtgttgaaac tcaaacattg caaaagtggg tggcaatatt    4920
cagtgcttaa cactttctta gcgttggtac atctgagaaa tgagtgctca ggtggattt    4980
atcctcgcaa gcatgttgtt ataagaattg tgggtgtgcc tatcataaca attgttttct    5040
gtatcttgaa aaagtattct ccacatttta aatgttttat attagagaat tctttaatgc    5100
acacttgtca aatatatata tatagtacca atgttacctt tttatttttt gttttagatg    5160
taagagcatg ctcatatgtt aggtacttac ataaattgtt acattatttt ttcttatgta    5220
ataccttttt gtttgtttat gtggttcaaa tatattcttt ccttaaactc ttaaaaaaaa    5280
aa                                                                   5282
```

<210> SEQ ID NO 13
<211> LENGTH: 470
<212> TYPE: PRT
<213> ORGANISM: homo sapiens

<400> SEQUENCE: 13

```
Met Asp Pro Gly Gln Gln Pro Pro Gln Pro Ala Pro Gln Gly Gln
1               5                   10                  15

Gly Gln Pro Pro Ser Gln Pro Gln Gly Gln Gly Pro Pro Ser Gly
                20                  25                  30

Pro Gly Gln Pro Ala Pro Ala Ala Thr Gln Ala Ala Pro Gln Ala Pro
                35                  40                  45

Pro Ala Gly His Gln Ile Val His Val Arg Gly Asp Ser Glu Thr Asp
                50                  55                  60

Leu Glu Ala Leu Phe Asn Ala Val Met Asn Pro Lys Thr Ala Asn Val
65                  70                  75                  80

Pro Gln Thr Val Pro Met Arg Leu Arg Lys Leu Pro Asp Ser Phe Phe
                85                  90                  95
```

```
Lys Pro Pro Glu Pro Lys Ser His Ser Arg Gln Ala Ser Thr Asp Ala
            100                 105                 110

Gly Thr Ala Gly Ala Leu Thr Pro Gln His Val Arg Ala His Ser Ser
        115                 120                 125

Pro Ala Ser Leu Gln Leu Gly Ala Val Ser Pro Gly Thr Leu Thr Pro
    130                 135                 140

Thr Gly Val Val Ser Gly Pro Ala Ala Thr Pro Thr Ala Gln His Leu
145                 150                 155                 160

Arg Gln Ser Ser Phe Glu Ile Pro Asp Asp Val Pro Leu Pro Ala Gly
                165                 170                 175

Trp Glu Met Ala Lys Thr Ser Ser Gly Gln Arg Tyr Phe Leu Asn His
            180                 185                 190

Ile Asp Gln Thr Thr Thr Trp Gln Asp Pro Arg Lys Ala Met Leu Ser
        195                 200                 205

Gln Met Asn Val Thr Ala Pro Thr Ser Pro Pro Val Gln Gln Asn Met
    210                 215                 220

Met Asn Ser Ala Ser Ala Met Asn Gln Arg Ile Ser Gln Ser Ala Pro
225                 230                 235                 240

Val Lys Gln Pro Pro Pro Leu Ala Pro Gln Ser Pro Gln Gly Gly Val
                245                 250                 255

Met Gly Gly Ser Asn Ser Asn Gln Gln Gln Met Arg Leu Gln Gln
            260                 265                 270

Leu Gln Met Glu Lys Glu Arg Leu Arg Leu Lys Gln Gln Glu Leu Leu
        275                 280                 285

Arg Gln Val Arg Pro Gln Ala Met Arg Asn Ile Asn Pro Ser Thr Ala
    290                 295                 300

Asn Ser Pro Lys Cys Gln Glu Leu Ala Leu Arg Ser Gln Leu Pro Thr
305                 310                 315                 320

Leu Glu Gln Asp Gly Gly Thr Gln Asn Pro Val Ser Ser Pro Gly Met
                325                 330                 335

Ser Gln Glu Leu Arg Thr Met Thr Thr Asn Ser Ser Asp Pro Phe Leu
            340                 345                 350

Asn Ser Gly Thr Tyr His Ser Arg Asp Glu Ser Thr Asp Ser Gly Leu
        355                 360                 365

Ser Met Ser Ser Tyr Ser Val Pro Arg Thr Pro Asp Asp Phe Leu Asn
    370                 375                 380

Ser Val Asp Glu Met Asp Thr Gly Asp Thr Ile Asn Gln Ser Thr Leu
385                 390                 395                 400

Pro Ser Gln Gln Asn Arg Phe Pro Asp Tyr Leu Glu Ala Ile Pro Gly
                405                 410                 415

Thr Asn Val Asp Leu Gly Thr Leu Glu Gly Asp Gly Met Asn Ile Glu
            420                 425                 430

Gly Glu Glu Leu Met Pro Ser Leu Gln Glu Ala Leu Ser Ser Asp Ile
        435                 440                 445

Leu Asn Asp Met Glu Ser Val Leu Ala Ala Thr Lys Leu Asp Lys Glu
    450                 455                 460

Ser Phe Leu Thr Trp Leu
465                 470

<210> SEQ ID NO 14
<211> LENGTH: 5294
<212> TYPE: DNA
<213> ORGANISM: homo sapiens
```

```
<400> SEQUENCE: 14
gccgccgcca gggaaaagaa agggaggaag gaaggaacaa gaaaaggaaa taaagagaaa      60
ggggaggcgg ggaaaggcaa cgagctgtcc ggcctccgtc aagggagttg gagggaaaaa     120
gttctcaggc gccgcaggtc cgagtgcctc gcagcccctc ccgaggcgca gccgccagac     180
cagtggagcc ggggcgcagg gcggggcgg aggcgccggg gcggggatg cggggccgcg      240 gcgcagcccc ccggccctga gagcgaggac agcgccgccc ggcccgcagc cgtcgccgct     300
tctccacctc ggcccgtgga gccggggcgt ccggcgtag ccctcgctcg cctgggtcag     360
ggggtgcgcg tcggggagg cagaagccat ggatcccggg cagcagccgc cgcctcaacc      420
ggccccccag ggccaagggc agccgccttc gcagcccccg caggggcagg gccgccgtc      480 cggacccggg caaccggcac ccgcggcgac ccaggcggcg ccgcaggcac ccccgccgg      540 gcatcagatc gtgcacgtcc gcggggactc ggagaccgac ctggaggcgc tcttcaacgc     600
cgtcatgaac cccaagacgg ccaacgtgcc ccagaccgtg cccatgaggc tccggaagct     660
gcccgactcc ttcttcaagc cgccggagcc caaatcccac tcccgacagg ccagtactga     720
tgcaggcact gcaggagccc tgactccaca gcatgttcga gctcattcct ctccagcttc     780
tctgcagttg ggagctgttt ctcctgggac actgaccccc actggagtag tctctggccc     840
agcagctaca cccacagctc agcatcttcg acagtcttct tttgagatac ctgatgatgt     900
acctctgcca gcaggttggg agatggcaaa gacatcttct ggtcagagat acttcttaaa     960
tcacatcgat cagacaacaa catggcagga ccccaggaag gccatgctgt cccagatgaa    1020
cgtcacagcc cccaccagtc caccagtgca gcagaatatg atgaactcgg cttcagccat    1080
gaaccagaga atcagtcaga gtgctccagt gaaacagcca ccacccctgg ctccccagag    1140
cccacaggga ggcgtcatgg gtggcagcaa ctccaaccag cagcaacaga tgcgactgca    1200
gcaactgcag atggagaagg agaggctgcg gctgaaacag caagaactgc ttcggcaggt    1260
gaggccacag gcaatgcgga atatcaatcc cagcacagca aattctccaa aatgtcagga    1320
gttagccctg cgtagccagt taccaacact ggagcaggat ggtgggactc aaaatccagt    1380
gtcttctccc gggatgtctc aggaattgag aacaatgacg accaaatagct cagatccttt    1440 ccttaacagt ggcacctatc actctcgaga tgagagtaca gacagtggac taagcatgag    1500
cagctacagt gtccctcgaa ccccagatga cttcctgaac agtgtggatg agatggatac    1560
aggtgatact atcaaccaaa gcaccctgcc ctcacagcag aaccgtttcc cagactacct    1620
tgaagccatt cctgggacaa atgtggacct tggaacactg gaaggagatg gaatgaacat    1680
agaaggagag gagctgatgc caagtctgca ggaagctttg agttctgaca tccttaatga    1740
catggagtct gttttggctg ccaccaagct agataaagaa agctttctta catggttata    1800
gagccctcag gcagactgaa ttctaaatct gtgaaggatc taaggagaca catgcaccgg    1860
aaatttccat aagccagttg cagttttcag gctaatacag aaaaagatga acaaacgtcc    1920
agcaagatac tttaatcctc tattttgctc ttccttgtcc attgctgctg ttaatgtatt    1980
gctgacctct ttcacagttg gctctaaaga atcaaaagaa aaaaactttt tatttctttt    2040
gctattaaaa ctactgttca ttttgggggc tggggaagt gagcctgttt ggatgatgga     2100
tgccattcct tttgcccagt taaatgttca ccaatcattt taactaaata ctcagactta    2160
gaagtcagat gcttcatgtc acagcattta gtttgttcaa cagttgtttc ttcagcttcc    2220
tttgtccagt ggaaaaacat gatttactgg tctgacaagc caaaaatgtt atatctgata    2280
ttaaatactt aatgctgatt tgaagagata gctgaaacca aggctgaaga ctgttttact    2340
```

```
ttcagtattt tcttttcctc ctagtgctat cattagtcac ataatgacct tgattttatt    2400
ttaggagctt ataaggcatg agacaatttc catataaata tattaattat tgccacatac    2460
tctaatatag attttggtgg ataattttgt gggtgtgcat tttgttctgt tttgttgggt    2520
tttttgtttt ttttgttttt ggcagggtcg gtgggggggt tggttggttg gttggttttg    2580
tcggaaccta ggcaaatgac catattagtg aatctgttaa tagttgtagc ttgggatggt    2640
tattgtagtt gttttggtaa aatcttcatt tcctggtttt ttttaccacc ttatttaaat    2700
ctcgattatc tgctctctct tttatataca tacacacacc caaacataac atttataata    2760
gtgtggtagt ggaatgtatc cttttttagg tttccctgct ttccagttaa ttttttaaaat   2820
ggtagcgctt tgtatgcatt tagaatacat gactagtagt ttatatttca ctggtagttt    2880
aaatctggtt ggggcagtct gcagatgttt gaagtagttt agtgttctag aaagagctat    2940
tactgtggat agtgcctagg ggagtgctcc acgccctctg ggcatacggt agatattatc    3000
tgatgaattg gaaaggagca aaccagaaat ggctttattt tctcccttgg actaattttt    3060
aagtctcgat tggaattcag tgagtaggtt cataatgtgc atgacagaaa taagctttat    3120
agtggtttac cttcatttag ctttggaagt tttctttgcc ttagttttgg aagtaaattc    3180
tagtttgtag ttctcatttg taatgaacac attaacgact agattaaaat attgccttca    3240
agattgttct tacttacaag acttgctcct acttctatgc tgaaaattga ccctggatag    3300
aatactataa ggttttgagt tagctggaaa agtgatcaga ttaataaatg tatattggta    3360
gttgaattta gcaaagaaat agagataatc atgattatac ctttattttt acaggaagag    3420
atgatgtaac tagagtatgt gtctacagga gtaataatgg tttccaaaga gtatttttta    3480
aaggaacaaa acgagcatga attaactctt caatataagc tatgaagtaa tagttggttg    3540
tgaattaaag tggcaccagc tagcacctct gtgttttaag ggtctttcaa tgtttctaga    3600
ataagccctt attttcaagg gttcataaca ggcataaaat ctcttctcct ggcaaaagct    3660
gctatgaaaa gcctcagctt gggaagatag attttttttcc ccccaattac aaaatctaag   3720
tattttggcc cttcaatttg gaggagggca aaagttggaa gtaagaagtt ttatttaag    3780
tactttcagt gctcaaaaaa atgcaatcac tgtgttgtat ataatagttc ataggttgat    3840
cactcataat aattgactct aaggctttta ttaagaaaac agcagaaaga ttaaatcttg    3900
aattaagtct gggggggaaat ggccactgca gatggagttt tagagtagta atgaaattct   3960
acctagaatg caaaattggg tatatgaatt acatagcatg ttgttgggat ttttttttaat   4020
gtgcagaaga tcaaagctac ttggaaggag tgcctataat ttgccagtag ccacagatta    4080
agattatatc ttatatatca gcagattagc tttagcttag ggggagggtg ggaaagtttg    4140
ggggggggt tgtgaagatt tagggggacc ttgatagaga actttataaa cttctttctc    4200
tttaataaag acttgtctta caccgtgctg ccattaaagg cagctgttct agagtttcag    4260
tcacctaagt acaccacaa aacaatatga atatggagat cttcctttac ccctcaactt    4320
taatttgccc agttatacct cagtgttgta gcagtactgt gatacctggc acagtgcttt    4380
gatcttacga tgccctctgt actgacctga aggagaccta agagtccttt ccctttttga    4440
gtttgaatca tagccttgat gtggtctctt gttttatgtc cttgttccta atgtaaaagt    4500
gcttaactgc ttcttggttg tattgggtag cattgggata agattttaac tgggtattct    4560
tgaattgctt ttacaataaa ccaattttat aatctttaaa tttatcaact ttttacattt    4620
gtgttatttt cagtcagggc ttcttagatc tacttatggt tgatggagca cattgatttg    4680
```

|  |  |
|---|---|
| gagtttcaga tcttccaaag cactatttgt tgtaataact tttctaaatg tagtgccttt | 4740 |
| aaaggaaaaa tgaacacagg gaagtgactt tgctacaaat aatgttgctg tgttaagtat | 4800 |
| tcatattaaa tacatgcctt ctatatggaa catggcagaa agactgaaaa ataacagtaa | 4860 |
| ttaattgtgt aattcagaat tcataccaat cagtgttgaa actcaaacat tgcaaaagtg | 4920 |
| ggtggcaata ttcagtgctt aacactttc tagcgttggt acatctgaga aatgagtgct | 4980 |
| caggtggatt ttatcctcgc aagcatgttg ttataagaat tgtgggtgtg cctatcataa | 5040 |
| caattgtttt ctgtatcttg aaaaagtatt ctccacattt taaatgtttt atattagaga | 5100 |
| attctttaat gcacacttgt caaatatata tatatagtac caatgttacc tttttatttt | 5160 |
| ttgtttaga tgtaagagca tgctcatatg ttaggtactt acataaattg ttacattatt | 5220 |
| ttttcttatg taatacctt ttgtttgttt atgtggttca aatatattct ttccttaaac | 5280 |
| tcttaaaaaa aaaa | 5294 |

<210> SEQ ID NO 15
<211> LENGTH: 492
<212> TYPE: PRT
<213> ORGANISM: homo sapiens

<400> SEQUENCE: 15

```
Met Asp Pro Gly Gln Gln Pro Pro Gln Pro Ala Pro Gln Gly Gln
1               5                   10                  15

Gly Gln Pro Pro Ser Gln Pro Gln Gly Gly Pro Ser Gly
            20                  25                  30

Pro Gly Gln Pro Ala Pro Ala Ala Thr Gln Ala Ala Pro Gln Ala Pro
            35                  40                  45

Pro Ala Gly His Gln Ile Val His Val Arg Gly Asp Ser Glu Thr Asp
50                  55                  60

Leu Glu Ala Leu Phe Asn Ala Val Met Asn Pro Lys Thr Ala Asn Val
65                  70                  75                  80

Pro Gln Thr Val Pro Met Arg Leu Arg Lys Leu Pro Asp Ser Phe Phe
                85                  90                  95

Lys Pro Pro Glu Pro Lys Ser His Ser Arg Gln Ala Ser Thr Asp Ala
            100                 105                 110

Gly Thr Ala Gly Ala Leu Thr Pro Gln His Val Arg Ala His Ser Ser
            115                 120                 125

Pro Ala Ser Leu Gln Leu Gly Ala Val Ser Pro Gly Thr Leu Thr Pro
130                 135                 140

Thr Gly Val Val Ser Gly Pro Ala Ala Thr Pro Thr Ala Gln His Leu
145                 150                 155                 160

Arg Gln Ser Ser Phe Glu Ile Pro Asp Asp Val Pro Leu Pro Ala Gly
                165                 170                 175

Trp Glu Met Ala Lys Thr Ser Ser Gly Gln Arg Tyr Phe Leu Asn His
            180                 185                 190

Ile Asp Gln Thr Thr Thr Trp Gln Asp Pro Arg Lys Ala Met Leu Ser
            195                 200                 205

Gln Met Asn Val Thr Ala Pro Thr Ser Pro Pro Val Gln Gln Asn Met
210                 215                 220

Met Asn Ser Ala Ser Gly Pro Leu Pro Asp Gly Trp Glu Gln Ala Met
225                 230                 235                 240

Thr Gln Asp Gly Glu Ile Tyr Tyr Ile Asn His Lys Asn Lys Thr Thr
                245                 250                 255
```

```
Ser Trp Leu Asp Pro Arg Leu Asp Pro Arg Phe Ala Met Asn Gln Arg
            260                 265                 270

Ile Ser Gln Ser Ala Pro Val Lys Gln Pro Pro Leu Ala Pro Gln
    275                 280                 285

Ser Pro Gln Gly Gly Val Met Gly Gly Ser Asn Ser Asn Gln Gln Gln
    290                 295                 300

Gln Met Arg Leu Gln Gln Leu Gln Met Glu Lys Glu Arg Leu Arg Leu
305                 310                 315                 320

Lys Gln Gln Glu Leu Leu Arg Gln Val Arg Pro Gln Glu Leu Ala Leu
                325                 330                 335

Arg Ser Gln Leu Pro Thr Leu Glu Gln Asp Gly Gly Thr Gln Asn Pro
            340                 345                 350

Val Ser Ser Pro Gly Met Ser Gln Glu Leu Arg Thr Met Thr Thr Asn
        355                 360                 365

Ser Ser Asp Pro Phe Leu Asn Ser Gly Thr Tyr His Ser Arg Asp Glu
    370                 375                 380

Ser Thr Asp Ser Gly Leu Ser Met Ser Ser Tyr Ser Val Pro Arg Thr
385                 390                 395                 400

Pro Asp Asp Phe Leu Asn Ser Val Asp Glu Met Asp Thr Gly Asp Thr
                405                 410                 415

Ile Asn Gln Ser Thr Leu Pro Ser Gln Gln Asn Arg Phe Pro Asp Tyr
            420                 425                 430

Leu Glu Ala Ile Pro Gly Thr Asn Val Asp Leu Gly Thr Leu Glu Gly
                435                 440                 445

Asp Gly Met Asn Ile Glu Gly Glu Glu Leu Met Pro Ser Leu Gln Glu
            450                 455                 460

Ala Leu Ser Ser Asp Ile Leu Asn Asp Met Glu Ser Val Leu Ala Ala
465                 470                 475                 480

Thr Lys Leu Asp Lys Glu Ser Phe Leu Thr Trp Leu
                485                 490

<210> SEQ ID NO 16
<211> LENGTH: 5360
<212> TYPE: DNA
<213> ORGANISM: homo sapiens

<400> SEQUENCE: 16
gccgccgcca gggaaaagaa agggaggaag gaaggaacaa gaaaaggaaa taaagagaaa      60
ggggaggcgg ggaaaggcaa cgagctgtcc ggcctccgtc aagggagttg gagggaaaaa     120
gttctcaggc gccgcaggtc cgagtgcctc gcagcccctc ccgaggcgca gccgccagac     180
cagtggagcc ggggcgcagg gcggggcgg aggcgccggg gcggggatg cggggccgcg      240 gcgcagcccc ccggccctga gagcgaggac agcgccgccc ggcccgcagc cgtcgccgct     300
tctccacctc ggcccgtgga gccggggcgt ccgggcgtag ccctcgctcg cctgggtcag     360
ggggtgcgcg tcgggggagg cagaagccat ggatcccggg cagcagccgc cgcctcaacc     420
ggccccccag ggccaagggc agccgccttc gcagccccg caggggcagg gccgccgtc       480 cggacccggg caaccggcac ccgcggcgac ccaggcggcg ccgcaggcac ccccgccgg      540 gcatcagatc gtgcacgtcc gcggggactc ggagaccgac ctggaggcgc tcttcaacgc     600
cgtcatgaac cccaagacgg ccaacgtgcc ccagaccgtg cccatgaggc tccggaagct     660 gccccgactcc ttcttcaagc cgccggagcc caaatcccac tcccgacagg ccagtactga     720
tgcaggcact gcaggagccc tgactccaca gcatgttcga gctcattcct ctccagcttc     780
```

```
tctgcagttg ggagctgttt ctcctgggac actgaccccc actggagtag tctctggccc    840
agcagctaca cccacagctc agcatcttcg acagtcttct tttgagatac ctgatgatgt    900
acctctgcca gcaggttggg agatggcaaa gacatcttct ggtcagagat acttcttaaa    960
tcacatcgat cagacaacaa catggcagga ccccaggaag gccatgctgt cccagatgaa   1020
cgtcacagcc cccaccagtc caccagtgca gcagaatatg atgaactcgg cttcaggtcc   1080
tcttcctgat ggatgggaac aagccatgac tcaggatgga gaaatttact atataaacca   1140
taagaacaag accacctctt ggctagaccc aaggcttgac cctcgttttg ccatgaacca   1200
gagaatcagt cagagtgctc cagtgaaaca gccaccaccc ctggctcccc agagcccaca   1260
gggaggcgtc atgggtggca gcaactccaa ccagcagcaa cagatgcgac tgcagcaact   1320
gcagatggag aaggagaggc tgcggctgaa acagcaagaa ctgcttcggc aggtgaggcc   1380
acaggagtta gccctgcgta gccagttacc aacactggag caggatggtg ggactcaaaa   1440
tccagtgtct tctcccggga tgtctcagga attgagaaca atgacgacca atagctcaga   1500
tcctttcctt aacagtggca cctatcactc tcgagatgag agtacagaca gtggactaag   1560
catgagcagc tacagtgtcc ctcgaacccc agatgacttc ctgaacagtg tggatgagat   1620
ggatacaggt gatactatca accaaagcac cctgccctca cagcagaacc gtttcccaga   1680
ctaccttgaa gccattcctg gacaaatgt ggaccttgga acactggaag agatggaat   1740
gaacatagaa ggagaggagc tgatgccaag tctgcaggaa gctttgagtt ctgacatcct   1800
taatgacatg gagtctgttt tggctgccac caagctagat aaagaaagct ttcttacatg   1860
gttatagagc cctcaggcag actgaattct aaatctgtga aggatctaag gagacacatg   1920
caccggaaat ttccataagc cagttgcagt tttcaggcta atacagaaaa agatgaacaa   1980
acgtccagca agatacttta atcctctatt ttgctcttcc ttgtccattg ctgctgttaa   2040
tgtattgctg acctctttca cagttggctc taaagaatca aaagaaaaaa acttttatt    2100
tcttttgcta ttaaaactac tgttcatttt gggggctggg ggaagtgagc ctgtttggat   2160
gatggatgcc attccttttg cccagttaaa tgttcaccaa tcattttaac taaatactca   2220
gacttagaag tcagatgctt catgtcacag catttagttt gttcaacagt tgtttcttca   2280
gcttcctttg tccagtggaa aaacatgatt tactggtctg acaagccaaa atgttatat    2340
ctgatattaa atacttaatg ctgatttgaa gagatagctg aaaccaaggc tgaagactgt   2400
tttactttca gtattttctt ttcctcctag tgctatcatt agtcacataa tgaccttgat   2460
tttattttag gagcttataa ggcatgagac aatttccata taaatatatt aattattgcc   2520
acatactcta atatagattt tggtggataa ttttgtgggt gtgcattttg ttctgttttg   2580
ttgggttttt tgttttttt gttttggca gggtcggtgg gggggttggt tggttggttg    2640
gttttgtcgg aacctaggca aatgaccata ttagtgaatc tgttaatagt tgtagcttgg   2700
gatggttatt gtagttgttt tggtaaaatc ttcatttcct ggttttttt accacccat    2760
ttaaatctcg attatctgct ctctctttta tatacataca cacacccaaa cataacattt   2820
ataaatgtgt ggtagtggaa tgtatccttt tttaggtttc cctgctttcc agttaatttt   2880
taaaatggta gcgctttgta tgcatttaga atacatgact agtagtttat atttcactgg   2940
tagtttaaat ctggttgggg cagtctgcag atgtttgaag tagtttagtg ttctagaaag   3000
agctattact gtggatagtg cctaggggag tgctccacgc cctctgggca tacggtagat   3060
attatctgat gaattggaaa ggagcaaacc agaaatggct ttattttctc ccttggacta   3120
```

```
atttttaagt ctcgattgga attcagtgag taggttcata atgtgcatga cagaaataag    3180
ctttatagtg gtttaccttc atttagcttt ggaagttttc tttgccttag ttttggaagt    3240
aaattctagt ttgtagttct catttgtaat gaacacatta acgactagat taaaatattg    3300
ccttcaagat tgttcttact tacaagactt gctcctactt ctatgctgaa aattgaccct    3360
ggatagaata ctataaggtt ttgagttagc tggaaaagtg atcagattaa taaatgtata    3420
ttggtagttg aatttagcaa agaaatagag ataatcatga ttatacctt attttacag    3480 gaagagatga tgtaactaga gtatgtgtct acaggagtaa taatggtttc caaagagtat    3540
tttttaaagg aacaaaacga gcatgaatta actcttcaat ataagctatg aagtaatagt    3600
tggttgtgaa ttaaagtggc accagctagc acctctgtgt tttaagggtc tttcaatgtt    3660
tctagaataa gcccttattt tcaagggttc ataacaggca taaatctct tctcctggca    3720 aaagctgcta tgaaaagcct cagcttggga agatagattt ttttcccccc aattacaaaa    3780
tctaagtatt ttggcccttc aatttggagg agggcaaaag ttggaagtaa gaagttttat    3840
tttaagtact ttcagtgctc aaaaaaatgc aatcactgtg ttgtatataa tagttcatag    3900
gttgatcact cataataatt gactctaagg cttttattaa gaaaacagca gaaagattaa    3960
atcttgaatt aagtctgggg ggaaatggcc actgcagatg gagttttaga gtagtaatga    4020
aattctacct agaatgcaaa attgggtata tgaattacat agcatgttgt tgggattttt    4080
tttaatgtgc agaagatcaa agctacttgg aaggagtgcc tataatttgc cagtagccac    4140
agattaagat tatatcttat atatcagcag attagcttta gcttaggggg agggtgggaa    4200
agtttggggg gggggttgtg aagatttagg gggaccttga tagagaactt tataaacttc    4260
tttctcttta ataaagactt gtcttacacc gtgctgccat taaaggcagc tgttctagag    4320
tttcagtcac ctaagtacac ccacaaaaca atatgaatat ggagatcttc ctttacccct    4380
caactttaat ttgcccagtt atacctcagt gttgtagcag tactgtgata cctggcacag    4440
tgctttgatc ttacgatgcc ctctgtactg acctgaagga gacctaagag tcctttccct    4500
ttttgagttt gaatcatagc cttgatgtgg tctcttgttt tatgtccttg ttcctaatgt    4560
aaaagtgctt aactgcttct tggttgtatt gggtagcatt gggataagat tttaactggg    4620
tattcttgaa ttgctttac aataaaccaa ttttataatc tttaaattta tcaactttt    4680 acatttgtgt tattttcagt cagggcttct tagatctact tatggttgat ggagcacatt    4740
gatttggagt ttcagatctt ccaaagcact atttgttgta ataactttc taaatgtagt    4800 gcctttaaag gaaaaatgaa cacagggaag tgactttgct acaaataatg ttgctgtgtt    4860
aagtattcat attaaataca tgccttctat atggaacatg gcagaaagac tgaaaaataa    4920
cagtaattaa ttgtgtaatt cagaattcat accaatcagt gttgaaactc aaacattgca    4980
aaagtgggtg gcaatattca gtgcttaaca cttttctagc gttggtacat ctgagaaatg    5040
agtgctcagg tggattttat cctcgcaagc atgttgttat aagaattgtg ggtgtgccta    5100
tcataacaat tgttttctgt atcttgaaaa agtattctcc acattttaaa tgttttatat    5160
tagagaattc tttaatgcac acttgtcaaa tatatatata tagtaccaat gttacctttt    5220
tattttttgt tttagatgta agagcatgct catatgttag gtacttacat aaaattgttac   5280 attattttt cttatgtaat acctttttgt ttgtttatgt ggttcaaata tattctttcc    5340
ttaaactctt aaaaaaaaaa                                                5360

<210> SEQ ID NO 17
<211> LENGTH: 508
```

<212> TYPE: PRT
<213> ORGANISM: homo sapiens

<400> SEQUENCE: 17

```
Met Asp Pro Gly Gln Gln Pro Pro Gln Pro Ala Pro Gln Gly Gln
1               5                   10                  15

Gly Gln Pro Pro Ser Gln Pro Pro Gln Gly Gly Pro Pro Ser Gly
                20                  25                  30

Pro Gly Gln Pro Ala Pro Ala Ala Thr Gln Ala Ala Pro Gln Ala Pro
            35                  40                  45

Pro Ala Gly His Gln Ile Val His Val Arg Gly Asp Ser Glu Thr Asp
        50                  55                  60

Leu Glu Ala Leu Phe Asn Ala Val Met Asn Pro Lys Thr Ala Asn Val
65                  70                  75                  80

Pro Gln Thr Val Pro Met Arg Leu Arg Lys Leu Pro Asp Ser Phe Phe
                85                  90                  95

Lys Pro Pro Glu Pro Lys Ser His Ser Arg Gln Ala Ser Thr Asp Ala
                100                 105                 110

Gly Thr Ala Gly Ala Leu Thr Pro Gln His Val Arg Ala His Ser Ser
            115                 120                 125

Pro Ala Ser Leu Gln Leu Gly Ala Val Ser Pro Gly Thr Leu Thr Pro
130                 135                 140

Thr Gly Val Val Ser Gly Pro Ala Ala Thr Pro Thr Ala Gln His Leu
145                 150                 155                 160

Arg Gln Ser Ser Phe Glu Ile Pro Asp Asp Val Pro Leu Pro Ala Gly
                165                 170                 175

Trp Glu Met Ala Lys Thr Ser Ser Gly Gln Arg Tyr Phe Leu Asn His
                180                 185                 190

Ile Asp Gln Thr Thr Thr Trp Gln Asp Pro Arg Lys Ala Met Leu Ser
            195                 200                 205

Gln Met Asn Val Thr Ala Pro Thr Ser Pro Pro Val Gln Gln Asn Met
210                 215                 220

Met Asn Ser Ala Ser Gly Pro Leu Pro Asp Gly Trp Glu Gln Ala Met
225                 230                 235                 240

Thr Gln Asp Gly Glu Ile Tyr Tyr Ile Asn His Lys Asn Lys Thr Thr
                245                 250                 255

Ser Trp Leu Asp Pro Arg Leu Asp Pro Arg Phe Ala Met Asn Gln Arg
                260                 265                 270

Ile Ser Gln Ser Ala Pro Val Lys Gln Pro Pro Pro Leu Ala Pro Gln
            275                 280                 285

Ser Pro Gln Gly Gly Val Met Gly Gly Ser Asn Ser Asn Gln Gln Gln
290                 295                 300

Gln Met Arg Leu Gln Leu Gln Met Glu Lys Glu Arg Leu Arg Leu
305                 310                 315                 320

Lys Gln Gln Glu Leu Leu Arg Gln Val Arg Pro Gln Ala Met Arg Asn
                325                 330                 335

Ile Asn Pro Ser Thr Ala Asn Ser Pro Lys Cys Gln Glu Leu Ala Leu
            340                 345                 350

Arg Ser Gln Leu Pro Thr Leu Glu Gln Asp Gly Gly Thr Gln Asn Pro
                355                 360                 365

Val Ser Ser Pro Gly Met Ser Gln Glu Leu Arg Thr Met Thr Thr Asn
            370                 375                 380

Ser Ser Asp Pro Phe Leu Asn Ser Gly Thr Tyr His Ser Arg Asp Glu
385                 390                 395                 400
```

```
Ser Thr Asp Ser Gly Leu Ser Met Ser Ser Tyr Ser Val Pro Arg Thr
                405                 410                 415
Pro Asp Asp Phe Leu Asn Ser Val Asp Glu Met Asp Thr Gly Asp Thr
            420                 425                 430
Ile Asn Gln Ser Thr Leu Pro Ser Gln Gln Asn Arg Phe Pro Asp Tyr
        435                 440                 445
Leu Glu Ala Ile Pro Gly Thr Asn Val Asp Leu Gly Thr Leu Glu Gly
    450                 455                 460
Asp Gly Met Asn Ile Glu Gly Glu Leu Met Pro Ser Leu Gln Glu
465                 470                 475                 480
Ala Leu Ser Ser Asp Ile Leu Asn Asp Met Glu Ser Val Leu Ala Ala
                485                 490                 495
Thr Lys Leu Asp Lys Glu Ser Phe Leu Thr Trp Leu
                500                 505

<210> SEQ ID NO 18
<211> LENGTH: 5408
<212> TYPE: DNA
<213> ORGANISM: homo sapiens

<400> SEQUENCE: 18
gccgccgcca gggaaaagaa agggaggaag gaaggaacaa gaaaaggaaa taaagagaaa      60
ggggaggcgg ggaaaggcaa cgagctgtcc ggcctccgtc aagggagttg gagggaaaaa     120
gttctcaggc gccgcaggtc cgagtgcctc gcagcccctc ccgaggcgca gccgccagac     180
cagtggagcc ggggcgcagg gcggggcgg aggcgccggg gcggggatg cggggccgcg     240 gcgcagcccc ccggccctga gagcgaggac agcgccgccc ggcccgcagc cgtcgccgct     300
tctccacctc ggcccgtgga gccggggcgt ccgggcgtag ccctcgctcg cctgggtcag     360
ggggtgcgcg tcggggagg cagaagccat ggatcccggg cagcagccgc cgcctcaacc     420
ggccccccag ggccaagggc agccgccttc gcagcccccg caggggcagg gcccgccgtc     480
cggacccggg caaccggcac ccgcggcgac ccaggcggcg ccgcaggcac ccccgccgg     540 gcatcagatc gtgcacgtcc gcggggactc ggagaccgac ctggaggcgc tcttcaacgc     600
cgtcatgaac cccaagacgg ccaacgtgcc ccagaccgtg cccatgaggc tccggaagct     660
gcccgactcc ttcttcaagc cgccggagcc caaatcccac tcccgacagg ccagtactga     720
tgcaggcact gcaggagccc tgactccaca gcatgttcga gctcattcct ctccagcttc     780
tctgcagttg ggagctgttt ctcctgggac actgaccccc actggagtag tctctggccc     840
agcagctaca cccacagctc agcatcttcg acagtcttct tttgagatac ctgatgatgt     900
acctctgcca gcaggttggg agatggcaaa gacatcttct ggtcagagat acttcttaaa     960
tcacatcgat cagacaacaa catggcagga ccccaggaag gccatgctgt cccagatgaa    1020
cgtcacagcc cccaccagtc caccagtgca gcagaatatg atgaactcgg cttcaggtcc    1080
tcttcctgat ggatgggaac aagccatgac tcaggatgga gaaatttact atataaacca    1140
taagaacaag accacctctt ggctagaccc aaggcttgac cctcgttttg ccatgaacca    1200
gagaatcagt cagagtgctc cagtgaaaca gccaccaccc ctggctcccc agagcccaca    1260
gggaggcgtc atgggtggca gcaactccaa ccagcagcaa cagatgcgac tgcagcaact    1320
gcagatggag aaggagaggc tgcggctgaa acagcaagaa ctgcttcggc aggtgaggcc    1380
acaggcaatg cggaatatca atcccagcac agcaaattct ccaaaatgtc aggagttagc    1440
cctgcgtagc cagttaccaa cactggagca ggatggtggg actcaaaatc cagtgtcttc    1500
```

```
tcccgggatg tctcaggaat tgagaacaat gacgaccaat agctcagatc ctttccttaa    1560
cagtggcacc tatcactctc gagatgagag tacagacagt ggactaagca tgagcagcta    1620
cagtgtccct cgaacccag atgacttcct gaacagtgtg gatgagatgg atacaggtga     1680
tactatcaac caaagcaccc tgccctcaca gcagaaccgt ttcccagact accttgaagc    1740
cattcctggg acaaatgtgg accttggaac actggaagga gatggaatga acatagaagg    1800
agaggagctg atgccaagtc tgcaggaagc tttgagttct gacatcctta atgacatgga    1860
gtctgttttg gctgccacca agctagataa agaaagcttt cttacatggt tatagagccc    1920
tcaggcagac tgaattctaa atctgtgaag gatctaagga gacacatgca ccggaaattt    1980
ccataagcca gttgcagttt tcaggctaat acagaaaaag atgaacaaac gtccagcaag    2040
atactttaat cctctatttt gctcttcctt gtccattgct gctgttaatg tattgctgac    2100
ctctttcaca gttggctcta aagaatcaaa agaaaaaac ttttattc ttttgctatt        2160 aaaactactg ttcattttgg gggctggggg aagtgagcct gtttggatga tggatgccat    2220
tccttttgcc cagttaaatg ttcaccaatc attttaacta aatactcaga cttagaagtc    2280
agatgcttca tgtcacagca tttagtttgt tcaacagttg tttcttcagc ttcctttgtc    2340
cagtggaaaa acatgattta ctggtctgac aagccaaaaa tgttatatct gatattaaat    2400
acttaatgct gatttgaaga gatagctgaa accaaggctg aagactgttt tactttcagt    2460
attttctttt cctcctagtg ctatcattag tcacataatg accttgattt tattttagga    2520
gcttataagg catgagacaa tttccatata aatatattaa ttattgccac atactctaat    2580
atagattttg gtggataatt ttgtgggtgt gcattttgtt ctgttttgtt gggttttttg    2640 tttttttgt ttttggcagg gtcggtgggg gggttggttg gttggttggt tttgtcggaa      2700
cctaggcaaa tgaccatatt agtgaatctg ttaatagttg tagcttggga tggttattgt    2760
agttgttttg gtaaaatctt catttcctgg ttttttttac caccttattt aaatctcgat    2820
tatctgctct ctcttttata tacatacaca cacccaaaca taacatttat aatagtgtgg    2880
tagtggaatg tatccttttt taggttttccc tgctttccag ttaattttta aaatggtagc   2940
gctttgtatg catttagaat acatgactag tagtttatat ttcactggta gtttaaatct    3000
ggttggggca gtctgcagat gttttgaagta gtttagtgtt ctagaaagag ctattactgt   3060
ggatagtgcc taggggagtg ctccacgccc tctgggcata cggtagatat tatctgatga   3120
attggaaagg agcaaaccag aaatggcttt attttctccc ttggactaat ttttaagtct    3180
cgattggaat tcagtgagta ggttcataat gtgcatgaca gaaataagct ttatagtggt    3240
ttaccttcat ttagctttgg aagttttctt tgccttagtt ttggaagtaa attctagttt    3300
gtagttctca tttgtaatga acacattaac gactagatta aaatattgcc ttcaagattg    3360
ttcttactta caagacttgc tcctacttct atgctgaaaa ttgaccctgg atagaatact    3420
ataaggtttt gagttagctg gaaaagtgat cagattaata aatgtatatt ggtagttgaa    3480
tttagcaaag aaatagagat aatcatgatt ataccttat ttttacagga agagatgatg     3540
taactagagt atgtgtctac aggagtaata atggtttcca agagtatttt tttaaaggaa    3600
caaaacgagc atgaattaac tcttcaatat aagctatgaa gtaatagttg gttgtgaatt    3660
aaagtggcac cagctagcac ctctgtgttt taagggtctt tcaatgtttc tagaataagc    3720
ccttattttc aagggttcat aacaggcata aaatctcttc tcctggcaaa agctgctatg    3780
aaaagcctca gcttgggaag atagattttt ttccccccaa ttacaaaatc taagtatttt    3840
```

```
ggcccttcaa tttggaggag ggcaaaagtt ggaagtaaga agttttattt taagtacttt    3900
cagtgctcaa aaaatgcaa tcactgtgtt gtatataata gttcataggt tgatcactca     3960
taataattga ctctaaggct tttattaaga aacagcaga aagattaaat cttgaattaa     4020
gtctgggggg aaatggccac tgcagatgga gttttagagt agtaatgaaa ttctacctag    4080
aatgcaaaat tgggtatatg aattacatag catgttgttg ggattttttt taatgtgcag    4140
aagatcaaag ctacttggaa ggagtgccta taatttgcca gtagccacag attaagatta   4200
tatcttatat atcagcagat tagctttagc ttaggggag ggtgggaaag tttgggggg     4260
gggttgtgaa gatttagggg gaccttgata gagaacttta taaacttctt tctctttaat   4320
aaagacttgt cttacaccgt gctgccatta aaggcagctg ttctagagtt tcagtcacct   4380
aagtacaccc acaaaacaat atgaatatgg agatcttcct ttacccctca actttaattt   4440
gcccagttat acctcagtgt tgtagcagta ctgtgatacc tggcacagtg ctttgatctt   4500
acgatgccct ctgtactgac ctgaaggaga cctaagagtc cttccctt ttgagtttga     4560
atcatagcct tgatgtggtc tcttgtttta tgtccttgtt cctaatgtaa aagtgcttaa   4620
ctgcttcttg gttgtattgg gtagcattgg gataagattt taactgggta ttcttgaatt   4680
gcttttacaa taaaccaatt ttataatctt taaatttatc aacttttac atttgtgtta    4740
ttttcagtca gggcttctta gatctactta tggttgatgg agcacattga tttggagttt   4800
cagatcttcc aaagcactat ttgttgtaat aacttttcta aatgtagtgc ctttaaagga   4860
aaaatgaaca cagggaagtg actttgctac aaataatgtt gctgtgttaa gtattcatat   4920
taaatacatg ccttctatat ggaacatggc agaaagactg aaaaataaca gtaattaatt   4980
gtgtaattca gaattcatac caatcagtgt tgaaactcaa acattgcaaa agtgggtggc   5040
aatattcagt gcttaacact tttctagcgt tggtacatct gagaaatgag tgctcaggtg   5100
gattttatcc tcgcaagcat gttgttataa gaattgtggg tgtgcctatc ataacaattg   5160
ttttctgtat cttgaaaaag tattctccac atttaaatg ttttatatta gagaattctt   5220
taatgcacac ttgtcaaata tatatatata gtaccaatgt tacctttta ttttttgttt    5280
tagatgtaag agcatgctca tatgttaggt acttacataa attgttacat tattttttct   5340
tatgtaatac cttttgtttt gtttatgtgg ttcaaatata ttctttcctt aaactcttaa   5400
aaaaaaaa                                                           5408
```

<210> SEQ ID NO 19
<211> LENGTH: 277
<212> TYPE: PRT
<213> ORGANISM: homo sapiens

<400> SEQUENCE: 19

```
Met Glu Asn Thr Glu Asn Ser Val Asp Ser Lys Ser Ile Lys Asn Leu
1               5                   10                  15

Glu Pro Lys Ile Ile His Gly Ser Glu Ser Met Asp Ser Gly Ile Ser
            20                  25                  30

Leu Asp Asn Ser Tyr Lys Met Asp Tyr Pro Glu Met Gly Leu Cys Ile
        35                  40                  45

Ile Ile Asn Asn Lys Asn Phe His Lys Ser Thr Gly Met Thr Ser Arg
    50                  55                  60

Ser Gly Thr Asp Val Asp Ala Ala Asn Leu Arg Glu Thr Phe Arg Asn
65                  70                  75                  80

Leu Lys Tyr Glu Val Arg Asn Lys Asn Asp Leu Thr Arg Glu Glu Ile
                85                  90                  95
```

```
Val Glu Leu Met Arg Asp Val Ser Lys Glu Asp His Ser Lys Arg Ser
            100                 105                 110

Ser Phe Val Cys Val Leu Leu Ser His Gly Glu Gly Ile Ile Phe
        115                 120                 125

Gly Thr Asn Gly Pro Val Asp Leu Lys Lys Ile Thr Asn Phe Phe Arg
    130                 135                 140

Gly Asp Arg Cys Arg Ser Leu Thr Gly Lys Pro Lys Leu Phe Ile Ile
145                 150                 155                 160

Gln Ala Cys Arg Gly Thr Glu Leu Asp Cys Gly Ile Glu Thr Asp Ser
                165                 170                 175

Gly Val Asp Asp Asp Met Ala Cys His Lys Ile Pro Val Glu Ala Asp
            180                 185                 190

Phe Leu Tyr Ala Tyr Ser Thr Ala Pro Gly Tyr Tyr Ser Trp Arg Asn
        195                 200                 205

Ser Lys Asp Gly Ser Trp Phe Ile Gln Ser Leu Cys Ala Met Leu Lys
    210                 215                 220

Gln Tyr Ala Asp Lys Leu Glu Phe Met His Ile Leu Thr Arg Val Asn
225                 230                 235                 240

Arg Lys Val Ala Thr Glu Phe Glu Ser Phe Ser Phe Asp Ala Thr Phe
                245                 250                 255

His Ala Lys Lys Gln Ile Pro Cys Ile Val Ser Met Leu Thr Lys Glu
            260                 265                 270

Leu Tyr Phe Tyr His
        275
```

<210> SEQ ID NO 20
<211> LENGTH: 2689
<212> TYPE: DNA
<213> ORGANISM: homo sapiens

<400> SEQUENCE: 20

```
acatctcccg gcggcgggcc gcggaagcag tgcagacgcg gctcctagcg gatgggtgct      60
attgtgaggc ggttgtagaa gagtttcgtg agtgctcgca gctcatacct gtggctgtgt     120
atccgtggcc acagctggtt ggcgtcgcct tgaaatccca ggccgtgagg agttagcgag     180
ccctgctcac actcggcgct ctggttttcg gtgggtgtgc cctgcacctg cctcttcccc     240
cattctcatt aataaaggta tccatggaga acactgaaaa ctcagtggat tcaaaatcca     300
ttaaaaattt ggaaccaaag atcatacatg gaagcgaatc aatggactct ggaatatccc     360
tggacaacag ttataaaatg gattatcctg agatgggttt atgtataata attaataata     420
agaattttca taaaagcact ggaatgacat ctcggtctgg tacagatgtc gatgcagcaa     480
acctcaggga acattcaga aacttgaaat atgaagtcag gaataaaaat gatcttacac       540
gtgaagaaat tgtggaattg atgcgtgatg tttctaaaga agatcacagc aaaaggagca     600
gttttgtttg tgtgcttctg agccatggtg aagaaggaat aattttttgga acaaatggac     660
ctgttgacct gaaaaaaata acaaactttt tcagagggga tcgttgtaga agtctaactg     720
gaaaacccaa actttcatt attcaggcct gccgtggtac agaactggac tgtggcattg      780
agacagacag tggtgttgat gatgacatgg cgtgtcataa aataccagtg gaggccgact     840
tcttgtatgc atactccaca gcacctggtt attattcttg gcgaaattca aaggatggct     900
cctggttcat ccagtcgctt tgtgccatgc tgaaacagta tgccgacaag cttgaattta     960
tgcacattct tacccgggtt aaccgaaagg tggcaacaga atttgagtcc ttttcctttg    1020
```

-continued

| | |
|---|---|
| acgctactttt tcatgcaaag aaacagattc catgtattgt tccatgctc acaaaagaac | 1080 |
| tctatttttta tcactaaaga aatggttggt tggtggtttt ttttagtttg tatgccaagt | 1140 |
| gagaagatgg tatatttggt actgtatttc cctctcattt tgacctactc tcatgctgca | 1200 |
| gagggtactt taagacatac tccttccatc aaatagaacc actatgaagc tacctcaaac | 1260 |
| ttccagtcag gtagttgcaa ttgaattaaa ttaggaataa ataaaaatgg atactggtgc | 1320 |
| agtcattatg agaggcaatg attgttaatt tacagctttc atgattagca agttacagtg | 1380 |
| atgctgtgct atgaattttc aagtaattgt gaaaagtta acattgaag taatgaattt | 1440 |
| ttatgatatt cccccactt aagactgtgt attctagttt tgtcaaactg tagaaatgat | 1500 |
| gatgtggaag aacttaggca tctgtgggca tggtcaaagg ctcaaaccttt tatttagaa | 1560 |
| ttgatataca cggatgactt aactgcattt ttagaccatt tatctgggat tatggttttg | 1620 |
| tgatgtttgt cctgaacact tttgttgtaa aaaataata ataatgttta atattgagaa | 1680 |
| agaaactaat attttatgtg agagaaagtg tgagcaaact aacttgactt ttaaggctaa | 1740 |
| aacttaacat tcatagaggg gtggagtttt aactgtaagg tgctacaatg cccctggatc | 1800 |
| taccagcata aatatcttct gatttgtccc tatgcatatc agttgagctt catataccag | 1860 |
| caatatatct gaagagctat tatataaaaa ccccaaactg ttgattatta gccaggtaat | 1920 |
| gtgaataaat tctataggaa catatgaaaa tacaacttaa ataataaaca gtggaatata | 1980 |
| aggaaagcaa taaatgaatg ggctgagctg cctgtaactt gagagtagat ggtttgagcc | 2040 |
| tgagcagaga catgactcag cctgttccat gaaggcagag ccatggacca cgcaggaagg | 2100 |
| gcctacagcc catttctcca tacgcactgg tatgtgtgga tgatgctgcc agggcgccat | 2160 |
| cgccaagtaa gaaagtgaag caaatcagaa acttgtgaag tggaaatgtt ctaaaggtgg | 2220 |
| tgaggcaata aaaatcatag tactctttgt agcaaaattc ttaagtatgt tattttctgt | 2280 |
| tgaagtttac aatcaaagga aaatagtaat gttttatact gtttactgaa agaaaaagac | 2340 |
| ctatgagcac ataggactct agacggcatc cagccggagg ccagagctga gccctcagcc | 2400 |
| cgggaggcag gctccaggcc tcagcaggtg cggagccgtc actgcaccaa gtctcactgg | 2460 |
| ctgtcagtat gacatttcac gggagatttc ttgttgctca aaaaatgagc tcgcatttgt | 2520 |
| caatgacagt ttcttttttc ttactagacc tgtaacttttt gtaaatacac atagcatgta | 2580 |
| atggtatctt aaagtgtgtt tctatgtgac aattttgtac aaatttgtta ttttccattt | 2640 |
| ttatttcaaa atatacattc aaacttaaaa ttaaaaaaaa aaaaaaaaa | 2689 |

<210> SEQ ID NO 21
<211> LENGTH: 277
<212> TYPE: PRT
<213> ORGANISM: homo sapiens

<400> SEQUENCE: 21

```
Met Glu Asn Thr Glu Asn Ser Val Asp Ser Lys Ser Ile Lys Asn Leu
1               5                   10                  15

Glu Pro Lys Ile Ile His Gly Ser Glu Ser Met Asp Ser Gly Ile Ser
            20                  25                  30

Leu Asp Asn Ser Tyr Lys Met Asp Tyr Pro Glu Met Gly Leu Cys Ile
        35                  40                  45

Ile Ile Asn Asn Lys Asn Phe His Lys Ser Thr Gly Met Thr Ser Arg
    50                  55                  60

Ser Gly Thr Asp Val Asp Ala Ala Asn Leu Arg Glu Thr Phe Arg Asn
65                  70                  75                  80
```

```
Leu Lys Tyr Glu Val Arg Asn Lys Asn Asp Leu Thr Arg Glu Glu Ile
                85                  90                  95
Val Glu Leu Met Arg Asp Val Ser Lys Glu Asp His Ser Lys Arg Ser
            100                 105                 110
Ser Phe Val Cys Val Leu Leu Ser His Gly Glu Glu Gly Ile Ile Phe
        115                 120                 125
Gly Thr Asn Gly Pro Val Asp Leu Lys Lys Ile Thr Asn Phe Phe Arg
    130                 135                 140
Gly Asp Arg Cys Arg Ser Leu Thr Gly Lys Pro Lys Leu Phe Ile Ile
145                 150                 155                 160
Gln Ala Cys Arg Gly Thr Glu Leu Asp Cys Gly Ile Glu Thr Asp Ser
                165                 170                 175
Gly Val Asp Asp Asp Met Ala Cys His Lys Ile Pro Val Glu Ala Asp
            180                 185                 190
Phe Leu Tyr Ala Tyr Ser Thr Ala Pro Gly Tyr Tyr Ser Trp Arg Asn
        195                 200                 205
Ser Lys Asp Gly Ser Trp Phe Ile Gln Ser Leu Cys Ala Met Leu Lys
    210                 215                 220
Gln Tyr Ala Asp Lys Leu Glu Phe Met His Ile Leu Thr Arg Val Asn
225                 230                 235                 240
Arg Lys Val Ala Thr Glu Phe Glu Ser Phe Ser Phe Asp Ala Thr Phe
                245                 250                 255
His Ala Lys Lys Gln Ile Pro Cys Ile Val Ser Met Leu Thr Lys Glu
            260                 265                 270
Leu Tyr Phe Tyr His
        275

<210> SEQ ID NO 22
<211> LENGTH: 2522
<212> TYPE: DNA
<213> ORGANISM: homo sapiens

<400> SEQUENCE: 22
acatctcccg gcggcgggcc gcggaagcag tgcagacgcg gctcctagcg gatgggtgct      60
attgtgaggc ggttgtagaa gttaataaag gtatccatgg agaacactga aaactcagtg     120
gattcaaaat ccattaaaaa tttggaacca aagatcatac atggaagcga atcaatggac     180
tctggaatat ccctggacaa cagttataaa atggattatc ctgagatggg ttatgtgtata    240 ataattaata ataagaattt tcataaaagc actggaatga catctcggtc tggtacagat     300
gtcgatgcag caaacctcag ggaaacattc agaaacttga aatatgaagt caggaataaa     360
aatgatctta cacgtgaaga aattgtggaa ttgatgcgtg atgtttctaa agaagatcac     420
agcaaaagga gcagttttgt ttgtgtgctt ctgagccatg gtgaagaagg aataattttt     480
ggaacaaatg gacctgttga cctgaaaaaa ataacaaact ttttcagagg ggatcgttgt     540
agaagtctaa ctggaaaacc caaacttttc attattcagg cctgccgtgg tacagaactg     600
gactgtggca ttgagacaga cagtggtgtt gatgatgaca tggcgtgtca taaaatacca     660
gtggaggccg acttcttgta tgcatactcc acagcacctg gttattattc ttggcgaaat     720
tcaaaggatg gctcctggtt catccagtcg ctttgtgcca tgctgaaaca gtatgccgac     780
aagcttgaat ttatgcacat tcttacccgg gttaaccgaa aggtggcaac agaatttgag     840
tccttttcct tgacgctac ttttcatgca aagaaacaga ttccatgtat tgtttccatg     900
ctcacaaaag aactctattt ttatcactaa agaaatggtt ggttggtggt ttttttttagt    960
```

```
ttgtatgcca agtgagaaga tggtatattt ggtactgtat ttccctctca ttttgaccta    1020
ctctcatgct gcagagggta ctttaagaca tactccttcc atcaaataga accactatga    1080
agctacctca aacttccagt caggtagttg caattgaatt aaattaggaa taaataaaaa    1140
tggatactgg tgcagtcatt atgagaggca atgattgtta atttacagct ttcatgatta    1200
gcaagttaca gtgatgctgt gctatgaatt ttcaagtaat tgtgaaaaag ttaaacattg    1260
aagtaatgaa ttttatgat attccccca cttaagactg tgtattctag ttttgtcaaa     1320
ctgtagaaat gatgatgtgg aagaacttag gcatctgtgg gcatggtcaa aggctcaaac   1380
cttatttta gaattgatat acacggatga cttaactgca tttttagacc atttatctgg    1440
gattatggtt ttgtgatgtt tgtcctgaac acttttgttg taaaaaaata ataataatgt   1500
ttaatattga gaaagaaact aatattttat gtgagagaaa gtgtgagcaa actaacttga   1560
ctttaaggc taaaacttaa cattcataga ggggtggagt tttaactgta aggtgctaca    1620
atgcccctgg atctaccagc ataaatatct tctgatttgt ccctatgcat atcagttgag   1680
cttcatatac cagcaatata tctgaagagc tattatataa aaaccccaaa ctgttgatta   1740
ttagccaggt aatgtgaata aattctatag gaacatatga aaatacaact taaataataa   1800
acagtggaat ataaggaaag caataaatga atgggctgag ctgcctgtaa cttgagagta   1860
gatggtttga gcctgagcag agacatgact cagcctgttc catgaaggca gagccatgga   1920
ccacgcagga agggcctaca gcccattcct ccatacgcac tggtatgtgt ggatgatgct   1980
gccagggcgc catcgccaag taagaaagtg aagcaaatca gaaacttgtg aagtggaaat   2040
gttctaaagg tggtgaggca ataaaaatca tagtactctt tgtagcaaaa ttcttaagta   2100
tgttattttc tgttgaagtt tacaatcaaa ggaaaatagt aatgttttat actgtttact   2160
gaaagaaaaa gacctatgag cacataggac tctagacggc atccagccgg aggccagagc   2220
tgagccctca gcccgggagg caggctccag gcctcagcag gtgcggagcc gtcactgcac   2280
caagtctcac tggctgtcag tatgacattt cacgggagat tcttgttgc tcaaaaaatg    2340
agctcgcatt tgtcaatgac agtttctttt ttcttactag acctgtaact tttgtaaata   2400
cacatagcat gtaatggtat cttaaagtgt gtttctatgt gacaattttg tacaaatttg   2460
ttattttcca tttttatttc aaaatataca ttcaaactta aaattaaaaa aaaaaaaaa    2520
aa                                                                 2522

<210> SEQ ID NO 23
<211> LENGTH: 2435
<212> TYPE: DNA
<213> ORGANISM: homo sapiens

<400> SEQUENCE: 23
aggggtggag agaaaagagg ggagggatgg ggggagggga aacaggagcg aggtgtctcc     60
ctagctcgct gcctctggca agtggagttt ttaaaaagct ccagcagatc atgtcatgac    120
gacttcgctg ctcctgcatc cacgctggcc ggagagcctt atgtacgtct atgaggacag    180
cgcggcggag agcggcatcg gcggcggcgg cggaggagga ggcggcggca cgggcggagc    240
gggggtggc tgcagcggag cgagccccgg caaagcccg agcatggatg gtctgggcag      300
cagctgcccg gccagccact gccgcgacct gcttccgcac cccgtgctgg gccgcccgcc    360
ggctccctg ggcgccctc agggcgccgt ctatacggac atcccggccc cggaggcggc     420
gcgcagtgt gcccgccgc ccgcaccccc cacctcgtcc agcgccaccc tgggctacgg     480
ctacccctc gggggcagct actacggctg ccgcctgtcg cacaacgtga acctgcagca    540
```

```
gaagccttgc gcctaccacc cgggcgataa atacccggag ccgtcgggcg ccctgcccgg    600
tgacgacctg tcctctaggg ccaaggagtt cgccttctac cccagcttcg ccagctccta    660
ccaggcgatg cccggctacc tggacgtgtc ggtggtgccc gggatcagcg ggcacccgga    720
gccgcgtcac gacgccctca tccccgtcga aggctaccag cactgggctc tctccaatgg    780
ctgggacagt caggtgtact gctccaagga gcagtcgcag tccgcccacc tctggaagtc    840
tcccttccca gacgtggttc ccctgcagcc cgaggtgagc agctaccggc gcgggcgcaa    900
gaaacgcgtg ccctacacta aggtgcagct gaaggagcta gagaaggaat acgcggctag    960
caagttcatc accaaagaga gcgccggcg catctccgcc accacgaacc tctctgagcg   1020
ccaggtaacc atctggttcc agaaccggcg ggtcaaagag aagaaggtgg tcagcaaatc   1080
gaaagcgcct catctccact ccacctgacc acccacccgc tgcttgcccc atctatttat   1140
gtctccgctt tgtaccataa ccgaacccac ggaaagacgc tgcgcgggtg cagaagagta   1200
tttaatgtta aggaaagaga agaaccgcgc cgcccggagg cagagaggct ccatggccgt   1260
gctgctgggc catccccaac tccctatccc atccccagcc tccacccca tccagatggg   1320 actcacgtgg cttcaacagc tttggaaatg ggtcccgagt gggccgtgcg aggaaggctg   1380
tcgacctcta ctcctccttg cgctcacctt gccagaaagt ctggtggcag cgcagagccc   1440
aatcattcca accaaagcag ggttggggaa tcccgaatgg ccccaattct tgcctcatcc   1500
tatgaccagg cttttagagg accttcccta agggcgcagc ttcggagcag atctgtcca   1560 gctcatactt ccttcgctg tccctcccgc actccttagg caagatttcc cagtaaagat   1620
tttctgtgcg tattttaaaa gtcgtgttaa tactcatgat aattattagg gacctggcag   1680
cgtgattgga gtatggatgt ttccgtaaaa gctggaattc cgtaaaagca ttgacgcagc   1740
ccctacactc catcccaacc aagaaactgc atttcctggg gccaggtggg agctgccttt   1800
gccccactgc ctcccctgtt ctgctctctc agtcaacatg tggaaatcca aggaggacaa   1860
agactccagc cacgctgcta ataggggctc ctctctcctc tctctctctc taggtggtaa   1920
ggttggggat tagtccaggt acagaagcag aactttttc taaggataaa catctcttcc   1980 aagggggatgg agagtgggtc cctcaacaaa gtccctgtcc agtcacctt ccatcagggc   2040 actagcccag gaatgactcc tcacactttc acctttactg atttccagag gaaagctaga   2100
ggatctagtt caagaggcaa gaagatctgg ccctcaatta gctagatgta gatgctgcct   2160
aacagttccc tcctcaaagg ccaccttggt gctgtggggg cccttgcct cttcccttcc   2220 cactggtgca ttacaaaaca gtgttctttt gaaatgttca tcaggaatag gcttttttaa   2280
aaaatgttgt gtatctgtat atagtattgt gatgtctgaa tgacaatgta ctgaatgcaa   2340
aaaggaaaaa aacccacaaa catgtttta aataaaata tctttttttg ccttgaaaaa   2400
aaaaaaaaaa aaaaaaaaa aaaaaaaaa aaaaa                                2435
```

<210> SEQ ID NO 24
<211> LENGTH: 330
<212> TYPE: PRT
<213> ORGANISM: homo sapiens

<400> SEQUENCE: 24

```
Met Thr Thr Ser Leu Leu Leu His Pro Arg Trp Pro Glu Ser Leu Met
1               5                   10                  15

Tyr Val Tyr Glu Asp Ser Ala Ala Glu Ser Gly Ile Gly Gly Gly Gly
            20                  25                  30
```

```
Gly Gly Gly Gly Gly Thr Gly Ala Gly Gly Cys Ser Gly
            35              40              45

Ala Ser Pro Gly Lys Ala Pro Ser Met Asp Gly Leu Gly Ser Ser Cys
 50                  55                  60

Pro Ala Ser His Cys Arg Asp Leu Leu Pro His Pro Val Leu Gly Arg
 65                  70                  75                  80

Pro Pro Ala Pro Leu Gly Ala Pro Gln Gly Ala Val Tyr Thr Asp Ile
                 85                  90                  95

Pro Ala Pro Glu Ala Ala Arg Gln Cys Ala Pro Pro Ala Pro Pro
            100                 105                 110

Thr Ser Ser Ser Ala Thr Leu Gly Tyr Gly Tyr Pro Phe Gly Gly Ser
            115                 120                 125

Tyr Tyr Gly Cys Arg Leu Ser His Asn Val Asn Leu Gln Gln Lys Pro
            130                 135                 140

Cys Ala Tyr His Pro Gly Asp Lys Tyr Pro Glu Pro Ser Gly Ala Leu
145                 150                 155                 160

Pro Gly Asp Asp Leu Ser Ser Arg Ala Lys Glu Phe Ala Phe Tyr Pro
                165                 170                 175

Ser Phe Ala Ser Ser Tyr Gln Ala Met Pro Gly Tyr Leu Asp Val Ser
            180                 185                 190

Val Val Pro Gly Ile Ser Gly His Pro Glu Pro Arg His Asp Ala Leu
            195                 200                 205

Ile Pro Val Glu Gly Tyr Gln His Trp Ala Leu Ser Asn Gly Trp Asp
210                 215                 220

Ser Gln Val Tyr Cys Ser Lys Glu Gln Ser Gln Ser Ala His Leu Trp
225                 230                 235                 240

Lys Ser Pro Phe Pro Asp Val Val Pro Leu Gln Pro Glu Val Ser Ser
                245                 250                 255

Tyr Arg Arg Gly Arg Lys Lys Arg Val Pro Tyr Thr Lys Val Gln Leu
            260                 265                 270

Lys Glu Leu Glu Lys Glu Tyr Ala Ala Ser Lys Phe Ile Thr Lys Glu
            275                 280                 285

Lys Arg Arg Arg Ile Ser Ala Thr Thr Asn Leu Ser Glu Arg Gln Val
290                 295                 300

Thr Ile Trp Phe Gln Asn Arg Arg Val Lys Glu Lys Lys Val Val Ser
305                 310                 315                 320

Lys Ser Lys Ala Pro His Leu His Ser Thr
            325                 330

<210> SEQ ID NO 25
<211> LENGTH: 1657
<212> TYPE: DNA
<213> ORGANISM: homo sapiens

<400> SEQUENCE: 25
gggtgctata gacgcacaaa cgaccgcgag ccacaaatca agcacacata tcaaaaaaca      60
aatgagctct tattttgtaa actcattttg cggtcgctat ccaaatggcc cggactacca    120
gttgcataat tatggagatc atagttccgt gagcgagcaa ttcagggact cggcgagcat    180
gcactccggc aggtacggct acggctacaa tggcatggat ctcagcgtcg ccgctcggg     240 ctccggccac tttggctccg gagagcgcgc ccgcagctac gctgccagcg ccagcgcggc    300
gcccgccgag cccaggtaca gccagccggc cacgtccacg cactctcctc agcccgatcc    360
gctgccctgc tccgccgtgg cccctcgcc cggcagcgac agccaccacg gcgggaaaaa     420
```

```
ctccctaagc aactccagcg gcgcctcggc cgacgccggc agcacccaca tcagcagcag    480 agaggggggtt ggcacggcgt ccggagccga ggaggacgcc cctgccagca gcgagcaggc   540
gagtgcgcag agcgagccga gcccggcgcc gcccgcccaa ccccagatct accctggat    600 gcgcaagctg cacataagtc atgacaacat aggcggcccg gaaggcaaaa gggcccggac   660
ggcctacacg cgctaccaga ccctggagct ggagaaggag ttccacttca accgttacct   720
gacccgcaga aggaggattg aaatagcaca tgctcttttgc ctctccgaga gacaaattaa  780
aatctggttc caaaaccgga gaatgaagtg gaaaaaagat aataagctga aaagcatgag   840
catggccgcg gcaggagggg ccttccgtcc ctgagtatct gagcgtttaa agtactgagc   900
agtattagcg gatcccgcgt agtgtcagta ctaaggtgac tttctgaaac tcccttgtgt   960
tccttctgtg aagaagccct gttctcgttg ccctaattca tctttttaatc atgagcctgt  1020 ttattgccat tatagcgcct gtataagtag atctgctttc tgttcatctc tttgtcctga   1080
atggctttgt cttgaaaaaa aatagatgtt ttaacttatt tatatgaagc aagctgtgtt   1140
acttgaagta actataacaa aaaaagaaaa gagaaaaaaa aacacacaaa aagtcccct    1200 tcaatctcgt ttagtgccaa tgttgtgtgt tgcactcaag ttgtttaact gtgcatgtgc   1260
gtggaagtgt tcctgtctca atagctccaa gctgttaaaa atatttttat tcaaactacc   1320
tatattcctt gtgtaattaa tgctgttgta gaggtgactt gatgagacac aacttgttcg   1380
acgtgtagtg actagtgact ctgtgatgaa aactgtgact ccaagcggtg tgtccctgcg   1440
tgcctttata ggaccctttg cacgaactct ggaagtggct cttataagcg cagcttcagt   1500
gatgtatgtt tttgtgaaca agttacaaa tattgtccaa gtctggctgt tttaagcaaa    1560
ctgtgatcag ctttttttt tttttttttt ttttgtatt tgttttttaag gaaaaaatac    1620 tgactggaac aaaaaataaa ctttctattg taagttc                            1657
```

<210> SEQ ID NO 26  
<211> LENGTH: 270  
<212> TYPE: PRT  
<213> ORGANISM: homo sapiens

<400> SEQUENCE: 26

```
Met Ser Ser Tyr Phe Val Asn Ser Phe Cys Gly Arg Tyr Pro Asn Gly
1               5                  10                  15

Pro Asp Tyr Gln Leu His Asn Tyr Gly Asp His Ser Ser Val Ser Glu
            20                  25                  30

Gln Phe Arg Asp Ser Ala Ser Met His Ser Gly Arg Tyr Gly Tyr Gly
        35                  40                  45

Tyr Asn Gly Met Asp Leu Ser Val Gly Arg Ser Gly Ser Gly His Phe
    50                  55                  60

Gly Ser Gly Glu Arg Ala Arg Ser Tyr Ala Ser Ala Ser Ala Ala
65                  70                  75                  80

Pro Ala Glu Pro Arg Tyr Ser Gln Pro Ala Thr Ser Thr His Ser Pro
                85                  90                  95

Gln Pro Asp Pro Leu Pro Cys Ser Ala Val Ala Pro Ser Pro Gly Ser
            100                 105                 110

Asp Ser His His Gly Gly Lys Asn Ser Leu Ser Asn Ser Ser Gly Ala
        115                 120                 125

Ser Ala Asp Ala Gly Ser Thr His Ile Ser Ser Arg Glu Gly Val Gly
    130                 135                 140

Thr Ala Ser Gly Ala Glu Glu Asp Ala Pro Ala Ser Ser Glu Gln Ala
145                 150                 155                 160
```

```
Ser Ala Gln Ser Glu Pro Ser Pro Ala Pro Ala Gln Pro Gln Ile
            165                 170                 175

Tyr Pro Trp Met Arg Lys Leu His Ile Ser His Asp Asn Ile Gly Gly
            180                 185                 190

Pro Glu Gly Lys Arg Ala Arg Thr Ala Tyr Thr Arg Tyr Gln Thr Leu
            195                 200                 205

Glu Leu Glu Lys Glu Phe His Phe Asn Arg Tyr Leu Thr Arg Arg Arg
            210                 215                 220

Arg Ile Glu Ile Ala His Ala Leu Cys Leu Ser Glu Arg Gln Ile Lys
225                 230                 235                 240

Ile Trp Phe Gln Asn Arg Arg Met Lys Trp Lys Lys Asp Asn Lys Leu
            245                 250                 255

Lys Ser Met Ser Met Ala Ala Ala Gly Gly Ala Phe Arg Pro
            260                 265                 270

<210> SEQ ID NO 27
<211> LENGTH: 11941
<212> TYPE: DNA
<213> ORGANISM: homo sapiens

<400> SEQUENCE: 27
```

| | | | | | |
|---|---|---|---|---|---|
| cacgcgcgcc | cggctggggg | atctcctccg | cgtgcccgaa | aggggatat | gccatttgga | 60 |
| catgtaattg | tcagcacggg | atctgagact | tccaaaaaat | gaagccggcg | acaggacttt | 120 |
| gggtctgggt | gagccttctc | gtggcggcgg | ggaccgtcca | gcccagcgat | tctcagtcag | 180 |
| tgtgtgcagg | aacggagaat | aaactgagct | ctctctctga | cctggaacag | cagtaccgag | 240 |
| ccttgcgcaa | gtactatgaa | actgtgagg | ttgtcatggg | caacctggag | ataaccagca | 300 |
| ttgagcacaa | ccgggacctc | tccttcctgc | ggtctgttcg | agaagtcaca | ggctacgtgt | 360 |
| tagtggctct | taatcagttt | cgttacctgc | ctctggagaa | tttacgcatt | attcgtggga | 420 |
| caaaacttta | tgaggatcga | tatgccttgg | caatattttt | aaactacaga | aaagatggaa | 480 |
| actttggact | tcaagaactt | ggattaaaga | acttgacaga | aatcctaaat | ggtggagtct | 540 |
| atgtagacca | gaacaaattc | ctttgttatg | cagacaccat | tcattggcaa | gatattgttc | 600 |
| ggaacccatg | gcttccaac | ttgactcttg | tgtcaacaaa | tggtagttca | ggatgtggac | 660 |
| gttgccataa | gtcctgtact | ggccgttgct | ggggacccac | agaaaatcat | tgccagactt | 720 |
| tgacaaggac | ggtgtgtgca | gaacaatgtg | acggcagatg | ctacggacct | tacgtcagtg | 780 |
| actgctgcca | tcgagaatgt | gctggaggct | gctcaggacc | taaggacaca | gactgctttg | 840 |
| cctgcatgaa | tttcaatgac | agtggagcat | gtgttactca | gtgtccccaa | acctttgtct | 900 |
| acaatccaac | cacctttcaa | ctggagcaca | atttcaatgc | aaagtacaca | tatgagcat | 960 |
| tctgtgtcaa | gaaatgtcca | cataactttg | tggtagattc | cagttcttgt | gtgcgtgcct | 1020 |
| gccctagttc | caagatggaa | gtagaagaaa | atgggattaa | aatgtgtaaa | ccttgcactg | 1080 |
| acatttgccc | aaaagcttgt | gatggcattg | gcacaggatc | attgatgtca | gctcagactg | 1140 |
| tggattccag | taacattgac | aaattcataa | actgtaccaa | gatcaatggg | aatttgatct | 1200 |
| ttctagtcac | tggtattcat | ggggacccett | acaatgcaat | tgaagccata | gacccagaga | 1260 |
| aactgaacgt | ctttcggaca | gtcagagaga | taacaggttt | cctgaacata | cagtcatggc | 1320 |
| caccaaacat | gactgacttc | agtgtttttt | ctaacctggt | gaccattggt | ggaagagtac | 1380 |
| tctatagtgg | cctgtccttg | cttatcctca | agcaacaggg | catcacctct | ctacagttcc | 1440 |
| agtccctgaa | ggaaatcagc | gcaggaaaca | tctatattac | tgacaacagc | aacctgtgtt | 1500 |

-continued

```
attatcatac cattaactgg acaacactct tcagcacaat caaccagaga atagtaatcc    1560
gggacaacag aaaagctgaa aattgtactg ctgaaggaat ggtgtgcaac catctgtgtt    1620
ccagtgatgg ctgttgggga cctgggccag accaatgtct gtcgtgtcgc cgcttcagta    1680
gaggaaggat ctgcatagag tcttgtaacc tctatgatgg tgaatttcgg gagtttgaga    1740
atggctccat ctgtgtggag tgtgaccccc agtgtgagaa gatggaagat ggcctcctca    1800
catgccatgg accgggtcct gacaactgta caaagtgctc tcattttaaa gatggcccaa    1860
actgtgtgga aaaatgtcca gatggcttac aggggggcaaa cagtttcatt ttcaagtatg    1920
ctgatccaga tcgggagtgc cacccatgcc atccaaactg cacccaaggg tgtaacggtc    1980
ccactagtca tgactgcatt tactacccat ggacgggcca ttccactttta ccacaacatg    2040
ctagaactcc cctgattgca gctggagtaa ttggtgggct cttcattctg gtcattgtgg    2100
gtctgacatt tgctgtttat gttagaagga gagcatcaa aaagaaaaga gccttgagaa    2160
gattcttgga acagagttg gtggaaccat taactcccag tggcacagca cccaatcaag    2220
ctcaacttcg tattttgaaa gaaactgagc tgaagagggt aaaagtcctt ggctcaggtg    2280
cttttggaac ggtttataaa ggtatttggg tacctgaagg agaaactgtg aagattcctg    2340
tggctattaa gattcttaat gagacaactg gtcccaaggc aaatgtggag ttcatggatg    2400
aagctctgat catggcaagt atggatcatc cacacctagt ccggttgctg ggtgtgtgtc    2460
tgagcccaac catccagctg gttactcaac ttatgcccca tggctgcctg ttggagtatg    2520
tccacgagca caaggataac attggatcac aactgctgct taactggtgt gtccagatag    2580
ctaagggaat gatgtacctg gaagaaagac gactcgttca tcgggatttg gcagcccgta    2640
atgtcttagt gaaatctcca aaccatgtga aaatcacaga ttttgggcta gccagactct    2700
tggaaggaga tgaaaaagag tacaatgctg atggaggaaa gatgccaatt aaatggatgg    2760
ctctggagtg tatacattac aggaaaattca cccatcagag tgacgtttgg agctatggag    2820
ttactatatg ggaactgatg acctttggag gaaaacccta tgatggaatt ccaacgcgag    2880
aaatccctga tttattagag aaaggagaac gtttgcctca gcctcccatc tgcactattg    2940
acgtttacat ggtcatggtc aaatgttgga tgattgatgc tgacagtaga cctaaattta    3000
aggaactggc tgctgagttt tcaaggatgg ctcgagaccc tcaaagatac ctagttattc    3060
agggtgatga tcgtatgaag cttcccagtc caaatgacag caagttcttt cagaatctct    3120
tgatgaaga ggatttggaa gatatgatgg atgctgagga gtacttggtc cctcaggctt    3180
tcaacatccc acctcccatc tatacttcca gagcaagaat tgactcgaat aggagtgaaa    3240
ttggacacag ccctcctcct gcctacaccc ccatgtcagg aaaccagttt gtataccgag    3300
atggaggttt tgctgctgaa caaggagtgt ctgtgcccta cagagcccca actagcacaa    3360
ttccagaagc tcctgtggca cagggtgcta ctgctgagat ttttgatgac tcctgctgta    3420
atggcaccct acgcaagcca gtggcacccc atgtccaaga ggacagtagc cccagaggt    3480
acagtgctga ccccaccgtg tttgccccag aacggagccc acgaggagag ctggatgagg    3540
aaggttacat gactcctatg cgagacaaac ccaaacaaga atacctgaat ccagtggagg    3600
agaacccttt tgtttctcgg agaaaaaatg gagaccttca agcattggat aatcccgaat    3660
atcacaatgc atccaatggt ccacccaagg ccgaggatga gtatgtgaat gagccactgt    3720
acctcaacac ctttgccaac accttgggaa aagctgagta cctgaagaac aacatactgt    3780
caatgccaga gaaggccaag aaagcgtttg acaaccctga ctactggaac cacagcctgc    3840
```

```
cacctcggag cacccttcag cacccagact acctgcagga gtacagcaca aaatattttt    3900
ataaacagaa tgggcggatc cggcctattg tggcagagaa tcctgaatac ctctctgagt    3960
tctccctgaa gccaggcact gtgctgccgc ctccaccttea cagacaccgg aatactgtgg   4020
tgtaagctca gttgtggttt tttaggtgga gagacacacc tgctccaatt tccccacccc   4080
cctctctttc tctggtggtc ttccttctac cccaaggcca gtagttttga cacttcccag   4140
tggaagatac agagatgcaa tgatagttat gtgcttacct aacttgaaca ttagagggaa    4200
agactgaaag agaaagatag gaggaaccac aatgtttctt catttctctg catgggttgg    4260
tcaggagaat gaaacagcta gagaaggacc agaaaatgta aggcaatgct gcctactatc    4320
aaactagctg tcactttttt tcttttttctt tttctttctt tgtttctttc ttcctcttct   4380
ttttttttt ttttttttaaa gcagatggtt gaaacaccca tgctatctgt tcctatctgc    4440
aggaactgat gtgtgcatat ttagcatccc tggaaatcat aataaagttt ccattagaac    4500
aaaagaataa cattttctat aacatatgat ggtgtctgaa attgagaatc cagtttcttt    4560
ccccagcagt ttctgtccta gcaagtaaga atggccaact caactttcat aatttaaaaa    4620
tctccattaa agttataact agtaattatg ttttcaacac tttttggttt ttttcatttt    4680
gttttgctct gaccgattcc tttatatttg ctcccctatt tttggcttta atttctaatt    4740
gcaaagatgt ttacatcaaa gcttcttcac agaatttaag caagaaatat tttaatatag    4800
tgaaatggcc actactttaa gtatacaatc tttaaaataa gaaagggagg ctaatatttt    4860
tcatgctatc aaattatctt caccctcatc ctttacattt ttcaacattt tttttctcc    4920
ataaatgaca ctacttgata ggccgttggt tgtctgaaga gtagaaggga aactaagaga    4980
cagttctctg tggttcagga aaactactga tactttcagg ggtggcccaa tgagggaatc    5040
cattgaactg gaagaaacac actggattgg gtatgtctac ctggcagata ctcagaaatg    5100
tagtttgcac ttaagctgta attttatttg ttctttttct gaactccatt ttggattttg    5160
aatcaagcaa tatggaagca accagcaaat taactaattt aagtacattt ttaaaaaaag    5220
agctaagata aagactgtgg aaatgccaaa ccaagcaaat taggaacctt gcaacggtat    5280
ccagggacta tgatgagagg ccagcacatt atcttcatat gtcacctttg ctacgcaagg    5340
aaatttgttc agttcgtata cttcgtaaga aggaatgcga gtaaggattg gcttgaattc    5400
catggaattt ctagtatgag actatttata tgaagtagaa ggtaactctt tgcacataaa    5460
ttggtataat aaaaagaaaa acacaaacat tcaaagctta gggataggtc cttgggtcaa    5520
aagttgtaaa taaatgtgaa acatcttctc atgcaattat tttattatcc aacacactaa    5580
tcttttgata ctttatataa ttcccttttct tcatatactg catccagtac tagaaccatc    5640
attattatgt atcattttga agaataccct gatgagatga aggatgagaa caaatgacag    5700
agatgagtct ccaagtaaag ggggcctcac atcaataatt aggaaactta gatataagtc    5760
gcccttttct gaaaattcta ccccaagtca tttagatttt taaaaaatat ttctaatgtt    5820
aaaatattgg gaccaaatta gaatcaatag tataagatta attaattaga gtaaaaatat    5880
ctattaaggc agagaaagtt tagagaaaaa aatccaaaga aatttgtgtt tcttcctatt    5940
ctgaacaagt aaatccatcc atccatccat ccaaacctcc tttatctaac tgtgtctact    6000
aaaagcacca tgttttgtgg ggaacactca gataaatgga atatcatcct caacttcaaa    6060
attctatgat ctaggagatt taattaaaat gacatttaa ttttctatg cgttccaaca     6120
atcagattgc atagtctctt ttgtgaatag ctgtcatata atcagttgta ctgtaagata    6180
tctccttaa actcatttgg gatataagtt aaacatcctt caaattgttg atgttgacaa     6240
```

```
acaggataat ttcaataata ttattcaaac ataaactggt ctaggagaat attgcatcac    6300
tgactaatta gcctatctag agtctaactt caccattaaa ccaaaagcag atggtggtcc    6360
ttggccaaga atattggaga cattggagtt ggttttttc taagctataa gaagtgaggc     6420
gagctgaaaa agtatggtag agcaggagaa gggtttgtga gattccttct agtgaagttc    6480
accctcaaac ttttcagggg taaagacaca gagtgattca ggggccacaa tctaatagct    6540
cagggctctc ctatccattc agagaagtct ctaggaaaag ggatctcata tcagtactta    6600
tgaaaaattg aatataagcc tcccttcta aataaatctg catcgagtca tcacagccct     6660 cttttggat actataccttt gattttttt ttctgattta caatatgcat atggttcta      6720 ctgggctata gaaagcagaa tcactcattt tggagaagga aaaatgaat agttaaaaca     6780 aacttttaac tgttaaggta acagaaatgt atttagtgaa tgtctctttc ctcctaagaa    6840
cacaagactt ctacatgttg ggtaataccct agagatgcat gtaggaataa tccaaaatga   6900
cccaaatgct ttataatagc accactttat aattctttg aatgattctc gtagtatata    6960
attgacttca gttgtttgag tgtttttgt tttattttg tccccctgg gaaaacatat       7020 ttcagcatgt ataagaggga gaaaaaagt ttcattcctt ccagagaata acttatttag    7080
tccagtaggg tagaattta aaatgtcagt taaagtcttc aaagtgcttg ggggatatc    7140 agattccaga ggccaattgt agcaattgaa atttgcagaa tcaattatgt aaatctgaga    7200
caaattagta ttaaaattac acggagtata ttttaaat cacccaactt tgtagattat      7260
acctattttg ggcaggtatg gaaaaatttt gcagttaaat gattgcctaa agaaagtggt    7320
aaacaggtga ggaaagatgg cctctgatct aggatagatc cagaaccaca aagcatctgc    7380
accacaaaag gtgttagact accaagcagc tcctggtttt ctgcatagta ttagtagcac    7440
agcttaggat gagaatcctt tctccagtaa cattcttaaa atagcatgaa aaacaacgca    7500
aaactcaaat ttctattaaa acacacaaac taaaatcaag tgattctttt ttgtagatta    7560
gggagaagga ctgaatatct aatttaagag aaggaatagt gtttaagtgt tatagtgtgt    7620
gagctaatac cttctaaagg aaagacatgg catgaagatt gtgcatactt acaatgctaa    7680
ggaaaaatca agaaaaggac tgtgtgaggc tctgctacta gatgaagttg gaaggactat    7740
taatgtgctt cttgaagtat caaaaatgaa aagaaaatta aaattgttta agcctgacag    7800
ggaaggatgt aaatacaagt ttttctagag ctctctaacc tttatttcaa aactggaatt    7860
attcatccat ctgtaattgt tgataattta actagtatat gtagttcata aggtaataga    7920
aaaggtgatc atgaaagcat gtatataact ggacagaacc acgataatgc tataagatgt    7980
agatttagtt aggttatcag atgttaaatg atttaatat tattaaataa atcaaactag    8040
aaaactaacc acaagtataa tgtaacaaag ttaaatgcag gatataaaaa tgtaggatgg    8100
attttgcata gtaaaagat aagtttgcca tttaaaattg ttgtttgttg ggtttagctg     8160
aaagtaggca tatatggttc cacttgggaa aacttgcttt aaagcattac aatgaacaat    8220 ttttctcat tctcttattc ctttatcact ttttaaatgt aaagaaaatt gtattattt      8280 attttttaa ataaacacca ccttgcagaa tttaataggc aaacatgtta catatgacta     8340
agtaagggtc ttcaagatga agtaaagaaa atgtaaatgt tctattacct tatgcagaga    8400
caaaaaaaaa aaggagtggt gtcatttagc tagcaaacaa acaaaataca gttaattggt    8460
gatatgtcct ttcttttctc actatgccct cttgcctcca aaaatgacaa caaagaatca    8520 caattttct gataaataaa tgctaaacca agcgtttcaa actattgcat tgccattctt     8580
```

```
ttggacttta gttattagaa tgatgattgt tatagggcaa atgagaaatc catgtgcatc    8640
agcttctagt tgttaaaaaa accagataaa ttaacttcta ctgtatactg tgggcagagg    8700
atcctagagc tgatcctaca acatcagctt ctagttgtta aaaaaaaaaa aagaaacaga    8760
taaattaact tctactgtat atactgtggg cagaggatct tactgtgcct ctgtttgtgt    8820
acatggactt cggtgtgtat cagtttgaag gacagccttg ccccatgtaa acatataaat    8880
gcagattggt atcgcctggt tgctatttgc ttaagaacaa atattataca gatgagatca    8940
ggcataattt taaaagatca ttatcagtgg agacctcatt attactgata ttacaatggg    9000
gccagttttt atacttctgg gtagaattaa taaaattttt ctgatcccag agatctgagt    9060
tctctctgca gttggaaaca agaagctgtt gtgggcattg tgtcgggcca ggggcccttg    9120
tgtttgtgtg ggcaaatatc ttttagcagt gtgagctgct tttttctttt cattaaaagt    9180
ctctctaaaa taatagaaat ttcagatact cggttcaagt ctcactgatt ttgtagaggt    9240
ccaaaaatgt aggatctgtc acttttgcag gcccctgcct cacctaattc ctggccaggt    9300
gacattttgg gcagaagtaa atgcttctat agtcacaagc taaaatgact ctaagcccca    9360
atttcacggg gggtattcac atgcttcctc tggaaaatac tctttgacag tcagctttgc    9420
aagtaagtga ttaccttgtt aggaatcaaa gaaaatgta tttctctctg acctttagag    9480
gaaaatagaa tccttccctt ttttgcccat tgacacaact ggcactgctc tcttcccttt    9540
ctaccaccct ggttcaaagt agtccccga tgctgtcctg ttccttcctt aagccatagt    9600
ggatctctga gatcctacac cccactttgt gaaacactga cttcatcttt gccctcgaat    9660
gcctgatttt ttcataagag attctagcaa tttggacact gtttaagtga actatcaaac    9720
taccgcatag agaatattta agctattaaa attatggttt cccatgaaga tcaattctct    9780
gtgtccttcc ctataggaat ttgagacgag ttagccctgt gatgaatctt gaaactcaca    9840
tatgtccaca tacacttggt agaacttcga tttaatcttt acataaaagc tgtacatata    9900
accaagaagt tattttttgcc agtaaattaa cttatttgct ttattcatct tatttggttc    9960
ctaatcgtaa atattttgta gctgctgtaa attttttttct cccaaatgag gagtcttatt   10020
atcataaagg taaaggctat tcagcttttga taaccacctg caattctttt ttggatcatt   10080
catccatcta acaaatacat aatgaggaca gttcatgtta atgaaaatcc atgttgttta   10140
atagaatgcc atcctttacc tacttttgct ctttatggac gttttttcttt tcatgctcta   10200 gtgagctttc cctatatcat gagaagtggt tatatttgtg caaatataca aatataggaa   10260
aacaaagatt catacctgta ggcaatagtc taacttgtcc aaaccacttt gcctttactg   10320 ctattttat ccccaatgcg tagatatttc ccccaggcct atagcctttg tgaaggaaag     10380
caaatcatac ctcctgtata ttgacacgaa tctggttttc aaatgtcatt tccagatttt   10440
ttagttaatt gggggttgtc cttttccctt aatgtgagag tcattttcct gtatatttct   10500
ggatctctca ggggctggga gggggagtg aggggactac aaccatagca ctccaagaac    10560 cctttttggga ttactccagt aatcaactac gaaagttatt ttctaaatgt agatatgtaa   10620
ggtgttcttt taaagtaagg tactttgaaa tatgtagcat aaactggtac tgctgttaaa   10680
tgggtcgatt attaaacgga gcagctgtgt gagggcagct aactttgaat gcctgtctcc   10740
ctggctggtg tgtctccttc tcatgttgag agcaccaggg attgcgtggc tgcatgctga   10800
aaccgcattt tcccatggtg tatgactagt tcatctcttt cttgagcacc attacaagaa   10860
gatcaaatga aaatgagatc aatgtggaag acaattcata gcacaaaaaa agtcatctta   10920
aatctactct caaacattca tcttatacat gcatcaaagt aatttactga catcagtttg   10980
```

```
ggtgagagag ggagtcactt tactgaaaag gcagaggctt aaggtgtata catttgtact   11040
cacttcctta ttttcttaac ttgtaagcag aaaacaagcc ctctctcttg tgaagtatct   11100
tcaaaggatt ggggtgcaaa aataccttgc tggtaagcca tcaatgtttt atttaaatcc   11160
ctgcattcaa agttagctgc cttttgaaa taaacaaaca aaaatacta ctgtatgttt     11220 gaaaatgtga atagtatttt tatagcttgt taaagacatg gctagttgca tttgtaaata   11280
agtataatgt tgctttgatt ttcttttgtg gacatcttta tttggaacat aattgtcttt   11340
agggttgatt tgtatataag taattggcct gtgattgttt cttttttggt tggaagttat   11400
cattttgaca ttacttgtga ttctgtgttc agcactattg tgatgtgttc aacctctgca   11460
ctcgcttaca caataggata tgccaattgt gtgtggtgta atgttatttt gattttttc   11520 catgttattg atgaaggatc atgcacctaa cacatactaa ctttttaat gttaggcata    11580 tttttagtat actttctctt attctttctt ctcctccaac cttttaccca tcctccttcc   11640
tttccctcat tcctgttgtt atttgagaat gagggagaaa cagtatttta catttatgta   11700
attaggcttt tccgttagtt ctcaaggatc ctcttttggc tcttgggaaa gaattgtacc   11760
tgtacaaggc aattatagaa tgcgaactgc tttgcctcat tccatactga tcatcccagc   11820
tgaacaattt gaaaactgtt ctgccttttt gttacatgaa tctgtcagaa atatatttt    11880 aatttaatat aaatgaaatt caataaaata tgaaacaaac gttaaaaaaa aaaaaaaaa    11940 a                                                                   11941
```

<210> SEQ ID NO 28
<211> LENGTH: 1308
<212> TYPE: PRT
<213> ORGANISM: homo sapiens

<400> SEQUENCE: 28

Met Lys Pro Ala Thr Gly Leu Trp Val Trp Val Ser Leu Leu Val Ala
1               5                   10                  15

Ala Gly Thr Val Gln Pro Ser Asp Ser Gln Ser Val Cys Ala Gly Thr
                20                  25                  30

Glu Asn Lys Leu Ser Ser Leu Ser Asp Leu Glu Gln Gln Tyr Arg Ala
            35                  40                  45

Leu Arg Lys Tyr Tyr Glu Asn Cys Glu Val Val Met Gly Asn Leu Glu
        50                  55                  60

Ile Thr Ser Ile Glu His Asn Arg Asp Leu Ser Phe Leu Arg Ser Val
65                  70                  75                  80

Arg Glu Val Thr Gly Tyr Val Leu Val Ala Leu Asn Gln Phe Arg Tyr
                85                  90                  95

Leu Pro Leu Glu Asn Leu Arg Ile Ile Arg Gly Thr Lys Leu Tyr Glu
                100                 105                 110

Asp Arg Tyr Ala Leu Ala Ile Phe Leu Asn Tyr Arg Lys Asp Gly Asn
            115                 120                 125

Phe Gly Leu Gln Glu Leu Gly Leu Lys Asn Leu Thr Glu Ile Leu Asn
        130                 135                 140

Gly Gly Val Tyr Val Asp Gln Asn Lys Phe Leu Cys Tyr Ala Asp Thr
145                 150                 155                 160

Ile His Trp Gln Asp Ile Val Arg Asn Pro Trp Pro Ser Asn Leu Thr
                165                 170                 175

Leu Val Ser Thr Asn Gly Ser Ser Gly Cys Gly Arg Cys His Lys Ser
                180                 185                 190

```
Cys Thr Gly Arg Cys Trp Gly Pro Thr Glu Asn His Cys Gln Thr Leu
        195                 200                 205
Thr Arg Thr Val Cys Ala Glu Gln Cys Asp Gly Arg Cys Tyr Gly Pro
    210                 215                 220
Tyr Val Ser Asp Cys Cys His Arg Glu Cys Ala Gly Gly Cys Ser Gly
225                 230                 235                 240
Pro Lys Asp Thr Asp Cys Phe Ala Cys Met Asn Phe Asn Asp Ser Gly
            245                 250                 255
Ala Cys Val Thr Gln Cys Pro Gln Thr Phe Val Tyr Asn Pro Thr Thr
            260                 265                 270
Phe Gln Leu Glu His Asn Phe Asn Ala Lys Tyr Thr Tyr Gly Ala Phe
        275                 280                 285
Cys Val Lys Lys Cys Pro His Asn Phe Val Val Asp Ser Ser Ser Cys
    290                 295                 300
Val Arg Ala Cys Pro Ser Ser Lys Met Glu Val Glu Glu Asn Gly Ile
305                 310                 315                 320
Lys Met Cys Lys Pro Cys Thr Asp Ile Cys Pro Lys Ala Cys Asp Gly
            325                 330                 335
Ile Gly Thr Gly Ser Leu Met Ser Ala Gln Thr Val Asp Ser Ser Asn
            340                 345                 350
Ile Asp Lys Phe Ile Asn Cys Thr Lys Ile Asn Gly Asn Leu Ile Phe
        355                 360                 365
Leu Val Thr Gly Ile His Gly Asp Pro Tyr Asn Ala Ile Glu Ala Ile
    370                 375                 380
Asp Pro Glu Lys Leu Asn Val Phe Arg Thr Val Arg Glu Ile Thr Gly
385                 390                 395                 400
Phe Leu Asn Ile Gln Ser Trp Pro Pro Asn Met Thr Asp Phe Ser Val
            405                 410                 415
Phe Ser Asn Leu Val Thr Ile Gly Gly Arg Val Leu Tyr Ser Gly Leu
            420                 425                 430
Ser Leu Leu Ile Leu Lys Gln Gln Gly Ile Thr Ser Leu Gln Phe Gln
        435                 440                 445
Ser Leu Lys Glu Ile Ser Ala Gly Asn Ile Tyr Ile Thr Asp Asn Ser
    450                 455                 460
Asn Leu Cys Tyr Tyr His Thr Ile Asn Trp Thr Thr Leu Phe Ser Thr
465                 470                 475                 480
Ile Asn Gln Arg Ile Val Ile Arg Asp Asn Arg Lys Ala Glu Asn Cys
            485                 490                 495
Thr Ala Glu Gly Met Val Cys Asn His Leu Cys Ser Ser Asp Gly Cys
            500                 505                 510
Trp Gly Pro Gly Pro Asp Gln Cys Leu Ser Cys Arg Arg Phe Ser Arg
        515                 520                 525
Gly Arg Ile Cys Ile Glu Ser Cys Asn Leu Tyr Asp Gly Glu Phe Arg
    530                 535                 540
Glu Phe Glu Asn Gly Ser Ile Cys Val Glu Cys Asp Pro Gln Cys Glu
545                 550                 555                 560
Lys Met Glu Asp Gly Leu Leu Thr Cys His Gly Pro Gly Pro Asp Asn
            565                 570                 575
Cys Thr Lys Cys Ser His Phe Lys Asp Gly Pro Asn Cys Val Glu Lys
            580                 585                 590
Cys Pro Asp Gly Leu Gln Gly Ala Asn Ser Phe Ile Phe Lys Tyr Ala
        595                 600                 605
```

```
Asp Pro Asp Arg Glu Cys His Pro Cys His Pro Asn Cys Thr Gln Gly
            610                 615                 620
Cys Asn Gly Pro Thr Ser His Asp Cys Ile Tyr Tyr Pro Trp Thr Gly
625                 630                 635                 640
His Ser Thr Leu Pro Gln His Ala Arg Thr Pro Leu Ile Ala Ala Gly
                645                 650                 655
Val Ile Gly Gly Leu Phe Ile Leu Val Ile Gly Leu Thr Phe Ala
            660                 665                 670
Val Tyr Val Arg Arg Lys Ser Ile Lys Lys Arg Ala Leu Arg Arg
        675                 680                 685
Phe Leu Glu Thr Glu Leu Val Glu Pro Leu Thr Pro Ser Gly Thr Ala
690                 695                 700
Pro Asn Gln Ala Gln Leu Arg Ile Leu Lys Glu Thr Glu Leu Lys Arg
705                 710                 715                 720
Val Lys Val Leu Gly Ser Gly Ala Phe Gly Thr Val Tyr Lys Gly Ile
                725                 730                 735
Trp Val Pro Glu Gly Glu Thr Val Lys Ile Pro Val Ala Ile Lys Ile
            740                 745                 750
Leu Asn Glu Thr Thr Gly Pro Lys Ala Asn Val Glu Phe Met Asp Glu
            755                 760                 765
Ala Leu Ile Met Ala Ser Met Asp His Pro His Leu Val Arg Leu Leu
770                 775                 780
Gly Val Cys Leu Ser Pro Thr Ile Gln Leu Val Thr Gln Leu Met Pro
785                 790                 795                 800
His Gly Cys Leu Leu Glu Tyr Val His Glu His Lys Asp Asn Ile Gly
                805                 810                 815
Ser Gln Leu Leu Leu Asn Trp Cys Val Gln Ile Ala Lys Gly Met Met
            820                 825                 830
Tyr Leu Glu Glu Arg Arg Leu Val His Arg Asp Leu Ala Ala Arg Asn
        835                 840                 845
Val Leu Val Lys Ser Pro Asn His Val Lys Ile Thr Asp Phe Gly Leu
850                 855                 860
Ala Arg Leu Leu Glu Gly Asp Glu Lys Glu Tyr Asn Ala Asp Gly Gly
865                 870                 875                 880
Lys Met Pro Ile Lys Trp Met Ala Leu Glu Cys Ile His Tyr Arg Lys
                885                 890                 895
Phe Thr His Gln Ser Asp Val Trp Ser Tyr Gly Val Thr Ile Trp Glu
            900                 905                 910
Leu Met Thr Phe Gly Gly Lys Pro Tyr Asp Gly Ile Pro Thr Arg Glu
        915                 920                 925
Ile Pro Asp Leu Leu Glu Lys Gly Glu Arg Leu Pro Gln Pro Pro Ile
        930                 935                 940
Cys Thr Ile Asp Val Tyr Met Val Met Val Lys Cys Trp Met Ile Asp
945                 950                 955                 960
Ala Asp Ser Arg Pro Lys Phe Lys Glu Leu Ala Ala Glu Phe Ser Arg
                965                 970                 975
Met Ala Arg Asp Pro Gln Arg Tyr Leu Val Ile Gln Gly Asp Asp Arg
            980                 985                 990
Met Lys Leu Pro Ser Pro Asn Asp Ser Lys Phe Phe Gln Asn Leu Leu
        995                 1000                1005
Asp Glu Glu Asp Leu Glu Asp Met Met Asp Ala Glu Glu Tyr Leu
    1010                1015                1020
```

Val Pro Gln Ala Phe Asn Ile Pro Pro Ile Tyr Thr Ser Arg
1025            1030            1035

Ala Arg Ile Asp Ser Asn Arg Ser Glu Ile Gly His Ser Pro Pro
1040            1045            1050

Pro Ala Tyr Thr Pro Met Ser Gly Asn Gln Phe Val Tyr Arg Asp
1055            1060            1065

Gly Gly Phe Ala Ala Glu Gln Gly Val Ser Val Pro Tyr Arg Ala
1070            1075            1080

Pro Thr Ser Thr Ile Pro Glu Ala Pro Val Ala Gln Gly Ala Thr
1085            1090            1095

Ala Glu Ile Phe Asp Asp Ser Cys Cys Asn Gly Thr Leu Arg Lys
1100            1105            1110

Pro Val Ala Pro His Val Gln Glu Asp Ser Ser Thr Gln Arg Tyr
1115            1120            1125

Ser Ala Asp Pro Thr Val Phe Ala Pro Glu Arg Ser Pro Arg Gly
1130            1135            1140

Glu Leu Asp Glu Glu Gly Tyr Met Thr Pro Met Arg Asp Lys Pro
1145            1150            1155

Lys Gln Glu Tyr Leu Asn Pro Val Glu Glu Asn Pro Phe Val Ser
1160            1165            1170

Arg Arg Lys Asn Gly Asp Leu Gln Ala Leu Asp Asn Pro Glu Tyr
1175            1180            1185

His Asn Ala Ser Asn Gly Pro Pro Lys Ala Glu Asp Glu Tyr Val
1190            1195            1200

Asn Glu Pro Leu Tyr Leu Asn Thr Phe Ala Asn Thr Leu Gly Lys
1205            1210            1215

Ala Glu Tyr Leu Lys Asn Asn Ile Leu Ser Met Pro Glu Lys Ala
1220            1225            1230

Lys Lys Ala Phe Asp Asn Pro Asp Tyr Trp Asn His Ser Leu Pro
1235            1240            1245

Pro Arg Ser Thr Leu Gln His Pro Asp Tyr Leu Gln Glu Tyr Ser
1250            1255            1260

Thr Lys Tyr Phe Tyr Lys Gln Asn Gly Arg Ile Arg Pro Ile Val
1265            1270            1275

Ala Glu Asn Pro Glu Tyr Leu Ser Glu Phe Ser Leu Lys Pro Gly
1280            1285            1290

Thr Val Leu Pro Pro Pro Tyr Arg His Arg Asn Thr Val Val
1295            1300            1305

<210> SEQ ID NO 29
<211> LENGTH: 11893
<212> TYPE: DNA
<213> ORGANISM: homo sapiens

<400> SEQUENCE: 29
cacgcgcgcc cggctggggg atctcctccg cgtgcccgaa aggggatat gccatttgga      60 catgtaattg tcagcacggg atctgagact tccaaaaaat gaagccggcg acaggacttt     120
gggtctgggt gagccttctc gtggcggcgg ggaccgtcca gcccagcgat tctcagtcag     180
tgtgtgcagg aacggagaat aaactgagct ctctctctga cctggaacag cagtaccgag     240
ccttgcgcaa gtactatgaa aactgtgagg ttgtcatggg caacctggag ataaccagca     300
ttgagcacaa ccgggacctc tccttcctgc ggtctgttcg agaagtcaca ggctacgtgt     360
tagtggctct taatcagttt cgttacctgc ctctggagaa tttacgcatt attcgtggga     420

```
caaaacttta tgaggatcga tatgccttgg caatattttt aaactacaga aaagatggaa    480
actttggact tcaagaactt ggattaaaga acttgacaga aatcctaaat ggtggagtct    540
atgtagacca gaacaaattc ctttgttatg cagacaccat tcattggcaa gatattgttc    600
ggaacccatg gccttccaac ttgactcttg tgtcaacaaa tggtagttca ggatgtggac    660
gttgccataa gtcctgtact ggccgttgct ggggacccac agaaaatcat tgccagactt    720
tgacaaggac ggtgtgtgca gaacaatgtg acggcagatg ctacggacct tacgtcagtg    780
actgctgcca tcgagaatgt gctggaggct gctcaggacc taaggacaca gactgctttg    840
cctgcatgaa tttcaatgac agtggagcat gtgttactca gtgtcccccaa acctttgtct    900
acaatccaac cacctttcaa ctggagcaca atttcaatgc aaagtacaca tatggagcat    960
tctgtgtcaa gaaatgtcca cataactttg tggtagattc cagttcttgt gtgcgtgcct   1020
gccctagttc caagatggaa gtagaagaaa atgggattaa aatgtgtaaa ccttgcactg   1080
acatttgccc aaaagcttgt gatggcattg cacaggatc attgatgtca gctcagactg    1140
tggattccag taacattgac aaattcataa actgtaccaa gatcaatggg aatttgatct   1200
ttctagtcac tggtattcat ggggacccctt acaatgcaat tgaagccata gacccagaga   1260
aactgaacgt ctttcggaca gtcagagaga taacaggttt cctgaacata cagtcatggc   1320
caccaaacat gactgacttc agtgtttttt ctaacctggt gaccattggt ggaagagtac   1380
tctatagtgg cctgtccttg cttatcctca agcaacaggg catcacctct ctacagttcc   1440
agtccctgaa ggaaatcagc gcaggaaaca tctatattac tgacaacagc aacctgtgtt   1500
attatcatac cattaactgg acaacactct tcagcacaat caaccagaga atagtaatcc   1560
gggacaacag aaaagctgaa aattgtactg ctgaaggaat ggtgtgcaac catctgtgtt   1620
ccagtgatgc ctgttgggga cctgggccag accaatgtct gtcgtgtcgc cgcttcagta   1680
gaggaaggat ctgcatagag tcttgtaacc tctatgatgg tgaatttcgg gagtttgaga   1740
atggctccat ctgtgtggag tgtgacccc agtgtgagaa gatggaagat ggcctcctca   1800
catgccatgg accgggtcct gacaactgta caaagtgctc tcatttaaa gatggcccaa   1860
actgtgtgga aaaatgtcca gatggcttac aggggggcaaa cagtttcatt ttcaagtatg   1920
ctgatccaga tcgggagtgc acccatgcc atccaaactg cacccaaggg tgtaacggtc   1980
ccactagtca tgactgcatt tactaccat ggacgggcca ttccacttta ccacaacatg   2040
ctagaactcc cctgattgca gctggagtaa ttggtgggct cttcattctg gtcattgtgg   2100
gtctgacatt tgctgtttat gttagaagga gagcatcaa aaagaaaaga gccttgagaa   2160
gattcttgga aacagagttg gtggaaccat taactcccag tggcacagca cccaatcaag   2220
ctcaacttcg tattttgaaa gaaactgagc tgaagagggt aaaagtcctt ggctcaggtg   2280
cttttggaac ggtttataaa ggtatttggg tacctgaagg agaaactgtg aagattcctg   2340
tggctattaa gattcttaat gagacaactg gtcccaaggc aaatgtggag ttcatggatg   2400
aagctctgat catggcaagt atggatcatc cacacctagt ccggttgctg ggtgtgtgtc   2460
tgagcccaac catccagctg gttactcaac ttatgcccca tggctgcctg ttggagtatg   2520
tccacgagca aggataac attggatcac aactgctgct taactggtgt gtccagatag   2580
ctaagggaat gatgtacctg gaagaaagac gactcgttca tcgggatttg gcagcccgta   2640
atgtcttagt gaaatctcca aaccatgtga aaatcacaga ttttgggcta gccagactct   2700
tggaaggaga tgaaaagag tacaatgctg atggaggaaa gatgccaatt aaatggatgg   2760
ctctggagtg tatacattac aggaaattca cccatcagag tgacgtttgg agctatggag   2820
```

```
ttactatatg ggaactgatg accttgggag gaaaaccct atgatggaatt ccaacgcgag    2880 aaatccctga tttattagag aaaggagaac gtttgcctca gcctcccatc tgcactattg    2940
acgtttacat ggtcatggtc aaatgttgga tgattgatgc tgacagtaga cctaaattta   3000
aggaactggc tgctgagttt tcaaggatgg ctcgagaccc tcaaagatac ctagttattc   3060
agggtgatga tcgtatgaag cttcccagtc caaatgacag caagttcttt cagaatctct   3120
tggatgaaga ggatttggaa gatatgatgg atgctgagga gtacttggtc cctcaggctt   3180
tcaacatccc acctcccatc tatacttcca gagcaagaat tgactcgaat aggaaccagt   3240
ttgtataccg agatggaggt tttgctgctg aacaaggagt gtctgtgccc tacagagccc   3300
caactagcac aattccagaa gctcctgtgg cacagggtgc tactgctgag atttttgatg   3360
actcctgctg taatggcacc ctacgcaagc cagtggcacc ccatgtccaa gaggacagta   3420
gcacccagag gtacagtgct gaccccaccg tgtttgcccc agaacggagc ccacgaggag   3480
agctggatga ggaaggttac atgactccta tgcgagacaa acccaaacaa gaatacctga   3540
atccagtgga ggagaaccct tttgtttctc ggagaaaaaa tggagacctt caagcattgg   3600
ataatcccga atatcacaat gcatccaatg gtccacccaa ggccgaggat gagtatgtga   3660
atgagccact gtacctcaac acctttgcca acaccttggg aaaagctgag tacctgaaga   3720
acaacatact gtcaatgcca gagaaggcca agaaagcgtt tgacaaccct gactactgga   3780
accacagcct gccacctcgg agcacccttc agcacccaga ctacctgcag gagtacagca   3840
caaaatattt ttataaacag aatgggcgga tccggcctat tgtggcagag aatcctgaat   3900
acctctctga gttctccctg aagccaggca ctgtgctgcc gcctccacct acagacacc    3960 ggaatactgt ggtgtaagct cagttgtggt tttttaggtg gagagacaca cctgctccaa   4020
tttccccacc cccctctctt tctctggtgg tcttccttct accccaaggc cagtagtttt   4080
gacacttccc agtggaagat acagagatgc aatgatagtt atgtgcttac ctaacttgaa   4140
cattagaggg aaagactgaa agagaaagat aggaggaacc acaatgtttc ttcatttctc   4200
tgcatgggtt ggtcaggaga atgaaacagc tagagaagga ccagaaaatg taaggcaatg   4260
ctgcctacta tcaaactagc tgtcactttt tttcttttc ttttcttc tttgtttctt     4320 tcttcctctt cttttttttt tttttttta aagcagatgg ttgaaacacc catgctatct   4380
gttcctatct gcaggaactg atgtgtgcat atttagcatc cctggaaatc ataataaagt   4440
ttccattaga acaaaagaat aacatttct ataacatatg atggtgtctg aaattgagaa    4500
tccagtttct ttccccagca gtttctgtcc tagcaagtaa gaatggccaa ctcaactttc   4560
ataatttaaa aatctccatt aaagttataa ctagtaatta tgttttcaac acttttggt    4620 ttttttcatt ttgttttgct ctgaccgatt cctttatatt tgctccccta tttttggctt   4680
taatttctaa ttgcaaagat gtttacatca aagcttcttc acagaattta agcaagaaat   4740
attttaatat agtgaaatgg ccactacttt aagtatacaa tctttaaaat aagaaaggga   4800
ggctaatatt tttcatgcta tcaaattatc ttcaccctca tcctttacat ttttcaacat   4860 tttttttttct ccataaatga cactacttga taggccgttg gttgtctgaa gagtagaagg   4920
gaaactaaga gacagttctc tgtggttcag gaaaactact gatactttca ggggtggccc    4980
aatgagggaa tccattgaac tggaagaaac acactggatt gggtatgtct acctggcaga    5040
tactcagaaa tgtagtttgc acttaagctg taatttttatt tgttcttttt ctgaactcca    5100
ttttggattt tgaatcaagc aatatggaag caaccagcaa attaactaat ttaagtacat    5160
```

```
tttaaaaaa agagctaaga taaagactgt ggaaatgcca aaccaagcaa attaggaacc    5220
ttgcaacggt atccagggac tatgatgaga ggccagcaca ttatcttcat atgtcacctt    5280
tgctacgcaa ggaaatttgt tcagttcgta tacttcgtaa gaaggaatgc gagtaaggat    5340
tggcttgaat tccatggaat ttctagtatg agactattta tatgaagtag aaggtaactc    5400
tttgcacata aattggtata ataaaaagaa aaacacaaac attcaaagct tagggatagg    5460
tccttgggtc aaaagttgta aataaatgtg aaacatcttc tcatgcaatt attttattat    5520
ccaacacact aatcttttga tactttatat aattcccttt cttcatatac tgcatccagt    5580
actagaacca tcattattat gtatcatttt gaaagaatac ctgatgagat gaaggatgag    5640
aacaaatgac agagatgagt ctccaagtaa agggggcctc acatcaataa ttaggaaact    5700
tagatataag tcgccctttt ctgaaaattc taccccaagt catttagatt tttaaaaaat    5760
atttctaatg ttaaaatatt gggaccaaat tagaatcaat agtataagat taattaatta    5820
gagtaaaaat atctattaag gcagagaaag tttagagaaa aaaatccaaa gaaatttgtg    5880
tttcttccta ttctgaacaa gtaaatccat ccatccatcc atccaaacct cctttatcta    5940
actgtgtcta ctaaaagcac catgttttgt ggggaacact cagataaatg gaatatcatc    6000
ctcaacttca aaattctatg atctaggaga tttaattaaa atgacatttt aatttttcta    6060
tgcgttccaa caatcagatt gcatagtctc ttttgtgaat agctgtcata taatcagttg    6120
tactgtaaga tatctccttt aaactcattt gggatataag ttaaacatcc ttcaaattgt    6180
tgatgttgac aaacaggata atttcaataa tattattcaa acataaactg gtctaggaga    6240
atattgcatc actgactaat tagcctatct agagtctaac ttcaccatta aaccaaaagc    6300
agatggtggt ccttggccaa gaatattgga gacattggag ttggtttttt tctaagctat    6360
aagaagtgag gcgagctgaa aaagtatggt agagcaggag aagggtttgt gagattcctt    6420
ctagtgaagt tcaccctcaa acttttcagg ggtaaagaca cagagtgatt caggggccac    6480
aatctaatag ctcagggctc tcctatccat tcagagaagt ctctaggaaa agggatctca    6540
tatcagtact tatgaaaaat tgaatataag cctcccttc taaataaatc tgcatcgagt    6600
catcacagcc ctctttttgg atactatacc ttgatttttt ttttctgatt tacaatatgc    6660
atatggtttc tactgggcta tagaaagcag aatcactcat tttggagaag gaaaaaatga    6720
atagttaaaa caaacttta actgttaagg taacagaaat gtatttagtg aatgtctctt    6780
tcctcctaag aacacaagac ttctacatgt tgggtaatac ctagagatgc atgtaggaat    6840
aatccaaaat gacccaaatg ctttataata gcaccacttt ataattcttt tgaatgattt    6900
ctgtagtata taattgactt cagttgtttg agtgttttt gttttatttt tgtccccct    6960 gggaaaacat atttcagcat gtataagagg gagaaaaaa gtttcattcc ttccagagaa    7020
taacttattt agtccagtag ggtagaattt taaaatgtca gttaaagtct tcaaagtgct    7080 tgggggggata tcagattcca gaggccaatt gtagcaattg aaatttgcag aatcaattat    7140
gtaaatctga gacaaattag tattaaaatt acacggagta tatttttaa atcacccaac    7200 tttgtagatt atacctattt tgggcaggta tggaaaaatt ttgcagttaa atgattgcct    7260
aaagaaagtg gtaaacaggt gaggaaagat ggcctctgat ctaggataga tccagaacca    7320
caaagcatct gcaccacaaa aggtgttaga ctaccaagca gctcctggtt ttctgcatag    7380
tattagtagc acagcttagg atgagaatcc tttctccagt aacattctta aaatagcatg    7440 aaaacaacg caaaactcaa atttctatta aaacacacaa actaaaatca agtgattctt    7500
ttttgtagat tagggagaag gactgaatat ctaatttaag agaaggaata gtgtttaagt    7560
```

```
gttatagtgt gtgagctaat accttctaaa ggaaagacat ggcatgaaga ttgtgcatac    7620
ttacaatgct aaggaaaaat caagaaaagg actgtgtgag gctctgctac tagatgaagt    7680
tggaaggact attaatgtgc ttcttgaagt atcaaaaatg aaaagaaaat taaaattgtt    7740
taagcctgac agggaaggat gtaaatacaa gttttttctag agctctctaa cctttatttc    7800
aaaactggaa ttattcatcc atctgtaatt gttgataatt taactagtat atgtagttca    7860
taaggtaata gaaaaggtga tcatgaaagc atgtatataa ctggacagaa ccacgataat    7920
gctataagat gtagatttag ttaggttatc agatgttaaa tgattttaat attattaaat    7980
aaatcaaact agaaaactaa ccacaagtat aatgtaacaa agttaaatgc aggatataaa    8040
aatgtaggat ggattttgca tagtaaaaag ataagtttgc catttaaaat tgttgtttgt    8100
tgggtttagc tgaaagtagg catatatggt tccacttggg aaaacttgct ttaaagcatt    8160
acaatgaaca attttttctc attctcttat tcctttatca cttttttaaat gtaaagaaaa    8220 ttgtatttat ttatttttttt aaataaacac caccttgcag aatttaatag gcaaacatgt    8280
tacatatgac taagtaaggg tcttcaagat gaagtaaaga aaatgtaaat gttctattac    8340
cttatgcaga gacaaaaaaa aaaggagtg gtgtcattta gctagcaaac aaacaaaata    8400
cagttaattg gtgatatgtc cttttctttc tcactatgcc ctcttgcctc caaaaatgac    8460
aacaaagaat cacaatttt ctgataaata aatgctaaac caagcgtttc aaactattgc    8520
attgccattc ttttggactt tagttattag aatgatgatt gttatagggc aaatgagaaa    8580
tccatgtgca tcagcttcta gttgttaaaa aaaccagata aattaacttc tactgtatac    8640
tgtgggcaga ggatcctaga gctgatccta caacatcagc ttctagttgt taaaaaaaaa    8700
aaaagaaaca gataaattaa cttctactgt atatactgtg ggcagaggat cttactgtgc    8760
ctctgtttgt gtacatggac ttcggtgtgt atcagtttga aggacagcct tgccccatgt    8820
aaacatataa atgcagattg gtatcgcctg gttgctattt gcttaagaac aaatattata    8880
cagatgagat caggcataat tttaaaagat cattatcagt ggagacctca ttattactga    8940
tattacaatg gggccagttt ttatacttct gggtagaatt aataaaattt ttctgatccc    9000
agagatctga gttctctctg cagttggaaa caagaagctg ttgtgggcat tgtgtcgggc    9060
caggggccct tgtgtttgtg tgggcaaata tcttttagca gtgtgagctg cttttttctt    9120
ttcattaaaa gtctctctaa aataatagaa atttcagata ctcggttcaa gtctcactga    9180
ttttgtagag gtccaaaaat gtaggatctg tcacttttgc aggcccctgc ctcacctaat    9240
tcctggccag gtgacatttt gggcagaagt aaatgcttct atagtcacaa gctaaaatga    9300
ctctaagccc caatttcacg gggggtattc acatgcttcc tctggaaaat actctttgac    9360
agtcagcttt gcaagtaagt gattaccttg ttaggaatca agaaaaatg tatttctctc    9420 tgacctttag aggaaaatag aatccttccc ttttttgccc attgacacaa ctggcactgc    9480
tctcttccct ttctaccacc ctggttcaaa gtagtccccc gatgctgtcc tgttcctttc    9540
ttaagccata gtggatctct gagatcctac accccacttt gtgaaacact gacttcatct    9600
ttgccctcga atgcctgatt ttttcataag agattctagc aatttggaca ctgtttaagt    9660
gaactatcaa actaccgcat agagaatatt taagctatta aaattatggt ttcccatgaa    9720
gatcaattct ctgtgtcctt ccctatagga atttgagacg agttagccct gtgatgaatc    9780
ttgaaactca catatgtcca catacacttg gtagaacttc gatttaatct ttacataaaa    9840
gctgtacata taaccaagaa gttatttttg ccagtaaatt aacttatttg ctttattcat    9900
```

-continued

```
cttatttggt tcctaatcgt aaatattttg tagctgctgt aaatttttt ctcccaaatg    9960 aggagtctta ttatcataaa ggtaaaggct attcagcttt gataaccacc tgcaattctt   10020
ttttggatca ttcatccatc taacaaatac ataatgagga cagttcatgt taatgaaaat   10080
ccatgttgtt aatagaatg ccatccttta cctactttg ctctttatgg acgtttttct    10140
tttcatgctc tagtgagctt tccctatatc atgagaagtg gttatatttg tgcaaatata   10200
caaatatagg aaaacaaaga ttcatacctg taggcaatag tctaacttgt ccaaaccact   10260
ttgcctttac tgctatttt atccccaatg cgtagatatt tccccaggc ctatagcctt     10320 tgtgaaggaa agcaaatcat acctcctgta tattgacacg aatctggttt tcaaatgtca   10380
tttccagatt ttttagttaa ttgggggttg tccttttccc ttaatgtgag agtcattttc   10440
ctgtatattt ctggatctct caggggctgg gagggggag tgaggggact acaaccatag    10500
cactccaaga acccttttgg gattactcca gtaatcaact acgaaagtta ttttctaaat   10560
gtagatatgt aaggtgttct tttaaagtaa ggtactttga aatatgtagc ataaactggt   10620
actgctgtta aatgggtcga ttattaaacg gagcagctgt gtgagggcag ctaactttga   10680
atgcctgtct ccctggctgg tgtgtctcct tctcatgttg agagcaccag ggattgcgtg   10740
gctgcatgct gaaaccgcat tttcccatgg tgtatgacta gttcatctct ttcttgagca   10800
ccattacaag aagatcaaat gaaaatgaga tcaatgtgga agacaattca tagcacaaaa   10860
aaagtcatct taaatctact ctcaaacatt catcttatac atgcatcaaa gtaatttact   10920
gacatcagtt tgggtgagag agggagtcac tttactgaaa aggcagaggc ttaaggtgta   10980
tacatttgta ctcacttcct tatttcttta acttgtaagc agaaaacaag ccctctctct   11040
tgtgaagtat cttcaaagga ttggggtgca aaaataccttt gctggtaagc catcaatgtt   11100
ttatttaaat ccctgcattc aaagttagct gccttttga aataaacaaa caaaaaatac    11160
tactgtatgt ttgaaaatgt gaatagtatt tttatagctt gttaaagaca tggctagttg   11220
catttgtaaa taagtataat gttgctttga ttttcttttg tggacatctt tatttggaac   11280
ataattgtct ttagggttga tttgtatata agtaattggc ctgtgattgt ttcttttttg   11340
gttggaagtt atcattttga cattacttgt gattctgtgt tcagcactat tgtgatgtgt   11400
tcaacctctg cactcgctta cacaatagga tatgccaatt gtgtgtggtg taatgttatt   11460 ttgattttt tccatgttat tgatgaagga tcatgcacct aacacatact aacttttta    11520 atgttaggca tatttttagt atactttctc ttattctttc ttctcctcca accttttacc   11580
catcctcctt cctttccctc attcctgttg ttatttgaga atgagggaga aacagtattt   11640
tacatttatg taattaggct tttccgttag ttctcaagga tcctcttttg gctcttggga   11700
aagaattgta cctgtacaag gcaattatag aatgcgaact gctttgcctc attccatact   11760
gatcatccca gctgaacaat ttgaaaactg ttctgccttt ttgttacatg aatctgtcag   11820
aaatatattt ttaatttaat ataaatgaaa ttcaataaaa tatgaaacaa acgttaaaaa   11880
aaaaaaaaaa aaa                                                      11893

<210> SEQ ID NO 30
<211> LENGTH: 1292
<212> TYPE: PRT
<213> ORGANISM: homo sapiens

<400> SEQUENCE: 30

Met Lys Pro Ala Thr Gly Leu Trp Val Trp Val Ser Leu Leu Val Ala
1               5                   10                  15
```

```
Ala Gly Thr Val Gln Pro Ser Asp Ser Gln Ser Val Cys Ala Gly Thr
                20                  25                  30

Glu Asn Lys Leu Ser Ser Leu Ser Asp Leu Glu Gln Gln Tyr Arg Ala
            35                  40                  45

Leu Arg Lys Tyr Tyr Glu Asn Cys Glu Val Val Met Gly Asn Leu Glu
        50                  55                  60

Ile Thr Ser Ile Glu His Asn Arg Asp Leu Ser Phe Leu Arg Ser Val
65                  70                  75                  80

Arg Glu Val Thr Gly Tyr Val Leu Val Ala Leu Asn Gln Phe Arg Tyr
                85                  90                  95

Leu Pro Leu Glu Asn Leu Arg Ile Ile Arg Gly Thr Lys Leu Tyr Glu
            100                 105                 110

Asp Arg Tyr Ala Leu Ala Ile Phe Leu Asn Tyr Arg Lys Asp Gly Asn
        115                 120                 125

Phe Gly Leu Gln Glu Leu Gly Leu Lys Asn Leu Thr Glu Ile Leu Asn
130                 135                 140

Gly Gly Val Tyr Val Asp Gln Asn Lys Phe Leu Cys Tyr Ala Asp Thr
145                 150                 155                 160

Ile His Trp Gln Asp Ile Val Arg Asn Pro Trp Pro Ser Asn Leu Thr
                165                 170                 175

Leu Val Ser Thr Asn Gly Ser Ser Gly Cys Gly Arg Cys His Lys Ser
            180                 185                 190

Cys Thr Gly Arg Cys Trp Gly Pro Thr Glu Asn His Cys Gln Thr Leu
        195                 200                 205

Thr Arg Thr Val Cys Ala Glu Gln Cys Asp Gly Arg Cys Tyr Gly Pro
210                 215                 220

Tyr Val Ser Asp Cys His Arg Glu Cys Ala Gly Gly Cys Ser Gly
225                 230                 235                 240

Pro Lys Asp Thr Asp Cys Phe Ala Cys Met Asn Phe Asn Asp Ser Gly
                245                 250                 255

Ala Cys Val Thr Gln Cys Pro Gln Thr Phe Val Tyr Asn Pro Thr Thr
            260                 265                 270

Phe Gln Leu Glu His Asn Phe Asn Ala Lys Tyr Thr Tyr Gly Ala Phe
        275                 280                 285

Cys Val Lys Lys Cys Pro His Asn Phe Val Val Asp Ser Ser Ser Cys
290                 295                 300

Val Arg Ala Cys Pro Ser Ser Lys Met Glu Val Glu Glu Asn Gly Ile
305                 310                 315                 320

Lys Met Cys Lys Pro Cys Thr Asp Ile Cys Pro Lys Ala Cys Asp Gly
                325                 330                 335

Ile Gly Thr Gly Ser Leu Met Ser Ala Gln Thr Val Asp Ser Ser Asn
            340                 345                 350

Ile Asp Lys Phe Ile Asn Cys Thr Lys Ile Asn Gly Asn Leu Ile Phe
        355                 360                 365

Leu Val Thr Gly Ile His Gly Asp Pro Tyr Asn Ala Ile Glu Ala Ile
370                 375                 380

Asp Pro Glu Lys Leu Asn Val Phe Arg Thr Val Arg Glu Ile Thr Gly
385                 390                 395                 400

Phe Leu Asn Ile Gln Ser Trp Pro Pro Asn Met Thr Asp Phe Ser Val
                405                 410                 415

Phe Ser Asn Leu Val Thr Ile Gly Gly Arg Val Leu Tyr Ser Gly Leu
            420                 425                 430
```

```
Ser Leu Leu Ile Leu Lys Gln Gln Gly Ile Thr Ser Leu Gln Phe Gln
        435                 440                 445

Ser Leu Lys Glu Ile Ser Ala Gly Asn Ile Tyr Ile Thr Asp Asn Ser
450                 455                 460

Asn Leu Cys Tyr Tyr His Thr Ile Asn Trp Thr Thr Leu Phe Ser Thr
465                 470                 475                 480

Ile Asn Gln Arg Ile Val Ile Arg Asp Asn Arg Lys Ala Glu Asn Cys
                485                 490                 495

Thr Ala Glu Gly Met Val Cys Asn His Leu Cys Ser Ser Asp Gly Cys
            500                 505                 510

Trp Gly Pro Gly Pro Asp Gln Cys Leu Ser Cys Arg Arg Phe Ser Arg
        515                 520                 525

Gly Arg Ile Cys Ile Glu Ser Cys Asn Leu Tyr Asp Gly Glu Phe Arg
    530                 535                 540

Glu Phe Glu Asn Gly Ser Ile Cys Val Glu Cys Asp Pro Gln Cys Glu
545                 550                 555                 560

Lys Met Glu Asp Gly Leu Leu Thr Cys His Gly Pro Gly Pro Asp Asn
                565                 570                 575

Cys Thr Lys Cys Ser His Phe Lys Asp Gly Pro Asn Cys Val Glu Lys
            580                 585                 590

Cys Pro Asp Gly Leu Gln Gly Ala Asn Ser Phe Ile Phe Lys Tyr Ala
        595                 600                 605

Asp Pro Asp Arg Glu Cys His Pro Cys His Pro Asn Cys Thr Gln Gly
    610                 615                 620

Cys Asn Gly Pro Thr Ser His Asp Cys Ile Tyr Tyr Pro Trp Thr Gly
625                 630                 635                 640

His Ser Thr Leu Pro Gln His Ala Arg Thr Pro Leu Ile Ala Ala Gly
                645                 650                 655

Val Ile Gly Gly Leu Phe Ile Leu Val Ile Val Gly Leu Thr Phe Ala
            660                 665                 670

Val Tyr Val Arg Arg Lys Ser Ile Lys Lys Arg Ala Leu Arg Arg
        675                 680                 685

Phe Leu Glu Thr Glu Leu Val Glu Pro Leu Thr Pro Ser Gly Thr Ala
        690                 695                 700

Pro Asn Gln Ala Gln Leu Arg Ile Leu Lys Glu Thr Glu Leu Lys Arg
705                 710                 715                 720

Val Lys Val Leu Gly Ser Gly Ala Phe Gly Thr Val Tyr Lys Gly Ile
                725                 730                 735

Trp Val Pro Glu Gly Glu Thr Val Lys Ile Pro Val Ala Ile Lys Ile
            740                 745                 750

Leu Asn Glu Thr Thr Gly Pro Lys Ala Asn Val Glu Phe Met Asp Glu
        755                 760                 765

Ala Leu Ile Met Ala Ser Met Asp His Pro His Leu Val Arg Leu Leu
    770                 775                 780

Gly Val Cys Leu Ser Pro Thr Ile Gln Leu Val Thr Gln Leu Met Pro
785                 790                 795                 800

His Gly Cys Leu Leu Glu Tyr Val His Glu His Lys Asp Asn Ile Gly
                805                 810                 815

Ser Gln Leu Leu Leu Asn Trp Cys Val Gln Ile Ala Lys Gly Met Met
            820                 825                 830

Tyr Leu Glu Glu Arg Arg Leu Val His Arg Asp Leu Ala Ala Arg Asn
        835                 840                 845
```

```
Val Leu Val Lys Ser Pro Asn His Val Lys Ile Thr Asp Phe Gly Leu
850                 855                 860

Ala Arg Leu Leu Glu Gly Asp Glu Lys Glu Tyr Asn Ala Asp Gly Gly
865                 870                 875                 880

Lys Met Pro Ile Lys Trp Met Ala Leu Glu Cys Ile His Tyr Arg Lys
                885                 890                 895

Phe Thr His Gln Ser Asp Val Trp Ser Tyr Gly Val Thr Ile Trp Glu
                900                 905                 910

Leu Met Thr Phe Gly Gly Lys Pro Tyr Asp Gly Ile Pro Thr Arg Glu
                915                 920                 925

Ile Pro Asp Leu Leu Glu Lys Gly Glu Arg Leu Pro Gln Pro Pro Ile
930                 935                 940

Cys Thr Ile Asp Val Tyr Met Val Met Val Lys Cys Trp Met Ile Asp
945                 950                 955                 960

Ala Asp Ser Arg Pro Lys Phe Lys Glu Leu Ala Ala Glu Phe Ser Arg
                965                 970                 975

Met Ala Arg Asp Pro Gln Arg Tyr Leu Val Ile Gln Gly Asp Asp Arg
                980                 985                 990

Met Lys Leu Pro Ser Pro Asn Asp Ser Lys Phe Phe Gln Asn Leu Leu
                995                 1000                1005

Asp Glu Glu Asp Leu Glu Asp Met Met Asp Ala Glu Glu Tyr Leu
     1010                1015                1020

Val Pro Gln Ala Phe Asn Ile Pro Pro Pro Ile Tyr Thr Ser Arg
     1025                1030                1035

Ala Arg Ile Asp Ser Asn Arg Asn Gln Phe Val Tyr Arg Asp Gly
     1040                1045                1050

Gly Phe Ala Ala Glu Gln Gly Val Ser Val Pro Tyr Arg Ala Pro
     1055                1060                1065

Thr Ser Thr Ile Pro Glu Ala Pro Val Ala Gln Gly Ala Thr Ala
     1070                1075                1080

Glu Ile Phe Asp Asp Ser Cys Cys Asn Gly Thr Leu Arg Lys Pro
     1085                1090                1095

Val Ala Pro His Val Gln Glu Asp Ser Ser Thr Gln Arg Tyr Ser
     1100                1105                1110

Ala Asp Pro Thr Val Phe Ala Pro Glu Arg Ser Pro Arg Gly Glu
     1115                1120                1125

Leu Asp Glu Glu Gly Tyr Met Thr Pro Met Arg Asp Lys Pro Lys
     1130                1135                1140

Gln Glu Tyr Leu Asn Pro Val Glu Glu Asn Pro Phe Val Ser Arg
     1145                1150                1155

Arg Lys Asn Gly Asp Leu Gln Ala Leu Asp Asn Pro Glu Tyr His
     1160                1165                1170

Asn Ala Ser Asn Gly Pro Pro Lys Ala Glu Asp Glu Tyr Val Asn
     1175                1180                1185

Glu Pro Leu Tyr Leu Asn Thr Phe Ala Asn Thr Leu Gly Lys Ala
     1190                1195                1200

Glu Tyr Leu Lys Asn Asn Ile Leu Ser Met Pro Glu Lys Ala Lys
     1205                1210                1215

Lys Ala Phe Asp Asn Pro Asp Tyr Trp Asn His Ser Leu Pro Pro
     1220                1225                1230

Arg Ser Thr Leu Gln His Pro Asp Tyr Leu Gln Glu Tyr Ser Thr
     1235                1240                1245
```

Lys Tyr Phe Tyr Lys Gln Asn Gly Arg Ile Arg Pro Ile Val Ala
1250                1255                1260

Glu Asn Pro Glu Tyr Leu Ser Glu Phe Ser Leu Lys Pro Gly Thr
1265                1270                1275

Val Leu Pro Pro Pro Pro Tyr Arg His Arg Asn Thr Val Val
1280                1285                1290

<210> SEQ ID NO 31
<211> LENGTH: 2973
<212> TYPE: DNA
<213> ORGANISM: homo sapiens

<400> SEQUENCE: 31

| | | |
|---|---|---|
| gggccgctct ctgacatcag agctgctgta gagcggagag gggcaggggt gaagggccac | 60 | |
| ggtggtgcaa cccaccactt cctccaagga ggagctgaga ggaacaggaa gtgtcaggac | 120 | |
| tttacgaccc gcgcctccag ctgaggtttc tagacgtgac ccagggcaga ctggtagcaa | 180 | |
| agccccacg cccagccagg agcaccgccg aggactccag cacaccgagg acatgctgg | 240 | |
| gcctgcgccc cccactgctc gccctggtgg ggctgctctc cctcgggtgc gtcctctctc | 300 | |
| aggagtgcac gaagttcaag gtcagcagct gccgggaatg catcgagtcg gggcccggct | 360 | |
| gcacctggtg ccagaagctg aacttcacag ggccggggga tcctgactcc attcgctgcg | 420 | |
| acaccccggc cacagctgctc atgaggggct gtgcggctga cgacatcatg gaccccacaa | 480 | |
| gcctcgctga aacccaggaa gaccacaatg ggggccagaa gcagctgtcc cacaaaaag | 540 | |
| tgacgcttta cctgcgacca ggccaggcag cagcgttcaa cgtgaccttc cggcgggcca | 600 | |
| agggctaccc catcgacctg tactatctga tggacctctc ctactccatg cttgatgacc | 660 | |
| tcaggaatgt caagaagcta ggtggcgacc tgctccgggc cctcaacgag atcaccgagt | 720 | |
| ccggccgcat tggcttcggg tccttcgtgg acaagaccgt gctgccgttc gtgaacacgc | 780 | |
| accctgataa gctgcgaaac ccatgcccca caaggagaa agagtgccag ccccgtttg | 840 | |
| ccttcaggca cgtgctgaag ctgaccaaca actccaacca gtttcagacc gaggtcggga | 900 | |
| agcagctgat ttccggaaac ctggatgcac ccgagggtgg gctggacgcc atgatgcagg | 960 | |
| tcgccgcctg cccggaggaa atcggctggc gcaacgtcac gcggctgctg gtgtttgcca | 1020 | |
| ctgatgacgg cttccattc gcgggcgacg ggaagctggg cgccatcctg acccccaacg | 1080 | |
| acggccgctg tcacctggag gacaacttgt acaagaggag caacgaattc gactacccat | 1140 | |
| cggtgggcca gctggcgcac aagctggctg aaaacaacat ccagcccatc ttcgcggtga | 1200 | |
| ccagtaggat ggtgaagacc tacgagaaac tcaccgagat catccccaag tcagccgtgg | 1260 | |
| gggagctgtc tgaggactcc agcaatgtgg tccatctcat taagaatgct acaataaac | 1320 | |
| tctcctccag ggtcttcctg gatcacaacg ccctccccga caccctgaaa gtcacctacg | 1380 | |
| actccttctg cagcaatgga gtgacgcaca ggaaccagcc cagaggtgac tgtgatggcg | 1440 | |
| tgcagatcaa tgtcccgatc accttccagg tgaaggtcac ggccacagag tgcatccagg | 1500 | |
| agcagtcgtt tgtcatccgg gcgctgggct tcacggacat agtgaccgtg caggttcttc | 1560 | |
| cccagtgtga gtgccggtgc cggaccagag cagagaccgc agcctctgc catggcaagg | 1620 | |
| gcttcttgga gtgcggcatc tgcaggtgtg acactggcta cattgggaaa aactgtgagt | 1680 | |
| gccagacaca gggccggagc agccaggagc tggaaggaag ctgccggaag gacaacaact | 1740 | |
| ccatcatctg ctcagggctg ggggactgtg tctgcgggca gtgcctgtgc cacaccagcg | 1800 | |
| acgtccccgg caagctgata tacgggcagt actgcgagtg tgacaccatc aactgtgagc | 1860 | |

-continued

| | |
|---|---|
| gctacaacgg ccaggtctgc ggcggcccgg ggaggggggct ctgcttctgc gggaagtgcc | 1920 |
| gctgccaccc gggctttgag ggctcagcgt gccagtgcga gaggaccact gagggctgcc | 1980 |
| tgaacccgcg cgtgttgag tgtagtggtc gtggccggtg ccgctgcaac gtatgcgagt | 2040 |
| gccattcagg ctaccagctg cctctgtgcc aggagtgccc cggctgcccc tcaccctgtg | 2100 |
| gcaagtacat ctcctgcgcc gagtgcctga agttcgaaaa gggccccttt gggaagaact | 2160 |
| gcagcgcggc gtgtccgggc ctgcagctgt cgaacaaccc cgtgaagggc aggacctgca | 2220 |
| aggagaggga ctcagagggc tgctgggtgg cctacacgct ggagcagcag gacgggatgg | 2280 |
| accgctacct catctatgtg gatgagagcc gagagtgtgt ggcaggcccc aacatcgccg | 2340 |
| ccatcgtcgg gggcaccgtg gcaggcatcg tgctgatcgg cattctcctg ctggtcatct | 2400 |
| ggaaggctct gatccacctg agcgacctcc gggagtacag gcgctttgag aaggagaagc | 2460 |
| tcaagtccca gtggaacaat gataatcccc ttttcaagag cgccaccacg acggtcatga | 2520 |
| accccaagtt tgctgagagt taggagcact tggtgaagac aaggccgtca ggacccacca | 2580 |
| tgtctgcccc atcacgcggc cgagacatgg cttgccacag ctcttgagga tgtcaccaat | 2640 |
| taaccagaaa tccagttatt ttccgccctc aaaatgacag ccatggccgg ccgggtgctt | 2700 |
| ctgggggctc gtcgggggga cagctccact ctgactggca cagtctttgc atggagactt | 2760 |
| gaggagggag ggcttgaggt tggtgaggtt aggtgcgtgt ttcctgtgca agtcaggaca | 2820 |
| tcagtctgat taaaggtggt gccaatttat ttacatttaa acttgtcagg gtataaaatg | 2880 |
| acatcccatt aattatattg ttaatcaatc acgtgtatag aaaaaaaata aaacttcaat | 2940 |
| acaggctgtc catggaaaaa aaaaaaaaaa aaa | 2973 |

<210> SEQ ID NO 32
<211> LENGTH: 2963
<212> TYPE: DNA
<213> ORGANISM: homo sapiens

<400> SEQUENCE: 32

| | |
|---|---|
| acaggcatcc agggtgagga aggctgccca caggcatcca gggtgaggaa ggcagcccac | 60 |
| actttcttg gagacacatc cccaaagaag tcctcacgtg gctccgtttg gcagaaacc | 120 |
| atgaattgaa cgggaaaaga aatatgtcaa gtatcagaaa gaagagtggc atgctttgac | 180 |
| agcaagtgga ctccgagtcc agggcagagc ctcagttagg gacatgctgg gcctgcgccc | 240 |
| cccactgctc gccctggtgg ggctgctctc cctcgggtgc gtcctctctc aggagtgcac | 300 |
| gaagttcaag gtcagcagct gccgggaatg catcgagtcg gggcccggct gcacctggtg | 360 |
| ccagaagctg aacttcacag ggccggggga tcctgactcc attcgctgcg cacccggcc | 420 |
| acagctgctc atgagggct gtgcggctga cgacatcatg gacccacaa gcctcgctga | 480 |
| aacccaggaa gaccacaatg ggggccagaa gcagctgtcc ccacaaaaag tgacgcttta | 540 |
| cctgcgacca ggccaggcag cagcgttcaa cgtgaccttc cggcgggcca agggctaccc | 600 |
| catcgacctg tactatctga tggacctctc ctactccatg cttgatgacc tcaggaatgt | 660 |
| caagaagcta ggtggcgacc tgctccgggc cctcaacgag atcaccgagt ccggccgcat | 720 |
| tggcttcggg tccttcgtgg acaagaccgt gctgccgttc gtgaacacgc accctgataa | 780 |
| gctgcgaaac ccatgcccca caaggagaa agagtgccag ccccgttg ccttcaggca | 840 |
| cgtgctgaag ctgaccaaca actccaacca gtttcagacc gaggtcggga agcagctgat | 900 |
| ttccggaaac ctggatgcac ccgagggtgg gctggacgcc atgatgcagg tcgccgcctg | 960 |

```
cccggaggaa atcggctggc gcaacgtcac gcggctgctg gtgtttgcca ctgatgacgg   1020
cttccatttc gcgggcgacg ggaagctggg cgccatcctg acccccaacg acggccgctg   1080
tcacctggag gacaacttgt acaagaggag caacgaattc gactacccat cggtgggcca   1140
gctggcgcac aagctggctg aaaacaacat ccagcccatc ttcgcggtga ccagtaggat   1200
ggtgaagacc tacgagaaac tcaccgagat catccccaag tcagccgtgg gggagctgtc   1260
tgaggactcc agcaatgtgg tccatctcat taagaatgct acaataaac tctcctccag   1320 ggtcttcctg gatcacaacg ccctccccga caccctgaaa gtcacctacg actccttctg   1380
cagcaatgga gtgacgcaca ggaaccagcc cagaggtgac tgtgatggcg tgcagatcaa   1440
tgtcccgatc accttccagg tgaaggtcac ggccacagag tgcatccagg agcagtcgtt   1500
tgtcatccgg gcgctgggct tcacggacat agtgaccgtg caggttcttc cccagtgtga   1560
gtgccggtgc cgggaccaga gcagagaccg cagcctctgc catggcaagg gcttcttgga   1620
gtgcggcatc tgcaggtgtg acactggcta cattgggaaa aactgtgagt gccagacaca   1680
gggccggagc agccaggagc tggaaggaag ctgccggaag acaacaact ccatcatctg   1740 ctcagggctg ggggactgtg tctgcgggca gtgcctgtgc cacaccagcg acgtccccgg   1800
caagctgata tacgggcagt actgcgagtg tgacaccatc aactgtgagc gctacaacgg   1860
ccaggtctgc ggcggcccgg ggaggggggct ctgcttctgc gggaagtgcc gctgccaccc   1920
gggctttgag ggctcagcgt gccagtgcga ggaccact gagggctgcc tgaacccgcg   1980
gcgtgttgag tgtagtggtc gtggccggtg ccgctgcaac gtatgcgagt gccattcagg   2040
ctaccagctg cctctgtgcc aggagtgccc cggctgcccc tcaccctgtg caagtacat   2100 ctcctgcgcc gagtgcctga agttcgaaaa gggccccttt gggaagaact gcagcgcggc   2160
gtgtccgggc ctgcagctgt cgaacaaccc cgtgaagggc aggacctgca aggagaggga   2220
ctcagagggc tgctgggtgg cctacacgct ggagcagcag gacgggatgg accgctacct   2280
catctatgtg gatgagagcc gagagtgtgt ggcaggcccc aacatcgccg ccatcgtcgg   2340
gggcaccgtg gcaggcatcg tgctgatcgg cattctcctg ctggtcatct ggaaggctct   2400
gatccacctg agcgacctcc gggagtacag gcgctttgag aaggagaagc tcaagtccca   2460
gtggaacaat gataatcccc ttttcaagag cgccaccacg acggtcatga ccccaagtt   2520 tgctgagagt taggagcact tggtgaagac aaggccgtca ggacccacca tgtctgcccc   2580
atcacgcggc cgagacatgg cttgccacag ctcttgagga tgtcaccaat taaccagaaa   2640
tccagttatt ttccgccctc aaaatgacag ccatggccgg ccgggtgctt ctggggggctc   2700 gtcgggggga cagctccact ctgactggca cagtcttttgc atggagactt gaggagggag   2760
ggcttgaggt tggtgaggtt aggtgcgtgt ttcctgtgca agtcaggaca tcagtctgat   2820
taaaggtggt gccaatttat ttacatttaa acttgtcagg gtataaaatg acatcccatt   2880
aattatattg ttaatcaatc acgtgtatag aaaaaaaata aaacttcaat acaggctgtc   2940
catggaaaaa aaaaaaaaaa aaa                                           2963
```

<210> SEQ ID NO 33
<211> LENGTH: 769
<212> TYPE: PRT
<213> ORGANISM: homo sapiens

<400> SEQUENCE: 33

```
Met Leu Gly Leu Arg Pro Pro Leu Leu Ala Leu Val Gly Leu Leu Ser
1               5                   10                  15
```

```
Leu Gly Cys Val Leu Ser Gln Glu Cys Thr Lys Phe Lys Val Ser Ser
            20                  25                  30
Cys Arg Glu Cys Ile Glu Ser Gly Pro Gly Cys Thr Trp Cys Gln Lys
            35                  40                  45
Leu Asn Phe Thr Gly Pro Gly Asp Pro Asp Ser Ile Arg Cys Asp Thr
 50                  55                  60
Arg Pro Gln Leu Leu Met Arg Gly Cys Ala Ala Asp Asp Ile Met Asp
 65                  70                  75                  80
Pro Thr Ser Leu Ala Glu Thr Gln Glu Asp His Asn Gly Gly Gln Lys
             85                  90                  95
Gln Leu Ser Pro Gln Lys Val Thr Leu Tyr Leu Arg Pro Gly Gln Ala
            100                 105                 110
Ala Ala Phe Asn Val Thr Phe Arg Arg Ala Lys Gly Tyr Pro Ile Asp
            115                 120                 125
Leu Tyr Tyr Leu Met Asp Leu Ser Tyr Ser Met Leu Asp Asp Leu Arg
130                 135                 140
Asn Val Lys Lys Leu Gly Gly Asp Leu Leu Arg Ala Leu Asn Glu Ile
145                 150                 155                 160
Thr Glu Ser Gly Arg Ile Gly Phe Gly Ser Phe Val Asp Lys Thr Val
            165                 170                 175
Leu Pro Phe Val Asn Thr His Pro Asp Lys Leu Arg Asn Pro Cys Pro
            180                 185                 190
Asn Lys Glu Lys Glu Cys Gln Pro Pro Phe Ala Phe Arg His Val Leu
            195                 200                 205
Lys Leu Thr Asn Asn Ser Asn Gln Phe Gln Thr Glu Val Gly Lys Gln
210                 215                 220
Leu Ile Ser Gly Asn Leu Asp Ala Pro Glu Gly Gly Leu Asp Ala Met
225                 230                 235                 240
Met Gln Val Ala Ala Cys Pro Glu Glu Ile Gly Trp Arg Asn Val Thr
            245                 250                 255
Arg Leu Leu Val Phe Ala Thr Asp Asp Gly Phe His Phe Ala Gly Asp
            260                 265                 270
Gly Lys Leu Gly Ala Ile Leu Thr Pro Asn Asp Gly Arg Cys His Leu
            275                 280                 285
Glu Asp Asn Leu Tyr Lys Arg Ser Asn Glu Phe Asp Tyr Pro Ser Val
290                 295                 300
Gly Gln Leu Ala His Lys Leu Ala Glu Asn Asn Ile Gln Pro Ile Phe
305                 310                 315                 320
Ala Val Thr Ser Arg Met Val Lys Thr Tyr Glu Lys Leu Thr Glu Ile
            325                 330                 335
Ile Pro Lys Ser Ala Val Gly Glu Leu Ser Glu Asp Ser Ser Asn Val
            340                 345                 350
Val His Leu Ile Lys Asn Ala Tyr Asn Lys Leu Ser Ser Arg Val Phe
            355                 360                 365
Leu Asp His Asn Ala Leu Pro Asp Thr Leu Lys Val Thr Tyr Asp Ser
    370                 375                 380
Phe Cys Ser Asn Gly Val Thr His Arg Asn Gln Pro Arg Gly Asp Cys
385                 390                 395                 400
Asp Gly Val Gln Ile Asn Val Pro Ile Thr Phe Gln Val Lys Val Thr
            405                 410                 415
Ala Thr Glu Cys Ile Gln Glu Gln Ser Phe Val Ile Arg Ala Leu Gly
            420                 425                 430
```

Phe Thr Asp Ile Val Thr Val Gln Val Leu Pro Gln Cys Glu Cys Arg
    435                 440                 445

Cys Arg Asp Gln Ser Arg Asp Arg Ser Leu Cys His Gly Lys Gly Phe
    450                 455                 460

Leu Glu Cys Gly Ile Cys Arg Cys Asp Thr Gly Tyr Ile Gly Lys Asn
465                 470                 475                 480

Cys Glu Cys Gln Thr Gln Gly Arg Ser Ser Gln Glu Leu Glu Gly Ser
                485                 490                 495

Cys Arg Lys Asp Asn Asn Ser Ile Ile Cys Ser Gly Leu Gly Asp Cys
                500                 505                 510

Val Cys Gly Gln Cys Leu Cys His Thr Ser Asp Val Pro Gly Lys Leu
                515                 520                 525

Ile Tyr Gly Gln Tyr Cys Glu Cys Asp Thr Ile Asn Cys Glu Arg Tyr
                530                 535                 540

Asn Gly Gln Val Cys Gly Gly Pro Gly Arg Gly Leu Cys Phe Cys Gly
545                 550                 555                 560

Lys Cys Arg Cys His Pro Gly Phe Glu Gly Ser Ala Cys Gln Cys Glu
                565                 570                 575

Arg Thr Thr Glu Gly Cys Leu Asn Pro Arg Arg Val Glu Cys Ser Gly
                580                 585                 590

Arg Gly Arg Cys Arg Cys Asn Val Cys Glu Cys His Ser Gly Tyr Gln
                595                 600                 605

Leu Pro Leu Cys Gln Glu Cys Pro Gly Cys Pro Ser Pro Cys Gly Lys
                610                 615                 620

Tyr Ile Ser Cys Ala Glu Cys Leu Lys Phe Glu Lys Gly Pro Phe Gly
625                 630                 635                 640

Lys Asn Cys Ser Ala Ala Cys Pro Gly Leu Gln Leu Ser Asn Asn Pro
                645                 650                 655

Val Lys Gly Arg Thr Cys Lys Glu Arg Asp Ser Glu Gly Cys Trp Val
                660                 665                 670

Ala Tyr Thr Leu Glu Gln Gln Asp Gly Met Asp Arg Tyr Leu Ile Tyr
                675                 680                 685

Val Asp Glu Ser Arg Glu Cys Val Ala Gly Pro Asn Ile Ala Ala Ile
                690                 695                 700

Val Gly Gly Thr Val Ala Gly Ile Val Leu Ile Gly Ile Leu Leu Leu
705                 710                 715                 720

Val Ile Trp Lys Ala Leu Ile His Leu Ser Asp Leu Arg Glu Tyr Arg
                725                 730                 735

Arg Phe Glu Lys Glu Lys Leu Lys Ser Gln Trp Asn Asn Asp Asn Pro
                740                 745                 750

Leu Phe Lys Ser Ala Thr Thr Thr Val Met Asn Pro Lys Phe Ala Glu
                755                 760                 765

Ser

<210> SEQ ID NO 34
<211> LENGTH: 2928
<212> TYPE: DNA
<213> ORGANISM: homo sapiens

<400> SEQUENCE: 34
gaggagctga gaggaacagg aagtgtcagg actttacgac ccgcgcctcc agctgaggtt    60
tctagacgtg acccagggca gactggtagc aaagccccca cgcccagcca ggagcaccgc   120
cgaggactcc agcacaccga gggacatgct gggcctgcgc cccccactgc tcgccctggt   180

```
ggggctgctc tccctcgggt gcgggcggcc cagagcaccc actcaccagc cggcctcgtc    240
cctcagtcct ctctcaggag tgcacgaagt tcaaggtcag cagctgccgg gaatgcatcg    300
agtcggggcc cggctgcacc tggtgccaga agctgaactt cacagggccg ggggatcctg    360
actccattcg ctgcgacacc cggccacagc tgctcatgag gggctgtgcg gctgacgaca    420
tcatggaccc cacaagcctc gctgaaaccc aggaagacca caatgggggc cagaagcagc    480
tgtccccaca aaaagtgacg ctttacctgc gaccaggcca ggcagcagcg ttcaacgtga    540
ccttccggcg ggccaagggc tacccccatc gacctgtacta tctgatggac ctctcctact    600
ccatgcttga tgacctcagg aatgtcaaga agctaggtgg cgacctgctc cgggccctca    660
acgagatcac cgagtccggc cgcattggct tcgggtcctt cgtggacaag accgtgctgc    720
cgttcgtgaa cacgcaccct gataagctgc gaaacccatg ccccaacaag gagaaagagt    780
gccagccccc gtttgccttc aggcacgtgc tgaagctgac caacaactcc aaccagtttc    840
agaccgaggt cgggaagcag ctgatttccg gaaacctgga tgcacccgag ggtgggctgg    900
acgccatgat gcaggtcgcc gcctgcccgg aggaaatcgg ctggcgcaac gtcacgcggc    960
tgctggtgtt tgccactgat gacggcttcc atttcgcggg cgacgggaag ctgggcgcca    1020
tcctgacccc caacgacggc cgctgtcacc tggaggacaa cttgtacaag aggagcaacg    1080
aattcgacta cccatcggtg ggccagctgg cgcacaagct ggctgaaaac aacatccagc    1140
ccatcttcgc ggtgaccagt aggatggtga agacctacga gaaactcacc gagatcatcc    1200
ccaagtcagc cgtgggggag ctgtctgagg actccagcaa tgtggtccat ctcattaaga    1260
atgcttacaa taaactctcc tccagggtct tcctggatca caacgccctc cccgacaccc    1320
tgaaagtcac ctacgactcc ttctgcagca atggagtgac gcacaggaac cagcccagag    1380
gtgactgtga tggcgtgcag atcaatgtcc cgatcacctt ccaggtgaag gtcacggcca    1440
cagagtgcat ccaggagcag tcgtttgtca tccgggcgct gggcttcacg acatagtga    1500 ccgtgcaggt tcttccccag tgtgagtgcc ggtgccggga ccagagcaga accgcagcc    1560 tctgccatgg caagggcttc ttggagtgcg catctgcag tgtgacact ggctacattg    1620 ggaaaaactg tgagtgccag acacagggcc ggagcagcca ggagctggaa ggaagctgcc    1680
ggaaggacaa caactccatc atctgctcag gctggggga ctgtgtctgc gggcagtgcc    1740
tgtgccacac cagcgacgtc cccggcaagc tgatatacgg gcagtactgc gagtgtgaca    1800
ccatcaactg tgagcgctac aacggccagg tctgcggcgg cccggggagg gggctctgct    1860
tctgcgggaa gtgccgctgc cacccgggct tgagggctc agcgtgccag tgcgagagga    1920
ccactgaggg ctgcctgaac ccgcggcgtg ttgagtgtag tggtcgtggc cggtgccgct    1980
gcaacgtatg cgagtgccat tcaggctacc agctgcctct gtgccaggag tgccccggct    2040
gcccctcacc ctgtggcaag tacatctcct gcgccgagtg cctgaagttc gaaaagggcc    2100
cctttgggaa gaactgcagc gcggcgtgtc cgggcctgca gctgtcgaac accccgtga    2160 agggcaggac ctgcaaggag agggactcag agggctgctg ggtggcctac acgctggagc    2220
agcaggacgg gatggaccgc tacctcatct atgtggatga gagccgagag tgtgtggcag    2280
gccccaacat cgccgccatc gtcggggggca ccgtggcagg catcgtgctg atcggcattc    2340
tcctgctggt catctggaag gctctgatcc acctgagcga cctccgggag tacaggcgct    2400
ttgagaagga gaagctcaag tcccagtgga acaatgataa tcccctttc aagagcgcca    2460 ccacgacggt catgaacccc aagtttgctg agagttagga gcacttggtg aagacaaggc    2520
```

-continued

| | | |
|---|---|---|
| cgtcaggacc caccatgtct gccccatcac gcggccgaga catggcttgc cacagctctt | 2580 |
| gaggatgtca ccaattaacc agaaatccag ttatttccg ccctcaaaat gacagccatg | 2640 |
| gccggccggg tgcttctggg ggctcgtcgg ggggacagct ccactctgac tggcacagtc | 2700 |
| tttgcatgga gacttgagga gggagggctt gaggttggtg aggttaggtg cgtgtttcct | 2760 |
| gtgcaagtca ggacatcagt ctgattaaag gtggtgccaa tttatttaca tttaaacttg | 2820 |
| tcagggtata aaatgacatc ccattaatta tattgttaat caatcacgtg tatagaaaaa | 2880 |
| aaataaaact tcaatacagg ctgtccatgg aaaaaaaaaa aaaaaaaa | 2928 |

<210> SEQ ID NO 35
<211> LENGTH: 700
<212> TYPE: PRT
<213> ORGANISM: homo sapiens

<400> SEQUENCE: 35

Met Arg Gly Cys Ala Ala Asp Asp Ile Met Asp Pro Thr Ser Leu Ala
1               5                   10                  15

Glu Thr Gln Glu Asp His Asn Gly Gly Gln Lys Gln Leu Ser Pro Gln
            20                  25                  30

Lys Val Thr Leu Tyr Leu Arg Pro Gly Gln Ala Ala Phe Asn Val
        35                  40                  45

Thr Phe Arg Arg Ala Lys Gly Tyr Pro Ile Asp Leu Tyr Tyr Leu Met
    50                  55                  60

Asp Leu Ser Tyr Ser Met Leu Asp Asp Leu Arg Asn Val Lys Lys Leu
65                  70                  75                  80

Gly Gly Asp Leu Leu Arg Ala Leu Asn Glu Ile Thr Glu Ser Gly Arg
                85                  90                  95

Ile Gly Phe Gly Ser Phe Val Asp Lys Thr Val Leu Pro Phe Val Asn
            100                 105                 110

Thr His Pro Asp Lys Leu Arg Asn Pro Cys Pro Asn Lys Glu Lys Glu
        115                 120                 125

Cys Gln Pro Pro Phe Ala Phe Arg His Val Leu Lys Leu Thr Asn Asn
    130                 135                 140

Ser Asn Gln Phe Gln Thr Glu Val Gly Lys Gln Leu Ile Ser Gly Asn
145                 150                 155                 160

Leu Asp Ala Pro Glu Gly Gly Leu Asp Ala Met Met Gln Val Ala Ala
                165                 170                 175

Cys Pro Glu Glu Ile Gly Trp Arg Asn Val Thr Arg Leu Leu Val Phe
            180                 185                 190

Ala Thr Asp Asp Gly Phe His Phe Ala Gly Asp Gly Lys Leu Gly Ala
        195                 200                 205

Ile Leu Thr Pro Asn Asp Gly Arg Cys His Leu Glu Asp Asn Leu Tyr
    210                 215                 220

Lys Arg Ser Asn Glu Phe Asp Tyr Pro Ser Val Gly Gln Leu Ala His
225                 230                 235                 240

Lys Leu Ala Glu Asn Asn Ile Gln Pro Ile Phe Ala Val Thr Ser Arg
                245                 250                 255

Met Val Lys Thr Tyr Glu Lys Leu Thr Glu Ile Ile Pro Lys Ser Ala
            260                 265                 270

Val Gly Glu Leu Ser Glu Asp Ser Ser Asn Val Val His Leu Ile Lys
        275                 280                 285

Asn Ala Tyr Asn Lys Leu Ser Ser Arg Val Phe Leu Asp His Asn Ala
    290                 295                 300

```
Leu Pro Asp Thr Leu Lys Val Thr Tyr Asp Ser Phe Cys Ser Asn Gly
305                 310                 315                 320

Val Thr His Arg Asn Gln Pro Arg Gly Asp Cys Asp Gly Val Gln Ile
            325                 330                 335

Asn Val Pro Ile Thr Phe Gln Val Lys Val Thr Ala Thr Glu Cys Ile
            340                 345                 350

Gln Glu Gln Ser Phe Val Ile Arg Ala Leu Gly Phe Thr Asp Ile Val
            355                 360                 365

Thr Val Gln Val Leu Pro Gln Cys Glu Cys Arg Cys Arg Asp Gln Ser
370                 375                 380

Arg Asp Arg Ser Leu Cys His Gly Lys Gly Phe Leu Glu Cys Gly Ile
385                 390                 395                 400

Cys Arg Cys Asp Thr Gly Tyr Ile Gly Lys Asn Cys Glu Cys Gln Thr
            405                 410                 415

Gln Gly Arg Ser Ser Gln Glu Leu Glu Gly Ser Cys Arg Lys Asp Asn
            420                 425                 430

Asn Ser Ile Ile Cys Ser Gly Leu Gly Asp Cys Val Cys Gly Gln Cys
            435                 440                 445

Leu Cys His Thr Ser Asp Val Pro Gly Lys Leu Ile Tyr Gly Gln Tyr
450                 455                 460

Cys Glu Cys Asp Thr Ile Asn Cys Glu Arg Tyr Asn Gly Gln Val Cys
465                 470                 475                 480

Gly Gly Pro Gly Arg Gly Leu Cys Phe Cys Gly Lys Cys Arg Cys His
            485                 490                 495

Pro Gly Phe Glu Gly Ser Ala Cys Gln Cys Glu Arg Thr Thr Glu Gly
            500                 505                 510

Cys Leu Asn Pro Arg Arg Val Glu Cys Ser Gly Arg Gly Arg Cys Arg
            515                 520                 525

Cys Asn Val Cys Glu Cys His Ser Gly Tyr Gln Leu Pro Leu Cys Gln
530                 535                 540

Glu Cys Pro Gly Cys Pro Ser Pro Cys Gly Lys Tyr Ile Ser Cys Ala
545                 550                 555                 560

Glu Cys Leu Lys Phe Glu Lys Gly Pro Phe Gly Lys Asn Cys Ser Ala
            565                 570                 575

Ala Cys Pro Gly Leu Gln Leu Ser Asn Asn Pro Val Lys Gly Arg Thr
            580                 585                 590

Cys Lys Glu Arg Asp Ser Glu Gly Cys Trp Val Ala Tyr Thr Leu Glu
            595                 600                 605

Gln Gln Asp Gly Met Asp Arg Tyr Leu Ile Tyr Val Asp Glu Ser Arg
610                 615                 620

Glu Cys Val Ala Gly Pro Asn Ile Ala Ala Ile Val Gly Gly Thr Val
625                 630                 635                 640

Ala Gly Ile Val Leu Ile Gly Ile Leu Leu Leu Val Ile Trp Lys Ala
            645                 650                 655

Leu Ile His Leu Ser Asp Leu Arg Glu Tyr Arg Arg Phe Glu Lys Glu
            660                 665                 670

Lys Leu Lys Ser Gln Trp Asn Asn Asp Asn Pro Leu Phe Lys Ser Ala
            675                 680                 685

Thr Thr Thr Val Met Asn Pro Lys Phe Ala Glu Ser
690                 695                 700

<210> SEQ ID NO 36
<211> LENGTH: 5553
<212> TYPE: DNA
```

<213> ORGANISM: homo sapiens

<400> SEQUENCE: 36

```
gtgtgaatgc ttcattcgcc tcacaaacaa ccacagaacc acaagtgcgg tgcaaacttt      60
ctccaggagg acagcaagaa gtctctggtt tttaaatggt taatctccgc aggtcactac     120
cagccaccga gaccaacaga gtcatttaag gctgcaagca gtatttacaa cagagggtac     180
aagttctatc tgaaaaaaaa aggagggact atggcatcaa acagcctctt cagcacagtg     240
acaccatgtc agcaaaactt cttttgggat ccgagcacca gccggcgctt cagcccccc      300
tccagcagcc tgcagcccgg caaaatgagc gacgtgagcc cggtggtggc tgcgcaacag     360
cagcagcaac agcagcagca gcaacagcag cagcagcagc agcaacagca gcagcagcag     420
caggaggcgg cggcggcggc tgcggcggcg gcggcggctg cggcggcggc agctgcagtg     480
ccccggttgc ggccgcccca cgacaaccgc accatggtgg agatcatcgc cgaccacccg     540
gccgaactcg tccgcaccga cagccccaac ttcctgtgct cggtgctgcc ctcgcactgg     600
cgctgcaaca agaccctgcc cgtggccttc aaggtggtag ccctcggaga ggtaccagat     660
gggactgtgg ttactgtcat ggcgggtaac gatgaaaatt attctgctga gctccggaat     720
gcctctgctg ttatgaaaaa ccaagtagca aggttcaacg atctgagatt tgtgggccgg     780
agtggacgag gcaagagttt caccttgacc ataaccgtct tcacaaatcc tccccaagta     840
gctacctatc acagagcaat taagttaca gtagatggac tcgggaacc cagaaggcac      900
agacagaagc ttgatgactc taaacctagt ttgttctctg accgcctcag tgatttaggg     960
cgcattcctc atcccagtat gagagtaggt gtcccgcctc agaacccacg gccctccctg    1020
aactctgcac caagtccttt taatccacaa ggacagagtc agattacaga ccccaggcag    1080
gcacagtctt ccccgccgtg gtcctatgac cagtcttacc cctcctacct gagccagatg    1140
acgtccccgt ccatccactc taccaccccg ctgtcttcca cacggggcac tgggcttcct    1200
gccatcaccg atgtgcctag gcgcatttca gatgatgaca ctgccaccte tgacttctgc    1260
ctctggcctt ccactctcag taagaagagc caggcaggtg cttcagaact gggccctttt    1320
tcagacccca ggcagttccc aagcatttca tccctcactg agagccgctt ctccaaccca    1380
cgaatgcact atccagccac ctttacttac accccgccag tcacctcagg catgtccctc    1440
ggtatgtccg ccaccactca ctaccacacc tacctgccac cacccctaccc cggctcttcc    1500
caaagccaga gtggacccct tccagaccagc agcactccat atctctacta tggcacttcg    1560
tcaggatcct atcagtttcc catggtgccg gggggagacc ggtctccttc cagaatgctt    1620
ccgccatgca ccaccacctc gaatggcagc acgctattaa atccaaattt gcctaaccag    1680
aatgatggtg ttgacgctga tggaagccac agcagttccc caactgtttt gaattctagt    1740
ggcagaatgg atgaatctgt ttggcgacca tattgaaatt cctcagcagt ggcccagtgg    1800
tatctggggg ccacatccca cacgtatcaa tatatacata tatagagaga gtgcatatat    1860
atgtatatcg attagctatc tacaaagtgc ctatttttta gaagattttt cattcactca    1920
ctcagtcatg atcttgcagc cataagaggg tagatattga gaagcagaag gctcaagaga    1980
gacaattgca atcgagcttc agattgttta ctatttaaga tgtacttta caaaggaaca    2040
aagaagggaa aaggtatttt tgtttttgtt gtttggtctg ttatcatcaa taacctgttc    2100
atatgccaat tcagagaggt ggactccagg ttcaggaggg agaagagcaa agccgcttcc    2160
tctctgtgct ttgaaacttc acaccctcac ggtggcagct gtgtatgac cagtgccctc    2220
cgcagacagc tcacaaaacc agttgaggtg cactaaaggg acatgaggta gaatggatgc    2280
```

```
ttccatcaca gtaccatcat tcagaataac tcttccaatt tctgctttca gacatgctgc    2340
aggtcctcat ctgaactgtt gggttcgttt tttttttttt ttttcctgct ccaagaaagt    2400
gacttcaaaa ataactgatc aggatagatt attttatttt acttttaac actccttctc     2460 cccttttccc actgaaccaa aaagaaatcc catccctaaa acctgccttc tccttttatg    2520
caaaactgaa aatggcaata cattattata gccataatgg tatagatagt gattgcgttt    2580
ggctatgtgt tgttttcttt tttttaaat tatgaatatg tgtaaaatct gaggtaactt     2640
gctaacgtga atggtcatat aactttaaag atatatttat aattatttaa tgacatttgg    2700
acccttgaaa catttcttag tgtattgata tgttgacttc ggtctctaaa agtgctcttt    2760
attaaataac aaatttcttc agtggtctag agccatatct gaaatattgc taagcaattt    2820
cagttcatcc aggcacaatg tgattttaaa aaatacttcc atctccaaat attttagata    2880
tagattgttt ttgtgatgta tgaaggaaat gttatgttta gttctttcag atctttgaat    2940
gcctctaaca cagctttgcc ttctaaagcg gtaattaggg atttaaaaaa caacctttag    3000 cccttttatca gcatgaaatg ctggagtgat gtggttttct aatttctttg gggtaattat   3060
gactcttgtc atattaaaaa gacaagcaca agtaaatcat tgaactacag aaaaatgttc    3120
tgtggtttca tagttaagca aaactctaaa tcgccaggct tcatagcaaa gacatagtca    3180
gctaaaagcc gcacatgtgg atagagggtt caattatgag acacctagta caggagagca    3240
aaattgcacc agagattctt aaccaaccag ccttaccaaa caacacaaca ggggaacccc    3300
aatctgcctt acccaaggcc ccactggcag ctttccacag aatttgcatt tagaggagca    3360
gaatgacatc actgtccttt gggagtaggt cctctgaaaa ggcagcaggt tccagcaggt    3420
agctgagctg agaggacata tggcccacgg ggacctacag acagcctttg acatttgtat    3480
ttcttacaat ggagggccaa ggagggcaag gggctgtgga gtttggtgtc tactagtgtg    3540
tatgaatttg agctagagtc cttctgtggc atgcactttg accactcctg gcagtcacat    3600
ggcagatttc caagtgcaaa tccttaatcc aaacaaggat catctaatga caccaccagg    3660
ccaatccctg ctctcctccc cgaaaagtca gggtccccttc attggaatcc tccacccacc    3720
caagcagaat ttagcagaga tttgccttca aaccctaacg gccccttgt tctctggtcc     3780 ttctcaaacc caccttttgta ggccacccag cattgcagga cagcgtgtgg ggcagctgga   3840
cctgtgcttc ctgcctggga gtctcccttg gaattcatcc tgactccttc taataaaaat    3900
ggatgggaaa gcaaaacact ttgccttcta aaggccgtat accaagtatg cttagataaa    3960
taagccactt ttctattact taagtaagaa ggaagtagta attgatacta tttattgttt    4020
gtgtgtggta gcttgaagca caccactgtc catttatttg taagtgtaaa atatgtgtgt    4080
ttgtttcagc agcacttaaa aaagccagtg tctggttaca catttcaatt ttaattaatt   4140
gacataaaaa tgctaccgcc agtgccagct gcatcctatt taattaaaaa ggtactatat    4200
ttgtacatta ttttttaatg ttaaaagggc ttttttaagt ttacagtaca cataccgagt    4260
gactttaggg atgcttttgt gttgaaatgt tactatagtg gctgcaggca gcaacccaga    4320
aacactttag aagctttttt tccttgggaa aaattcaagc acttcttccc tccaccctca    4380
ctccaaccac cccaatgggg gtaattcaca tttcttagaa caaattctgc cctttttgg    4440 tctagggatt aaaattttgt ttttctttct ttctttttt ttttttttca ctgaacccctt     4500 aatttgcact gggtcatgtg tttgatttgt gatttcaaga ccaaagcaaa gtcttactac    4560
tactgtggaa ccatgtacta gttcctggga attaaaatag cgtggttctc tttgtagcac    4620
```

```
aaacattgct ggaatttgca gtcttttcaa tgcagccaca ttttatcca tttcagttgt   4680 ctcacaaatt ttaacccata tcagagttcc agaacaggta ccacagcttt ggttttagat   4740
tagtggaata acattcagcc cagaactgag aaactcaaca gattaactat cgtttgctct   4800
ttagacggtc tcactgcctc tcacttgcca gagcccttc aaaatgagca gagaagtcca    4860
caccattagg gaccatctgt gataaattca gaagggagga gatgtgtgta cagctttaag   4920
gattccctca attccgagga aagggactgg cccagaatcc aggttaatac atggaaacac   4980
gaagcattag caaaagtaat aattatacct atggtatttg aaagaacaat aataaaagac   5040
acttcttcca aaccttgaat tgttgtttt tagaaaacga atgcatttaa aaatattttc    5100
tatgtgagaa ttttttagat gtgtgtttac ttcatgttta caaataactg tttgcttttt   5160
aatgcagtac tttgaaatat atcagccaaa accataactt acaataattt cttaggtatt   5220
ctgaataaaa ttccatttct tttggatatg ctttaccatt cttaggtttc tgtggaacaa   5280
aaatatttgt agcattttgt gtaaatacaa gctttcattt ttattttttc caattgctat   5340
tgcccaagaa ttgctttcca tgcacatatt gtaaaaattc cgctttgtgc cacaggtcat   5400
gattgtggat gagtttactc ttaacttcaa agggactatt tgtattgtat gttgcaactg   5460
taaattgaat tatttggcat ttttctcatg attgtaaatat taatttgaag tttgaattta   5520
attttcaata aaatggcttt tttggttttg tta                                5553
```

<210> SEQ ID NO 37
<211> LENGTH: 521
<212> TYPE: PRT
<213> ORGANISM: homo sapiens

<400> SEQUENCE: 37

```
Met Ala Ser Asn Ser Leu Phe Ser Thr Val Thr Pro Cys Gln Gln Asn
1               5                   10                  15

Phe Phe Trp Asp Pro Ser Thr Ser Arg Arg Phe Ser Pro Pro Ser Ser
                20                  25                  30

Ser Leu Gln Pro Gly Lys Met Ser Asp Val Ser Pro Val Val Ala Ala
            35                  40                  45

Gln Gln Gln Gln Gln Gln Gln Gln Gln Gln Gln Gln Gln Gln Gln Gln
        50                  55                  60

Gln Gln Gln Gln Gln Gln Gln Glu Ala Ala Ala Ala Ala Ala Ala Ala
65                  70                  75                  80

Ala Ala Ala Ala Ala Ala Ala Ala Val Pro Arg Leu Arg Pro Pro
                85                  90                  95

His Asp Asn Arg Thr Met Val Glu Ile Ile Ala Asp His Pro Ala Glu
            100                 105                 110

Leu Val Arg Thr Asp Ser Pro Asn Phe Leu Cys Ser Val Leu Pro Ser
        115                 120                 125

His Trp Arg Cys Asn Lys Thr Leu Pro Val Ala Phe Lys Val Val Ala
    130                 135                 140

Leu Gly Glu Val Pro Asp Gly Thr Val Val Thr Val Met Ala Gly Asn
145                 150                 155                 160

Asp Glu Asn Tyr Ser Ala Glu Leu Arg Asn Ala Ser Ala Val Met Lys
                165                 170                 175

Asn Gln Val Ala Arg Phe Asn Asp Leu Arg Phe Val Gly Arg Ser Gly
            180                 185                 190

Arg Gly Lys Ser Phe Thr Leu Thr Ile Thr Val Phe Thr Asn Pro Pro
        195                 200                 205
```

```
Gln Val Ala Thr Tyr His Arg Ala Ile Lys Val Thr Val Asp Gly Pro
    210                 215                 220
Arg Glu Pro Arg Arg His Arg Gln Lys Leu Asp Asp Ser Lys Pro Ser
225                 230                 235                 240
Leu Phe Ser Asp Arg Leu Ser Asp Leu Gly Arg Ile Pro His Pro Ser
                245                 250                 255
Met Arg Val Gly Val Pro Pro Gln Asn Pro Arg Pro Ser Leu Asn Ser
            260                 265                 270
Ala Pro Ser Pro Phe Asn Pro Gln Gly Gln Ser Gln Ile Thr Asp Pro
        275                 280                 285
Arg Gln Ala Gln Ser Ser Pro Pro Trp Ser Tyr Asp Gln Ser Tyr Pro
    290                 295                 300
Ser Tyr Leu Ser Gln Met Thr Ser Pro Ser Ile His Ser Thr Thr Pro
305                 310                 315                 320
Leu Ser Ser Thr Arg Gly Thr Gly Leu Pro Ala Ile Thr Asp Val Pro
                325                 330                 335
Arg Arg Ile Ser Asp Asp Asp Thr Ala Thr Ser Asp Phe Cys Leu Trp
            340                 345                 350
Pro Ser Thr Leu Ser Lys Lys Ser Gln Ala Gly Ala Ser Glu Leu Gly
        355                 360                 365
Pro Phe Ser Asp Pro Arg Gln Phe Pro Ser Ile Ser Ser Leu Thr Glu
    370                 375                 380
Ser Arg Phe Ser Asn Pro Arg Met His Tyr Pro Ala Thr Phe Thr Tyr
385                 390                 395                 400
Thr Pro Pro Val Thr Ser Gly Met Ser Leu Gly Met Ser Ala Thr Thr
                405                 410                 415
His Tyr His Thr Tyr Leu Pro Pro Pro Tyr Pro Gly Ser Ser Gln Ser
            420                 425                 430
Gln Ser Gly Pro Phe Gln Thr Ser Ser Thr Pro Tyr Leu Tyr Tyr Gly
        435                 440                 445
Thr Ser Ser Gly Ser Tyr Gln Phe Pro Met Val Pro Gly Gly Asp Arg
    450                 455                 460
Ser Pro Ser Arg Met Leu Pro Pro Cys Thr Thr Thr Ser Asn Gly Ser
465                 470                 475                 480
Thr Leu Leu Asn Pro Asn Leu Pro Asn Gln Asn Asp Gly Val Asp Ala
                485                 490                 495
Asp Gly Ser His Ser Ser Ser Pro Thr Val Leu Asn Ser Ser Gly Arg
            500                 505                 510
Met Asp Glu Ser Val Trp Arg Pro Tyr
        515                 520

<210> SEQ ID NO 38
<211> LENGTH: 5487
<212> TYPE: DNA
<213> ORGANISM: homo sapiens

<400> SEQUENCE: 38
gtgtgaatgc ttcattcgcc tcacaaacaa ccacagaacc acaagtgcgg tgcaaacttt      60
ctccaggagg acagcaagaa gtctctggtt tttaaatggt taatctccgc aggtcactac     120
cagccaccga gaccaacaga gtcatttaag gctgcaagca gtatttacaa cagagggtac     180
aagttctatc tgaaaaaaaa aggagggact atggcatcaa acagcctctt cagcacagtg     240
acaccatgtc agcaaaactt cttttgggat ccgagcacca gccggcgctt cagccccccc     300
tccagcagcc tgcagcccgg caaaatgagc gacgtgagcc cggtggtggc tgcgcaacag     360
```

```
cagcagcaac agcagcagca gcaacagcag cagcagcagc agcaacagca gcagcagcag    420
caggaggcgg cggcggcggc tgcggcggcg gcggcggctg cggcggcggc agctgcagtg    480
ccccggttgc ggccgcccca cgacaaccgc accatggtgg agatcatcgc cgaccacccg    540
gccgaactcg tccgcaccga cagccccaac ttcctgtgct cggtgctgcc ctcgcactgg    600
cgctgcaaca agaccctgcc cgtggccttc aaggtggtag ccctcggaga ggtaccagat    660
gggactgtgg ttactgtcat ggcgggtaac gatgaaaatt attctgctga gctccggaat    720
gcctctgctg ttatgaaaaa ccaagtagca aggttcaacg atctgagatt tgtgggccgg    780
agtggacgag gcaagagttt caccttgacc ataaccgtct tcacaaatcc tccccaagta    840
gctacctatc acagagcaat taaagttaca gtagatggac ctcgggaacc cagaaggcac    900
agacagaagc ttgatgactc taaacctagt ttgttctctg accgcctcag tgatttaggg    960
cgcattcctc atcccagtat gagagtaggt gtcccgcctc agaacccacg gccctccctg   1020
aactctgcac caagtccttt taatccacaa ggacagagtc agattacaga ccccaggcag   1080
gcacagtctt ccccgccgtg gtcctatgac cagtcttacc cctcctacct gagccagatg   1140
acgtccccgt ccatccactc taccaccccg ctgtcttcca cacggggcac tgggcttcct   1200
gccatcaccg atgtgcctag gcgcatttca ggtgcttcag aactgggccc tttttcagac   1260
cccaggcagt tcccaagcat ttcatccctc actgagagcc gcttctccaa cccacgaatg   1320
cactatccag ccacctttac ttacaccccg ccagtcacct caggcatgtc cctcggtatg   1380
tccgccacca ctcactacca cacctacctg ccaccaccct accccggctc ttcccaaagc   1440
cagagtggac ccttccagac cagcagcact ccatatctct actatggcac ttcgtcagga   1500
tcctatcagt ttcccatggt gccgggggga gaccggtctc cttccagaat gcttccgcca   1560
tgcaccacca cctcgaatgg cagcacgcta ttaaatccaa atttgcctaa ccagaatgat   1620
ggtgttgacg ctgatggaag ccacagcagt tccccaactg ttttgaattc tagtggcaga   1680
atggatgaat ctgtttggcg accatattga aattcctcag cagtggccca gtggtatctg   1740
ggggccacat cccacacgta tcaatatata catatataga gagagtgcat atatatgtat   1800
atcgattagc tatctacaaa gtgcctattt tttagaagat ttttcattca ctcactcagt   1860
catgatcttg cagccataag agggtagata ttgagaagca gaaggctcaa gagagacaat   1920
tgcaatcgag cttcagattg tttactattt aagatgtact tttacaaagg aacaaagaag   1980
ggaaaaggta ttttgttttt tgttgtttgg tctgttatca tcaataacct gttcatatgc   2040
caattcagag aggtggactc caggttcagg agggagaaga gcaaagccgc ttcctctctg   2100
tgctttgaaa cttcacaccc tcacggtggc agctgtgtat ggaccagtgc cctccgcaga   2160
cagctcacaa aaccagttga ggtgcactaa agggacatga ggtagaatgg atgcttccat   2220
cacagtacca tcattcagaa taactcttcc aatttctgct ttcagacatg ctgcaggtcc   2280
tcatctgaac tgttgggttc gttttttttt tttttttttcc tgctccaaga aagtgacttc   2340
aaaaataact gatcaggata gattatttta ttttactttt taacactcct tctcccctttt   2400 tcccactgaa ccaaaaagaa atcccatccc taaaacctgc cttctccttt tatgcaaaac   2460
tgaaaatggc aatacattat tatagccata atggtataga tagtgattgc gtttggctat   2520
gtgttgtttt cttttttttt aaattatgaa tatgtgtaaa atctgaggta acttgctaac   2580
gtgaatggtc ataaacttt aaagatatat ttataattat ttaatgacat ttggacccttt   2640 gaaacatttc ttagtgtatt gatatgttga cttcggtctc taaaagtgct ctttattaaa   2700
```

```
taacaaattt cttcagtggt ctagagccat atctgaaata ttgctaagca atttcagttc    2760
atccaggcac aatgtgattt taaaaaatac ttccatctcc aaatatttta gatatagatt    2820
gtttttgtga tgtatgaagg aaatgttatg tttagttctt tcagatcttt gaatgcctct    2880
aacacagctt tgccttctaa agcggtaatt agggatttaa aaacaacct ttagcccttt     2940 atcagcatga aatgctggag tgatgtggtt ttctaatttc tttggggtaa ttatgactct    3000
tgtcatatta aaagacaag cacaagtaaa tcattgaact acagaaaaat gttctgtggt     3060
ttcatagtta agcaaaactc taaatcgcca ggcttcatag caaagacata gtcagctaaa    3120
agccgcacat gtggatagag ggttcaatta tgagacacct agtacaggag agcaaaattg    3180
caccagagat tcttaaccaa ccagccttac caaacaacac aacaggggaa ccccaatctg    3240
ccttacccaa ggccccactg gcagctttcc acagaatttg catttagagg agcagaatga    3300
catcactgtc ctttgggagt aggtcctctg aaaaggcagc aggttccagc aggtagctga    3360
gctgagagga catatggccc acggggacct acagacagcc tttgacattt gtatttctta    3420
caatggaggg ccaaggaggg caaggggctg tggagtttgg tgtctactag tgtgtatgaa    3480
tttgagctag agtccttctg tggcatgcac tttgaccact cctggcagtc acatggcaga    3540
tttccaagtg caaatcctta atccaaacaa ggatcatcta atgacaccac caggccaatc    3600
cctgctctcc tccccgaaaa gtcagggtcc cttcattgga atcctccacc cacccaagca    3660
gaatttagca gagatttgcc ttcaaaccct aacggccccc ttgttctctg gtccttctca    3720
aacccacctt tgtaggccac ccagcattgc aggacagcgt gtgggcagc tggacctgtg     3780 cttcctgcct gggagtctcc cttggaattc atcctgactc cttctaataa aaatggatgg    3840
gaaagcaaaa cactttgcct tctaaaggcc gtataccaag tatgcttaga taaataagcc    3900
acttttctat tacttaagta agaaggaagt agtaattgat actatttatt gtttgtgtgt    3960
ggtagcttga agcacaccac tgtccattta tttgtaagtg taaaatatgt gtgtttgttt    4020
cagcagcact taaaaaagcc agtgtctggt tacacatttc aatttaatt aattgacata     4080 aaaatgctac cgccagtgcc agctgcatcc tatttaatta aaaaggtact atatttgtac    4140 attattttt aatgttaaaa gggctttttt aagtttacag tacacatacc gagtgacttt     4200
agggatgctt ttgtgttgaa atgttactat agtggctgca ggcagcaacc cagaaacact    4260
ttagaagctt tttttccttg ggaaaaattc aagcacttct tccctccacc ctcactccaa    4320
ccaccccaat gggggtaatt cacatttctt agaacaaatt ctgcccttt ttggtctagg     4380 gattaaaatt ttgttttct ttctttcttt tttttttttt ttcactgaac ccttaatttg     4440
cactgggtca tgtgtttgat ttgtgatttc aagaccaaag caaagtctta ctactactgt    4500
ggaaccatgt actagttcct gggaattaaa atagcgtggt tctctttgta gcacaaacat    4560
tgctggaatt tgcagtcttt tcaatgcagc cacattttta tccatttcag ttgtctcaca    4620
aattttaacc catatcagag ttccagaaca ggtaccacag ctttggtttt agattagtgg    4680
aataacattc agcccagaac tgagaaactc aacagattaa ctatcgtttg ctctttagac    4740
ggtctcactg cctctcactt gccagagccc tttcaaaatg agcagagaag tccacaccat    4800
tagggaccat ctgtgataaa ttcagaaggg aggagatgtg tgtacagctt taaggattcc    4860
ctcaattccg aggaaaggga ctggcccaga atccaggtta atacatggaa acacgaagca    4920
ttagcaaaag taataattat acctatggta tttgaaagaa caataataaa agacacttct    4980
tccaaacctt gaatttgttg tttttagaaa acgaatgcat ttaaaaatat tttctatgtg    5040 agaattttt agatgtgtgt ttacttcatg tttacaaata actgtttgct ttttaatgca    5100
```

-continued

```
gtactttgaa atatatcagc caaaaccata acttacaata atttcttagg tattctgaat   5160
aaaattccat ttcttttgga tatgctttac cattcttagg tttctgtgga acaaaaatat   5220
ttgtagcatt ttgtgtaaat acaagctttc atttttattt tttccaattg ctattgccca   5280
agaattgctt tccatgcaca tattgtaaaa attccgcttt gtgccacagg tcatgattgt   5340
ggatgagttt actcttaact tcaaagggac tatttgtatt gtatgttgca actgtaaatt   5400
gaattatttg gcatttttct catgattgta atattaattt gaagtttgaa tttaattttc   5460
aataaaatgg ctttttttggt tttgtta                                      5487

<210> SEQ ID NO 39
<211> LENGTH: 499
<212> TYPE: PRT
<213> ORGANISM: homo sapiens

<400> SEQUENCE: 39

Met Ala Ser Asn Ser Leu Phe Ser Thr Val Thr Pro Cys Gln Gln Asn
1               5                   10                  15

Phe Phe Trp Asp Pro Ser Thr Ser Arg Arg Phe Ser Pro Pro Ser Ser
            20                  25                  30

Ser Leu Gln Pro Gly Lys Met Ser Asp Val Ser Pro Val Val Ala Ala
        35                  40                  45

Gln Gln Gln Gln Gln Gln Gln Gln Gln Gln Gln Gln Gln Gln Gln Gln
    50                  55                  60

Gln Gln Gln Gln Gln Gln Glu Ala Ala Ala Ala Ala Ala Ala Ala Ala
65                  70                  75                  80

Ala Ala Ala Ala Ala Ala Ala Ala Val Pro Arg Leu Arg Pro Pro
                85                  90                  95

His Asp Asn Arg Thr Met Val Glu Ile Ile Ala Asp His Pro Ala Glu
            100                 105                 110

Leu Val Arg Thr Asp Ser Pro Asn Phe Leu Cys Ser Val Leu Pro Ser
        115                 120                 125

His Trp Arg Cys Asn Lys Thr Leu Pro Val Ala Phe Lys Val Val Ala
    130                 135                 140

Leu Gly Glu Val Pro Asp Gly Thr Val Val Thr Val Met Ala Gly Asn
145                 150                 155                 160

Asp Glu Asn Tyr Ser Ala Glu Leu Arg Asn Ala Ser Ala Val Met Lys
                165                 170                 175

Asn Gln Val Ala Arg Phe Asn Asp Leu Arg Phe Val Gly Arg Ser Gly
            180                 185                 190

Arg Gly Lys Ser Phe Thr Leu Thr Ile Thr Val Phe Thr Asn Pro Pro
        195                 200                 205

Gln Val Ala Thr Tyr His Arg Ala Ile Lys Val Thr Val Asp Gly Pro
    210                 215                 220

Arg Glu Pro Arg Arg His Arg Gln Lys Leu Asp Asp Ser Lys Pro Ser
225                 230                 235                 240

Leu Phe Ser Asp Arg Leu Ser Asp Leu Gly Arg Ile Pro His Pro Ser
                245                 250                 255

Met Arg Val Gly Val Pro Pro Gln Asn Pro Arg Pro Ser Leu Asn Ser
            260                 265                 270

Ala Pro Ser Pro Phe Asn Pro Gln Gly Gln Ser Gln Ile Thr Asp Pro
        275                 280                 285

Arg Gln Ala Gln Ser Ser Pro Pro Trp Ser Tyr Asp Gln Ser Tyr Pro
    290                 295                 300
```

```
Ser Tyr Leu Ser Gln Met Thr Ser Pro Ser Ile His Ser Thr Thr Pro
305                 310                 315                 320

Leu Ser Ser Thr Arg Gly Thr Gly Leu Pro Ala Ile Thr Asp Val Pro
                325                 330                 335

Arg Arg Ile Ser Gly Ala Ser Glu Leu Gly Pro Phe Ser Asp Pro Arg
            340                 345                 350

Gln Phe Pro Ser Ile Ser Ser Leu Thr Glu Ser Arg Phe Ser Asn Pro
        355                 360                 365

Arg Met His Tyr Pro Ala Thr Phe Thr Tyr Thr Pro Pro Val Thr Ser
    370                 375                 380

Gly Met Ser Leu Gly Met Ser Ala Thr Thr His Tyr His Thr Tyr Leu
385                 390                 395                 400

Pro Pro Pro Tyr Pro Gly Ser Ser Gln Ser Gln Ser Gly Pro Phe Gln
                405                 410                 415

Thr Ser Ser Thr Pro Tyr Leu Tyr Tyr Gly Thr Ser Ser Gly Ser Tyr
                420                 425                 430

Gln Phe Pro Met Val Pro Gly Gly Asp Arg Ser Pro Ser Arg Met Leu
        435                 440                 445

Pro Pro Cys Thr Thr Thr Ser Asn Gly Ser Thr Leu Leu Asn Pro Asn
    450                 455                 460

Leu Pro Asn Gln Asn Asp Gly Val Asp Ala Asp Gly Ser His Ser Ser
465                 470                 475                 480

Ser Pro Thr Val Leu Asn Ser Ser Gly Arg Met Asp Glu Ser Val Trp
                485                 490                 495

Arg Pro Tyr

<210> SEQ ID NO 40
<211> LENGTH: 2358
<212> TYPE: DNA
<213> ORGANISM: homo sapiens

<400> SEQUENCE: 40
aaactcacac aacaactctt ccccgctgag aggagacagc cagtgcgact ccaccctcca    60
gctcgacggc agccgccccg gccgacagcc ccgagacgac agcccggcgc gtcccggtcc   120
ccacctccga ccaccgccag cgctccaggc cccgccgctc cccgctcgcc gccaccgcgc   180
cctccgctcc gcccgcagtg ccaaccatga ccgccgccag tatgggcccc gtccgcgtcg   240
ccttcgtggt cctcctcgcc ctctgcagcc ggccggccgt cggccagaac tgcagcgggc   300
cgtgccggtg cccggacgag ccggcgccgc gctgccggc gggcgtgagc ctcgtgctgg   360
acggctgcgg ctgctgccgc gtctgcgcca gcagctgggc gagctgtgc accgagcgcg   420 accctgcga cccgcacaag ggcctcttct gtgacttcgg ctccccggcc aaccgcaaga   480
tcggcgtgtg caccgccaaa gatggtgctc cctgcatctt cggtggtacg gtgtaccgca   540
gcggagagtc cttccagagc agctgcaagt accagtgcac gtgcctggac ggggcggtgg   600
gctgcatgcc cctgtgcagc atggacgttc gtctgcccag ccctgactgc ccttcccga   660 ggagggtcaa gctgcccggg aaatgctgcg aggagtgggt gtgtgacgag cccaaggacc   720
aaaccgtggt tgggcctgcc ctcgcggctt accgactgga agacacgttt ggcccagacc   780
caactatgat tagagccaac tgcctggtcc agaccacaga gtggagcgcc tgttccaaga   840
cctgtgggat gggcatctcc acccgggtta ccaatgacaa cgcctcctgc aggctagaga   900
agcagagccg cctgtgcatg gtcaggcctt gcgaagctga cctggaagag aacattaaga   960
```

```
aggggcaaaaa gtgcatccgt actcccaaaa tctccaagcc tatcaagttt gagctttctg    1020
gctgcaccag catgaagaca taccgagcta aattctgtgg agtatgtacc gacggccgat    1080
gctgcacccc ccacagaacc accaccctgc cggtggagtt caagtgccct gacggcgagg    1140
tcatgaagaa gaacatgatg ttcatcaaga cctgtgcctg ccattacaac tgtcccggag    1200
acaatgacat ctttgaatcg ctgtactaca ggaagatgta cggagacatg gcatgaagcc    1260
agagagtgag agacattaac tcattagact ggaacttgaa ctgattcaca tctcattttt    1320
ccgtaaaaat gatttcagta gcacaagtta tttaaatctg ttttttctaac tgggggaaaa    1380 gattcccacc caattcaaaa cattgtgcca tgtcaaacaa atagtctatc aacccccagac    1440 actggtttga agaatgttaa gacttgacag tggaactaca ttagtacaca gcaccagaat    1500
gtatattaag gtgtggcttt aggagcagtg ggagggtacc agcagaaagg ttagtatcat    1560
cagatagcat cttatacgag taatatgcct gctatttgaa gtgtaattga aaggaaaaat    1620
tttagcgtgc tcactgacct gcctgtagcc ccagtgacag ctaggatgtg cattctccag    1680
ccatcaagag actgagtcaa gttgttcctt aagtcagaac agcagactca gctctgacat    1740
tctgattcga atgacactgt tcaggaatcg gaatcctgtc gattagactg gacagcttgt    1800
ggcaagtgaa tttgcctgta acaagccaga ttttttaaaa tttatattgt aaatattgtg    1860
tgtgtgtgtg tgtgtgtata tatatatata tgtacagtta tctaagttaa tttaaagttg    1920
tttgtgcctt tttattttg ttttaatgc tttgatattt caatgttagc ctcaatttct    1980
gaacaccata ggtagaatgt aaagcttgtc tgatcgttca aagcatgaaa tggatactta    2040
tatgaaaatt ctgctcagat agaatgacag tccgtcaaaa cagattgttt gcaaagggga    2100
ggcatcagtg tccttggcag gctgatttct aggtaggaaa tgtggtagcc tcactttaa    2160 tgaacaaatg gcctttatta aaaactgagt gactctatat agctgatcag tttttttcacc    2220 tggaagcatt tgtttctact ttgatatgac tgttttcgg acagtttatt tgttgagagt    2280
gtgaccaaaa gttacatgtt tgcacctttc tagttgaaaa taaagtgtat atttttccta    2340 taaaaaaaa aaaaaaaa                                                   2358
```

<210> SEQ ID NO 41
<211> LENGTH: 349
<212> TYPE: PRT
<213> ORGANISM: homo sapiens

<400> SEQUENCE: 41

```
Met Thr Ala Ala Ser Met Gly Pro Val Arg Val Ala Phe Val Val Leu
1               5                   10                  15

Leu Ala Leu Cys Ser Arg Pro Ala Val Gly Gln Asn Cys Ser Gly Pro
                20                  25                  30

Cys Arg Cys Pro Asp Glu Pro Ala Pro Arg Cys Pro Ala Gly Val Ser
            35                  40                  45

Leu Val Leu Asp Gly Cys Gly Cys Cys Arg Val Cys Ala Lys Gln Leu
        50                  55                  60

Gly Glu Leu Cys Thr Glu Arg Asp Pro Cys Asp Pro His Lys Gly Leu
65                  70                  75                  80

Phe Cys Asp Phe Gly Ser Pro Ala Asn Arg Lys Ile Gly Val Cys Thr
                85                  90                  95

Ala Lys Asp Gly Ala Pro Cys Ile Phe Gly Gly Thr Val Tyr Arg Ser
            100                 105                 110

Gly Glu Ser Phe Gln Ser Ser Cys Lys Tyr Gln Cys Thr Cys Leu Asp
        115                 120                 125
```

```
Gly Ala Gly Cys Met Pro Leu Cys Ser Met Asp Val Arg Leu Pro
        130                 135                 140

Ser Pro Asp Cys Pro Phe Pro Arg Arg Val Lys Leu Pro Gly Lys Cys
145                 150                 155                 160

Cys Glu Glu Trp Val Cys Asp Glu Pro Lys Asp Gln Thr Val Val Gly
                165                 170                 175

Pro Ala Leu Ala Ala Tyr Arg Leu Glu Asp Thr Phe Gly Pro Asp Pro
                180                 185                 190

Thr Met Ile Arg Ala Asn Cys Leu Val Gln Thr Thr Glu Trp Ser Ala
        195                 200                 205

Cys Ser Lys Thr Cys Gly Met Gly Ile Ser Thr Arg Val Thr Asn Asp
    210                 215                 220

Asn Ala Ser Cys Arg Leu Glu Lys Gln Ser Arg Leu Cys Met Val Arg
225                 230                 235                 240

Pro Cys Glu Ala Asp Leu Glu Glu Asn Ile Lys Lys Gly Lys Lys Cys
                245                 250                 255

Ile Arg Thr Pro Lys Ile Ser Lys Pro Ile Lys Phe Glu Leu Ser Gly
                260                 265                 270

Cys Thr Ser Met Lys Thr Tyr Arg Ala Lys Phe Cys Gly Val Cys Thr
        275                 280                 285

Asp Gly Arg Cys Cys Thr Pro His Arg Thr Thr Thr Leu Pro Val Glu
    290                 295                 300

Phe Lys Cys Pro Asp Gly Glu Val Met Lys Lys Asn Met Met Phe Ile
305                 310                 315                 320

Lys Thr Cys Ala Cys His Tyr Asn Cys Pro Gly Asp Asn Asp Ile Phe
                325                 330                 335

Glu Ser Leu Tyr Tyr Arg Lys Met Tyr Gly Asp Met Ala
                340                 345

<210> SEQ ID NO 42
<211> LENGTH: 430
<212> TYPE: PRT
<213> ORGANISM: homo sapiens

<400> SEQUENCE: 42

Met Gln Arg Ser Arg Ala Gly Ala Asp Glu Ala Ala Leu Leu Leu Ala
1               5                   10                  15

Gly Leu Ala Leu Arg Glu Leu Glu Pro Gly Cys Gly Ser Pro Gly Arg
                20                  25                  30

Gly Arg Arg Gly Pro Arg Pro Gly Pro Gly Asp Glu Ala Ala Pro Ala
        35                  40                  45

Leu Gly Arg Arg Gly Lys Gly Ser Gly Pro Glu Ala Gly Ala Asp
    50                  55                  60

Gly Leu Ser Arg Gly Glu Arg Gly Pro Arg Arg Ala Ala Val Pro Glu
65                  70                  75                  80

Leu Ser Ala Gln Pro Ala Gly Ser Pro Arg Ala Ser Leu Ala Gly Ser
                85                  90                  95

Asp Gly Gly Gly Gly Gly Ser Ala Arg Ser Ser Gly Ile Ser Leu
                100                 105                 110

Gly Tyr Asp Gln Arg His Gly Ser Pro Arg Ser Gly Arg Ser Asp Pro
        115                 120                 125

Arg Pro Gly Pro Gly Pro Pro Ser Val Gly Ser Ala Arg Ser Ser Val
    130                 135                 140
```

```
Ser Ser Leu Gly Ser Arg Gly Ser Ala Gly Ala Tyr Ala Asp Phe Leu
145                 150                 155                 160

Pro Pro Gly Ala Cys Pro Ala Pro Ala Arg Ser Pro Glu Pro Ala Gly
            165                 170                 175

Pro Ala Pro Phe Pro Leu Pro Ala Leu Pro Leu Pro Pro Gly Arg Glu
        180                 185                 190

Gly Gly Pro Ser Ala Ala Glu Arg Arg Leu Glu Ala Leu Thr Arg Glu
    195                 200                 205

Leu Glu Arg Ala Leu Glu Ala Arg Thr Ala Arg Asp Tyr Phe Gly Ile
210                 215                 220

Cys Ile Lys Cys Gly Leu Gly Ile Tyr Gly Ala Gln Gln Ala Cys Gln
225                 230                 235                 240

Ala Met Gly Ser Leu Tyr His Thr Asp Cys Phe Thr Cys Asp Ser Cys
            245                 250                 255

Gly Arg Arg Leu Arg Gly Lys Ala Phe Tyr Asn Val Gly Glu Lys Val
            260                 265                 270

Tyr Cys Gln Glu Asp Phe Leu Tyr Ser Gly Phe Gln Gln Thr Ala Asp
        275                 280                 285

Lys Cys Ser Val Cys Gly His Leu Ile Met Glu Met Ile Leu Gln Ala
290                 295                 300

Leu Gly Lys Ser Tyr His Pro Gly Cys Phe Arg Cys Ser Val Cys Asn
305                 310                 315                 320

Glu Cys Leu Asp Gly Val Pro Phe Thr Val Asp Val Glu Asn Asn Ile
            325                 330                 335

Tyr Cys Val Arg Asp Tyr His Thr Val Phe Ala Pro Lys Cys Ala Ser
            340                 345                 350

Cys Ala Arg Pro Ile Leu Pro Ala Gln Gly Cys Glu Thr Thr Ile Arg
        355                 360                 365

Val Val Ser Met Asp Arg Asp Tyr His Val Ala Cys Tyr His Cys Glu
370                 375                 380

Asp Cys Gly Leu Gln Leu Ser Gly Glu Glu Gly Arg Arg Cys Tyr Pro
385                 390                 395                 400

Leu Ala Gly His Leu Leu Cys Arg Arg Cys His Leu Arg Arg Leu Gln
            405                 410                 415

Pro Gly Pro Leu Pro Ser Pro Thr Val His Val Thr Glu Leu
        420                 425                 430

<210> SEQ ID NO 43
<211> LENGTH: 2204
<212> TYPE: DNA
<213> ORGANISM: homo sapiens

<400> SEQUENCE: 43
atgcagcgct ccagggcggg cgcggacgag gcggccctac tcctggccgg gctggccctg      60
cgggagctgg agcccgggtg cggctctccc ggtcggggc ggcgggggcc gcggcctggg      120
cctggagacg aggcggcgcc gcgctgggc cgcagaggga agggcagcgg cggccccgag       180
gccggggcgg acggactgag ccgcggggag cggggtcccc ggcgcgcggc ggttccggag      240
ctcagcgcgc agcctgcggg cagcccacgg gccagcctgg cggggtccga cggcggcggc      300
ggtggcggca gcgcccgatc cagcggcatc agcctgggct acgaccagcg ccacggcagc      360
ccgcgctccg gtcgctcgga cccgcgtccc gtcccgggc gccttcggt gggcagcgcc       420 cgctccagcg tttccagcct cggctcccgg ggctcggccg gcgcctacgc tgacttcctc      480
```

```
ccgcccggcg cctgccccgc gcccgctcgc tccccggagc ctgcggggcc ggctcccttc    540
ccgctgcctg cactcccgct gcccctggcc cgggagggcg gcccaagcgc ggccgagcgg    600
cggctggagg cgctcacccg ggagctggag cgggcgctcg aggcgcgcac ggcgcgggac    660
tacttcggca tttgcatcaa gtgtgggctt ggcatctacg gagcccagca ggcgtgccag    720
gcaatgggga gtctttatca cactgactgc ttcacctgcg actcgtgtgg gagacgactc    780
cgtgggaagg cgttctacaa cgtgggtgag aaagtgtact gccaggagga cttcctgtac    840
tccgggttcc agcagacggc cgacaaatgc agcgtgtgtg gacatctcat catggaaatg    900
atcctgcagg ccctgggcaa gtcctaccac ccaggctgct ccggtgctc cgtgtgcaat    960
gagtgcctgg acggggttcc cttcaccgtg gacgtggaga caacatcta ctgcgtgcga   1020
gactatcaca cggttttgc accaaaatgc gcctcctgtg cccgtcctat cctccctgca   1080
cagggctgcg agacaaccat ccgtgtggtg tccatggaca gagactacca cgtggcatgt   1140
taccactgtg aggactgcgg gctgcagctg agcggggagg agggacgccg ttgctatccc   1200
ctggcgggcc acctactgtg tcgtcgttgc cacctgcggc gcctccaacc tgggcctctt   1260
ccctcaccca ctgtgcacgt cactgagctc tgagcagggg aaaacccgtc cctgggccgg   1320
ggtgggtgtg ggtgtggagg gagggcccgc gtgggtggcc ctggtcagcg tcaggggagc   1380
tccctccaat cagtttccca ccgagctgct gtctgcaggg gccggacccc cgcgtggaag   1440
cttctattta ttcaccgtct gtgcctgctc aagtcacttc cctgcgggcc ctgcctccca   1500
cccaccccat caccagcttt ccacttggag gcccctgtg cctgcagcc tcagggtagg    1560
ccgtgggtca ccaggctgga gagggcccct gccttggcca ggggtgcgag gtgacccggc   1620
tgcattgctg ggtgggagct gctgtctgtt gttcaggggc ctggcccccg ccctccccc    1680
cgaccccgac ctcgcaaagc gcactcccgg gcagggtgtg gtctggaagg cggggctggc   1740
ggggacatgg gtgttcctgc atctcctagc gcagttcctg ctggtgggtg aagggtgcc    1800
tggtttaggc ggggtcccag gagggggtga ggggtgacac ccttggggag ggggcctgca   1860
aagggcactg cctgtggcca cgtggtgtct gtgggaattg gtcctgggga ctttgatggg   1920
tgtttgcggc cccagttgcc gccctgctcc ctcttccagg gctcctggct tgggccccc    1980
gacccccctg ctcagctcgg gaaaatcccc gtgcggctcc agccccgggt cacgctcagg   2040
agcgatgaga ggggcgccct ggccacgctt caggaaagcc tgtgtctgcg cgcggggcaa   2100
ggggctccac gacaaaagga caagatttga cttaaattaa gttttttccct tgaggatatt   2160
ttcattttct ttaaaagaat ataattttct tctaagatct tgga                    2204
```

<210> SEQ ID NO 44
<211> LENGTH: 335
<212> TYPE: PRT
<213> ORGANISM: homo sapiens

<400> SEQUENCE: 44

```
Met Asp Asn Ala Arg Met Asn Ser Phe Leu Glu Tyr Pro Ile Leu Ser
1               5                   10                  15

Ser Gly Asp Ser Gly Thr Cys Ser Ala Arg Ala Tyr Pro Ser Asp His
            20                  25                  30

Arg Ile Thr Thr Phe Gln Ser Cys Ala Val Ser Ala Asn Ser Cys Gly
        35                  40                  45

Gly Asp Asp Arg Phe Leu Val Gly Arg Gly Val Gln Ile Gly Ser Pro
    50                  55                  60
```

His His His His His His His His Pro Gln Pro Ala Thr Tyr
65                  70                  75                  80

Gln Thr Ser Gly Asn Leu Gly Val Ser Tyr Ser His Ser Cys Gly
                85                  90                  95

Pro Ser Tyr Gly Ser Gln Asn Phe Ser Ala Pro Tyr Ser Pro Tyr Ala
            100                 105                 110

Leu Asn Gln Glu Ala Asp Val Ser Gly Gly Tyr Pro Gln Cys Ala Pro
        115                 120                 125

Ala Val Tyr Ser Gly Asn Leu Ser Ser Pro Met Val Gln His His His
130                 135                 140

His His Gln Gly Tyr Ala Gly Gly Ala Val Gly Ser Pro Gln Tyr Ile
145                 150                 155                 160

His His Ser Tyr Gly Gln Glu His Gln Ser Leu Ala Leu Ala Thr Tyr
                165                 170                 175

Asn Asn Ser Leu Ser Pro Leu His Ala Ser His Gln Glu Ala Cys Arg
            180                 185                 190

Ser Pro Ala Ser Glu Thr Ser Ser Pro Ala Gln Thr Phe Asp Trp Met
        195                 200                 205

Lys Val Lys Arg Asn Pro Pro Lys Thr Gly Lys Val Gly Glu Tyr Gly
210                 215                 220

Tyr Leu Gly Gln Pro Asn Ala Val Arg Thr Asn Phe Thr Thr Lys Gln
225                 230                 235                 240

Leu Thr Glu Leu Glu Lys Glu Phe His Phe Asn Lys Tyr Leu Thr Arg
                245                 250                 255

Ala Arg Arg Val Glu Ile Ala Ala Ser Leu Gln Leu Asn Glu Thr Gln
            260                 265                 270

Val Lys Ile Trp Phe Gln Asn Arg Arg Met Lys Gln Lys Lys Arg Glu
        275                 280                 285

Lys Glu Gly Leu Leu Pro Ile Ser Pro Ala Thr Pro Pro Gly Asn Asp
290                 295                 300

Glu Lys Ala Glu Glu Ser Ser Glu Lys Ser Ser Ser Pro Cys Val
305                 310                 315                 320

Pro Ser Pro Gly Ser Ser Thr Ser Asp Thr Leu Thr Thr Ser His
            325                 330                 335

<210> SEQ ID NO 45
<211> LENGTH: 2561
<212> TYPE: DNA
<213> ORGANISM: homo sapiens

<400> SEQUENCE: 45
attcatatca ttttctttct ccggccccat ggaggaagtg agaaagttgg cacagtcacg      60
ccgggcttcg caggaccagg tcactcagtg acagatggac aatgcaagaa tgaactcctt     120
cctggaatac cccatactta gcagtggcga ctcggggacc tgctcagccc gagcctaccc     180
ctcggaccat aggattacaa ctttccagtc gtgcgcggtc agcgccaaca gttgcggcgg     240
cgacgaccgc ttcctagtgg cagggggggt gcagatcggt tcgccccacc accaccacca     300
ccaccaccat caccaccccc agccggctac ctaccagact ccggggaacc tgggggtgtc     360
ctactcccac tcaagttgtg gtccaagcta tggctcacag aacttcagtg cgccttacag     420
cccctacgcg ttaaatcagg aagcagacgt aagtggtggg tacccccagt gcgctcccgc     480
tgtttactct ggaaatctct catctcccat ggtccagcat caccaccacc accagggtta     540
tgctgggggc gcggtgggct cgcctcaata cattcaccac tcatatggac aggagcacca     600

```
gagcctggcc ctggctacgt ataataactc cttgtcccct ctccacgcca gccaccaaga    660
agcctgtcgc tcccccgcat cggagacatc ttctccagcg cagacttttg actggatgaa    720
agtcaaaaga aaccctccca aaacagggaa agttggagag tacggctacc tgggtcaacc    780
caacgcggtg cgcaccaact tcactaccaa gcagctcacg gaactggaga aggagttcca    840
cttcaacaag tacctgacgc gcgcccgcag ggtggagatc gctgcatccc tgcagctcaa    900
cgagacccaa gtgaagatct ggttccagaa ccgccgaatg aagcaaaaga acgtgagaa     960 ggagggtctc ttgcccatct ctccggccac cccgccagga acgacgaga aggccgagga     1020 atcctcagag aagtccagct cttcgccctg cgttccttcc ccggggtctt ctacctcaga    1080
cactctgact acctcccact gaggcggctc cagccccaga caacagccca ggcatctcct    1140
tgggctggga cttcttaccc aaagcacatg cttagcttat ctttctttcc atttacagtc    1200
tctttcttcc tttctaatcc tatctgggga gctcctggcc aggataatat atttgcagat    1260
aattctggac cagagacttg gtgcgggggtt aacaccttca tccagattgg gtgccagcat    1320 acatttctg gtgggcctta acatccctcc tgcttttagg agaattcaca gaacctactg     1380
ttcctttcag atgaccttttt ggaaaatagt tcccttttgcc aacagaaaca tgccagaagg    1440
aatcttctca tcttttatct aactatatgt acagctctcc cctcccttgt ccttgaaagt    1500
aggatatagc gaaaggcgag tccaggagct caggaagaag agatgcacta tatgtttaca    1560
caattaattc atcccttaat ttaagtcatt ttcatgtgtg tgagtttgct ggttgtaaat    1620
actttgtcct aagagattta tctttataca gattttctag aaatgtttag gttactaaaa    1680
cagggtgggc aaactctcta aactggtaca attttatagg tgaaagaaaa aattccctca    1740
tttaaaccca atcagatgcc tcagagggta gccttgattt gttcttacag ttaagaagcc    1800
ctgcagagca caaacttcag aaacccggct tcctgtgcta agtctttccc aatctctacc    1860
cctttcttct cgggccaccc tctgtttaaa atttgtgctg ggttattcag aacctaaaag    1920
tattattcaa accaatttct tccttccaca gttatcttag ctggatataa tgtattttca    1980
gctcaattgt taatgtgatg gatggcacaa tgaatgtata ttttgtgtta ttcgtgaata    2040
gtcttttgca tgtcgcacaa tgtttgatgt ccccaaagta ccacactgag ttctatcagt    2100
tatcctttgt gagcctatga tattccccat ttcctgtaca atcatgaaca gctctgagat    2160
cctggagtga tatgatccag agcagagttt acgggtctta ggatgtctgt aataaataaa    2220
tatactcaag tttcaggtat gcttaagcat ccgtgtattt ggctgggcta caatttgtta    2280
attcctatga agttggcaca tttcatgagg ggaaagggag aagggtggta atatttttca    2340
aagagatggg cctttttcttg aataaaagtt aataacagct cctttattat aatcaaagct    2400
cataatggaa aaaagactg atgaagaaat ttatgaagca gatttatttt tgaaacaaac    2460
atggatactt cctgggtcaa gtgctaacct tttcacctcc aactggatgt tgacgtatat    2520
ataaacagaa ctcccttcaa aagccaaaaa aaaaaaaaa a                        2561
```

<210> SEQ ID NO 46
<211> LENGTH: 137
<212> TYPE: PRT
<213> ORGANISM: homo sapiens

<400> SEQUENCE: 46

Met Asp Asn Ala Arg Met Asn Ser Phe Leu Glu Tyr Pro Ile Leu Ser
1               5                   10                  15

```
Ser Gly Asp Ser Gly Thr Cys Ser Ala Arg Ala Tyr Pro Ser Asp His
        20                  25                  30
Arg Ile Thr Thr Phe Gln Ser Cys Ala Val Ser Ala Asn Ser Cys Gly
            35                  40                  45
Gly Asp Asp Arg Phe Leu Val Gly Arg Gly Val Gln Ile Gly Ser Pro
 50                  55                  60
His His His His His His His His Pro Gln Pro Ala Thr Tyr
 65                  70                  75                  80
Gln Thr Ser Gly Asn Leu Gly Val Ser Tyr Ser His Ser Ser Cys Gly
                85                  90                  95
Pro Ser Tyr Gly Ser Gln Asn Phe Ser Ala Pro Tyr Ser Pro Tyr Ala
            100                 105                 110
Leu Asn Gln Glu Ala Asp Pro Pro Arg Ser Leu Ser Leu Pro Arg Ile
        115                 120                 125
Gly Asp Ile Phe Ser Ser Ala Asp Phe
    130                 135
```

<210> SEQ ID NO 47
<211> LENGTH: 2358
<212> TYPE: DNA
<213> ORGANISM: homo sapiens

<400> SEQUENCE: 47

```
attcatatca ttttcttct ccggccccat ggaggaagtg agaaagttgg cacagtcacg      60
ccgggcttcg caggaccagg tcactcagtg acagatggac aatgcaagaa tgaactcctt    120
cctggaatac cccatactta gcagtggcga ctcggggacc tgctcagccc gagcctaccc    180
ctcggaccat aggattacaa ctttccagtc gtgcgcggtc agcgccaaca gttgcgcggg    240
cgacgaccgc ttcctagtgg gcaggggggt gcagatcggt cgccccacc accaccacca    300
ccaccaccat cacccccccc agccggctac ctaccagact ccggaacc tgggggtgtc     360
ctactcccac tcaagttgtg gtccaagcta tggctcacag aacttcagtg cgccttacag    420
cccctacgcg ttaaatcagg aagcagaccc accaagaagc ctgtcgctcc cccgcatcgg    480
agacatcttc tccagcgcag acttttgact ggatgaaagt caaaagaaac cctcccaaaa    540
cagggaaagt tggagagtac ggctacctgg tcaacccaa cgcggtgcgc accaacttca    600
ctaccaagca gctcacggaa ctggagaagg agttccactt caacaagtac ctgacgcgcg    660
cccgcagggt ggagatcgct gcatccctgc agctcaacga dcccaagtg aagatctggt    720
tccagaaccg ccgaatgaag caaaagaaac gtgagaagga gggtctcttg cccatctctc    780
cggccacccc gccaggaaac gacgagaagg ccgaggaatc ctcagagaag tccagctctt    840
cgccctgcgt tccttcccg gggtcttcta cctcagacac tctgactacc tcccactgag    900
gcggctccag ccccagacaa cagcccaggc atctccttgg gctgggactt cttacccaaa    960
gcacatgctt agcttatctt tctttccatt tacagtctct ttcttccttt ctaatcctat   1020
ctggggagct cctggccagg ataatatatt tgcagataat tctggaccag agacttggtg   1080
cggggttaac accttcatcc agattgggtg ccagcataca ttttctggtg ggccttaaca   1140
tccctcctgc ttttaggaga attcacgaaa cctactgttc ctttcagatg accttttgga   1200
aaatagttcc ctttgccaac agaaacatgc cagaaggaat cttctcatct tttatctaac   1260
tatatgtaca gctctcccct cccttgtcct tgaaagtagg atatagcgaa aggcgagtcc   1320
aggagctcag gaagaagaga tgcactatat gtttacacaa ttaattcatc ccttaattta   1380
```

```
agtcattttc atgtgtgtga gtttgctggt tgtaaatact ttgtcctaag agatttatct    1440
ttatacagat tttctagaaa tgtttaggtt actaaaacag ggtgggcaaa ctctctaaac    1500
tggtacaatt ttataggtga agaaaaaaat tccctcattt aaacccaatc agatgcctca    1560
gagggtagcc ttgatttgtt cttacagtta agaagccctg cagagcacaa acttcagaaa    1620
cccggcttcc tgtgctaagt ctttcccaat ctctaccct ttcttctcgg gccaccctct     1680
gtttaaaatt tgtgctgggt tattcagaac ctaaaagtat tattcaaacc aatttcttcc    1740
ttccacagtt atcttagctg gatataatgt attttcagct caattgttaa tgtgatggat    1800
ggcacaatga atgtatattt tgtgttattc gtgaatagtc ttttgcatgt cgcacaatgt    1860
ttgatgtccc caaagtacca cactgagttc tatcagttat cctttgtgag cctatgatat    1920
tccccatttc ctgtacaatc atgaacagct ctgagatcct ggagtgatat gatccagagc    1980
agagtttacg ggtcttagga tgtctgtaat aaataaatat actcaagttt caggtatgct    2040
taagcatccg tgtatttggc tgggctacaa tttgttaatt cctatgaagt tggcacattt    2100
catgagggga aagggagaag ggtggtaaat attttcaaag agatgggcct tttcttgaat    2160
aaaagttaat aacagctcct ttattataat caaagctcat aatggaaaaa aagactgatg    2220
aagaaattta tgaagcagat ttattttga aacaaacatg gatacttcct gggtcaagtg     2280
ctaacctttt cacctccaac tggatgttga cgtatatata aacagaactc ccttcaaaag    2340
ccaaaaaaaa aaaaaaaa                                                  2358
```

<210> SEQ ID NO 48
<211> LENGTH: 508
<212> TYPE: PRT
<213> ORGANISM: homo sapiens
<220> FEATURE:
<221> NAME/KEY: MISC_FEATURE
<222> LOCATION: (127)..(127)
<223> OTHER INFORMATION: can be phosphorylated

<400> SEQUENCE: 48

```
Met Asp Pro Gly Gln Gln Pro Pro Gln Pro Ala Pro Gln Gly Gln
1               5                   10                  15

Gly Gln Pro Pro Ser Gln Pro Gln Gly Gly Pro Pro Ser Gly
            20                  25                  30

Pro Gly Gln Pro Ala Pro Ala Thr Gln Ala Ala Pro Gln Ala Pro
        35                  40                  45

Pro Ala Gly His Gln Ile Val His Val Arg Gly Asp Ser Glu Thr Asp
    50                  55                  60

Leu Glu Ala Leu Phe Asn Ala Val Met Asn Pro Lys Thr Ala Asn Val
65                  70                  75                  80

Pro Gln Thr Val Pro Met Arg Leu Arg Lys Leu Pro Asp Ser Phe Phe
                85                  90                  95

Lys Pro Pro Glu Pro Lys Ser His Ser Arg Gln Ala Ser Thr Asp Ala
            100                 105                 110

Gly Thr Ala Gly Ala Leu Thr Pro Gln His Val Arg Ala His Ser Ser
        115                 120                 125

Pro Ala Ser Leu Gln Leu Gly Ala Val Ser Pro Gly Thr Leu Thr Pro
    130                 135                 140

Thr Gly Val Val Ser Gly Pro Ala Ala Thr Pro Thr Ala Gln His Leu
145                 150                 155                 160

Arg Gln Ser Ser Phe Glu Ile Pro Asp Asp Val Pro Leu Pro Ala Gly
                165                 170                 175
```

```
Trp Glu Met Ala Lys Thr Ser Ser Gly Gln Arg Tyr Phe Leu Asn His
            180                 185                 190

Ile Asp Gln Thr Thr Thr Trp Gln Asp Pro Arg Lys Ala Met Leu Ser
        195                 200                 205

Gln Met Asn Val Thr Ala Pro Thr Ser Pro Pro Val Gln Gln Asn Met
    210                 215                 220

Met Asn Ser Ala Ser Gly Pro Leu Pro Asp Gly Trp Glu Gln Ala Met
225                 230                 235                 240

Thr Gln Asp Gly Glu Ile Tyr Tyr Ile Asn His Lys Asn Lys Thr Thr
                245                 250                 255

Ser Trp Leu Asp Pro Arg Leu Asp Pro Arg Phe Ala Met Asn Gln Arg
            260                 265                 270

Ile Ser Gln Ser Ala Pro Val Lys Gln Pro Pro Leu Ala Pro Gln
        275                 280                 285

Ser Pro Gln Gly Gly Val Met Gly Gly Ser Asn Ser Asn Gln Gln Gln
    290                 295                 300

Gln Met Arg Leu Gln Gln Leu Gln Met Glu Lys Glu Arg Leu Arg Leu
305                 310                 315                 320

Lys Gln Gln Glu Leu Leu Arg Gln Val Arg Pro Gln Ala Met Arg Asn
                325                 330                 335

Ile Asn Pro Ser Thr Ala Asn Ser Pro Lys Cys Gln Glu Leu Ala Leu
            340                 345                 350

Arg Ser Gln Leu Pro Thr Leu Glu Gln Asp Gly Gly Thr Gln Asn Pro
        355                 360                 365

Val Ser Ser Pro Gly Met Ser Gln Glu Leu Arg Thr Met Thr Thr Asn
    370                 375                 380

Ser Ser Asp Pro Phe Leu Asn Ser Gly Thr Tyr His Ser Arg Asp Glu
385                 390                 395                 400

Ser Thr Asp Ser Gly Leu Ser Met Ser Ser Tyr Ser Val Pro Arg Thr
                405                 410                 415

Pro Asp Asp Phe Leu Asn Ser Val Asp Glu Met Asp Thr Gly Asp Thr
            420                 425                 430

Ile Asn Gln Ser Thr Leu Pro Ser Gln Gln Asn Arg Phe Pro Asp Tyr
        435                 440                 445

Leu Glu Ala Ile Pro Gly Thr Asn Val Asp Leu Gly Thr Leu Glu Gly
    450                 455                 460

Asp Gly Met Asn Ile Glu Gly Glu Glu Leu Met Pro Ser Leu Gln Glu
465                 470                 475                 480

Ala Leu Ser Ser Asp Ile Leu Asn Asp Met Glu Ser Val Leu Ala Ala
                485                 490                 495

Thr Lys Leu Asp Lys Glu Ser Phe Leu Thr Trp Leu
            500                 505

<210> SEQ ID NO 49
<211> LENGTH: 20
<212> TYPE: PRT
<213> ORGANISM: Artificial sequence
<220> FEATURE:
<223> OTHER INFORMATION: Cell Permeable Caspase-3 Inhibitor I
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (20)..(20)
<223> OTHER INFORMATION: C' aldehyde conjugated peptide
```

```
<400> SEQUENCE: 49

Ala Ala Val Ala Leu Leu Pro Ala Val Leu Leu Ala Leu Leu Ala Pro
1               5                   10                  15

Asp Glu Val Asp
            20

<210> SEQ ID NO 50
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 50
gcgacctgga agtccaacta                                             20

<210> SEQ ID NO 51
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 51
atctgcttgg agcccacat                                              19

<210> SEQ ID NO 52
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 52
gcatcaagtg tgggcttggc                                             20

<210> SEQ ID NO 53
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 53
gttgtagaac gccttcccac                                             20

<210> SEQ ID NO 54
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 54
gcagatgcta cggaccttac g                                           21

<210> SEQ ID NO 55
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 55
gacactgagt aacacatgct cc                                          22
```

```
<210> SEQ ID NO 56
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 56
tcaggtgtac tgctccaagg                                               20

<210> SEQ ID NO 57
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 57
cagctgcacc ttagtgtagg g                                             21

<210> SEQ ID NO 58
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 58
tctcgttgcc ctaattcatc tttt                                          24

<210> SEQ ID NO 59
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 59
cattcaggac aaagagatga acagaa                                        26

<210> SEQ ID NO 60
<211> LENGTH: 906
<212> TYPE: PRT
<213> ORGANISM: Homo sapiens

<400> SEQUENCE: 60

Met Thr Ala Val His Ala Gly Asn Ile Asn Phe Lys Trp Asp Pro Lys
1               5                   10                  15

Ser Leu Glu Ile Arg Thr Leu Ala Val Glu Arg Leu Leu Glu Pro Leu
                20                  25                  30

Val Thr Gln Val Thr Thr Leu Val Asn Thr Asn Ser Lys Gly Pro Ser
            35                  40                  45

Asn Lys Lys Arg Gly Arg Ser Lys Lys Ala His Val Leu Ala Ala Ser
        50                  55                  60

Val Glu Gln Ala Thr Glu Asn Phe Leu Glu Lys Gly Asp Lys Ile Ala
65                  70                  75                  80

Lys Glu Ser Gln Phe Leu Lys Glu Glu Leu Val Ala Ala Val Glu Asp
                85                  90                  95

Val Arg Lys Gln Gly Asp Leu Met Lys Ala Ala Ala Gly Glu Phe Ala
                100                 105                 110
```

```
Asp Asp Pro Cys Ser Ser Val Lys Arg Gly Asn Met Val Arg Ala Ala
            115                 120                 125

Arg Ala Leu Leu Ser Ala Val Thr Arg Leu Leu Ile Leu Ala Asp Met
    130                 135                 140

Ala Asp Val Tyr Lys Leu Leu Val Gln Leu Lys Val Val Glu Asp Gly
145                 150                 155                 160

Ile Leu Lys Leu Arg Asn Ala Gly Asn Glu Gln Asp Leu Gly Ile Gln
                165                 170                 175

Tyr Lys Ala Leu Lys Pro Glu Val Asp Lys Leu Asn Ile Met Ala Ala
            180                 185                 190

Lys Arg Gln Gln Glu Leu Lys Asp Val Gly His Arg Asp Gln Met Ala
    195                 200                 205

Ala Ala Arg Gly Ile Leu Gln Lys Asn Val Pro Ile Leu Tyr Thr Ala
210                 215                 220

Ser Gln Ala Cys Leu Gln His Pro Asp Val Ala Ala Tyr Lys Ala Asn
225                 230                 235                 240

Arg Asp Leu Ile Tyr Lys Gln Leu Gln Gln Ala Val Thr Gly Ile Ser
                245                 250                 255

Asn Ala Ala Gln Ala Thr Ala Ser Asp Asp Ala Ser Gln His Gln Gly
            260                 265                 270

Gly Gly Gly Gly Glu Leu Ala Tyr Ala Leu Asn Asn Phe Asp Lys Gln
    275                 280                 285

Ile Ile Val Asp Pro Leu Ser Phe Ser Glu Glu Arg Phe Arg Pro Ser
290                 295                 300

Leu Glu Glu Arg Leu Glu Ser Ile Ile Ser Gly Ala Ala Leu Met Ala
305                 310                 315                 320

Asp Ser Ser Cys Thr Arg Asp Asp Arg Arg Glu Arg Ile Val Ala Glu
                325                 330                 335

Cys Asn Ala Val Arg Gln Ala Leu Gln Asp Leu Leu Ser Glu Tyr Met
            340                 345                 350

Gly Asn Ala Gly Arg Lys Glu Arg Ser Asp Ala Leu Asn Ser Ala Ile
    355                 360                 365

Asp Lys Met Thr Lys Lys Thr Arg Asp Leu Arg Arg Gln Leu Arg Lys
370                 375                 380

Ala Val Met Asp His Val Ser Asp Ser Phe Leu Glu Thr Asn Val Pro
385                 390                 395                 400

Leu Leu Val Leu Ile Glu Ala Ala Lys Asn Gly Asn Glu Lys Glu Val
                405                 410                 415

Lys Glu Tyr Ala Gln Val Phe Arg Glu His Ala Asn Lys Leu Ile Glu
            420                 425                 430

Val Ala Asn Leu Ala Cys Ser Ile Ser Asn Asn Glu Glu Gly Val Lys
    435                 440                 445

Leu Val Arg Met Ser Ala Ser Gln Leu Glu Ala Leu Cys Pro Gln Val
450                 455                 460

Ile Asn Ala Ala Leu Ala Leu Ala Ala Lys Pro Gln Ser Lys Leu Ala
465                 470                 475                 480

Gln Glu Asn Met Asp Leu Phe Lys Glu Gln Trp Glu Lys Gln Val Arg
                485                 490                 495

Val Leu Thr Asp Ala Val Asp Asp Ile Thr Ser Ile Asp Asp Phe Leu
            500                 505                 510

Ala Val Ser Glu Asn His Ile Leu Glu Asp Val Asn Lys Cys Val Ile
    515                 520                 525
```

```
Ala Leu Gln Glu Lys Asp Val Asp Gly Leu Asp Arg Thr Ala Gly Ala
        530                 535                 540
Ile Arg Gly Arg Ala Ala Arg Val Ile His Val Val Thr Ser Glu Met
545                 550                 555                 560
Asp Asn Tyr Glu Pro Gly Val Tyr Thr Glu Lys Val Leu Glu Ala Thr
                565                 570                 575
Lys Leu Leu Ser Asn Thr Val Met Pro Arg Phe Thr Glu Gln Val Glu
            580                 585                 590
Ala Ala Val Glu Ala Leu Ser Ser Asp Pro Ala Gln Pro Met Asp Glu
        595                 600                 605
Asn Glu Phe Ile Asp Ala Ser Arg Leu Val Tyr Asp Gly Ile Arg Asp
610                 615                 620
Ile Arg Lys Ala Val Leu Met Ile Arg Thr Pro Glu Glu Leu Asp Asp
625                 630                 635                 640
Ser Asp Phe Glu Thr Glu Asp Phe Asp Val Arg Ser Arg Thr Ser Val
                645                 650                 655
Gln Thr Glu Asp Asp Gln Leu Ile Ala Gly Gln Ser Ala Arg Ala Ile
            660                 665                 670
Met Ala Gln Leu Pro Gln Glu Gln Lys Ala Lys Ile Ala Glu Gln Val
        675                 680                 685
Ala Ser Phe Gln Glu Glu Lys Ser Lys Leu Asp Ala Glu Val Ser Lys
        690                 695                 700
Trp Asp Asp Ser Gly Asn Asp Ile Ile Val Leu Ala Lys Gln Met Cys
705                 710                 715                 720
Met Ile Met Met Glu Met Thr Asp Phe Thr Arg Gly Lys Gly Pro Leu
                725                 730                 735
Lys Asn Thr Ser Asp Val Ile Ser Ala Ala Lys Lys Ile Ala Glu Ala
            740                 745                 750
Gly Ser Arg Met Asp Lys Leu Gly Arg Thr Ile Ala Asp His Cys Pro
        755                 760                 765
Asp Ser Ala Cys Lys Gln Asp Leu Leu Ala Tyr Leu Gln Arg Ile Ala
        770                 775                 780
Leu Tyr Cys His Gln Leu Asn Ile Cys Ser Lys Val Lys Ala Glu Val
785                 790                 795                 800
Gln Asn Leu Gly Gly Glu Leu Val Val Ser Gly Val Asp Ser Ala Met
                805                 810                 815
Ser Leu Ile Gln Ala Ala Lys Asn Leu Met Asn Ala Val Val Gln Thr
            820                 825                 830
Val Lys Ala Ser Tyr Val Ala Ser Thr Lys Tyr Gln Lys Ser Gln Gly
        835                 840                 845
Met Ala Ser Leu Asn Leu Pro Ala Val Ser Trp Lys Met Lys Ala Pro
        850                 855                 860
Glu Lys Lys Pro Leu Val Lys Arg Glu Lys Gln Asp Glu Thr Gln Thr
865                 870                 875                 880
Lys Ile Lys Arg Ala Ser Gln Lys Lys His Val Asn Pro Val Gln Ala
                885                 890                 895
Leu Ser Glu Phe Lys Ala Met Asp Ser Ile
                900                 905

<210> SEQ ID NO 61
<211> LENGTH: 27
<212> TYPE: PRT
<213> ORGANISM: Mus musculus
<220> FEATURE:
<221> NAME/KEY: MISC_FEATURE
```

<223> OTHER INFORMATION: partial sequence alpha catenin

<400> SEQUENCE: 61

Lys Ala Leu Lys Pro Glu Val Asp Lys Leu Asn Ile Met Ala Ala Lys
1               5                   10                  15

Arg Gln Gln Glu Leu Lys Asp Val Gly Asn Arg
            20                  25

<210> SEQ ID NO 62
<211> LENGTH: 27
<212> TYPE: PRT
<213> ORGANISM: Homo sapience
<220> FEATURE:
<221> NAME/KEY: MISC_FEATURE
<223> OTHER INFORMATION: partial sequence alpha catenin

<400> SEQUENCE: 62

Lys Ala Leu Lys Pro Glu Val Asp Lys Leu Asn Ile Met Ala Ala Lys
1               5                   10                  15

Arg Gln Gln Glu Leu Lys Asp Val Gly His Arg
            20                  25

<210> SEQ ID NO 63
<211> LENGTH: 27
<212> TYPE: PRT
<213> ORGANISM: Rattus novergicus
<220> FEATURE:
<221> NAME/KEY: MISC_FEATURE
<223> OTHER INFORMATION: partial sequence alpha catenin

<400> SEQUENCE: 63

Arg Ala Leu Lys Pro Glu Val Asp Lys Leu Asn Ile Met Ala Ala Lys
1               5                   10                  15

Arg Gln Gln Glu Leu Lys Asp Val Gly His Arg
            20                  25

<210> SEQ ID NO 64
<211> LENGTH: 27
<212> TYPE: PRT
<213> ORGANISM: Gallus gallus
<220> FEATURE:
<221> NAME/KEY: MISC_FEATURE
<223> OTHER INFORMATION: partial sequence alpha catenin

<400> SEQUENCE: 64

Lys Ala Leu Lys Pro Glu Val Asp Lys Leu Asn Ile Met Ala Ala Lys
1               5                   10                  15

Arg Gln Gln Glu Leu Lys Asp Val Gly His Arg
            20                  25

<210> SEQ ID NO 65
<211> LENGTH: 27
<212> TYPE: PRT
<213> ORGANISM: Dabio reiro
<220> FEATURE:
<221> NAME/KEY: MISC_FEATURE
<223> OTHER INFORMATION: partial sequence alpha catenin

<400> SEQUENCE: 65

Lys Ala Leu Lys Pro Glu Val Asp Lys Leu Asn Met Met Ala Ala Lys
1               5                   10                  15

Arg Gln Gln Glu Leu Lys Asp Val His His Lys
            20                  25

```
<210> SEQ ID NO 66
<211> LENGTH: 27
<212> TYPE: PRT
<213> ORGANISM: Mus musculus
<220> FEATURE:
<221> NAME/KEY: MISC_FEATURE
<223> OTHER INFORMATION: partial sequence alpha catenin

<400> SEQUENCE: 66

Glu Leu Val Val Ser Gly Val Asp Ser Ala Met Ser Leu Ile Gln Ala
1               5                   10                  15

Ala Lys Asn Leu Met Asn Ala Val Val Gln Thr
            20                  25

<210> SEQ ID NO 67
<211> LENGTH: 27
<212> TYPE: PRT
<213> ORGANISM: Homo sapience
<220> FEATURE:
<221> NAME/KEY: MISC_FEATURE
<223> OTHER INFORMATION: partial sequence alpha catenin

<400> SEQUENCE: 67

Glu Leu Val Val Ser Gly Val Asp Ser Ala Met Ser Leu Ile Gln Ala
1               5                   10                  15

Ala Lys Asn Leu Met Asn Ala Val Val Gln Thr
            20                  25

<210> SEQ ID NO 68
<211> LENGTH: 27
<212> TYPE: PRT
<213> ORGANISM: Rattus novergicus
<220> FEATURE:
<221> NAME/KEY: MISC_FEATURE
<223> OTHER INFORMATION: partial sequence alpha catenin

<400> SEQUENCE: 68

Glu Leu Val Val Ser Gly Val Asp Ser Ala Met Ser Leu Ile Gln Ala
1               5                   10                  15

Ala Lys Asn Leu Met Asn Ala Val Val Gln Thr
            20                  25

<210> SEQ ID NO 69
<211> LENGTH: 27
<212> TYPE: PRT
<213> ORGANISM: Gallus gallus
<220> FEATURE:
<221> NAME/KEY: MISC_FEATURE
<223> OTHER INFORMATION: partial sequence alpha catenin

<400> SEQUENCE: 69

Glu Leu Val Val Ser Gly Val Asp Ser Ala Met Ser Leu Ile Gln Ala
1               5                   10                  15

Ala Lys Asn Leu Met Asn Ala Val Val Gln Thr
            20                  25

<210> SEQ ID NO 70
<211> LENGTH: 27
<212> TYPE: PRT
<213> ORGANISM: Dabio reiro
<220> FEATURE:
<221> NAME/KEY: MISC_FEATURE
<223> OTHER INFORMATION: partial sequence alpha catenin
```

```
<400> SEQUENCE: 70

Glu Leu Val Val Ser Gly Leu Asp Ser Ala Met Ser Leu Ile Gln Ala
1               5                   10                  15

Ala Lys Asn Leu Met Asn Ser Val Val Ser Thr
            20                  25

<210> SEQ ID NO 71
<211> LENGTH: 4
<212> TYPE: PRT
<213> ORGANISM: Artificial sequence
<220> FEATURE:
<223> OTHER INFORMATION: Caspase-3 inhibitor
<220> FEATURE:
<221> NAME/KEY: MOD_RES
<222> LOCATION: (1)..(1)
<223> OTHER INFORMATION: benzyloxycarbonyl conjugated
<220> FEATURE:
<221> NAME/KEY: MOD_RES
<222> LOCATION: (1)..(1)
<223> OTHER INFORMATION: O-Methyl
<220> FEATURE:
<221> NAME/KEY: MOD_RES
<222> LOCATION: (2)..(2)
<223> OTHER INFORMATION: O-Methyl
<220> FEATURE:
<221> NAME/KEY: MOD_RES
<222> LOCATION: (4)..(4)
<223> OTHER INFORMATION: O-Methyl
<220> FEATURE:
<221> NAME/KEY: MOD_RES
<222> LOCATION: (4)..(4)
<223> OTHER INFORMATION: fluoromethylketone conjugated

<400> SEQUENCE: 71

Asp Glu Val Asp
1

<210> SEQ ID NO 72
<211> LENGTH: 4
<212> TYPE: PRT
<213> ORGANISM: Artificial sequence
<220> FEATURE:
<223> OTHER INFORMATION: Caspase-3 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: chloromethyl ketone conjugated

<400> SEQUENCE: 72

Asp Glu Val Asp
1

<210> SEQ ID NO 73
<211> LENGTH: 4
<212> TYPE: PRT
<213> ORGANISM: Artificial sequence
<220> FEATURE:
<223> OTHER INFORMATION: Caspase-3 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: CHO conjugated
```

```
<400> SEQUENCE: 73

Glu Ser Met Asp
1

<210> SEQ ID NO 74
<211> LENGTH: 4
<212> TYPE: PRT
<213> ORGANISM: Artificial sequence
<220> FEATURE:
<223> OTHER INFORMATION: Caspase-3 inhibitor
<220> FEATURE:
<221> NAME/KEY: MOD_RES
<222> LOCATION: (1)..(1)
<223> OTHER INFORMATION: benzyloxycarbonyl conjugated
<220> FEATURE:
<221> NAME/KEY: MOD_RES
<222> LOCATION: (1)..(1)
<223> OTHER INFORMATION: O-Methyl
<220> FEATURE:
<221> NAME/KEY: MOD_RES
<222> LOCATION: (4)..(4)
<223> OTHER INFORMATION: O-Methyl
<220> FEATURE:
<221> NAME/KEY: MOD_RES
<222> LOCATION: (4)..(4)
<223> OTHER INFORMATION: fluoromethylketone conjugated

<400> SEQUENCE: 74

Asp Gln Met Asp
1

<210> SEQ ID NO 75
<211> LENGTH: 4
<212> TYPE: PRT
<213> ORGANISM: Artificial sequence
<220> FEATURE:
<223> OTHER INFORMATION: Caspase-3 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: CHO

<400> SEQUENCE: 75

Asp Glu Val Asp
1

<210> SEQ ID NO 76
<211> LENGTH: 4
<212> TYPE: PRT
<213> ORGANISM: Artificial sequence
<220> FEATURE:
<223> OTHER INFORMATION: Caspase cleavage site

<400> SEQUENCE: 76

Pro Glu Val Asp
1

<210> SEQ ID NO 77
<211> LENGTH: 4
<212> TYPE: PRT
<213> ORGANISM: Artificial sequence
<220> FEATURE:
<223> OTHER INFORMATION: Caspase cleavage site
```

-continued

```
<400> SEQUENCE: 77

Ser Gly Val Asp
1
```

USE OF CASPASE-3 INHIBITORS AND CASPASE-3 ACTIVATORS IN THE MANUFACTURE OF MEDICAMENT FOR TREATING CANCER AND WOUND HEALING

RELATED APPLICATIONS

This application is a National Phase of PCT Patent Application No. PCT/IB2017/056364 having International filing date of Oct. 13, 2017, which claims the benefit of priority of Israel Patent Application No. 248468 filed on Oct. 13, 2016. The contents of the above applications are all incorporated by reference as if fully set forth herein in their entirety.

SEQUENCE LISTING STATEMENT

The ASCII file, entitled 77183SequenceListing.txt, created on Apr. 5, 2019, comprising 265,890 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to methods of selecting a treatment for a cancer by analyzing activity of Yes associated protein 1 (YAP) in cancer cells of the subject, and, more particularly, but not exclusively, to methods of treating cancer using anti-caspase-3 agents such as caspase-3 inhibitors.

A fundamental mechanism for proper development and tissue homeostasis is apoptosis, which is responsible for the elimination of undesired and potentially dangerous cells (1-6). Apoptosis culminates in the activation of caspases, which are a class of cysteine proteases that are expressed as inactive zymogens in almost all cells (7-10). Of the caspase family, Caspase-3 plays an instrumental role in apoptosis and is responsible for cleaving a variety of important structural proteins to implement the cell death program (11). However, the lethal activity of Caspase-3 can be retained and refocused to achieve cellular remodeling, differentiation as well as for regulating the release of mitogens to promote compensatory proliferation (12-17).

The skin epidermis is comprised of three distinct compartments: the hair follicle (HF), sebaceous gland (SG) and the interfollicular epidermis (IFE) (18). The HF cycles between phases of growth (anagen), destruction (catagen) and rest (telogen) and is fueled by subpopulations of HF stem cells (HFSCs) that reside within the bulge (19-20). During catagen, apoptosis eliminates the lower transient portion of the HF in a cohort fashion, while the permanent upper part of the pilosebaceous unit including the bulge and SG remain intact (15, 19). In contrast to the HF, the SG is found to be in a constant state of renewal (19). The basal layer of the SG is composed of proliferating cells situated along the SG proliferative zone (SGPZ), which differentiate and give rise to lipid-filled sebocytes in the inner compartment of the SG (FIG. 1A). As differentiated sebocytes mature they progressively accumulate lipids and are pushed toward the necrotic zone (NZ) where they erupt and release their sebum (21) (FIG. 1A). While the HF and IFE have been the focus of numerous investigations, incredibly little is known regarding the homeostasis of the SG, the mechanisms regulating the size of this unique miniorgan, and whether it is regulated by apoptotic machinery proteins.

One fundamental signaling module that has been established as a master regulator of organ size is the Hippo pathway. Central to the Hippo pathway is the transcriptional co-activator Yes-associated protein (YAP), which becomes activated upon dephosphorylation to induce expression of genes that drive proliferation and attenuate apoptosis. Dysregulation of YAP activity has been found to yield significant implications, including massive tissue overgrowth and tumor development (24-26). In the skin, YAP has been found to play an important role in regulating epidermal proliferation and tissue expansion by acting downstream of α-Catenin in a Hippo-independent fashion (27-29). Specifically, α-Catenin sequesters YAP at cell junctions, thereby repressing its transcriptional activity by limiting its liberation. Deletion of Ctnna1, encoding α-Catenin, has been shown to drive hyperproliferation of epidermal cells via enhanced YAP activity. However, very little is known regarding the mechanisms regulating the liberation of YAP from α-Catenin.

Additional background art includes US 20120303057 (Choy Young Bid); Fuchs Y. and Steller H. 2011 [Cell 147(4), 742-758]; Fuchs Y. and Steller H. 2015 [Nature Review Molecular Cell Biology 16(6):329-44]; Li F, et al. 2010 [Sci Signal. 2010 Feb. 23; 3(110):ra13]; Tseng A S, et al. 2007 [Dev Biol. 2007 Jan. 1; 301(1):62-9]; Liu X., et al. 2015 [Mol Cell. 2015 Apr. 16; 58(2): 284-296]; Huang Q., et al., 2012 [Nat. Med. 17(7): 860-866)]; Li Xiu Juan et al. 2013(a) ["3,3'-Diindolylmethane suppresses the growth of gastric cancer cells via activation of the Hippo signaling pathway". Oncology reports, 2013, 30(5): 2419-2416] and Li, Xiu Juan, et al., 2013(b) ["DIM inhibitis growth of human gastric cancer through modulation of the hippo signaling pathway". Proceedings: ACCR $104^{th}$ Annual Meeting 2013 (Apr. 6-10, 2013].

SUMMARY OF THE INVENTION

According to an aspect of some embodiments of the present invention there is provided a method of selecting a treatment for a cancer in a subject in need thereof, the method comprising analyzing activity of Yes associated protein 1 (YAP) in cancer cells of the subject, wherein an up-regulation in activity of the YAP above a predetermined level as compared to an activity of the YAP in a matching non-cancerous tissue classifies the subject suitable for treatment of cancer with a caspase 3 inhibitor.

According to an aspect of some embodiments of the present invention there is provided a method of treating a subject having cancer, comprising: (a) testing suitability of the subject for treatment according to some embodiments of the invention, and (b)

treating the subject with a therapeutically effective amount of a caspase-3 inhibitor, thereby treating the subject.

Use of a therapeutically effective amount of a caspase-3 inhibitor in the manufacture of a medicament for treating cancer, wherein the cancer cells of the cancer exhibit up-regulation in activity of Yes associated protein (YAP) above a predetermined level as compared to an activity of the YAP in a matching non-cancerous tissue.

According to an aspect of some embodiments of the present invention there is provided a method of improving wound healing in a subject, comprising administering to a wounded area of the subject a wound healing effective amount of a caspase-3 activator, the therapeutically effective amount of the caspase-3 being capable of increasing activity of Yes associated protein 1 (YAP) above a predetermined level as compared to a wounded area of a subject non-treated by the caspase-3 activator, thereby improving the wound healing in the subject.

Use of an effective amount of a wound healing caspase-3 activator for the manufacture of a medicament for the treatment of a wound in a local manner in a subject, wherein said effective amount of said caspase-3 is capable of increasing activity of Yes associated protein 1 (YAP) above a predetermined level as compared to a wounded area of a subject non-treated by said caspase-3 activator.

According to some embodiments of the invention, the method further comprising analyzing cellular localization of the YAP, wherein an increased nuclear localization of the YAP above a predetermined level as compared to nuclear localization of the YAP in a matching non-cancerous tissue classifies the subject suitable for treatment of cancer with a caspase 3 inhibitor.

According to some embodiments of the invention, the cancer is a solid tumor.

According to some embodiments of the invention, the cancer is characterized by the up-regulation the activity of the YAP above the predetermined threshold as compared to the matching non-cancerous tissue is selected from the group consisting of glioma, head and neck cancer, esophageal cancer, sarcoma, non small cell lung cancer, breast cancer, ovarian cancer, uterine cancer, gastric cancer, melanoma, colorectal cancer, bladder cancer, prostate cancer, liver cancer and pancreatic cancer.

According to some embodiments of the invention, the caspase-3 inhibitor is selected from the group consisting of Ivachtin, z-DEVD-fmk (SEQ ID NO: 71), Z-VAD(OMe)-FMK, Z-FA-FMK, Ac-DEVD-CMK (SEQ ID NO: 72), Q-VD-OPH, Caspase-3/7 Inhibitor I (5-[(S)-(+)-2-(Methoxymethyl)pyrrolidino]sulfonylisatin), Caspase Inhibitor X (BI-9B12), Z-Asp-2,6-dichlorobenzoyloxymethylketone, DICA, Caspase-3 Inhibitor I cell permeable (Ac-AAVALLPAVLLALLAPDEVD-CHO, SEQ ID NO: 49), Ac-VAD-cho, Ac-ESMD-CHO (SEQ ID NO: 73, and Z-Asp-OMe-Gln-Met-Asp-OMe-FMK (SEQ ID NO: 74).

According to some embodiments of the invention, the method further comprising administering to the subject a chemotherapeutic drug.

According to some embodiments of the invention, the chemotherapy drug is a BRAF inhibitor.

According to some embodiments of the invention, the BRAF inhibitor is vemurafenib (marketed as Zelboraf).

According to some embodiments of the invention, the method further comprising treating the subject with radiation therapy.

According to some embodiments of the invention, the activity of the YAP is characterized by coactivation of the transcription of the TEAD (TEA domain) complex.

According to some embodiments of the invention, the caspase-3 activator is selected from the group consisting of PAC-1, and ABT-199.

According to some embodiments of the invention, the caspase-3 activator does induce apoptosis in the cells.

According to some embodiments of the invention, the administering is performed by topical administration to the wounded area of the subject.

According to some embodiments of the invention, the administering is performed by peripheral administration to the subject.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-I demonstrate that caspase-3 does not instruct sebocyte elimination. FIG. 1A—Schematic representation of sebaceous gland stem cell (SG SC) differentiation and their location in the sebaceous gland. Basement Membrane (BM); Proliferating Zone (PZ); Maturing Zone (MZ); Necrotic Zone (NZ). FIG. 1B—Tail whole mounts stained for activated caspase-3 (CP3), keratin-15 (K15) and 4',6-diamidino-2-phenylindole (DAPI, blue/purple). IFD, infundibulum; HS, hair shaft; ES, epithelial stand. FIG. 1C—Immunofluorescence staining of tail whole mounts for K15, TUNEL and DAPI cells. JZ, junctional zone. FIG. 1D—Zoom in of catagenic epithelial (regressing) strand stained for CP3, K15, TUNEL and DAPI. Arrow indicating apoptotic cell expressing both CP3 and TUNEL. FIG. 1E—Immunofluorescence staining of tail whole mounts for K15, CP9 and DAPI cells. FIG. 1F—Zoom in of catagenic epithelial strand stained for CP9, TUNEL and DAPI. FIG. 1G—Percentage of PZ SG cells that are positive CP3 and negative for TUNEL. FIG. 1H—Quantifications of $CP3^+$/$CP7^+$/$CP9^+$ cells in different zones of the pilosebaceous unit. FIG. 1I—Quantifications of cells positive for CP3 and TUNEL, CP7 and TUNEL and CP9 and TUNEL in different zones of the pilosebaceous unit. Scale bars, 100 µm (FIG. 1B), 50 µm (FIG. 1C), 50 µm (FIG. 1E), 50 µm (FIGS. 1D and 1F).

FIGS. 2A-W demonstrate that caspase-3 regulates sebaceous gland size and cell proliferation. FIG. 2A—Images showing the effect of Caspase 3 deletion on animal's fur. FIGS. 2B-C—Oil-red-O staining of sebaceous glands from wild type (WT; FIG. 2B) and $Casp3^{-/-}$ (FIG. 2C) tailskin. FIGS. 2D-E—Quantification of SG length (FIG. 2E) and area (FIG. 2D) in WT and $Casp3^{-/-}$ (also marked as "C3"). FIGS. 2F-G—Quantification of cell number (FIG. 2F) and proliferating cells (FIG. 2G) in the SG of WT and $Casp3^{-/-}$ (also marked as "C3") tailskin. FIGS. 2H-I—Confocal Z-stack images of WT (FIG. 2H) and $Caspase\ 3^{-/-}$ (FIG. 2I) tail whole mounts stained for Ki67 and K15. Nuclear counterstain was with DAPI. Inset in each of FIGS. 2H and 2I is a blow up of three SGs. FIGS. 2J-K—Quantification of SG length (FIG. 2K) and width (FIG. 2J) in tailskin following 7 days of CP3 chemical inhibition with Ivachtin and z-DEVD-fmk (SEQ ID NO: 71). NT, non treated. FIGS.

2L-M images of a dorsal skin (FIG. 2L) and earskin (FIG. 2M) showing expression of K15 expression in the SG of earskin versus expression in the bulge of dorsal skin, isolated from K15-GFP reporter mice. FIGS. 2N-O—FACS analyses of ear skin cells isolated from K15-GFP reporter mice. FACS-purified integrin α6+ cells were resorted for K15$^+$CD34$^-$Sca1$^-$. FIGS. 2P-Q—Quantification of cell number (FIG. 2P) and colony number formation (FIG. 2Q) of K15$^+$CD34$^-$Sca1$^-$ isolated cells treated with z-DEVD-fmk (SEQ ID NO: 71) for 14 days. FIG. 2R—Dorsalskin (upper panel) and earskin (lower panel) isolated from Krt1-15-EGFP reporter mice. In dorsalskin EGFP labeled cells are seen solely in the HF bulge and hair germ (upper panel) while in the earskin EGFP is highly expressed in the SGPZ (lower panel). FIG. 2S—FACS analyses of dorsalskin (upper panel) and earskin (lower panel) cells isolated from Krt1-15-EGFP reporter mice. FACS-purified integrin α6$^+$ cells were resorted for CD34, Sca1 and EGFP. The results demonstrate that the present inventors were able to isolate SGPZ cells. FIG. 2T—Quantification of SG width (left panel) and length (right panel) in mice treated with DMSO or ABT-199 for 7 days (n=40 individual SGs). FIG. 2U—Quantification of CP3$^+$ cells (left panel) and proliferating cells (right panel) in the SGs of mice treated with DMSO or ABT-199 for 7 days (n=30 individual SGs). FIG. 2V-W—Quantification of proliferating (FIG. 2V) and CP3$^+$ FIG. 2W) cells in the SGs of mice treated with DMSO or PAC-1 for 5 days (n=35 individual SGs). Data are shown as mean±SEM. * P<0.05; (P<0.01) and * (P<0.005) indicates statistical significance of comparison to control by two-tailed unpaired student t-test comparing levels in WT vs. KO samples or control vs. treated samples. Denotation: Wild Type, WT, and Caspase 3$^{-/-}$, Casp3$^{-/-}$. Scale bars, 100 µm (FIGS. 2B-C), 100 µm (FIGS. 2H-I), 10 µm (FIG. 2L), 20 µm (FIG. 2M), 10 µm (FIG. 2R, insets), 100 µm (FIG. 2R).

Figure 3O:
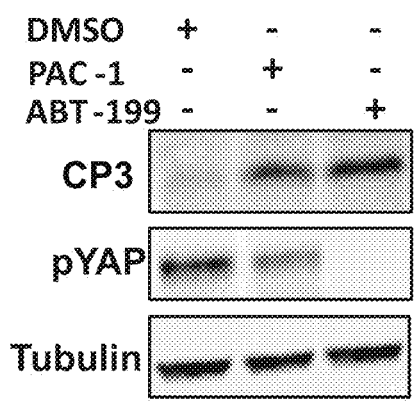

FIGS. 3A-O demonstrate that caspase-3 regulates activation of YAP. FIGS. 3A-B—Confocal Z-stack of SGs from WT (FIG. 3A) and Casp3$^{-/-}$ (FIG. 3B) mice stained for YAP, K15 and DAPI. FIG. 3C—A histogram depicting quantification of nuclear YAP cells in WT and Casp3$^{-/-}$ mice. FIG. 3D—Nuclear and cytoplasmic proteins isolated from WT and Casp3$^{-/-}$ dorsal skins were subjected to immunoblot analysis using antibodies against YAP and Histone 3, H3, as a control. FIGS. 3E-F—images depicting dorsal whole mount (DWM) staining for YAP (red), Ki67 (green) and DAPI (blue) following Caspase-3 inhibition with z-DEVD-fmk (SEQ ID NO: 71, FIG. 3F) or control (DMSO, FIG. 3E). FIGS. 3G—Immunoblot analysis of proteins isolated from dorsal skin of DMSO, Ivachtin or z-DEVD-fmk (SEQ ID NO: 71) treated mice using antibodies against phospho-YAP (pYAP) and α-tubulin as a control. FIG. 3H—Immunostaining of K15$^+$CD34$^-$Sca1$^-$ isolated cells with YAP (red), Ki67 (orange), α-catenin (green) and DAPI (blue). FIG. 3I—A histogram depicting quantification of K15$^+$CD34$^-$Sca1$^-$ cells positive for nuclear YAP after treatment with DMSO, Ivachtin or z-DEVD-fmk (SEQ ID NO: 71) for 14 days. FIGS. 3J-K—Immunostaining of HaCaT cells for YAP (green; middle image), Ki67 (red; right image) and DAPI (blue; left image) following treatment with z-DEVD-fmk (SEQ ID NO: 71, FIG. 3K) or control (DMSO, FIG. 3J). FIG. 3L—A histogram depicting quantification of nuclear YAP after treatment with DMSO, Ivachtin or z-DEVD-fmk (SEQ ID NO: 71) in low confluence (purple bars) or EGTA (peach bars) treated HaCaT cells. FIG. 3M—A histogram depicting RT-PCR analysis. RNA isolated from HaCaT cells treated with DMSO or z-DEVD-fmk (SEQ ID NO: 71) was subjected to Real-Time PCR analysis for YAP target genes. Values shown were normalized to Rp1p0 (Ribosomal protein lateral stalk subunit P0) relative to levels in DMSO treated cells. Data are shown as mean±SEM, n=3; FIG. 3N—Confocal Z-stacks of SGs from WT (upper panels) and Casp3$^{-/-}$ (lower panels) mice stained for YAP, Ki67 and DAPI (nuclear counterstain) as indicated in the panel. Shown is also a merge image of the YAP, Ki67 and DAPI stains. FIG. 3O—Immunoblot analysis of proteins isolated from integrin α6$^+$CD34$^-$EGFP$^{high}$ cells treated with DMSO, PAC-1 or ABT-199 using antibodies against phospho-YAP (pYAP), caspase-3 and α-Tubulin as control. *** (P<0.005) indicates statistical significance of comparison to control. Denotation: z-DEVD-fmk (SEQ ID NO: 71): DEVD. Scale bars: 50 µm (FIGS. 3A-B), 100 µm (FIGS. 3E-F), 100 µm (FIG. 3H), 100 µm (FIGS. 3J-K).

FIGS. 4A-S demonstrate that α-catenin is cleaved by caspase 3. FIG. 4A—Crystal structure of α-Catenin protein (PDB: 4IGG) showing Caspase-3 possible cleavage sites at the N-(Cyan) and C-(Gold) terminus. Schematic representation of mouse α-Catenin protein showing vinculin homology domains (VH) and location of cleavage sites. FIG. 4B—Coomassie staining of in vitro cleavage of recombinant human α-catenin protein by human CP3 in the absence or presence of CP3 inhibitor (Ac-DEVD-CHO, SEQ ID NO: 75). Arrows indicate the two cleavage products at approximately 17 and 14 kDa. FIG. 4C—Proteins isolated from HaCaT cells were subjected to in vitro cleavage reaction with human CP3 and analyzed using western blot for α-catenin N- and C-terminus and 14-3-3. FIG. 4D—Proteins isolated from HaCaT cells were subjected to co-immunoprecipitation with an antibody against α-Catenin. Pull-down complexes were subjected to in vitro cleavage with CP3 and analyzed using antibodies against α-Catenin and 14-3-3. FIGS. 4E-F—Endogenous proteins isolated from dorsalskin were subjected to co-immunoprecipitation with an antibody against α-Catenin (FIG. 4E) or YAP (FIG. 4F) and pull down complexes were analyzed by Western blot using antibodies against CP3 and YAP. FIG. 4G—An integrin α6$^+$CD34$^-$EGFP$^{high}$ SGPZ cell stained with α-Catenin (green), CP3 (red) antibodies and DAPI (blue). FIG. 4H—Immunoblot analysis of proteins isolated from dorsalskin of animals treated with DMSO, Ivachtin and z-DEVD-fmk (SEQ ID NO: 71) with α-Catenin and tubulin antibodies. FIG. 4I—Immunostaining of z-DEVD-fmk (SEQ ID NO: 71) treated HaCaT cells with α-Catenin (red) and DAPI (blue). Inset shows DMSO treated cells. FIGS. 4J-L—Confocal Z-stack of SGs from control (DMSO, FIG. 4J), Ivachtin (FIG. 4K), and z-DEVD-fmk (SEQ ID NO: 71, FIG. 4L)— treated mice stained for α-Catenin (red) and DAPI (blue). FIG. 4M—Coomassie staining of in vitro cleavage of recombinant human α-Catenin protein by recombinant human caspase-3. Arrow indicates the decrease of the full length α-Catenin at approximately 100 kDa. FIG. 4N—Coomassie staining of in vitro cleavage of recombinant human α-Catenin protein by human caspase-3 in the absence or presence of caspase-3 inhibitor (Ac-DEVD-CHO, SEQ ID NO: 75). Arrows indicate the two cleavage products at approximately 17 and 14 kDa. FIG. 4O—Immunoblot analysis of proteins isolated from integrin α6$^+$CD34$^-$EGFP$^{high}$ cells treated with DMSO or PAC-1 using antibodies against CP3, α-Catenin and α-Tubulin as control. FIG. 4P—Proteins isolated from HaCaT cells were subjected to co-IP with an antibody against α-Catenin. Pull-down complexes were subjected to in vitro cleavage with cleaved caspase-3. Upon cleavage of α-Catenin, cleaved products (CL) were collected to assess liberation products. Additionally, α-Catenin (EL) was eluted and the present inventors have analyzed the levels of full length α-Catenin. Data indicate that upon caspase-3 cleavage 14-3-3 is released from α-Catenin. Heavy chain (HC) panel demonstrates that caspase-3 does not cleave IgG or protein G. FIG. 4Q—Immunoblot analysis of proteins isolated from tailskin of animals treated with DMSO or Ivachtin stained with α-Catenin and αTubulin antibodies. FIG. 4R—Immunostaining of an integrin α6$^+$CD34$^-$EGFP$^{high}$ SGPZ cell with antibodies against α-Catenin, CP3 and with DAPI. FIG. 4S—Immunostaining of z-DEVD-fmk-treated HaCaT cells with α-Catenin and DAPI. Inset shows DMSO-treated cells. Denotation: z-DEVD-fmk (SEQ ID NO: 71), DEVD; α-Catenin, αCat; caspase-3, CP3. Scale bars: Scale bars, 5 μm (FIG. 4G), 5 μm (FIG. 4I), 50 μm (FIGS. 4J-L), 5 μm (FIGS. 4R and 4S).

Figure 5A:
Figure 5B:
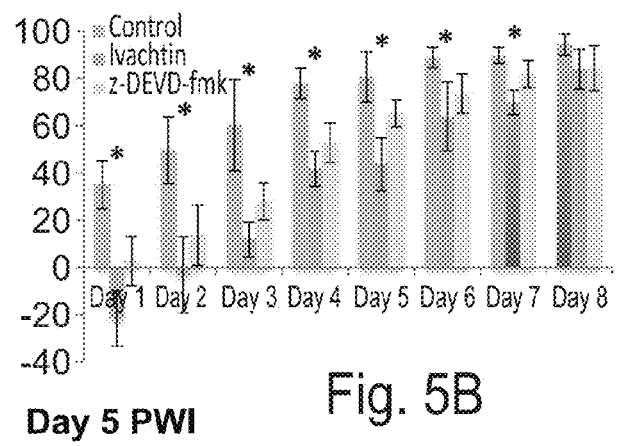
Figure 5C:
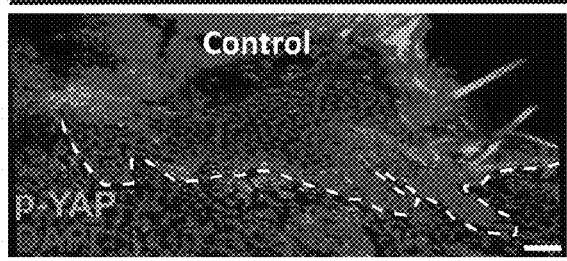
Figure 5D:
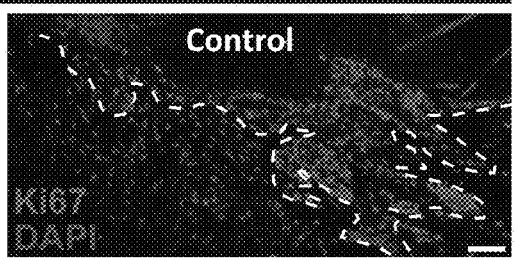
Figure 5E:
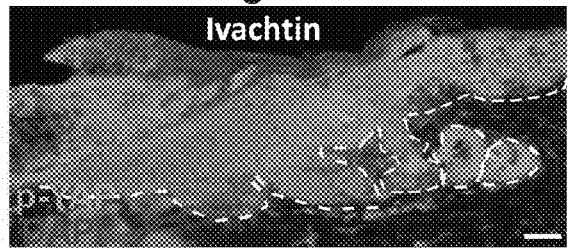
Figure 5F:
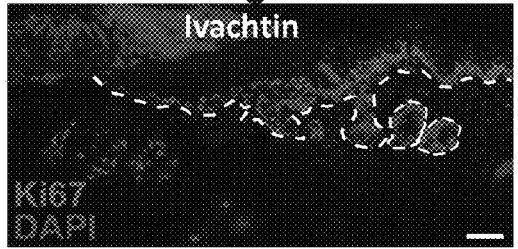
Figure 5G:
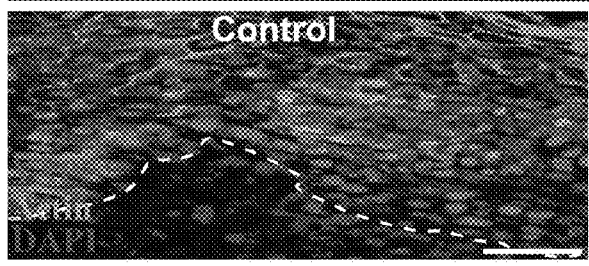
Figure 5I:
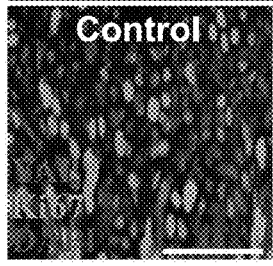
Figure 5J:
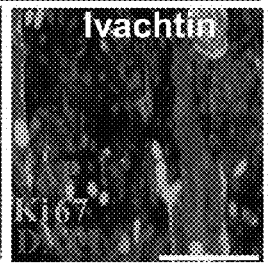
Figure 5H:
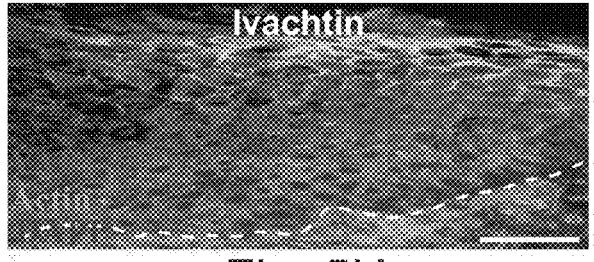
Figure 5K:
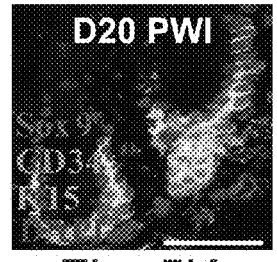
Figure 5L:
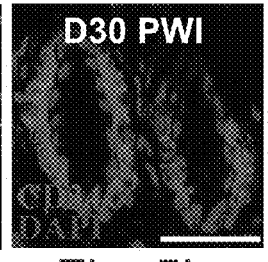

FIGS. 5A-L show that caspase-3 regulates YAP dependent wound healing. FIG. 5A—Representative picture of DMSO (control; left 1mouse), Ivachtin (middle mouse) and z-DEVD-fmk (SEQ ID NO: 71, right mouse) treated animals 3 days post wound infliction (PWI). Excision wounds (1 cm$^2$) were inflicted on dorsal skin of 8-week-old [n=10]. Ivachtin and z-DEVD-fmk (SEQ ID NO: 71) were injected daily (sub-cutaneously) during the wound healing process. FIG. 5B—Re-epithelialization dynamics of skins at different times PWI. Percentage of wound coverage (i.e., the percentage of area of the wound which is healed and covered with a new skin layer out of the total area of wound) was calculated versus original wound size. Blue bars: DMSO; Red bars: Ivachtin; Green bars: z-DEVD-fmk (SEQ ID NO: 71) (Wound size was measured daily from D0 to D8 post wounding); FIGS. 5C-F—Immunofluorescence staining for α-Catenin (red) and p-YAP (green) 5 days PWI of animals treated with DMSO (FIGS. 5C-D) or Ivachtin (FIGS. 5E-F). Dashed line indicates dermis-epidermis border and arrow represents α-Catenin decrease along the expression gradient. FIGS. 5G-H—Immunofluorescence staining for YAP (red), actin (green) and DAPI (blue) 7 days PWI in DMSO (FIG. 5G) or Ivachtin (FIG. 5H) treated animals. Dashed line indicates dermis-epidermis border. FIGS. 5I-J—Immunofluorescence staining for Dorsal whole mount (DWM) stained for YAP (red), Ki67 (green) and DAPI (blue) 12 days PWI in DMSO (FIG. 5I) or Ivachtin (FIG. 5J) treated animals. FIGS. 5K-L—images depicting HF regeneration in DMSO treated animals stained for Sox9 (red), CD34 (yellow), K15 (green) and DAPI (blue) 20 days PWI (FIG. 5K) or 30 days PWI (FIG. 5L). Note that 12 days PWI, Ivachtin treated animal display a decreased number of nuclear YAP (red) and Ki67 (green) cells (FIGS. 5I-J). Denotation WB: wound border. Scale bars, 50 μm (FIG. 5C-F), 20 μm (FIG. 5G-L).

Figure 6H:
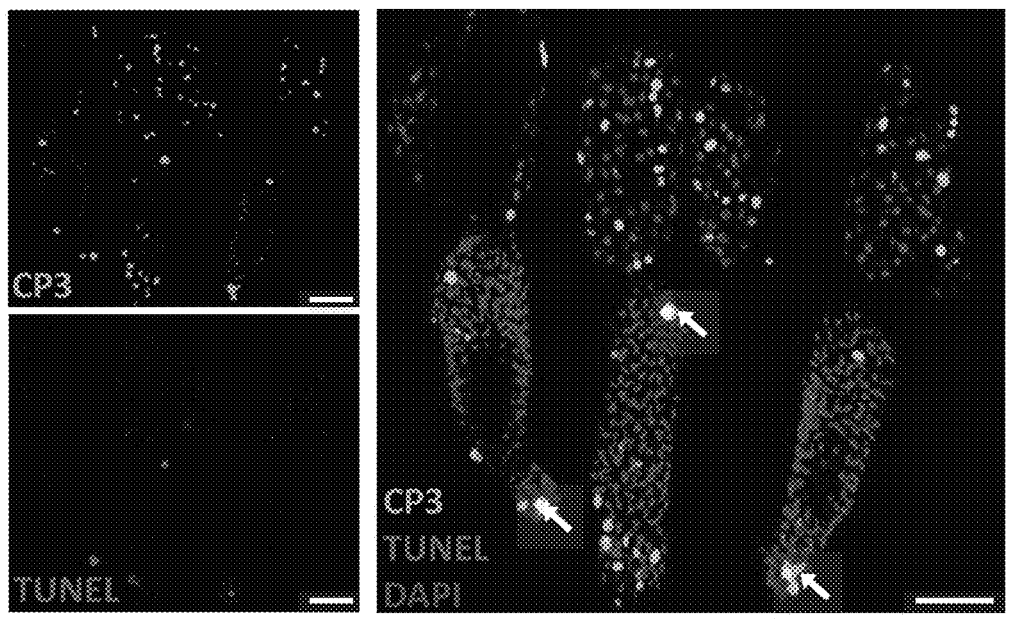
Figure 6I:
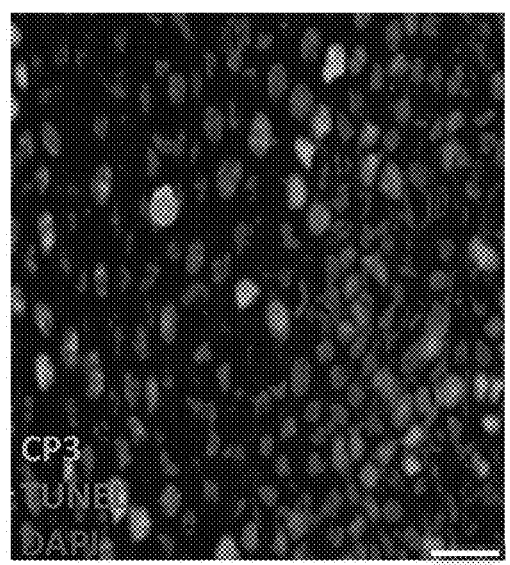

FIGS. 6A-I—Cleaved caspase-3 does not eliminate SG cells. FIG. 6A—Confocal Z-stack of SGs from WT mice stained for CP3, TUNEL and DAPI. Arrow indicating apoptotic cell in the SG expressing both CP3 and TUNEL. FIG. 6B—TWM stained for cleaved PARP (cPARP) and DAPI. Arrows indicate apoptotic cells in the regressing strand expressing cPARP. FIG. 6C—Immunofluorescence staining of P16 TWM for CP3, K15 and DAPI. FIG. 6D—Confocal Z-stack of catagenic ES from tailskin stained for CP3 and TUNEL. FIG. 6E—Confocal Z-stack of developing SG from P1 old mouse stained for CP3 and DAPI. FIGS. 6F-G—Tailskin stained for CP7, TUNEL and DAPI indicating staining in HFSC bulge and ES but not in the SG. Denotation: autofluorescence, AF. FIG. 6H—Confocal Z-stack of SGs from WT mice stained for CP3. TUNEL and DAPI. Arrow indicates apoptotic cells expressing both CP3 and TUNEL. FIG. 6I—Immunofluorescence staining of tailskin IFE (Interfollicular epidermis) for CP3, TUNEL and DAPI. Scale bars, 10 μm (FIG. 6B inner panel), 20 μm (FIGS. 6D, 6E, 6G), 50 μm (FIGS. 6A, 6B, and 6F), 100 μm (FIG. 6C).

Figure 7A:
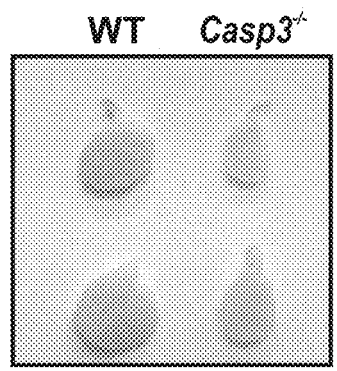
Figure 7B:
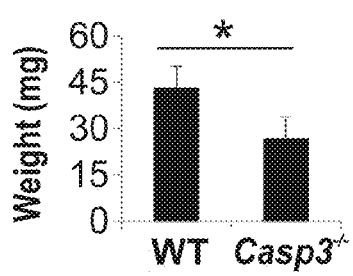
Figure 7C:
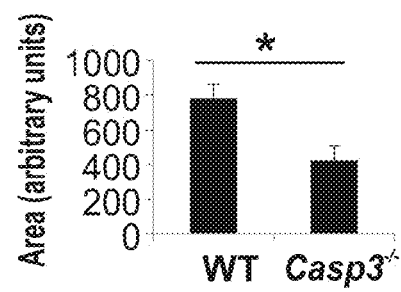
Figure 7D:
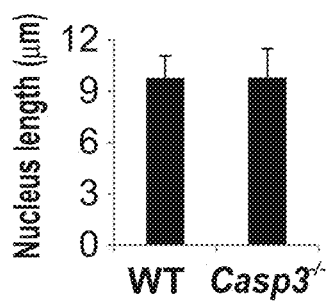
Figure 7E:
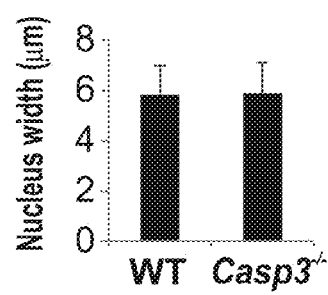
Figure 7F:
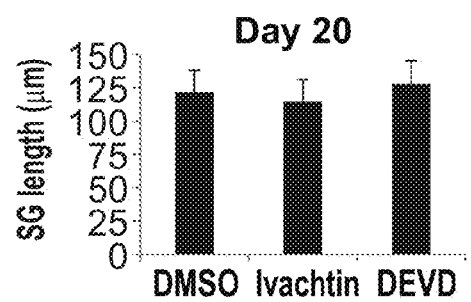
Figure 7G:
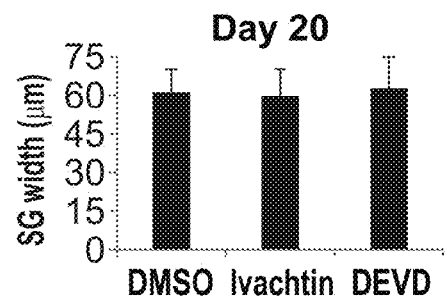
Figure 7H:
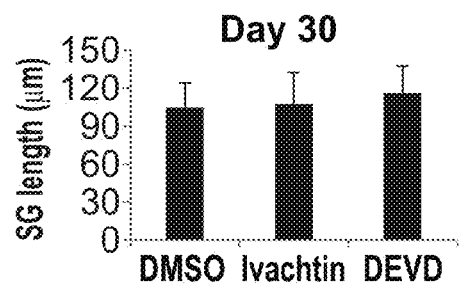
Figure 7I:
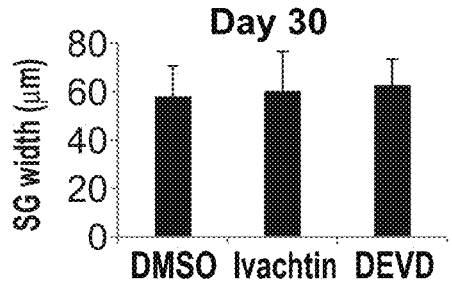
Figure 7J:
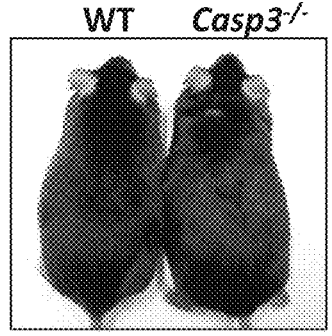
Figure 7K:
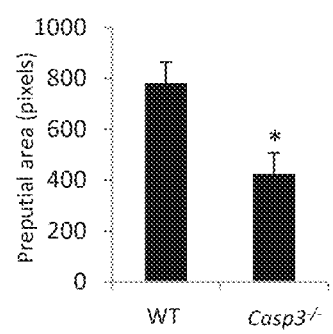
Figure 7L:
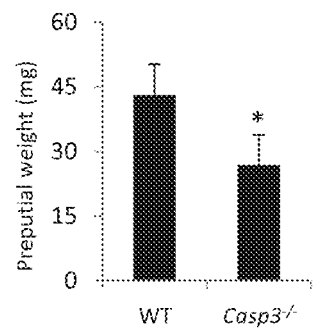

FIGS. 7A-L—Caspase-3 does not affect cell size but regulates the size of sebocyte-containing glands. FIG. 7A—Preputial glands from WT and Casp3$^{-/-}$ male mice. FIGS. 7B-C—Quantification of preputial weight and area in WT and Casp3$^{-/-}$ mice. (n=6). FIGS. 7D-E—Cell size quantification represented as nucleus length (μm) and width (μm) in the SGs of WT and Casp3$^{-/-}$ mice. (n=40) individual cells. FIGS. 7F-I—Quantification of SG length (FIGS. 7F and 7H, in μm) and width (FIGS. 7G and 7I, in μm) in tailskin following 20 (FIG. 7F, FIG. 7G) or 30 days (FIG. 7H, FIG. 7I) of caspase-3 chemical inhibition with Ivachtin and z-DEVD-fmk (SEO ID NO: 71). n=100 individual SGs. FIG. 7J—Effect of Casp3 deletion on glossiness of animal fur. FIGS. 7K and L—histograms depicting Quantification of preputial area (FIG. 7K, in pixels) and weight (FIG. 7L, in mg) in WT and Casp3$^{-/-7}$ mice (n=6). * (P<0.05) by two-tailed unpaired student t-test.

Figures 8A, 8B:
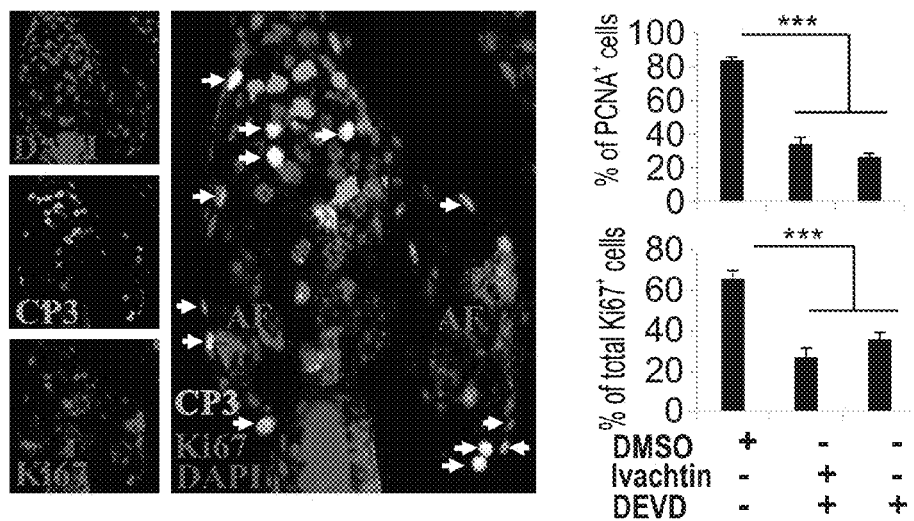
Figure 8C:
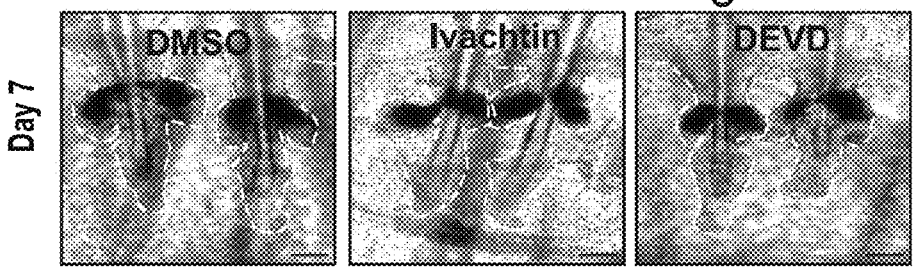
Figure 8D:
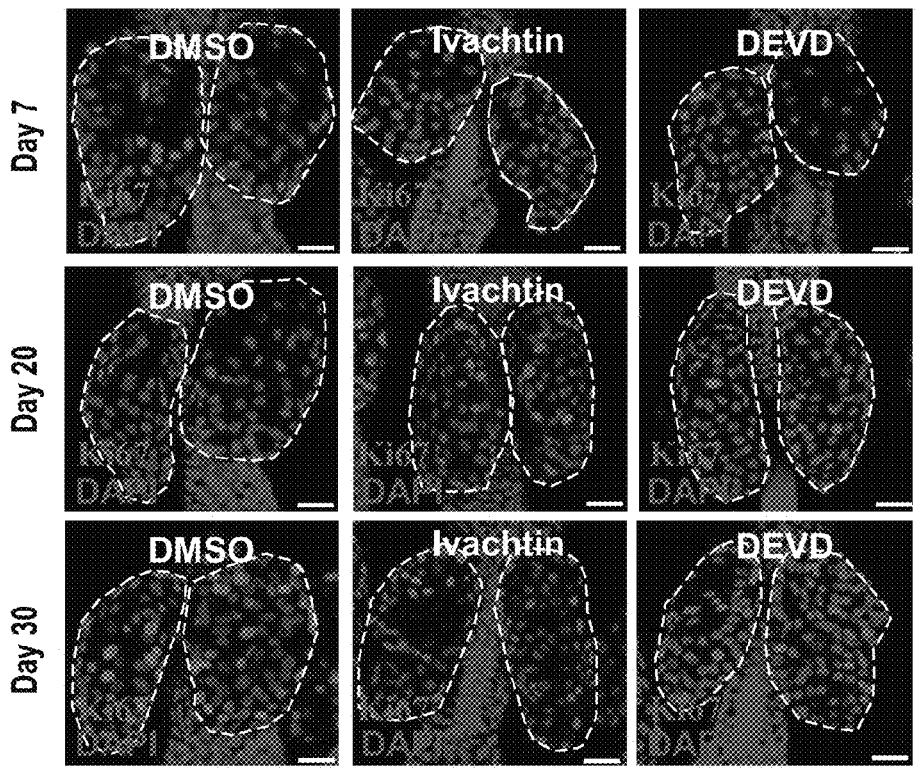

FIGS. 8A-D—Caspase-3 regulates cell proliferation. FIG. 8A—Co-localization of CP3 and Ki67 in proliferating sebocytes. Nuclear counterstain was with DAPI. Arrows indicate co-labelled CP3$^+$Ki67$^+$SGPZ cells. FIG. 8B—Quantification of integrin α6$^+$CD34$^-$EGFP$^{high}$ SGPZ cells positive for Ki67 or PCNA after treatment with DMSO, Ivachtin (daily) or z-DEVD-fmk (SEQ ID NO: 71) for five days. (n=250 individual cells). FIG. 8C—ORO staining of SGs from WT and caspase-3 inhibited mice seven days post treatment. FIG. 8D—Immunofluorescence staining for Ki67 and DAPI of SG from tailskin following 7, 20 and 30 days of treatment with Ivachtin and z-DEVD-fmk (SEQ ID NO: 71). *** (P<0.005) by two-tailed unpaired student t-test. Denotation: autofluorescence, AF denotes. Scale bars, 20 μm (FIG. 8A, FIG. 8D), 50 μm (FIG. 8C).

FIGS. 9A-F—Visualization, isolation and expansion of integrin α6$^+$CD34$^-$EGFP$^{high}$ SGPZ cells. FIGS. 9A-B—Dorsalskin and earskin isolated from Krt1-15-EGFP reporter mice. In dorsalskin EGFP-labeled cells are seen solely in the HF bulge and hair germ (FIG. 9A) while in the earskin EGFP is highly expressed in the SGPZ (FIG. 9B). FIG. 9C—Intravital imaging of Krt1-15-EGFP mice indicating that SGPZ cells highly express EGFP. FIG. 9D—FACS analysis of ear and dorsal skin cells isolated from Krt1-15-EGFP reporter mice. FACS-purified integrin α6+ cells were analyzed for Sca1, CD34 and EGFP. FIG. 9E—Colony formation of integrin α6$^+$CD34$^-$EGFP$^{high}$ isolated cells. FIG. 9F—ORO staining indicating that integrin α6$^+$CD34$^-$EGFP$^{high}$ cells are able to give rise to differentiated sebocyles in vitro. Integrin α6$^+$CD34$^-$Sca1$^+$ epidermal keratinocytes were used as control. Scale bars, 10 μm (FIG. 9A insets, FIG. 9C, FIG. 9E), 20 μm (FIG. 9F), 100 μm (FIG. 9A).

Figure 10E:
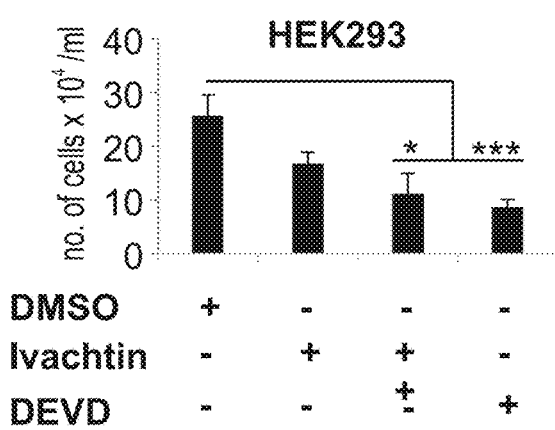
Figure 10F:
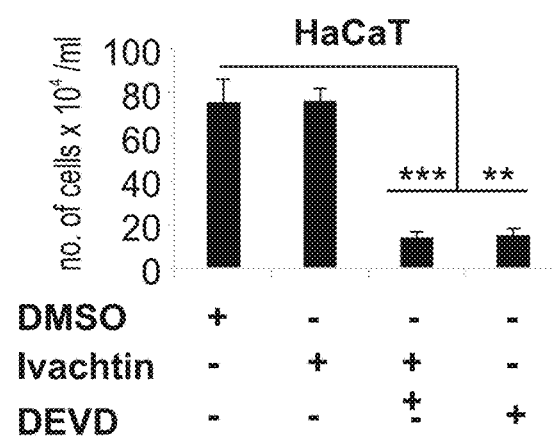
Figure 10G:
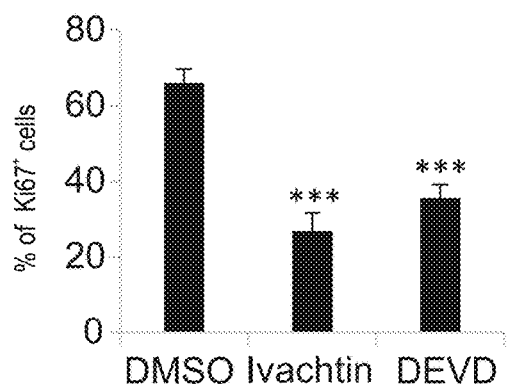
Figure 10H:
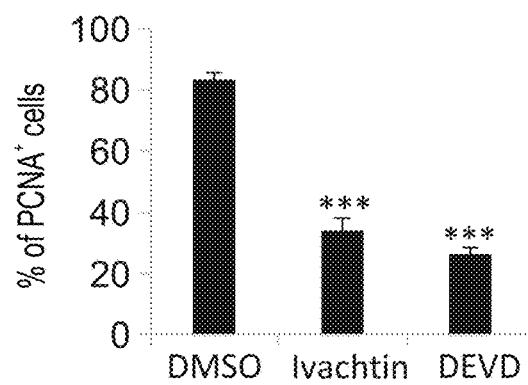

FIGS. 10A-H—Chemical Inhibition of Caspase-3 results in decreased proliferation and SGPZ cell number. Isolated integrin α6$^+$CD34$^-$EGFP$^{high}$ SGPZ cells (FIG. 10A), integrin α6$^+$CD34$^+$ HFSCs (FIG. 10B), HaCaT cells (FIG. 10C) and HEK293 cells (FIG. 10D) were seeded with Ivachtin or Z-DEVD-fmk (SEQ ID NO: 71), and grown for 7-14 days. Quantification of cell number for HEK293 (FIG. 10E) or HaCaT cells (FIG. 10F) treated with Ivachtin or Z-DEVD-fmk (SEQ ID NO: 71). + represents single administration of the inhibitors, ++ represents daily administration. The experiment was repeated 3 times in triplicates (n=3). * (P<0.05); (P<0.01) and * (P<0.005) by two-tailed unpaired student t-test. Scale bars, 10 µm (FIGS. 10A-D). FIG. 10G-H demonstrate that inhibition of caspase-3 results in decreased proliferation and SGPZ cell number. Isolated integrin α6+CD34−EGFP$^{high}$ SGPZ cells were seeded with Ivachtin or z-DEVD-fmk (SEQ ID NO: 71) and grown for 5-14 days. FIG. 10G—Quantification of integrin α6+CD34−EGFP$^{high}$ SGPZ cells positive for Ki67. FIG. 10H—Quantification of % of PCNA after treatment with DMSO, Ivachtin (daily) or z-DEVD-fmk (SEQ ID NO: 71) for five days (n=250 individual cells). *** P<0.005 by two-tailed unpaired student t-test. Scale bars, 10 µm (A).

FIGS. 11A-H—Caspase-3 regulates the activation of YAP. FIG. 11A—Co-labeling of YAP, Ki67 and DAPI in a tailskin SG. FIG. 11B—Decreased nuclear YAP localization in HEK293 cells treated with Z-DEVD-fmk (SEQ ID NO: 71). FIGS. 11C-D—Western blot analyses indicate that integrin α6+CD34−EGFP$^{high}$ SGPZ cells (FIG. 11C) and HEK293 (FIG. 11D) treated with z-DEVD-fmk (SEQ ID NO: 71) exhibit increased pYAP levels. β-actin or α-Tubulin levels were used as loading controls. FIGS. 11E-F—Densitometry was performed using Image Studio software. FIG. 11G—Immunostaining of HaCaT cells for YAP, Ki67 and DAPI following treatment with z-DEVD-fmk (SEQ ID NO: 71). FIG. 11H—Decreased nuclear YAP localization in Hek293 cells treated with Z-DEVD-fmk (SEQ ID NO: 71). Scale bars, 5 µm (FIG. 11B), 20 µm (FIG. 11A).

Figure 12C:
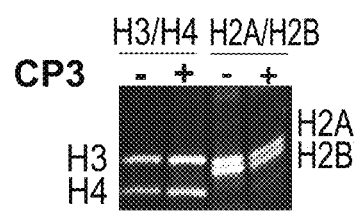
Figure 12D:
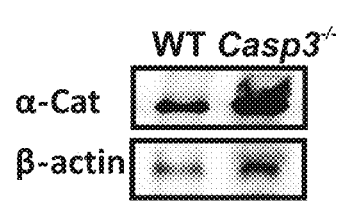
Figure 12E:
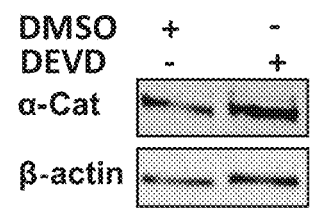
Figure 12F:
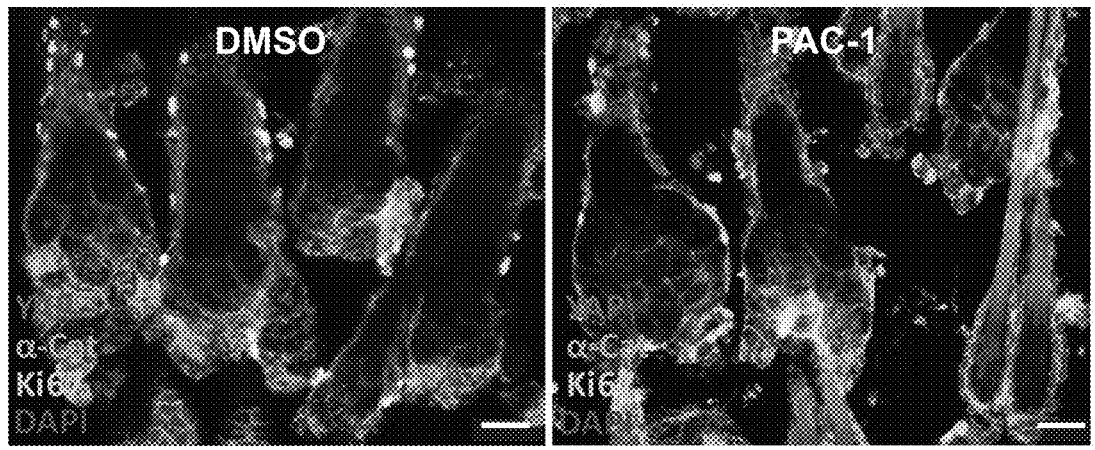

FIGS. 12A-F α-Catenin is a target of Caspase-3. FIG. 12A—Caspase-3 predicted cleavage sites within the α-Catenin amino acid sequences (highlighted in boxes) are conserved across a broad range of phyla (e.g., *Mus musculus, Homo sapiens, Rattus norvegicus, Gallus gallus,* and *Danio reiro*). Amino acid sequences were obtained from Ensembl release 89 www(dot)ensembl(dot)org). Conserved amino acids are shown in purple. FIG. 12B—Recombinant human α-Catenin (SEQ ID NO:60) was subjected to an in vitro caspase-3 cleavage reaction, followed by SDS/PAGE and Coomassie Blue staining as in FIG. 4B. The protein fragments were isolated and processed for mass spectrometry. The mass spectrometry data was analyzed using Proteome Discoverer 1.4 software using Sequest (Thermo) algorithm searching against the Uniprot database. The red peptides represent those who identified with the highest probability and the peptide highlighted with yellow represents those identified with lower probability from the two fragments. Predicted cleavage sites are indicated in cyan or gold. FIG. 12C—Coomassie staining of in vitro cleavage of recombinant mouse H3/H4 and H2A/H2B heterodimers by human CP3. Immunoblot analysis of proteins isolated from dorsalskin of WT and Casp3−/− mice (FIG. 12D) or from integrin α6+CD34−EGFP$^{high}$ SGPZ cells (FIG. 12E) employing α-Catenin and f3-Actin antibodies. FIG. 12F—Dorsal wholemount staining for YAP, Ki67, α-Catenin and DAPI following caspase-3 activation with PAC-1. Scale bars, 50 µm (FIG. 12F).

Figure 13A:
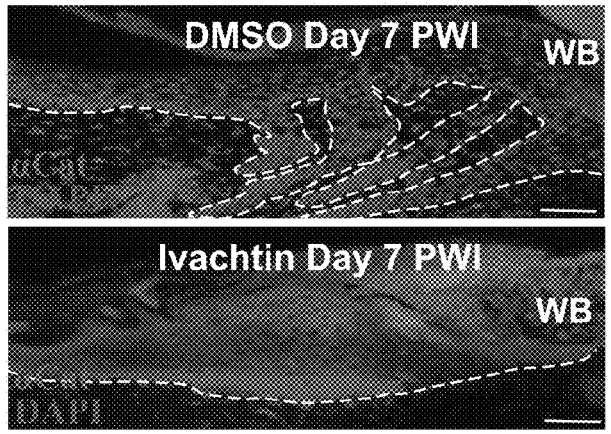
Figure 13B:
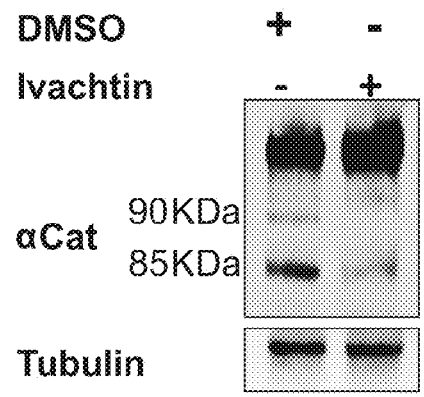
Figure 13C:
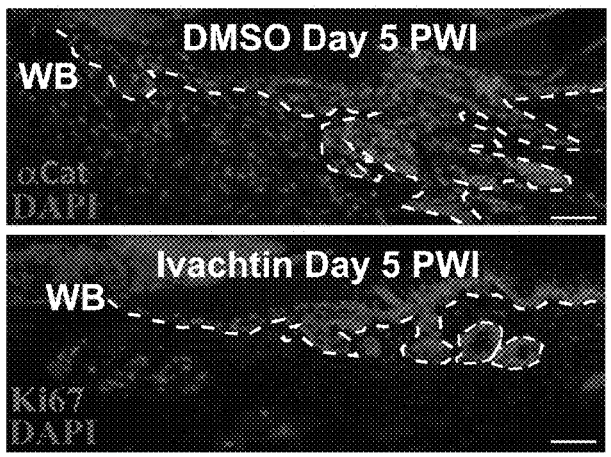
Figure 13D:
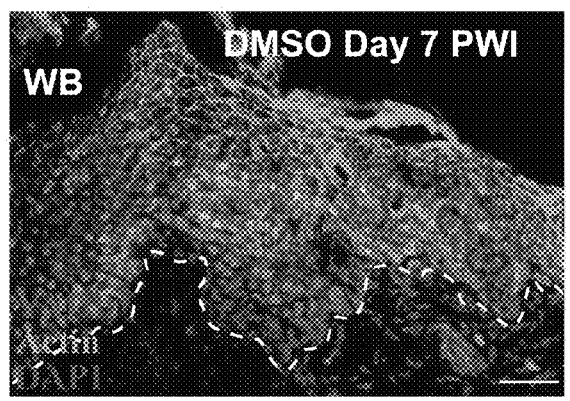
Figure 13E:
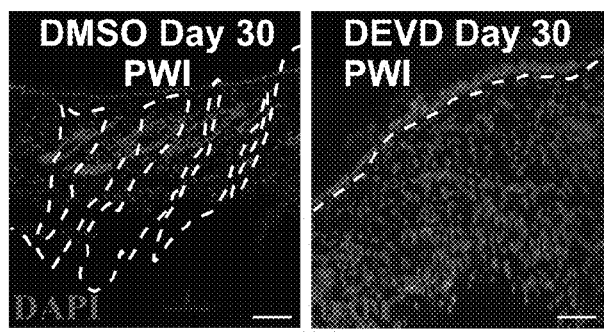

FIGS. 13A-E—Caspase-3 regulates YAP activation during wound healing and contributes to de novo hair follicle regeneration. FIG. 13A—Immunofluorescence staining for α-Catenin 7 days PWI indicates increased α-Catenin levels in the invading keratinocytes of Ivachtin treated animals. FIG. 13B—Proteins were isolated from wounded dorsalskin (7 days PWI) and subjected to Western blot analysis indicating impairment in cleavage of α-Catenin in Ivachtin-treated animals. FIG. 13C—Decreased proliferation in the wound border of caspase-3-inhibited animals. Actin was used to mark cell borders. FIG. 13D—Decreased nuclear YAP in the wound border of DEVD (z-DEVD-fmk, SEQ ID NO: 71) inhibited animals. FIG. 13E—De novo HF regeneration is inhibited in DEVD (z-DEVD-fmk, SEQ ID NO: 71) —treated mice. Denotation: wound border, WB. Scale bars, 50 µm (FIG. 13A, FIG. 13C, FIG. 13D), 100 µm (FIG. 13E).

FIGS. 14A-C depict inhibition of Caspase-3 attenuates proliferation of melanoma cells. FIGS. 14A-B Picture of control, and z-DEVD-fmk (SEQ ID NO: 71) treated melanoma cell lines (501A and 624-38) after 4 days of treatment. Caspase-3 inhibited melanoma cells exhibited delayed wound healing. FIG. 14C—Immunofluorescence of decreased Ki67+ cells (green) after 4 days of Caspase-3 inhibition. Scale bars, 20 µm (FIG. 14C right panels), 100 µm (FIG. 14A, FIG. 14B panels).

Figure 15A:
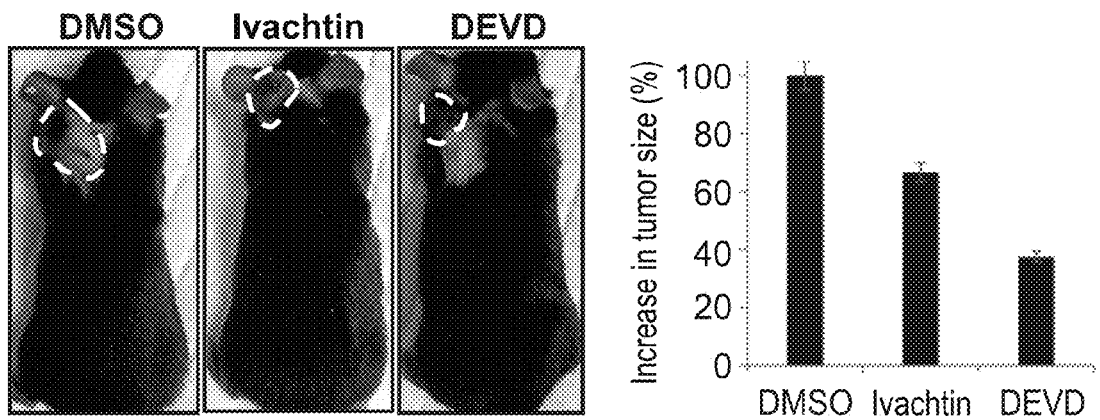
Figure 15B:
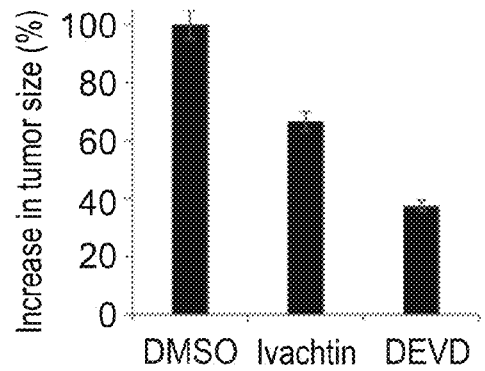
Figure 15C:
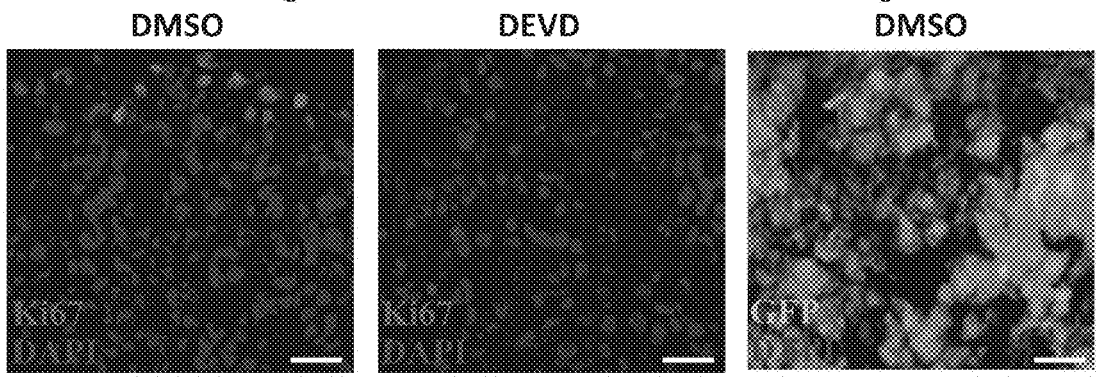
Figure 15D:
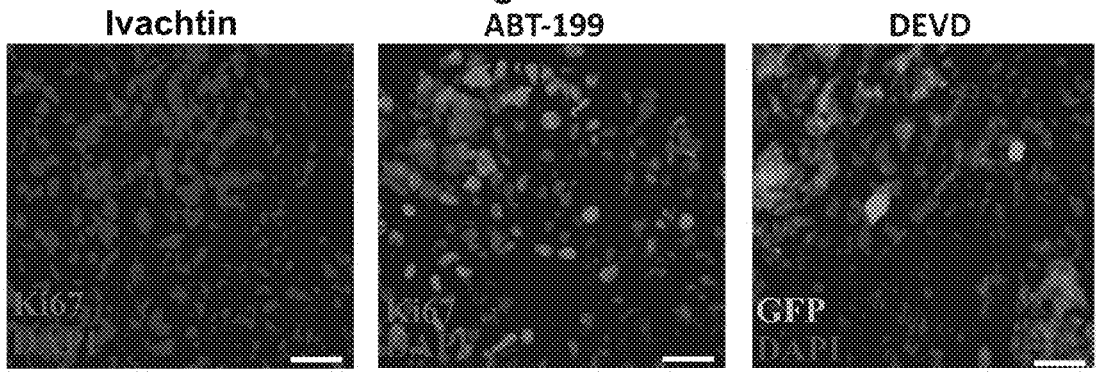
Figure 15E:
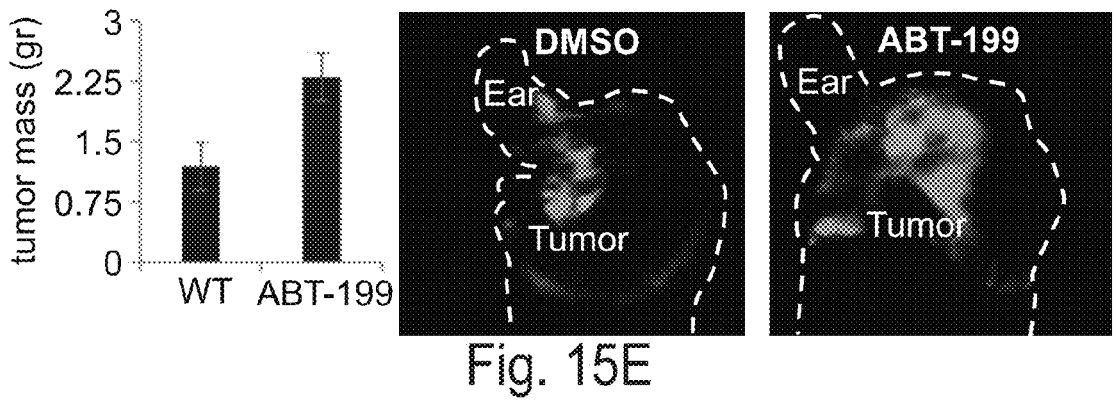

FIGS. 15A-E show that caspase-3 regulates proliferation and melanoma development in vivo. FIG. 15A—Melanoma cell were injected into recipient mice. Ten days post injection, tumor were treated with daily injections of DMSO, Ivachtin or z-DEVD-fmk (SEQ ID NO: 71). Representative image 6 days after first treatment. FIG. 15B—quantification of tumor development indicates inhibition of tumor size in response to caspase-3 inhibition. FIG. 15C—Extracted tumors were analyzed for proliferation using the Ki67 marker and the presence of GFP+ melanoma cells. FIG. 15D—Tumors treated with the caspase-3 activator ABT-199 result in a dramatic increase in tumor mass. FIG. 15E—Control and ABT-199 treated tumors were examined in vivo using the Maestro live imaging instrument indicating a striking increase in the melanotic tumor in response to caspase-3 activation. The histogram on the left shows increase in tumor mass following treatment with ABT-199. Scale bars, 20 µm.

Figures 16A, 16B:
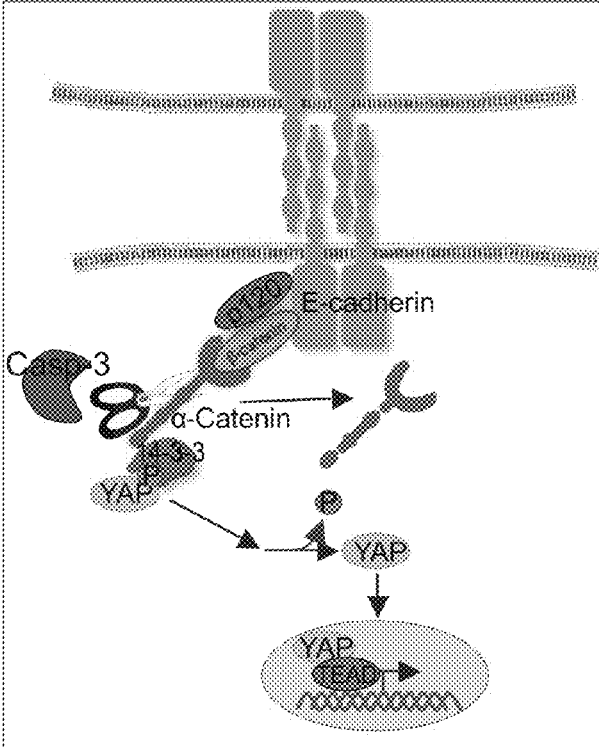

FIGS. 16A-B depict a model for caspase-3 mechanism of action. Proliferation signals, as in SG cell renewal or skin regeneration, promote caspase-3 cleavage of α-Catenin. α-Catenin retains YAP in the cytoplasm via interaction with 14-3-3 (27). Upon caspase-3 cleavage, 14-3-3 binding to α-Catenin is abrogated and YAP is dephosphorylated and translocates into the nucleus. When caspase-3 is deleted or inhibited, α-Catenin prevents YAP-mediated transcription by promoting its cytoplasmic localization. FIG. 16A—wild type; FIG. 16B—Caspase-3 deletion/inhibition.

Figure 17A:
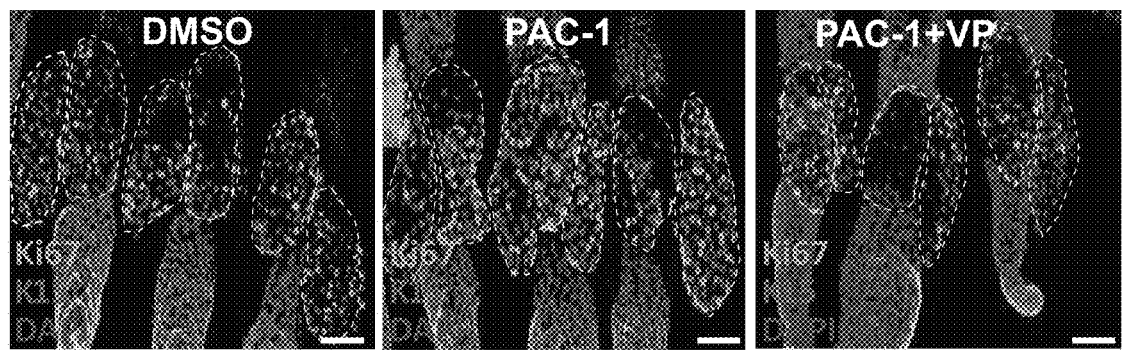
Figure 17B:
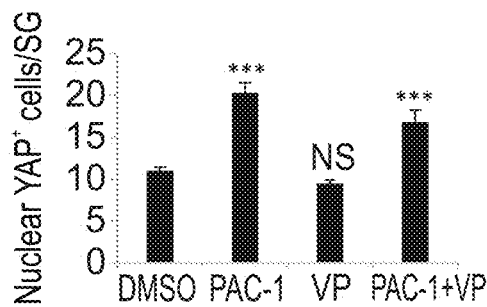
Figure 17C:
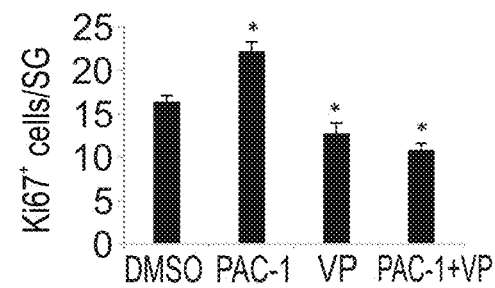
Figure 17D:
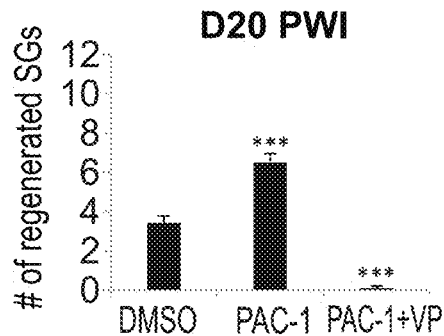
Figure 17E:
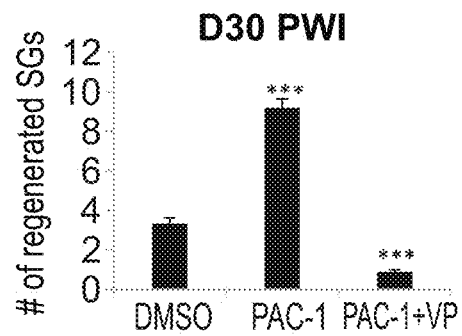
Figure 17F:
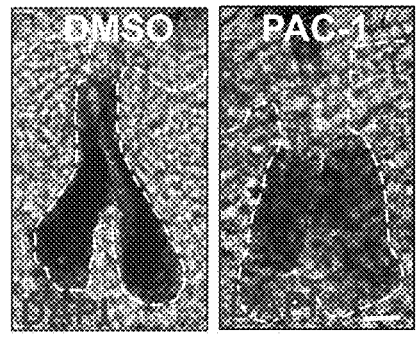
Figure 17G:
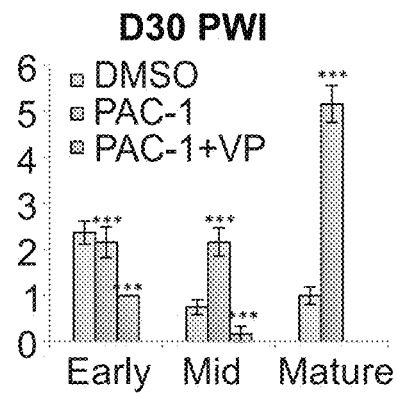

FIGS. 17A-G show that caspase-3 effect on SG size is YAP dependent. FIG. 17A—Confocal Z-stack of SGs from mice treated with DMSO (left panel), PAC-1 (middle panel) or PAC-1+Verteporfin (right panel) stained for Ki67, K15 and DAPI. FIG. 17B—Quantification of nuclear YAP+ cells in SGs of mice treated with DMSO, Verteporfin, PAC-1 or PAC-1+Verteporfin (n=50-100 individual SGs). FIG. 17C—Quantification of Ki67+ cells in SGs of mice treated the same as in FIG. 17B (n=50-100 individual SGs). FIGS. 17D and E—Quantification of de novo SG formation in mice treated with DMSO, PAC-1 or PAC-1+Verteporfin harvested 20 days PWI (post wound infliction) (FIG. 17D) and 30 days PWI (FIG. 17E). FIG. 17F—Confocal images comparing SG size from DMSO (left panel) and PAC-1 (right panel) treated mice. FIG. 17G—Quantification of regenerated de novo SGs at different phases in wounds treated with DMSO, PAC-1 or PAC-1+Verteporfin 30 days PWI. Data are shown as mean±SEM. *P<0.05; P<0.01; *P<0.005 by student t-test compared levels in DMSO and the other treatments. Denotation: Verteporfin, VP; Post wound infliction, PWI. Scale bars: 20 µm (FIG. 17F), 50 µm (FIG. 17A).

Figure 18A:
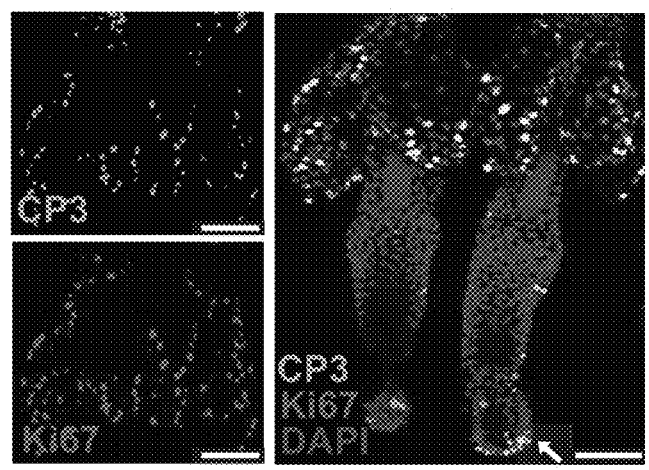
Figure 18B:
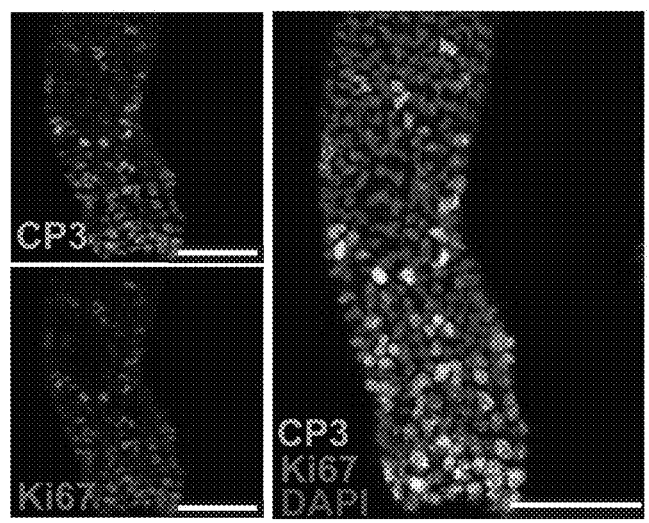
Figure 18C:
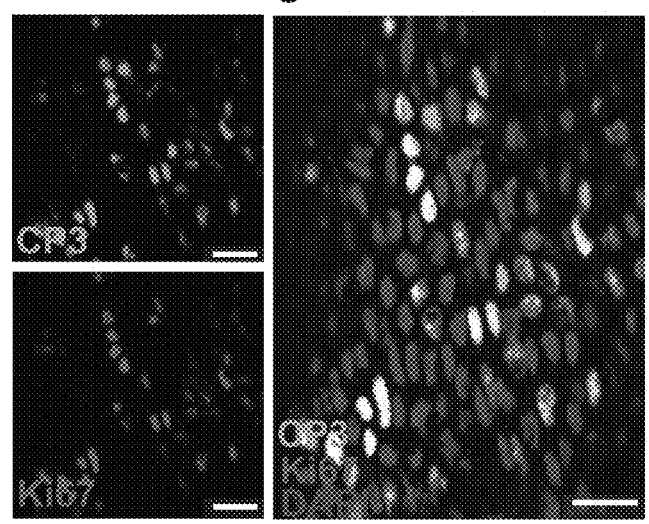

FIGS. 18A-C show the co-localization of caspase-3 and Ki67 in proliferating cells. FIG. 18A—Immunofluorescence staining of CP3 and Ki67 in proliferating cells of the SG and along the HF (hair follicle). Arrows indicate co-labelled CP3+/Ki67+ cells. FIG. 18B—Co-localization of CP3 and Ki67 in anagenic HF. FIG. 18C—Co-localization of CP3 and Ki67 in the tailskin IFE. Scale bars, 20 μm (FIGS. 18B, C), 50 μm (FIG. 18A).

FIGS. 19A-F show that caspase-3 regulates YAP-dependent wound healing. FIG. 19A—Representative picture of DMSO, Ivachtin and z-DEVD-fmk (SEQ ID NO: 71) —treated animals three days post wound infliction (PWI). Excision wounds (1 cm²) were inflicted on dorsal skin of eight-week old mice. Ivachtin and z-DEVD-fmk (SEQ ID NO: 71) were injected daily (sub-cutaneously) during the wound healing process. FIG. 19B—Reepithelialization dynamics of dorsalskins at different times PWI. Percentage of wound coverage was calculated versus original wound size. FIGS. 19C and D—Immunofluorescence staining for α-Catenin (red), pYAP and DAPI (blue) five days PWI. Arrow indicates an α-Catenin decrease along the expression gradient. FIG. 19E—Immunofluorescence staining for YAP (red), actin (green) and DAPI (blue) 7 days PWI in DMSO- or Ivachtin-treated animals. Dashed line indicates dermis-epidermis border. FIG. 19F—Mice were treated with DMSO (wt), Ivachtin, Verteporfin (VP), the YAP inhibitor, or both. The results indicate that no additive effect is seen when combining caspase-3 and YAP. Denotation: wound border, WB. Scale bars: 20 μm (FIG. 19D-G), 50 μm (FIG. 19C).

Figure 20A:
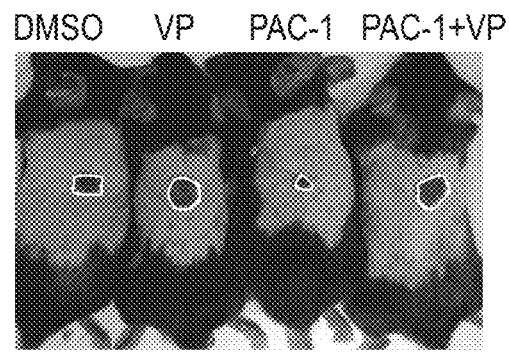
Figure 20B:
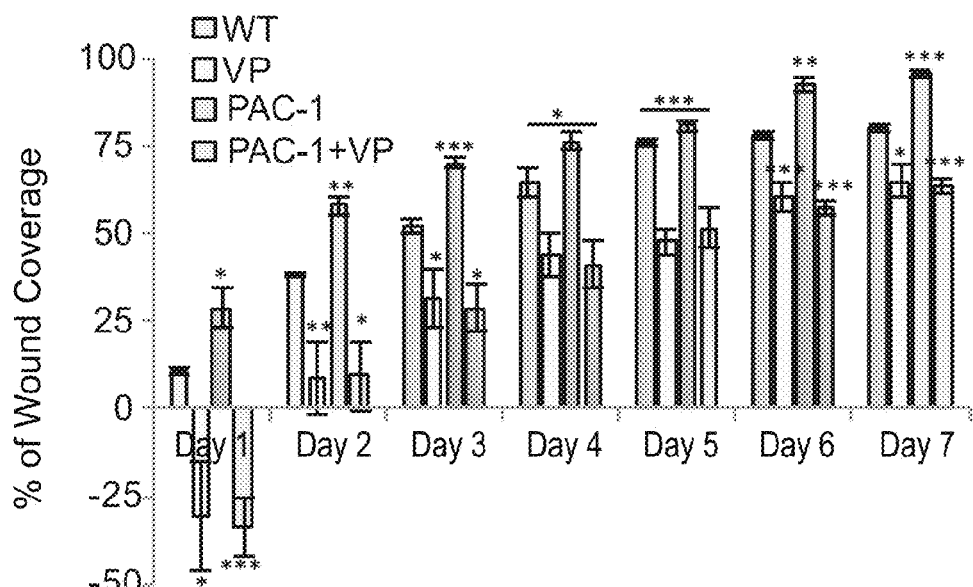
Figures 20C, 20D, 20E:
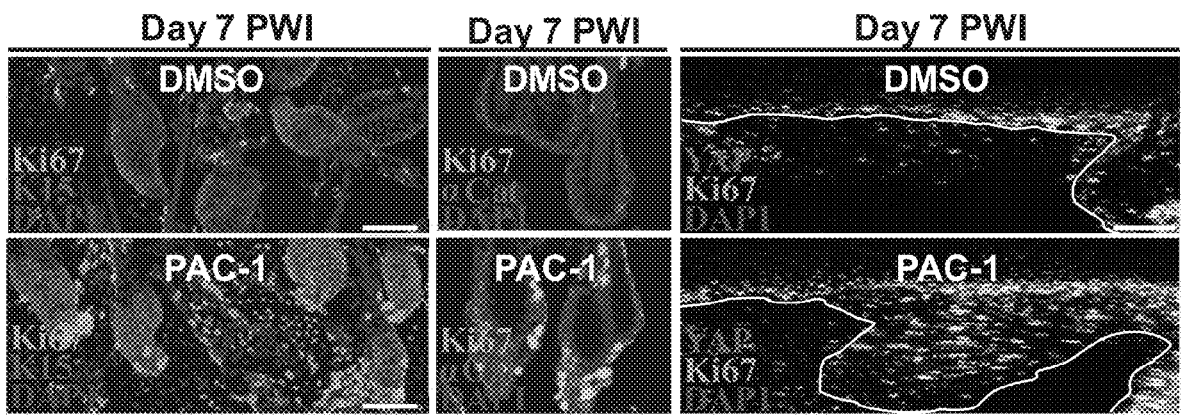

FIGS. 20A-E show that caspase-3 regulates YAP-dependent wound healing. FIG. 20A—Representative picture of DMSO, VP, PAC1 and a combination (PAC+VP) treated animals 7 days post wound infliction (PWI). Excision wounds (1 cm²) were inflicted on dorsal skin of eight-week old mice. VP and PAC-1 were injected daily (sub-cutaneously) during the wound healing process. FIG. 20B—Reepithelialization dynamics of dorsalskins at different times PWI. Percentage of wound coverage was calculated versus original wound size. The results indicate that activation of caspase-3 facilitates increased healing which can be negated by YAP inhibition. FIG. 20C—Immunofluorescence staining for Ki67 (green) and K15 (red) seven days PWI of DMSO (upper panel) or PAC-1 (lower panel) treated animals. Nuclear counterstaining was done by DAPI (blue). FIG. 20D—Immunofluorescence staining for α-Catenin (red), Ki67 (green) and DAPI (blue) 7 days PWI of DMSO (upper panel) or PAC-1 (lower panel) treated animals. FIG. 20E—Immunofluorescence staining for YAP (red), Ki67 (green) and DAPI (blue) 7 days PWI of DMSO (upper panel) or PAC-1 (lower panel) treated animals. Dashed line indicates dermis-epidermis border. Pac1-treated animals display an increased number of nuclear YAP and Ki67 cells. Denotation: wound border, WB. Scale bars: 20 μm (FIGS. 20D and E), 50 μm (FIG. 20C).

FIGS. 21A-F show that activation of caspase 3 dramatically accelerates tumor growth and proliferation. FIG. 21A—Mice injected with B16F10 cells ($10^6$) are able to generate melanoma in vivo. FIG. 21B—Growth of established tumors is accelerated when treated with a pro-apoptotic agent, ABT-199. FIG. 21C—Quantification of tumor weight (mg) in treated (ABT-199) and non-treated (DMSO) animals. FIG. 21D—Resected tumors stained for activated cleaved Caspase-3 (red) show higher expression in ABT-199-treated animals. FIG. 21E—Resected tumors stained for the proliferative marker Ki67 (red). FIG. 21F—Quantification of Ki67$^+$ melanoma cells in vivo after treatment with ABT-199 (marked as "ABT") as compared to control (DMASO treated). Denotation: CP3, Caspase-3.  ($P<0.01$), * ($P<0.001$).

FIGS. 22A-G show that inhibition of caspase 3 attenuates cancer cell proliferation and leads to increased cell death in vivo (FIGS. 22A-C) and in vitro (FIGS. 22D-F). FIG. 22A—Mice injected with B16F10 cells ($1\times10^6$) are able to generate melanoma in vivo. FIG. 22B—Growth of established tumors is hindered when treated with a specific, reversible Caspase-3 inhibitor (Ivachtin). FIG. 22C—A histogram displaying quantification of tumor weight (mg) in treated (with Ivachtin) and non-treated (DMSO) animals. FIG. 22D—Resected tumors stained for the proliferative marker Ki67 (red) and with the nuclear counterstain (DAPI, blue) in DMSO (no-treatment, left panel) or Ivachtin (treated, right panel) animals, show higher expression in non-treated (DMSO) animals. FIG. 22E—A histogram depicting quantification of Ki67$^+$ melanoma cells in vivo after treatment with Ivachtin. FIG. 22F—TUNEL assay performed in resected tumors in DMSO (no-treatment, left panel) or Ivachtin (treated, right panel) animals, showing enhanced cell death in Ivachtin-treated animals. FIG. 22G—A histogram depicting quantification of TUNEL$^+$ melanoma cells. Denotation: CP3, Caspase-3. Scale bars: 10 μm (FIGS. 22D and 22F). * ($P<0.05$).

Figure 23A:
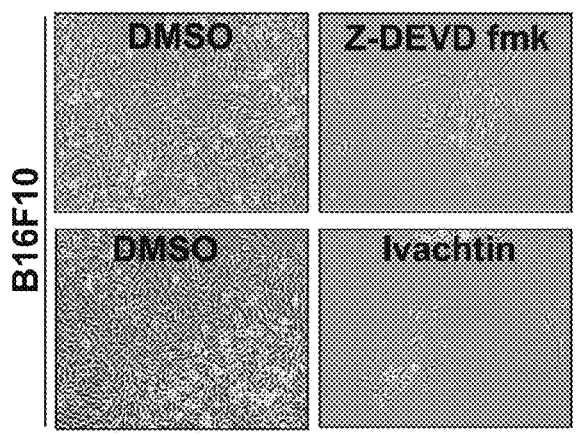
Figure 23B:
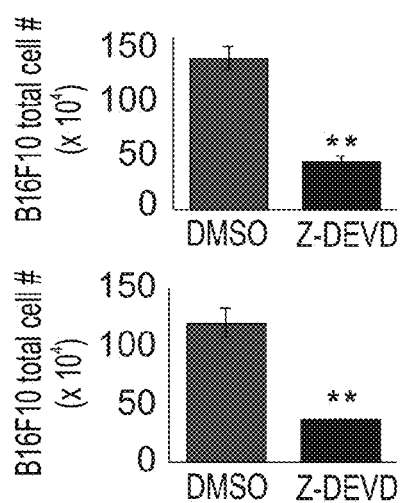
Figure 23C:
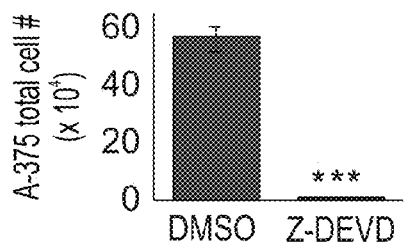
Figure 23D:
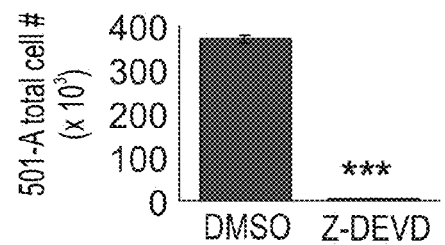
Figure 23E:
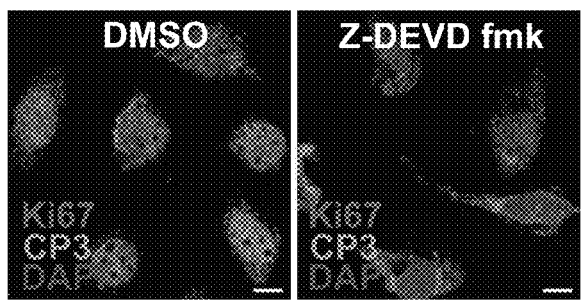
Figure 23G:
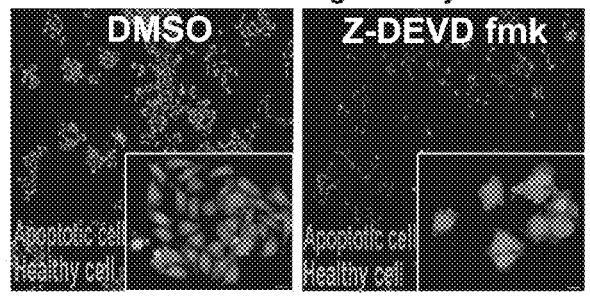
Figure 23F:
Figure 23H:

FIGS. 23A-H show that inhibition of caspase 3 attenuates cancer cell proliferation in vitro (FIGS. 23A-C) and leads to increased cell death in vitro (FIGS. 23D-F); FIG. 23A—Growth of B16F10 melanoma cells is hindered in the continuous presence of a specific irreversible Caspase-3 inhibitor (upper panels, DMSO and Z-DEVD-fmk (SEQ ID NO: 71); Lower panels, DMSO and Ivachtin). FIG. 23B—Histograms depicting quantifications of total cell number after treatment (upper panel, DMSO and Z-DEVD-fmk (SEQ ID NO: 71); Lower panel, DMSO and Ivachtin). FIG. 23C—A histogram depicting quantifications of A-375 total cells number after treatment with Z-DEVD-fmk (SEQ ID NO: 71). FIG. 23D—A histogram depicting quantifications of 501-A total cells number after treatment with Z-DEVD-fmk (SEQ ID NO: 71). FIG. 23E—Images depicting B16F10 melanoma cells stained for Ki67 (red), active cleaved Caspase-3 (green) and nuclear counterstain DAPI (blue). Cells treated with Z-DEVD-fmk (SEQ ID NO: 71) display reduced levels of proliferative cells. FIG. 23F—A histogram depicting quantification of Ki67$^+$ cells in non-treated (DMSO) and treated (Z-DEVD-fmk, SEQ ID NO: 71) media. FIG. 23G—Images depicting non-treated (DMSO) and Z-DEVD-fmk (SEQ ID NO: 71) treated B16F10 cells stained with acridine orange/ethidium bromide reveals viable (green) and dying (red) cells. FIG. 23H—A histogram depicting quantification of cell death in control (DMSO) and Z-DEVD-fmk (SEQ ID NO: 71) —treated cells. Insets are zoom in on specific cells, Denotation: CP3, Caspase-3. Scale bars: 100 μm.  ($P<0.01$), * ($P<0.001$).

Figure 24A:
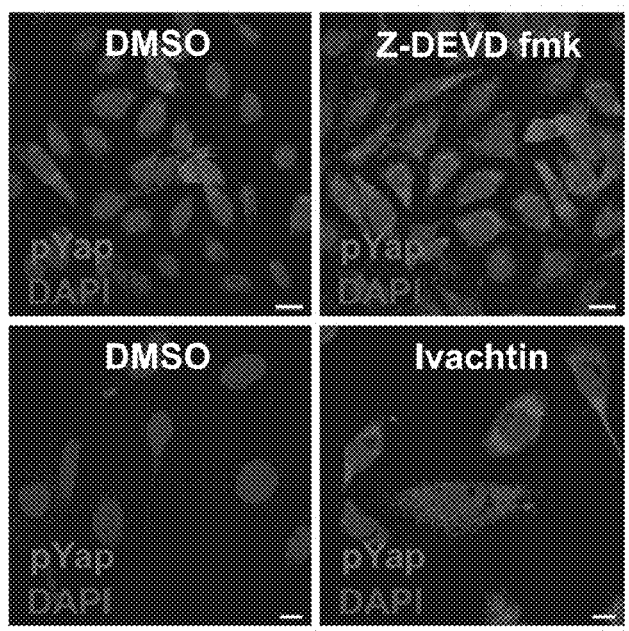
Figure 24B:
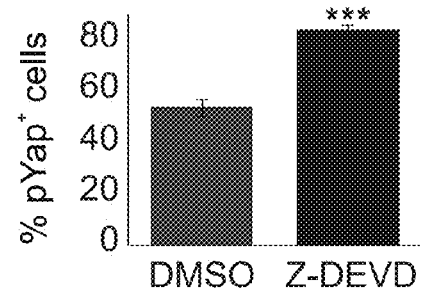
Figure 24C:
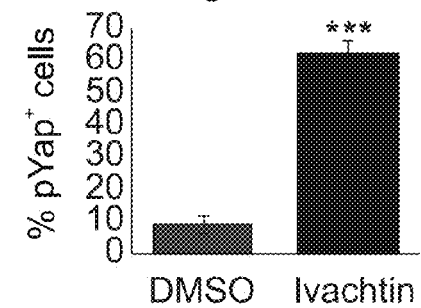
Figure 24D:
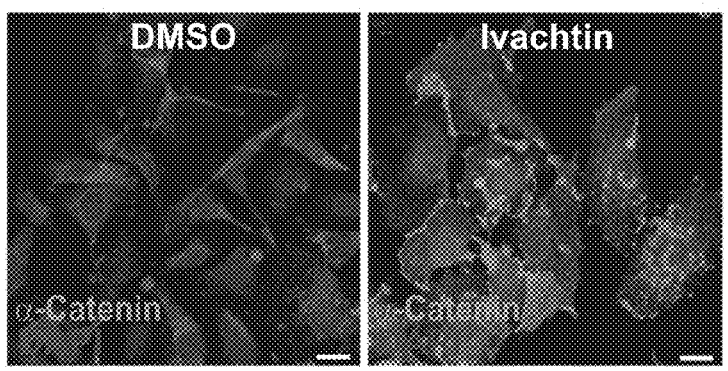
Figure 24E:
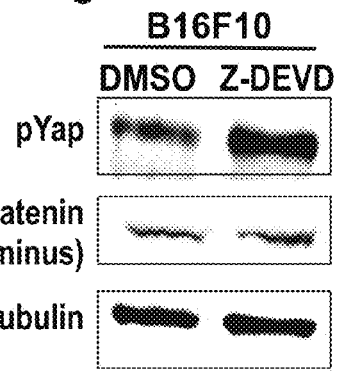

FIGS. 24A-E show that Caspase-3 regulates melanoma maintenance via the Yap signaling pathway. FIG. 24A—Images depicting B16F10 melanoma cells stained for pYAP (red). Cells were treated with DMSO, Z-DEVD-fmk (SEQ ID NO: 71) or Ivachtin. FIGS. 24B-C—Histograms depicting quantification of pYAP cells following treatment with Z-DEVD-fmk (SEQ ID NO: 71, FIG. 24B) or Ivachtin (FIG. 24C). FIG. 24D—Images depicting B16F10 melanoma cells stained for α-Catenin (green). Cells treated with Ivachtin present reduced expression of α-Catenin. FIG. 24E—Immunoblot analysis of proteins isolated from B16F10 melanoma cells using antibodies against pYAP, α-Catenin and α-Tubulin as control.

Figure 25A:
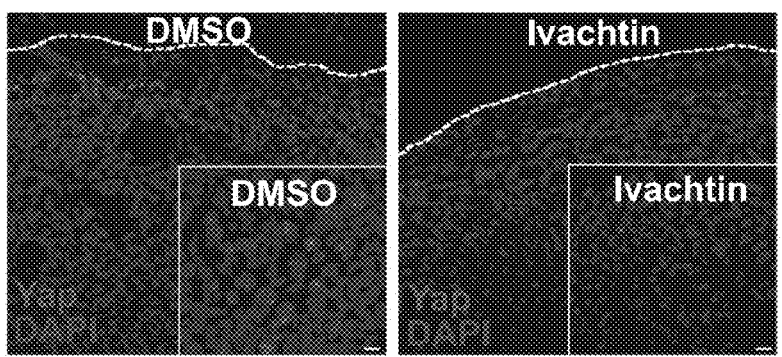
Figure 25B:
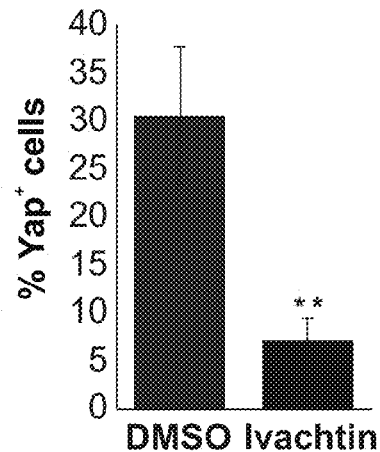

FIGS. 25A-B show that caspase 3 inhibition diminishes YAP signaling in melanoma cells in vivo. FIG. 25A—Resected tumors stained for YAP (red) show higher expression in non-treated (DMSO) animals. Scale bars: 20 μm; FIG. 25B—A histogram depicting quantification of YAP$^+$ melanoma cells in vivo after treatment. ** ($P<0.01$).

FIGS. 26A-F show that caspase-3 inhibition coupled with a chemical BRAF inhibitor attenuates proliferation of resistant melanoma cells in vitro and leads to increased cell death in a Yap-dependent fashion. FIG. 26A—Images showing that cell growth of A-375 melanoma cells is hindered in the continuous presence of a specific irreversible Caspase-3 inhibitor coupled with Vem (upper panels, Z-DEVD fmk (SEQ ID NO: 71)+Vem; Lower panels, Ivachtin+Vem). FIG. 26B—A histogram depicting quantifications of A-375 total cell number after treatment with Z-DEVD-fmk (SEQ ID NO: 71) and BRAF inhibitor (Vem) separate (blue) and combined (white). FIG. 26C—Cell growth of A-375 resistant melanoma cells is hindered in the continuous presence of a specific irreversible Caspase-3 inhibitor coupled with Vem (upper panels, Z-DEVD fmk (SEQ ID NO: 71)+Vem; Lower panels, Ivachtin+Vem). FIG. 26D—Quantifications of A-375 total cell number after treatment with Z-DEVD-fmk (SEQ ID NO: 71) and BRAF inhibitor (Vem) separate and combined: upper panel—Z-DEVD fmk (SEQ ID NO: 71)+Vem; lower panel—Ivachtin+Vem). FIG. 26E—Cell growth of LU-1205 resistant melanoma cells is hindered in the continuous presence of a specific irreversible Caspase-3 inhibitor coupled with Vem. FIG. 26F—A histogram depicting quantifications of LU-1205 resistant melanoma total cell number after treatment with Z-DEVD-fmk (SEQ ID NO: 71) and BRAF inhibitor (Vem) separate and combined.

Figure 27A:
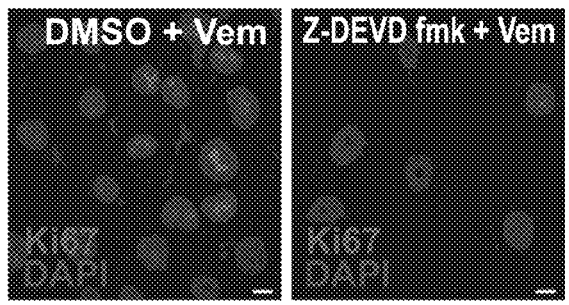
Figure 27C:
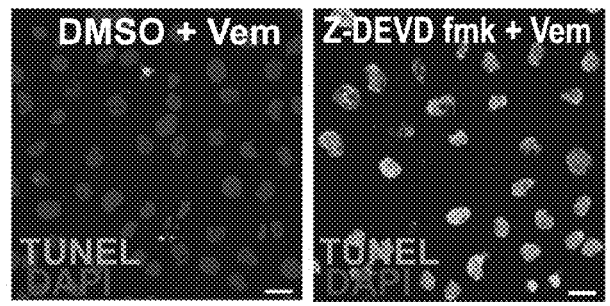
Figure 27B:
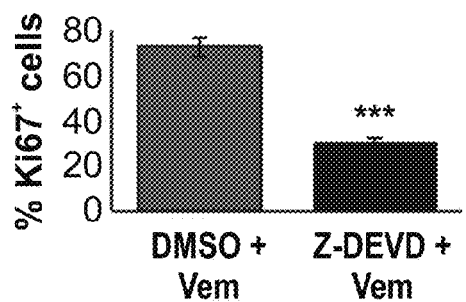
Figure 27D:
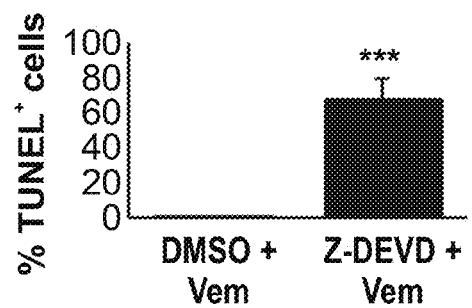

FIGS. 27A-D show that caspase-3 inhibition coupled with a chemical BRAF inhibitor attenuates proliferation of resistant melanoma cells in vitro and leads to increased cell death in a Yap-dependent fashion. FIG. 27A—A-375 resistant melanoma cells stained for Ki67 (red). Cells treated with Z-DEVD-fmk (SEQ ID NO: 71)+Vem display reduced levels of proliferative cells. FIG. 27B—A histogram depicting quantification of Ki67$^+$cells in non-treated and treated media. FIG. 27C—TUNEL assay performed on fixed A-375 resistant melanoma cells shows enhanced cell death in z-DEVD fmk (SEQ ID NO: 71)+Vem-treated cells. FIG. 27D—A histogram depicting quantification of TUNEL$^+$ melanoma cells.

Figure 28:
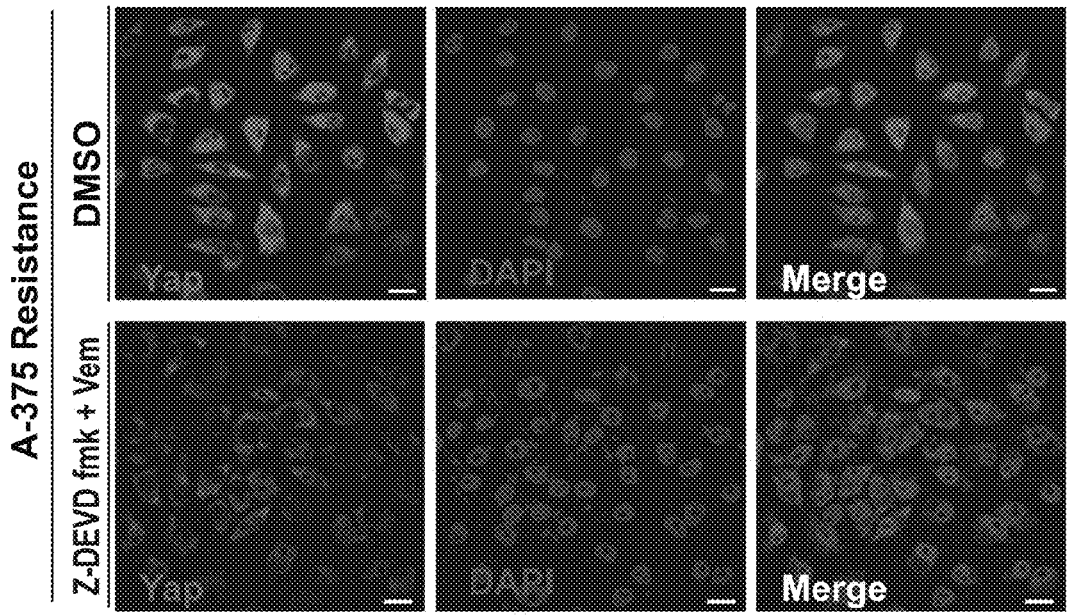

FIG. 28 shows that caspase 3 inhibition diminishes Yap signaling in resistant melanoma cells. Images of A-375 resistant melanoma cells that were treated with z-DEVD fmk (SEQ ID NO: 71) coupled with Vem and were stained for Yap (red). Cells treated with z-DEVD-fmk (SEQ ID NO: 71)+Vem show cytosolic Yap and lower expression than control cells. Denotation: Vem, Vemurafenib. Scale Bars: 10 μm  ($P<0.01$), * ($P<0.001$). These results shown that inhibition of caspase 3 coupled with BRAF inhibition attenuates expansion of resistant melanoma cells, drives cell death as well as impairs YAP activation.

FIGS. 29A-I demonstrate that feedback inhibition of caspase-3 activity is mediated through XIAP. FIG. 29A—Confocal Z-stack images of TWM stained for CP3, Ki67 and DAPI from WT and XIAP$^{-/-}$ mice. FIG. 29B—Quantification of proliferating Ki67+(upper histogram) and CP3+ (lower histogram) cells in the SG of WT and XIAP$^{-/-}$ tailskin (n=25 individual SGs). FIG. 29C—Quantification of SG length (upper histogram, measured in μm) and volume (lower histogram, measured in mm$^3$) in WT and XIAP$^{-/-}$ mice (n=30 individual SGs). FIG. 29D—Quantification of SG cells positive for CP3 or TUNEL in tailskins (n=25 individual SGs). FIG. 29E—Images of TWM stained for XIAP and DAPI from mice treated with DMSO, Verteporfin, PAC-1 or PAC-1+Verteporfin. FIG. 29F—Immunostaining of integrin α6$^+$CD34$^-$EGFP$^{high}$ cells for XIAP and DAPI following treatment with PAC-1. FIG. 29G—Quantification of XIAP signal intensity from integrin α6$^+$CD34$^-$EGFP$^{high}$ cells treated as described in FIG. 29F. FIG. 29H—RNA isolated from integrin α6$^+$CD34$^-$EGFP$^{high}$ cells treated with VP, PAC1 or a combination of both was subjected to RT-PCR analysis for XIAP expression. Values shown were normalized to Rp1p0, relative to levels in DMSO treated cells (n=3). FIG. 29I—Schematic model for caspase-3-YAP mechanism of action. Proliferation promoting signals, as occurring in SG cell renewal, promote caspase-3 cleavage of α-Catenin. Alpha-Catenin retains YAP in the cytoplasm via interaction with 14-3-3. Upon caspase-3 cleavage, 14-3-3 binding to α-Catenin is abrogated and YAP is dephosphorylated and translocates into the nucleus, where it regulates transcription of its target genes including XIAP. XIAP facilitates a feedback loop, by blocking caspase-3 activity. Upon caspase-3 deletion or inhibition, α-Catenin retains YAP in the cytoplasm, thus preventing YAP-mediated transcription. Denotation: z-DEVD-fmk (SEQ ID NO: 71), DEVD. Verteporfin, VP. Scale bars: 50 μm (FIGS. 29A, 29E), 20 μm (FIG. 29F).

DESCRIPTION OF SPECIFIC EMBODIMENTS OF THE INVENTION

The present invention, in some embodiments thereof, relates to methods of selecting a treatment for a cancer by analyzing activity of Yes associated protein 1 (YAP) in cancer cells of the subject, and, more particularly, but not exclusively, to methods of treating cancer using caspase-3 inhibitors.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have uncovered a surprising, non-apoptotic role of Caspase-3 in the skin and show that cleaved Caspase-3 regulates YAP-dependent organ size and regeneration.

Apoptosis culminates in the activation of Caspase-3, which is responsible for implementing the cell death program. The present inventors uncovered, for the first time, a non-apoptotic role of Caspase-3 as a key regulator of organ size and skin regeneration. Caspase-3 is specifically activated in the proliferating cells of the sebaceous gland (SG), but does not induce apoptosis and does not instruct cellular elimination. Deletion or chemical inhibition of Caspase-3 in vivo results in significant reduction of sebocyte cell number, proliferation and SG size. YAP, a vital transcription factor of the Hippo pathway, was inactivated in mice deficient for Caspase-3. Additionally, the present inventors show that α-Catenin, known to sequester YAP in the cytoplasm, is cleaved by Caspase-3 thus facilitating the activation and nuclear translocation of YAP, a vital regulator of organ size. Accordingly, activation of caspase-3 leads to YAP-dependent organ size augmentation, suggesting a novel mechanism, which governs the nuclear translocation of YAP. Finally, Caspase-3 inhibition delayed wound healing and hair follicle regeneration by diminishing YAP activity. This data unravels a non-canonical role of Caspase-3 as a fundamental regulator of YAP activation, organ size and regeneration. Taken together, the present inventors unravel a unique molecular mechanism where the apoptotic machinery is refocused to regulate cell proliferation and orchestrate organ size.

As described in Examples 1-8 hereinbelow, the present inventors have uncovered a surprising, non-apoptotic, role of caspase-3 as a key regulator of YAP-dependent cell proliferation, organ size and regeneration. Using the SG as a model, the present inventors sought to understand whether this unique organ, including its size, cell number and tissue expansion, could be governed by apoptotic machinery proteins. Intriguingly, the present inventors could detect active caspase-3 in dividing SG cells that were not undergoing apoptosis. Using inhibition and activation strategies of caspase-3, the present inventors were able to determine that cellular proliferation and SG size are contingent upon active caspase-3, and contrary to the straightforward expectation, inhibition of caspase-3 attenuates these modalities in vivo. Caspase-3 is specifically activated in the proliferating cells of the sebaceous gland (SG) where it does not instruct cellular elimination. Mice deficient for caspase-3 display significant reduction in sebocyte cell number and proliferation, resulting in a dramatic decrease in SG size. In caspase-$3^{-/-}$ mice, YAP, a known oncogene, was found to reside outside of the nucleus in an inactivated phosphorylated state. Additionally, the present inventors revealed that alpha-catenin, known to sequester YAP, is cleaved by caspase-3 in two distinct regions suggesting a novel mechanism in which caspase-3 can regulate the nuclear translocation of oncogenic YAP. Finally, chemical inhibition of caspase-3 inhibited keratinocyte proliferation and impaired wound healing and skin regeneration in a YAP dependent manner (FIGS. 2J, 2K, 2P, 2Q, 8C, 8D, 7F-I showing that inhibition of active caspase-3 impair organ size and cell proliferation; FIGS. 3G, 3H, 3I, 3L, 3M, showing that inhibition of active caspase-3 inhibits YAP activation; FIG. 4S, showing that inhibition of caspase-3 decreased alpha-catenin expression (the endogenous YAP inhibitor); FIGS. 10A-H showing that inhibition of active caspase-3 inhibits cell proliferation; FIGS. 11A-H showing that inhibition of active caspase-3 inhibits YAP activation). In addition, the Examples section show that inhibition of caspase-3 attenuates YAP-dependent regeneration (FIGS. 19A-F), impairs wound healing (FIGS. 19A-B), inhibits YAP activation (FIGS. 19C-E) and that there is no additive effect when inhibiting caspase-3 and YAP (FIG. 19F).

Upon further examination, the present inventors revealed that active caspase-3 is able to cleave α-Catenin. Without being bound by any theory, in this mechanism, α-Catenin is unable to sequester YAP, leading to its dephosphorylation and translocation into the nucleus. In line with this, stimulation of caspase-3 activity augments SG size, in a manner dependent upon YAP liberation from α-Catenin. Furthermore, the present inventors show that XIAP, a potent endogenous caspase inhibitor, serves as a target gene of YAP and is able to diminish caspase-3-mediated YAP signaling in vivo. Accordingly, the present inventors have found that deletion of XIAP results in a significant expansion in SG size. Without being bound by any theory, these findings suggest that XIAP is able to function as a strong feedback antagonist in vivo. In line with previous studies on YAP activation in the skin, and without being bound by any theory, the present inventors offer a mechanism to describe how YAP liberation is regulated and how SG size is governed by this unique module, thus there is an autonomous signaling crosstalk between the apoptotic core machinery and the YAP signaling pathway in the skin.

The Examples section further show that caspase activation results in increased organ size and cell proliferation (FIGS. 2T, 2U, 2V and 2W), that activation of caspase-3 activates YAP (FIG. 3O), that activation of caspase-3 drives YAP-dependent proliferation (FIGS. 17A-G), and that activation of caspase-3 drives YAP-dependent regeneration (FIGS. 17D-G).

Furthermore, the Examples section shows that activation of caspase-3 drives tissue regeneration (FIGS. 20A-B), and drives cell proliferation and tissue regeneration (FIGS. 20C-D).

In addition, the Examples section demonstrates that activation of caspase-3 accelerates tumor growth and cell proliferation (FIGS. 21A-F). On the other hand, inhibition of caspase-3 attenuates cancer cell proliferation and leads to increased cell death [FIGS. 22A-G; 23A-D (in vitro), 23E-H (in vivo)], attenuates YAP signaling in melanoma cells [FIGS. 24A-E (in vitro) and FIGS. 25A-B (in vivo)]. Furthermore, the Examples section demonstrate that inhibition of caspase-3 coupled with BRAF inhibition attenuates expansion of resistant melanoma cells (FIGS. 26A-F) and attenuates expansion of resistant melanoma cells, drives cell death as well as impairs YAP activation (FIGS. 27A-D and FIG. 28).

According to an aspect of some embodiments of the invention, there is provided a method of selecting a treatment for a cancer in a subject in need thereof, the method comprising analyzing activity of Yes associated protein 1 (YAP) in cancer cells of the subject, wherein an up-regulation in activity of the YAP above a predetermined level as compared to an activity of the YAP in a matching non-cancerous tissue classifies the subject suitable for treatment of cancer with a caspase 3 inhibitor.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "subject" includes mammals, preferably human beings at any age which suffer from the pathology. Preferably, this term encompasses individuals who are at risk to develop the pathology.

Selecting a treatment for a cancer (e.g., a treatment regimen for cancer) refers to a treatment plan that specifies the type of treatment, dosage, schedule and/or duration of a treatment provided to a subject in need thereof (e.g., a subject diagnosed with a pathology).

The selected treatment regimen can be an aggressive one which is expected to result in the best clinical outcome (e.g., complete cure of the pathology) or a more moderate one which may relief symptoms of the pathology yet results in incomplete cure of the pathology. It will be appreciated that in certain cases the more aggressive treatment regimen may be associated with some discomfort to the subject or adverse side effects (e.g., a damage to healthy cells or tissue). The type of treatment can include a surgical intervention (e.g., removal of lesion, diseased cells, tissue, or organ), a cell replacement therapy, an administration of a therapeutic drug (e.g., receptor agonists, antagonists, hormones, chemotherapy agents) in a local or a systemic mode, an exposure to radiation therapy using an external source (e.g., external beam) and/or an internal source (e.g., brachytherapy) and/or any combination thereof. The dosage, schedule and duration of treatment can vary, depending on the severity of pathology and the selected type of treatment, and those of skills in the art are capable of adjusting the type of treatment with the dosage, schedule and duration of treatment.

As mentioned above, the present inventors have uncovered that caspase-3 regulates activation of YAP. In the absence of active caspase-3 the YAP protein resides outside of the nucleus and is in an inactivated phosphorylated state. In the presence of active caspase-3, the alpha-catenin, which is known to sequester YAP in the cytoplasm, is cleaved by caspase-3 in two distinct regions, thus enabling the translocation of YAP into the nucleus and the further activation thereof.

The method of some embodiments of the invention requires analyzing the activity of Yes associated protein 1 (YAP) in cancer cells of the subject.

The terms "Yes associated protein 1" or "YAP", which are interchangeably used herein, refer to the downstream nuclear effector protein of the Hippo signaling pathway which is involved in development, growth, repair, and homeostasis. The gene encoding YAP is known to play a role in the development and progression of multiple cancers as a transcriptional regulator of this signaling pathway.

Several isoforms of YAP are known in the art, and the sequences of these isoforms can be obtained from various sources such as the National Center for Biotechnology Information (NCBI) data base. Isoform 1 (variant 1) [protein sequence GenBank Accession No. NP_001123617.1 (SEQ ID NO:1); RNA sequence GenBank Accession No. NM_001130145.2 (SEQ ID NO:2)] uses an alternate in-frame splice site in the 3' coding region, compared to variant 9; isoform 2 (variant 2) [protein sequence GenBank Accession No. NP_006097.2 (SEQ ID NO:3), RNA sequence GenBank Accession NO. NM_006106.4 (SEQ ID NO:4)] uses an alternate in-frame splice site and lacks two alternate exons in the coding region, compared to variant 9; isoform 3 (variant 3) [protein sequence GenBank Accession No. NP_001181973.1 (SEQ ID NO:5); RNA sequence GenBank Accession No. NM_001195044.1 (SEQ ID NO:6)] uses an alternate in-frame splice site and lacks an alternate exon in the 3' coding region, compared to variant 9; isoform 4 (variant 4) [protein sequence GenBank Accession No. NP_001181974.1 (SEQ ID NO:7), RNA sequence GenBank Accession No. NM_001195045.1 (SEQ ID NO:8)] differs in the 5' UTR and has multiple differences in the coding region, compared to variant 9; isoform 5 (variant 5) [protein sequence GenBank Accession No. NP_001269027.1 (SEQ ID NO:9), RNA sequence GenBank Accession No. NM_001282098.1 (SEQ ID NO:10)] lacks two alternate in-frame exons in the coding region, compared to variant 9; isoform 6 (variant 6) [protein sequence GenBank Accession No. NP_001269026.1 (SEQ ID NO:11), RNA sequence GenBank Accession No. NM_001282097.1 (SEQ ID NO:12)] lacks an in-frame exon and uses an alternate in-frame splice site in the coding region, compared to variant 9; isoform 7 (variant 7) [protein sequence GenBank Accession No. NP_001269028.1 (SEQ ID NO:13), RNA sequence GenBank Accession No. NM_001282099.1 (SEQ ID NO:14) lacks an alternate in-frame exon in the coding region, compared to variant 9; isoform 8 (variant 8) [protein sequence GenBank Accession No. NP_001269029.1 (SEQ ID NO:15), RNA sequence GenBank Accession No. NM_001282100.1 (SEQ ID NO:16)] lacks an alternate in-frame exon in the 3' coding region, compared to variant 9; isoform 9 (variant 9) [protein sequence GenBank Accession No. NP_001269030.1 (SEQ ID NO:17), RNA sequence GenBank Accession No. NM_001282101.1 (SEQ ID NO:18)] represents the longest transcript and encodes the longest isoform (9)

As described above, YAP acts as a transcriptional regulator of the of the Hippo signaling pathway and thus plays a role in the development and progression of multiple cancers. Active YAP protein translocates from the cytoplasma into the cell nucleus and functions there as a coactivator of TEA domain family members (TEAD), which are the major transcription factors driving YAP-mediated gene transcription. The activation of YAP is regulated by its phosphorylation, wherein phosphorylation of YAP at serine 127 (S127) leads to its retention in the cytoplasm, and phosphorylation of YAP on serine 381 (S381) leads to its ubiquitination and cytoplasmic degradation (Zhao B., et al., 2007, Genes Dev. 21: 2747-2761; Samar S., et al., 2016, JBC online publication Jul. 20, 2016; each of which is fully incorporated herein by reference in its entirety).

According to some embodiments of the invention, the activity of YAP can be determined by measuring transcription levels of the YAP target genes in the nucleus.

Non-limiting examples of YAP target genes include, HOXC13 [e.g., homeobox protein Hox-C13 as set forth by GenBank Accession Nos. NM_017410.2 (SEQ ID NO:23) and NP_059106.2 (SEQ ID NO:24)], HOXA5 [homeobox protein Hox-A5 as set forth by GenBank Accession Nos. NM_019102.3 (SEQ ID NO:25) and NP_061975.2 (SEQ ID NO:26)], ErbB4 [e.g., the receptor tyrosine-protein kinase erbB-4 isoform JM-a/CVT-1 precursor as set forth by GenBank Accession Nos. NM_005235.2 (SEQ ID NO:27) and NP_005226.1 (SEQ ID NO:28); and the receptor tyrosine-protein kinase erbB-4 isoform JM-a/CVT-2 precursor as set forth by GenBank Accession Nos. NM_001042599.1 (SEQ ID NO:29) and NP_001036064.1 (SEQ ID NO:30)], ITGB2 [e.g integrin beta-2 isoform 1 precursor set forth by GenBank Accession Nos. NM_000211.4 (SEQ ID NO:31), NM_001127491.2 (SEQ ID NO:32) and NP_000202.3 (SEQ ID NO:33); integrin beta-2 isoform 2 set forth by GenBank Accession Nos. NM_001303238.1 (SEQ ID NO:34) and NP_001290167.1 (SEQ ID NO:35)], RUNX2 [e.g., runt-related transcription factor 2 isoform as set forth by GenBank Accession Nos. NM_001024630.3 (SEQ ID NO:36) and NP_001019801.3 (SEQ ID NO:37); runt-related transcription factor 2 isoform b as set forth by GenBank Accession Nos. NM_001015051.3 (SEQ ID NO:38) NP_001015051.3 (SEQ ID NO:39)], CTGF [e.g connective tissue growth factor precursor as set forth by GenBank Accession Nos. NM_001901.2 (SEQ ID NO:40) and NP_001892.1 (SEQ ID NO:41)], WTIP [Wilms tumor 1 interacting protein; GenBank Accession No. NP_001073905.1 (protein, SEQ ID NO:42); and GenBank Accession No. NM_001080436.1 (RNA, SEQ ID NO:43)], Hoxa1 [homeobox A1; isoform (a) GenBank Accession No. NP_005513.1 (protein, SEQ ID NO:44) and GenBank Accession No. NM_005522.4 (RNA, SEQ ID NO:45); and isoform (b) GenBank Accession No. NP_705873.2 (protein, SEQ ID NO:46) and GenBank Accession No. NM_153620.2 (RNA, SEQ ID NO:47)]. Additional information can be found in Liu M et al., 2015. "YAP Regulates the Expression of Hoxa1 and Hoxc13 in Mouse and Human Oral and Skin Epithelial Tissues" Mo. Cell Biol. 35: 1449-61; and Xiaojing Wang et al. 2016; "YAP down-regulated its target CTGF to maintain stem cell pluripotency in human ovarian cancer stem-like cells"; Int. J. Clin. Exp. Pathol. 9: 6210-6216, each of which is fully incorporated herein by reference in its entirety).

Briefly, an assay which can determine the transcriptional activity of YAP on a target gene can be performed by determining the levels of transcripts of YAP downstream target genes by RT-PCR (reverse transcriptase—polymerase chain reaction). For example, HaCaT or HEK293 cells can be treated with or without caspase-3 inhibitors and the effect on YAP can be determined by determining the level of expression of the YAP target genes.

For example, as shown in FIG. 3M and described in Example 3 of the Examples section which follows, the effect of caspase-3 inhibitors is demonstrated by the decrease in activation of YAP target genes such as WTIP, ERBB4, HOXC14 and HOXA5 as determined by RT-PCR analysis.

Additionally or alternatively immunological assays such as Western blots, immunohistochemical assays and immunofluorescence can also be used to detect the activity of YAP using antibodies specific for YAP or inactive YAP (phosphorylated at Ser127 e.g., in the polypeptide set forth by SEQ ID NO:48 and/or by monitoring YAP cellular localization.

According to some embodiments of the invention, the activity of YAP can be determined by measuring the phosphorylation level, e.g., at amino acid serine 127 (S127) of the YAP polypeptide set forth by SEQ ID NO: 48. It should be noted that presence of unphosphorylated or dephosphorylated YAP indicates that the YAP is active.

According to the method of some embodiments of the invention, up-regulation in activity of YAP above a predetermined level as compared to an activity of the YAP in a matching non-cancerous tissue (or cell) classifies the subject as being suitable for treatment of cancer with a caspase 3 inhibitor.

According to some embodiments of the invention, the method further comprising analyzing cellular localization of the YAP, wherein an increased nuclear localization of the YAP above a predetermined level as compared to nuclear localization of the YAP in a matching non-cancerous tissue classifies the subject suitable for treatment of cancer with a caspase 3 inhibitor.

According to some embodiments of the invention, the translocation of YAP from the cytoplasma into the cell nucleus can be determined by various immunological assays. For example immunofluorescence staining or immunohistochemistry together with biochemical assays such as cellular fractionation, can be used to detect the localization of YAP in the nucleus or the cytoplasm thus determining its activity. Antibodies specific for the phosphorylated form of YAP on Ser127 (for humans) or Ser112 (for mice) only detect cytoplasmic localization of the protein. Antibodies specific for pan YAP protein can detect both cytoplasmic and nuclear localization of the protein thus distinguishing between inactive and active form respectively. A combination of these two antibodies can verify the translocation of YAP to the nucleus and thus its activation. Additional assays such as RT-PCR for target genes or immunofluorescence for target genes can be used to show that activation of YAP correlates with its nuclear translocation.

As used herein the term "above predetemined level" refers to an increase in the level of activity of YAP and/or an increase in the nuclear localization of YAP in the cancerous cell relative to a reference non-cancerous cell (e.g., a cell which is non-cancerous and which is obtained from a matching tissue as the original tissue/cell from which the cancer originates) which is higher than a predetermined threshold such as a about 10%, e.g., higher than about 20%, e.g., higher than about 30%, e.g., higher than about 40%, e.g., higher than about 50%, e.g., higher than about 60%, higher than about 70%, higher than about 80%, higher than about 90%, higher than about 2 times, higher than about three times, higher than about four time, higher than about five times, higher than about six times, higher than about seven times, higher than about eight times, higher than about nine times, higher than about 20 times, higher than about 50 times, higher than about 100 times, higher than about 200 times of at least one reference non-cancerous cell. The upregulation in the level of activity and/or the increase in nuclear localization of YAP can be also determined using logarithmic fold changes (e.g., in Log 2).

Thus, according to the method of some embodiments of the invention, a subject is suitable for treatment of the cancer with a caspase-3 inhibitor when the activity of YAP in the cancerous cells obtained from the cancer (e.g., tumor) of the subject is increased above a predetermined level as compared to the level of activity of YAP in a reference cell. Additionally or alternatively, the subject is suitable for treatment of the cancer with a caspase-3 inhibitor when an increased level above a predetermined level of YAP in the nucleus is present in the cancerous cells obtained from the cancer (e.g., tumor) of the subject as compared to the level of YAP in the nucleus of a reference cell.

As used herein the term "caspase-3" refers to a protein which is a member of the cysteine-aspartic acid protease (caspase) family. Sequential activation of caspases plays a central role in the execution-phase of cell apoptosis. Caspases exist as inactive proenzymes which undergo proteolytic processing at conserved aspartic residues to produce two subunits, large and small, that dimerize to form the active enzyme. Caspase-3 cleaves and activates caspases 6, 7 and 9, and is being processed by caspases 8, 9 and 10.

The caspase-3 gene (gene symbol is CASP3) encodes two isoformes. The sequences of these isoforms can be obtained from various sources such as the National Center for Biotechnology Information (NCBI) data base. Isoform 1 (variant alpha) [protein sequence GenBank Accession No. NP_004337.2 (SEQ ID NO:19), RNA sequence GenBank Accession No. NM_004346.3 (SEQ ID NO:20)] represents the longer transcript; isoform 2 variant (beta) [protein sequence GenBank Accession No. NP_116786.1 (SEQ ID NO:21); RNA sequence GenBank Accession No. NM_032991.2 (SEQ ID NO:22)] differs in the 5' UTR, compared to variant alpha.

According to an aspect of some embodiments of the invention, there is provided a method of treating a subject having cancer, the method comprising (a) testing suitability of the subject for treatment according to the method of some embodiments of the invention, and (b) treating the subject with a therapeutically effective amount of a caspase-3 inhibitor, thereby treating the subject.

Thus, the treatment with the anti-caspase-3 agents, such as caspase-3 inhibitors is efficient when cancer is characterized by increased activity of YAP in the cancerous cells as compared to reference cells.

The cancer can be a solid tumor or a non-solid tumor.

According to some embodiments of the invention, wherein the cancer which is characterized by the up-regulation the activity of the YAP above the predetermined threshold as compared to the matching non-cancerous tissue is selected from the group consisting of glioma, head and neck cancer, esophageal cancer, sarcoma, non small cell lung cancer, breast cancer, ovarian cancer, uterine cancer, gastric cancer, melanoma, colorectal cancer, bladder cancer, prostate cancer, liver cancer and pancreatic cancer.

Non-limiting examples of Caspase 3 inhibitors which can be used by the method of some embodiments of the invention include, but are not limited to, Z-VAD(OMe)-FMK [An irreversible and cell permeable broad-spectrum Caspase Inhibitor]; Z-FA-FMK [Inhibits effector, but not initiator caspases in vitro, and suppress some forms of apoptosis]; Z-DEVD-FMK [SEQ ID NO: 71, An inhibitor of caspase-3, caspase-6, caspase-7, and caspase-10]; Ac-DEVD-CMK

[SEQ ID NO: 72. A potent cell-permeable and irreversible caspase-3 inhibitor]; Q-VD-OPH [An inhibitor of caspase-3, caspase-1, caspase-8 and caspase-9]; Caspase-3/7 Inhibitor I (5-[(S)-(+)-2-(Methoxymethyl)pyrrolidino]sulfonylisatin) [An inhibitor of caspase-3, caspase-7 and Caspase-9]; Ivachtin [A potent, cell-permeable, reversible, non-competitive inhibitor of caspase-3]; Caspase Inhibitor X (BI-9B12) [A competitive inhibitor of caspase-3, caspase-7 and caspase-8]; Z-Asp-2,6-dichlorobenzoyloxymethylketone [A broad Caspase Inhibitor]; DICA [An inhibitor of caspase-3 and caspase-7]; Caspase-3 Inhibitor I, Cell Permeable (Ac-AAVALLPAVLLALLAPDEVD-CHO; SEQ ID NO:49) [An inhibitor of caspase-3, caspase-6, caspase-7, caspase-8, and caspase-10]; Ac-VAD-cho [Inhibits caspase-1,3,4,7]; Ac-ESMD-CHO [SEQ ID NO: 73, Inhibits caspase-3, 7]; Z-Asp-OMe-Gln-Met-Asp-OMe-FMK [SEQ ID NO: 74, Inhibits caspase-3, 6].

According to some embodiments of the invention, the method of treating the subject comprises combination therapy with anti-cancer treatment such as chemotherapeutic drug, radiation therapy, phototherapy and photodynamic therapy, surgery, nutritional therapy, ablative therapy, combined radiotherapy and chemotherapy, brachytherapy, proton beam therapy, immunotherapy, cellular therapy and photon beam radiosurgical therapy.

Anti-Cancer Drugs

Anti-cancer drugs that can be co-administered with the caspase-3 inhibitors of some embodiments of the invention include, but are not limited to Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofuirin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride. Additional antineoplastic agents include those disclosed in Chapter 52, Antineoplastic Agents (Paul Calabresi and Bruce A. Chabner), and the introduction thereto, 1202-1263, of Goodman and GILMAN'S "THE PHARMACOLOGICAL BASIS OF THERAPEUTICS", EIGHTH EDITION, 1990, MCGRAW-HILL, INC. (HEALTH PROFESSIONS DIVISION).

According to some embodiments of the invention, the chemotherapy drug is a BRAF inhibitor.

According to some embodiments of the invention, the BRAF inhibitor is vemurafenib (marketed as zelboraf).

Anti-Inflammatory Drugs

Anti inflammatory drugs that can be administered in combination with the anti-caspase-3 agents, such as the caspase-3 inhibitor(s) of some embodiment of the invention include but are not limited to Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lomoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Momiflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium.

Following are non-limiting examples of approved chemotherapy which can be co-administered with the caspase-3 inhibitors of some embodiments of the invention: abarelix, aldesleukin, aldesleukin, alemtuzumab, alitretinoin, allopurinol, altretamine, amifostine, anastrozole, arsenic trioxide, asparaginase, azacitidine, bevacuzimab, bexarotene, bleomycin, bortezomib, busulfan, calusterone, capecitabine, carboplatin, carmustine, celecoxib, cetuximab, cisplatin, cladribine, clofarabine, cyclophosphamide, cytarabine, dacarbazine, dactinomycin, actinomycin D, Darbepoetin alfa, Darbepoetin alfa, daunorubicin liposomal, daunorubicin, decitabine, Denileukin diftitox, dexrazoxane, dexrazoxane, docetaxel, doxorubicin, dromostanolone propionate, Elliott's B Solution, epirubicin, Epoetin alfa, erlotinib, estramustine, etoposide, exemestane, Filgrastim, floxuridine, fludarabine, fluorouracil 5-FU, fulvestrant, gefitinib, gemcitabine, gemtuzumab ozogamicin, goserelin acetate, histrelin acetate, hydroxyurea, Ibritumomab Tiuxetan, idarubicin, ifosfamide, imatinib mesylate, interferon alfa 2a, Interferon alfa-2b, irinotecan, lenalidomide, letrozole, leucovorin, Leuprolide Acetate, levamisole, lomustine, CCNU, meclorethamine, nitrogen mustard, megestrol acetate, melphalan, L-PAM, mercaptopurine 6-MP, mesna, methotrexate, mitomycin C, mitotane, mitoxantrone, nandrolone phenpropionate, nelarabine, Nofetumomab, Oprelvekin, Oprelvekin, oxaliplatin, paclitaxel, palifermin, pamidronate, pegademase, pegaspargase, Pegfilgrastim, pemetrexed disodium, pentostatin, pipobroman, plicamycin mithramycin, porfimer sodium, procarbazine, quinacrine, Rasburicase, Rituximab, sargramostim, sorafenib, streptozocin, sunitinib maleate, tamoxifen, temozolomide, teniposide VM-26, testolactone, thioguanine 6-TG, thiotepa, thiotepa, topotecan, toremifene, Tositumomab, Trastuzumab, tretinoin ATRA, Uracil Mustard, valrubicin, vinblastine, vinorelbine, zoledronate and zoledronic acid.

The method of some embodiments of the invention, further comprising treating the subject with radiation therapy.

As described in Example 3 of the Examples section which follows, and shown in FIGS. 5A-L and FIGS. 13A-E the present inventors have further uncovered that inhibition of caspase-3 impaired wound healing and thus suggest using caspase-3 activator(s) for improving wound healing.

Thus, according to an aspect of some embodiments of the invention there is provided a method of improving wound healing in a subject, comprising administering to a wounded area of the subject a wound healing effective amount of a caspase-3 activator, the therapeutically effective amount of the caspase-3 being capable of increasing activity of Yes associated protein 1 (YAP) as compared to a wounded area of a subject non-treated by the caspase-3 activator, thereby improving the wound healing in the subject.

The term "wound healing" refers to a process involving tissue growth that partially or totally closes a wound, e.g., repairs a breach in the dermis or epidermis and partially or totally restores the barrier properties of the skin, or repairs of the surface layers of a mucosal membrane.

The process of wound healing consists of three phases during which the injured tissue is repaired, regenerated, and new tissue is reorganized into a scar. These three phases are classified as: a) an inflammation phase which begins from day 0 e.g., to about 3 days, b) a cellular proliferation phase from about day 3 to about day 12, and c) a remodeling phase from about say 3 to about 6 months. Sometimes wound repair is hampered resulting in the formation of keloid.

In the inflammation phase, inflammatory cells, mostly neutrophils, enter the site of the wound followed by lymphocytes, monocytes, and later macrophages. The neutrophils that are stimulated begin to release proteases and reactive oxygen species into the surrounding medium with potential adverse effects on both the adjacent tissues and the invading microorganisms. The oxygen species known to be released by the neutrophils are superoxide ($O_2^-$) through the action of a plasma membrane-bound NADPH oxidase, hydrogen peroxide ($H_2O_2$) formed by action of dismutation of $O_2^-$, and HOCl produced by the action of myeloperoxidase with $H_2O_2$.

The proliferative phase consists of laying down new granulation tissue, and the formation of new blood vessels in the injured area. The fibroblasts, endothelial cells, and epithelial cells migrate in the wound site. These fibroblasts produce the collagen that is necessary for wound repair. Ascorbic acid is crucial in the formation of collagen. Several studies have demonstrated that ascorbic acid was capable of overcoming the reduced proliferative capacity of elderly dermal fibroblasts, as well as increasing collagen synthesis in elderly cells by similar degrees as in newborn cells even though the basal levels of collagen synthesis are age dependent.

In re-epithelialization, epithelial cells migrate from the free edges of the tissue across the wound. This event is succeeded by the proliferation of epithelial cells at the periphery of the wound. Research has also shown that re-epithelialization is enhanced by the presence of occlusive wound dressings which maintain a moisture barrier.

The final phase of wound healing, which is remodeling, is effected by both the replacement of granulation tissue with collagen and elastin fibers and the devascularization of the granulation tissue.

It should be noted that improving wound healing can include decreasing or shortening the time period required for the wound to heal, as well as improving quality of the healing process of a wound.

According to some embodiments of the invention improving wound healing comprises shortening the time period required for the wound to heal by at least 2%, at least 3%, at least 4%, at least 5%, at least 6%, at least 7%, at least 8%, at least 9%, at least 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, e.g., at least about 100% as compared to the time period required for the same (e.g., identical) wound to heal in the absence of administration of the caspase-3 activator to the subject under identical conditions.

The wound healing status can be documented using known scales. Two tools commonly used to monitor and quantify wound healing are the Pressure Ulcer Scale for Healing (PUSH), developed and validated by the NPUAP and others; and the Bates-Jensen Wound Assessment Tool (BWAT), developed and validated by Bates-Jensen and others.

Pressure Ulcer Scale for Healing (PUSH)—PUSH was designed to be a biologically accurate, easy to use, clinically practical instrument for pressure ulcer tracking over time and across care settings, such as for quantifying healing of venous and diabetic foot ulcers. PUSH considers three factors with respect to wound status: size in centimeters squared, tissue type present in wound bed, and exudate amount. Tissue type and exudate are each given a score of 0 to 4. Size comprises ten grades, with the largest size (>24 $cm^2$) having the highest score. Then the subscores for the three factors are added together for a total score. Definitions and scores from NPUAP for the tissue types begin with the most severe:

4, necrotic tissue (eschar): black, brown, or tan tissue that adheres firmly to the wound bed or ulcer edges and may be either firmer or softer than surrounding skin;

3, slough: yellow or white tissue that adheres to the ulcer bed in strings or thick clumps, or is mucinous (covered with mucus);

2, granulation tissue: pink or beefy red tissue with a shiny, moist, granular appearance;

1, epithelial tissue: for superficial ulcers, new pink or shiny tissue (skin) that grows in from the edges or as islands on the ulcer surface;

0, closed/resurfaced: the wound is completely covered with epithelium (new skin).

Bates-Jensen Wound Assessment Tool (BWAT)—The BWAT is a valid and reliable tool developed by Bates-Jensen that is used to assess and monitor healing of all types of wounds. It is more comprehensive than the PUSH tool. Bates-Jensen consists of 15 items, two of which (location and shape) are not scored. Scored items are: Size; Depth; Edges; Undermining; Necrotic tissue type; Necrotic tissue amount; Exudate type; Exudate amount; Skin color; Edema; Induration; Granulation; Epithelialization. Each item can be scored 1 to 5, with 1 being the best for that attribute. After each item is assessed and scored, the 13 subscores are summed to get a total score. Bates-Jensen has calculated that BWAT scores can be converted to PUSH scores since the two tools are highly correlated.

An additional asset of BWAT is using the score to measure wound severity. This is important, since the goal of wound care is to reduce wound severity. The total BWAT scores are divided into four severity categories: 13-20=minimal severity; 21-30=mild severity; 31-40=moderate severity; 41-65=extreme severity;

The BWAT has been adapted as a photographic wound assessment tool (PWAT) by Houghton et al. (2000). This variation includes 6 of the 13 items, also rated on a 1 to 5 scoring system. The six item subscores can then be summed to a total score. Like the other tools, this tool has been validated and is responsive to change in wound status.

According to some embodiments of the invention, the activity of YAP is characterized by coactivation of the transcription of the TEAD (TEA/ATTS domain) complex.

According to some embodiments of the invention, the caspase-3 activator is selected from the group consisting of PAC-1, ABT-199 and Apoptosis activator 2, PETCM.

According to some embodiments of the invention, administering the caspase-3 activator is performed by topical administration to the wounded area of the subject.

According to some embodiments of the invention, administering the caspase-3 activator is performed by peripheral administration to the subject.

The anti-caspase-3 agent (e.g., the caspase-3 inhibitor) or the caspase-3 activator of some embodiments of the invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the anti-caspase-3 agent (e.g., the caspase-3 inhibitor) or the caspase-3 activator accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

The term "tissue" refers to part of an organism consisting of cells designed to perform a function or functions. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuos infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (e.g., anti-caspase-3 agent such as caspase-3 inhibitor; or the caspase-3 activator) effective to prevent, alleviate or ameliorate symptoms of a disorder (e.g., treat the cancer or improve the wound healing) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is understood that any Sequence Identification Number (SEQ ID NO) disclosed in the instant application can refer to either a DNA sequence or a RNA sequence, depending on the context where that SEQ ID NO is mentioned, even if that SEQ ID NO is expressed only in a DNA sequence format or a RNA sequence format. For example, SEQ ID NO: 47 is expressed in a DNA sequence format (e.g., reciting T for thymine), but it can refer to either a DNA sequence that corresponds to an Hoxa1 nucleic acid sequence, or the RNA sequence of an RNA molecule nucleic acid sequence. Similarly, though some sequences are expressed in a RNA sequence format (e.g., reciting U for uracil), depending on the actual type of molecule being described, it can refer to either the sequence of a RNA molecule comprising a dsRNA, or the sequence of a DNA molecule that corresponds to the RNA sequence shown. In any event, both DNA and RNA molecules having the sequences disclosed with any substitutes are envisioned.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Methods

Mice—All animal studies were approved by the Committee on the Ethics of Animal Experiments of the Technion. $Casp3^{tm1Flv}$ ($Casp3^{-/-}$) and B6.Cg-Tg(Krt1-15-EGFP)2Cot/J were purchased from Jackson Laboratories.

Cell culture—The HaCaT and HEK293 cell lines were cultured in DMEM medium supplemented with 10% FBS, 1% P/S (Pen/Strep) and 1% L-glutamine. Integrin $\alpha 6^+CD34^+$ HFSCs and integrin $\alpha 6^+CD34^-EGFP^{high}$ SGPZ cells were isolated and cultured in HFSC media on sustaining J2 feeder cells. Serum was chelated for a calcium concentration of 50 µM. Treatment with Ivachtin, z-DEVD-fmk (SEQ ID NO: 71, 100 µM, AdooQ Bioscience) or DMSO (as control) was for 7 to 14 days, and renewed upon media change. Cells were fixed in 4% PFA for 10 minutes for immunofluorescence analysis or harvested for protein or RNA extraction.

Flow Cytometry—SGPZ cell isolation and FACS analysis were performed with K15-EGFP mice and CD34, integrin $\alpha 6$ and Sca1 antibodies. $K15-GFP^{high}$ cells were isolated from ears and dorsal skin of 8-week old B6.Cg-Tg(Krt1-15-EGFP)2Cot/J mice.

Immunofluorescence—Skins were embedded in OCT, frozen, sectioned, and fixed in 4% paraformaldehyde. Tail samples were treated with 5 mM EDTA for 4 hours at 37° C. to separate skin epithelium from dermis and fixed in formal saline for 2 hours at room temperature. Dorsal samples were treated with 5 mM EDTA for 6 hours at 37° C. to separate skin epithelium from dermis and fixed in formal saline for 1 hour at room temperature. Samples were blocked for 2 hours in Blocking buffer consisting of 10% Goat serum, 2% BSA, 0.2% Triton-X. Primary antibodies were diluted in blocking buffer and tissue/sections were incubated overnight at 4° C. Whole mounts or sections were washed at least 3 times with PBS. Secondary antibodies were incubated for 1 hour at room temperature followed by 4 washes with PBS. The following primary antibodies were used: YAP (Rabbit, 1:100, Cell Signalling, Mouse 1:100 Santa Cruz), pYAP (Rabbit, 1:100 Cell Signalling), α-E-Catenin (Rabbit, 1:100, Cell Signalling), Ki67 (Rabbit, 1:100, Abcam; Rat, 1:100, eBioscience), CD34 (Rat, 1:100, eBioscience), K15 (Mouse, 1:100, Thermo, Chicken, 1:1000, Abcam), Sox9 (Rabbit, 1:100, Millipore, Goat, 1:50, Santa Cruz). Cleaved-Caspase-3 (Rabbit, 1:100, Cell signalling), Phalloidin (1:250, Life Technologies). TUNEL was performed using ApopTag TdT (Millipore). Antibody staining was visualized using secondary antibodies conjugated to Alexa Fluor 488, Alexa Fluor 546, and Alexa Fluor 633. Analysis was performed on Zeiss LSM 880 confocal microscope. Oil-red-O staining was performed by incubating skin samples in 0.18% ORO for 10 minutes and washing with PBS.

Intravital confocal imaging—Eight week-old mice B6.Cg-Tg(Krt1-15-EGFP)2Cot/J were anaesthetized with isoflurane, and the skin around the head region was shaved using a mechanical trimmer and depilatory cream. The mouse was placed on a heated stage, and the head and the ear were supported by a custom-made stage constructed in our lab. A glass coverslip was placed against the skin in the junction region between the head and the ear. Anaesthesia was maintained throughout the course of the experiment with vaporized isoflurane delivered by a nose cone. Intravital imaging was performed using the Zeiss LSM 880 confocal microscope.

RNA extraction, reverse transcription and real-time PCR (RT-PCR)—RNA was isolated using Trizol (Sigma) and up to 2 µg of RNA were subjected to cDNA synthesis (Applied Biosystems). Real time PCR was carried out using the PerfeCTa SYBR Green FastMix (Quanta), with gene-specific primers [RpLp0 GCGACCTGGAAGTCCAACTA (SEQ ID NO:50) and ATCTGCTTGGAGCCCACAT (SEQ ID NO:51); WTIP GCATCAAGTGTGGGCTTGGC (SEQ ID NO:52) and GTTGTAGAACGCCTTCCCAC (SEQ ID NO:53); ErbB4 GCAGATGCTACGGACCTTACG (SEQ ID NO:54) and GACACTGAGTAACACATGCTCC (SEQ ID NO:55); HOXC13 TCAGGTGTACTGCTCCAAGG (SEQ ID NO:56) and CAGCTGCACCTTAGTGTAGGG (SEQ ID NO:57); HOXA5 TCTCGTTGCCCTAATT-CATCTTTT (SEQ ID NO:58) and CAT-TCAGGACAAAGAGATGAACAGAA (SEQ ID NO:59)]. Amplicon levels were analysed in triplicate and quantitated relative to a standard curve comprising cDNA, and values normalized to levels of the housekeeping gene (Rplp0 or Gapdh). Reactions were: 3 minutes at 95° C., then 40 cycles of 10 seconds at 95° C. and 30 seconds at 60° C. with addition of melt curve step: 10 seconds at 95° C., and increments of 0.5° C. every 5 seconds between 65° C. to 95° C.

Protein extraction, Western Blot and Co-immunoprecipitation—Skin tissues were disrupted using homogenizer. Cells were washed with ice-cold PBS and collected on ice before centrifugation (4,000 rpm, 5 minutes at 4° C.), lysed in lysis buffer with protease inhibitors, and then incubated on ice for 30 minutes. After centrifugation (14,000 rpm, 15 minutes at 4° C.), the proteins (supernatant) were removed and quantified (Bradford reagent, BioRad). The NE-PER Nuclear and Cytoplasmic Extraction Reagents Kit (Thermo Scientific) was used to separate cellular fractions. For CO-IP, equal amounts of cell lysates were incubated with antibody, and immunocomplexes were captured on Protein-A/G Agarose beads. Protein samples were denatured and resolved on 12.5% SDS-PAGE or gradient gel (4-20% Bio-Rad) and electrotransferred to a nitrocellulose membrane (Whatman). Membranes were blocked in 5% dry skimmed milk in PBS-T and incubated with primary antibodies (1:1000). The following antibodies were used: YAP (Cell Signalling; Santa Cruz), pYAP (Cell Signalling), α-E-Catenin (C-terminus, Cell Signalling; Santa Cruz), α-E-Catenin (N-terminus, Cell Signaling), Cleaved-Caspase-3 (Cell signalling), 14-3-3, α-tubulin, β-actin (Santa Cruz), H3 (Abcam).

Wound repair—50 day old mice received subcutaneous injections of Ivachtin or z-DEVD-fmk (SEQ ID NO: 71, 2.5 mg/kg, AdooQ Bioscience) two days prior to wound excision and for 11 days thereafter. For all wound repair experiments, mice were sedated with isofluorane. Mice were shaved with electric clippers and treated topically with a hair removal cream for a few minutes (Nair). Full-thickness excision wounds (1 cm$^2$) were generated on the dorsal skins and monitored for wound coverage. PWI, mice were individually housed. At the desired time PWI, mice were euthanized with $CO_2$ and the wounded skins were harvested and either embedded in OCT or prepared for whole mounts as described above or for protein extraction.

In Vitro Cleavage Assay—Recombinant human α-Catenin protein (2.5 µg; Abcam) and recombinant active-caspase 3 (100 ng; BD Bioscience) were incubated at 37° C. for 2 h in cleavage assay buffer (20 mM PIPES, 100 mM NaCl, 10 mM DTT, 1 mM EDTA, 0.1% (w/v) CHAPS, 10% sucrose, pH 7.2) containing either DMSO or Ac-DEVD-CHO (SEQ ID NO: 75. 1 µg; BD Bioscience) as indicated. Reactions were stopped by addition of Laemmli sample buffer, and subjected to SDS/PAGE.

Mass Spectrometry—To confirm caspase-3 cleavage of α-Catenin protein, an in vitro cleavage reaction, performed as previously described, was subjected to SDS/PAGE followed by Coomassie Blue staining. The protein bands corresponding to the cleavage fragments were subjected to in-gel tryptic digestion. Analysis of the peptides was performed by a Q-Exactive plus mass spectrometer (Thermo) in a positive mode using repetitively full MS scan followed by High energy Collision Dissociation (HCD) of the 10 most dominant ion selected from the first MS scan.

Data was analyzed using Proteome Discoverer 1.4 software Using Sequest (Thermo) algorithm searching against the Uniprot database. Semi quantitation was performed by calculating the peak area of each peptide based on its extracted ion currents (XICs). The area of the protein is the average of the three most intense peptides from each protein. Results were filtered with 1% false discovery rate.

Example 1

Caspase-3 is Activated in the Sebocyte Gland but Does Not Result in Execution of Apoptosis Experimental Results Caspase-3 does not instruct sebocyte elimination—The present inventors have utilized the mouse tailskin as a model and employed an antibody specific for the activated and cleaved version of Caspase-3. Three distinct locations were detected in which cells were positively marked (CP3$^+$) along the pilosebaceous unit: (I) the HF bulge, (II) the catagenic HF epithelial strand (ES) and (III) the SGPZ (FIG. 1B). Both CP3$^+$K15$^+$ HF stem cells (HFSCs) and catagenic ES keratinocytes underwent apoptosis as evident by TUNEL staining and apoptotic morphology (FIGS. 1B-D). Surprisingly, although cleaved Caspase-3 was highly expressed in a large number of cells along the SGPZ (34%) it did not instruct cellular elimination (FIG. 1B, FIG. 1C, and FIGS. 1H-I). This was evident as only a minor fraction SGPZ CP3$^+$ sebocytes were positive for TUNEL (<1%, 0.5±0.5%) and did not display any of the known characteristics of apoptosis including nuclear condensation, fragmentation and membrane blebbing (FIG. 1C, FIG. 1H, FIG. 1I, and FIGS. 6A and 6H).

Cleaved caspase-3 does not eliminate sebocyte gland cells—In addition, PARP, known to be a classical target of Caspase-3 during apoptosis (22), was not cleaved in SGPZ sebocytes but could be detected in cells in the lower portion of a catagenic HF (FIG. 6B). Interestingly, the activation of Caspase-3 could be visualized in the developing SG as early postnatal day 1 (P1) and was evident in the SGPZ cells during all phases of the HF cycle including telogen, anagen and catagen (FIGS. 6C-E). Intriguingly, the present inventors could also detect TUNEL$^-$ cleaved caspase-3$^+$ cells along the outer root sheath of the HF during anagen as well as in IFE keratinocytes (FIG. 6I and FIGS. 18A-C).

In the SG Caspase-9 specifically activates Caspase-3 but not Caspase-7, in a manner that does not instruct cellular elimination—As a next step the present inventors examined the activation of the initiator caspase, Caspase-9, known to reside upstream and activate both Caspase-3 and Caspase-7 in the intrinsic apoptotic cascade (1, 8, 15). The present inventors could clearly detect the activation of Caspase-9 and -7 in HFSCs and in cells along the ES, however only Caspase-9 but not Caspase-7 was activated in the SGPZ cells (FIGS. 1E-G, and FIG. 6F). Quantitative analysis indicated that 22±3% and less than 0.5±0.5% of SGPZ sebocytes were positive for cleaved Caspase-9 and Caspase-7 respectively (FIG. 1G). In contrast, co-localization of Caspase-3, Caspase-7, Caspase-9 and TUNEL was seen in both HFSCs and ES catagenic keratinocytes (FIG. 1I). This suggests that in the SG Caspase-9 specifically activates Caspase-3 but not Caspase-7, in a manner that does not instruct cellular elimination.

Example 2

Caspase-3 Regulates Sebaceous Gland Size and Cell Proliferation

Experimental Results

Caspase-3 regulates sebaceous gland size and cell proliferation—Given that Caspase-3 is activated in the SG but does not result in execution of apoptosis, the present inventors next sought out to examine the non-apoptotic function of Caspase-3. Employing Caspase-3-null mice (Casp3$^{-/-}$) the present inventors first noticed that the fur of Casp3$^{-/-}$ mice appeared less glossy than control wild-type (WT) littermates (FIG. 2A). Examination of Casp3$^{-/-}$ SGs, revealed that they are significantly smaller in comparison to control (FIGS. 2B-E). The area (per plane) of the Casp3$^{-/-}$ SGs was approximately 25% of WT and the length of the SG was significantly shorter (FIGS. 2B-C and FIGS. 2D-E). In parallel, the fur of Casp3$^{-/-}$ appeared less lustrous than control WT littermates (FIG. 7J). Of note, Casp3$^{-/-}$ SGs were positively stained with the Oil red O dye indicating that the sebocyte differentiation program can still occur in the absence of Caspase-3 (FIGS. 2B-C).

Caspase-3 does not affect cell size but regulates the size of sebocyte-containing glands—Furthermore, in Casp3$^{-/-}$ mice the male preputial gland, a holocrine modified SG, was also significantly smaller providing compelling evidence as to the essential role of Caspase-3 in controlling the size of sebocyte containing glands (FIGS. 7A-C).

Since alteration of SG size could be the result of an effect on either cell size or number the present inventors examined both these scenarios. As shown in FIGS. 7D-E and 2R the present inventors did not detect any alteration in the size of individual sebocytes, however the number of cells in Casp3$^{-/-}$ SGs was significantly decreased, encompassing only ~35-40% of the number of WT SGs (FIG. 2F). To investigate the consequences of Caspase-3 deficiency on sebocyte proliferation, the present inventors performed immunostaining with specific proliferative markers Ki67, revealing a four-fold decrease in the number of Casp3$^{-/-}$ proliferating sebocytes (FIG. 2G and FIGS. 2H-I). Strikingly, almost all Ki67$^+$ SGPZ cells were positive for cleaved caspase-3 staining (FIG. 8A and FIG. 18A), and the present inventors could also detect co-labeling in anagenic HFs cells and IFE keratinocytes (FIGS. 18B-C). These data indicate the decrease in sebocyte number in Casp3$^{-/-}$ SGs was attributed to a decrease in proliferation and expansion of sebocytes along the SGPZ.

Caspase-3 regulates cell proliferation—The present inventors next sought out to examine whether chemical inhibition of Caspase-3 would yield similar consequences. For this aim, two specific cell permeable Caspase-3 inhibitors were utilized: the reversible Ivachtin inhibitor and the non-reversible z-DEVD-fmk (SEQ ID NO: 71) inhibitor. Eight week old mice were subcutaneously injected with Ivachtin, z-DEVD-fmk or DMSO for 7 days and were then monitored for the effect on SG size and proliferation. Strikingly, both inhibitors resulted in a decrease in SG size (FIGS. 2J-K) and impaired proliferative rates, with z-DEVD-fmk (SEQ ID NO: 71) exerting a stronger effect (FIGS. 8A-D). In contrast, when mice were examined 20 and 30 days post injection, the size of the SG and the length, width and the number of proliferating cells returned to normal (FIGS. 7F-I, and FIG. 8C). Without being bound by any theory, these data suggest that Caspase-3 plays a key role in SG homeostasis and that the size of adult SG is subject to a constant flux.

Novel strategy for isolating PZSG cells—The next step was to isolate PZSG cells and examine the effect of Caspase-3 in vitro, however given that presently there are no markers that enable the isolation of these cells the present inventors employed a novel strategy. Here, the present inventors utilized B6.Cg-Tg(Krt1-15-EGFP)2Cot/J mice, originally engineered to mark K15$^+$ HFSCs in the dorsalskin (23). Employing wholemount confocal analysis and intravital imaging, the present inventors found that in contrast to dorsalskins where the EGFP is expressed in the bulge as well as the hair germ (HG), in the pilosebcous units of the ears EGFP is highly expressed in SGPZ cells (FIGS. 2L-M, 2R and FIGS. 9A-C). Additionally, as apposed to second telogen dorsal HFs which contain an old and a new bulge, earskin HFs displayed a single bulge and no HG. Therefore, the fluorescence activated cell sorting (FACS) strategy used antibodies for integrin α6 which marks all basal keratinocytes in the skin epidermis, e.g., IFE, SG and HF, the CD34 bulge HFSC marker as well as EGFP which labels both bulge HFSCs and SGPZ cells. In accordance with the confocal and intravital imaging data, the number of integrin α6$^+$CD34$^+$ HFSCs was significantly decreased (two-fold decreased) in earskin HFs when compared to dorsalskin (FIG. 2S). Furthermore, the present inventors could clearly detect a large population, expressing high levels of EGFP (integrin α6$^+$CD34$^-$K15-EGFP$^{high}$) in the pilosebaceous units of the ear (FIG. 2R, FIG. 2N, FIG. 9D). The present inventors isolated these integrin α6$^+$CD34$^-$EGFP$^{high}$ PZSG cells from 8 week old telogenic mice. These cells were easily expanded giving rise to holoclones as well as differentiated ORO$^+$ sebocytes (FIGS. 9E-F). Additionally, in contrast to differentiated Sca1$^+$ keratinocytes, integrin α6$^+$CD34$^-$ EGFP$^{high}$ SGPZ cells gave rise to differentiated ORO$^+$ sebocytes (FIG. 9F).

Chemical inhibition of Caspase-3 results in decreased cell number—The present inventors next examined whether Caspase-3 inhibition would impair the proliferation of isolated integrin α6$^+$CD34$^-$EGFP$^+$ cells. Initially z-DEVD-fmk (SEQ ID NO: 71) was added and the present inventors found that it dramatically inhibited both cell number as well as the number of formed colonies (FIGS. 2P-Q, FIG. 10A). In contrast, Ivachtin had very limited effect presumably due to its reversible nature (FIG. 10A). However, when cells were supplemented with Ivachtin daily a significant impairment in cellular expansion, e.g., proliferation and cell number was evident (FIG. 8B). Performing immunostaining with the proliferative markers Ki67 and PCNA, revealed a three-fold decrease in the number of z-DEVD-fmk (SEQ ID NO: 71) and Ivachtin treated cells (FIG. 8B, FIG. 10A). In order to examine whether Caspase-3 affects the expansion of other cell types the present inventors isolated integrin α6$^+$CD34$^+$ HFSCs from second telogen mice. These HFSCs as well as HaCaT keratinocytes and Hek293E3 cells were treated with z-DEVD-fmk (SEQ ID NO: 71) and Ivachtin (FIGS. 10G and 10H). In accordance with the previous findings either one treatment of z-DEVD-fmk (SEQ ID NO: 71) dramatically or daily treatment with Ivachtin impaired the expansion of both cell types (FIGS. 10B-F). In contrast, Ivachtin had very limited effect presumably due to its reversible nature. However, when cells were supplemented with Ivachtin daily a significant impairment in cellular proliferation and cell number was evident (FIGS. 10B-F).

Having established that caspase-3 inhibition affects SG size and cell proliferation in vitro and in vivo, the present inventors tested whether activation of caspase-3 would yield the opposite effect. For this aim, the present inventors employed the caspase-3 activators PAC-1 (reference 40) and ABT-199 (reference 41). Eight-week old mice, in second telogen, were subcutaneously injected with PAC-1 or ABT-199 for seven days and the present inventors monitored the effect on SG size and cell proliferation. The results clearly demonstrate that caspase-3 activators resulted in a significant increase in cell proliferation, caspase-3 activation and SG size (FIGS. 2V and 2W).

Example 3

Caspase-3 Regulates the Activation of YAP

YAP, the transcriptional co-activator of the Hippo pathway, is known to have a critical role in the regulation of organ size, while impaired regulation of its activity has been found lead to massive overgrowth of tissues (24-26). In the skin, YAP has been found to play an important role in regulating epidermal proliferation acting downstream of alpha-catenin (27-29). Since inhibition of Caspase-3 affected both proliferation and organ size the present inventors hypothesized that it might regulate YAP activity.

Experimental Results

Caspase-3 affects YAP localization in the cell—Conducting immunofluorescent staining for YAP, the present inventors found that in approximately 45% of control SGPZ cells, YAP is located in the nucleus (FIGS. 3A-C). As expected in many proliferating SGPZ cells the present inventors could detect an overlap between YAP and Ki67 while in the terminally differentiated sebocytes YAP was retained outside the nuclease and localized to distinct punctate (FIGS. 3A-B, FIG. 11A). In contrast, in Casp3$^{-/-}$ SGs only 5% of SGPZ cell displayed nuclear Yap (FIGS. 3A-C). In order to verify the effect of Caspase-3 on YAP localization, the present inventors performed nuclear and cytoplasm fractionation followed by Western blotting. The present inventors isolated skins from 8-week old WT and Casp3$^{-/-}$ mice and the results clearly indicate that the levels of nuclear YAP are decreased in Casp3$^{-/-}$ dorsalskin (FIG. 3D). Similar results were also evident upon in vivo administration of z-DEVD-fmk (SEQ ID NO: 71, FIGS. 3E-F).

Caspase-3 inhibitors affect phosphorylation of YAP—In the skin, phosphorylation at the S127 residue results in inactivation and retention of YAP in the cytoplasm (27). Therefore, the present inventors next examined the levels of phosphorylated YAP (pYAP) in both WT and Casp3$^{-/-}$ by conducting Western blotting. In accordance with the above findings, pYAP levels were extremely increased in the skin treated with Caspase-3 inhibitors (FIG. 3G).

Given that Caspase-3 inhibition hindered cell number and proliferation in vitro the present inventors next examined whether this was mediated via YAP in EGFP$^{high}$ SGPZ cells using K15$^+$ SGPZ cells. Administration of Caspase-3 inhibitors resulted in a dramatic decrease in the nuclear translocation of YAP (FIGS. 3H-I). Similar findings as to effect of caspase-3 inhibition on YAP activation and proliferation were also obtained in HaCaT and Hek293E3 cells (FIGS. 3J-K, FIGS. 11B-F). In line with this, activation of caspase-3 with PAC-1 and ABT-199 in EGFP$^{high}$ SGPZ cells significantly decreased the levels of pYAP (FIG. 3O).

In high cellular densities YAP has been shown to become inactive (27), however disruption of adherent junctions (AJ) with the calcium chelator, EGTA, results in the rapid nuclear translocation of YAP (27). The present inventors therefore supplemented high confluent HaCaT cultures with Caspase-3 inhibitors and monitored the effect on YAP localization upon EGTA treatment. In accordance with the previous findings a significant decrease in the levels of nuclear YAP was apparent in Caspase-3 inhibited cells (FIG. 3L).

Once YAP translocates to the nucleus it drives the expression of a variety of target genes (30). The present inventors therefore examined the induction of YAP dependent target genes in cells treated with z-DEVD-fmk (SEQ ID NO: 71). Interestingly, HOXC13 which plays a critical role in HF formation (31) was 5-fold decreased, while HOXA5 which has been reported to counteract stem cell traits by inhibiting Wnt signaling (32) was 2-fold decreased in z-DEVD (SEQ ID NO: 71) —treated cells (FIG. 3J). Additionally, the receptor tyrosine kinase ErbB4 was downregulated 6-fold while WTIP a member of the Ajuba family and an inhibitor of the Hippo pathway was downregulated 2-fold (FIG. 3M). Taken together these findings demonstrate that Caspase-3 is able to modulate the activation and nuclear translocation of YAP.

Example 4

Caspase-3 Functions Via YAP to Regulate SGPZ Cell Proliferation and SG Development Caspase-3 Functions Via YAP to Regulate SGPZ Cell Proliferation and SG Development The above data revealed that caspase-3 is able to regulate SGPZ cell proliferation as well SG expansion. Therefore, the present inventors investigated whether SG homeostasis is governed by YAP activity in a caspase-3 dependent manner. For this aim the present inventors employed the YAP chemical inhibitor, Verteporfin, which is known to inhibit the interaction between YAP and TEAD in the nucleus and block transcriptional activity (reference 42). The present inventor administered Verteporfin either alone or in combination with the caspase-3 activator PAC-1. The results indicated that PAC-1-treated mice displayed higher numbers of nuclear YAP$^+$/Ki67$^+$ cells (FIGS. 17A-C). As expected, Verteporfin treatment did not affect the nuclear translocation of YAP but was able to overcome the positive proliferative effect of PAC-1, thus suggesting that caspase-3 functions upstream of YAP activation (FIGS. 17B and C).

The wound healing process can stimulate de novo regeneration of HFs and SGs (reference 35). As such, the present inventors utilized this model to examine whether caspase-3 activation can drive SG development and maturation. Eight-week old mice were injected with DMSO, PAC-1 or PAC-1 along with Verteporfin for two days prior to wound infliction. Full thickness excision wounds (1 cm$^2$) were generated on the dorsalskins and skin samples were harvested 20 and 30 days post wound infliction. Examining de novo regeneration of SGs from the wound bed, the present inventors found that caspase-3 activation led to a striking increase in the number of regenerated SGs (FIGS. 17D and E). Importantly, YAP inhibition reversed these regenerative phenotypes, leading to a 10-fold reduction in the number of de novo formed SGs (FIGS. 17D and E). Notably, in PAC-1 treated mice, the regenerating skin contained significantly larger and more developed SGs (FIGS. 17F-G), while in Verteporfin-treated mice the low number of regenerative SGs did not develop into mature SGs. Together, these results show that YAP plays a key role in regulating SGPZ proliferation and SG development as a physiological downstream target of caspase-3.

Example 5

Alpha Catenin is Cleaved by Caspase-3

α-Catenin is Cleaved by Caspase-3

Since Caspase-3 functions as a cysteine protease, and without being bound by any theory, the present inventors hypothesized that it might liberate YAP and facilitate its activation by cleaving an upstream target. In the skin, α-Catenin, a key component of adherent junctions (AJ), is known to retain phosphorylated YAP (S127 residue) in the cytoplasm, via interaction with 14-3-3 (27). Performing bioinformatic analysis the present inventors found that α-Catenin encompasses two potential Caspase-3 cleavage sites located at either the N (PEVD, SEQ ID NO: 76) or C (SGVD, SEQ ID NO: 77) termini (FIG. 4A) suggesting that they might be accessed by caspase-3. Examining the evolutionary conservation of these sites, the present inventors found that they are highly conserved across different species (FIG. 11G).

Examining the crystal structure of α-Catenin the present inventors found that these cleavage sites are exposed suggesting that they might be accessed by Caspase-3 (FIG. 4A). In order to examine if Caspase-3 cleaves α-Catenin, the present inventors conducted an in vitro cleavage assay. Recombinant human cleaved Caspase-3 was incubated with α-Catenin for 2 hours and products were separated using SDS-electrophoresis and Coommasie staining. As a control, the present inventors used the Ac-DEVD-CHO (SEQ ID NO: 75) inhibitor and found no cleavage products (FIG. 4B). In contrast, the present inventors observed a dramatic decrease in the levels of full length α-Catenin (FIG. 4M) (Caspase-3 cleaved α-Catenin), giving rise to two novel bands at a molecular weight of ~14 kDa and ~17 kDa, which are similar to the sizes expected from the bioinformatic analysis (FIGS. 4B and 4N).

Purification and Mass-spectrometry of the cleavage products identified α-Catenin peptides matching to the predicted cleavage fragments (FIG. 12A). Additionally, under these conditions, Caspase-3 was not able to cleave either histones H2A/H2B or H3/H4 (FIG. 12B). These data demonstrate the substrate specificity of Caspase-3 to α-Catenin.

The present inventors next added cleaved Caspase-3 to the protein lysate extracted from HaCaT cells and conducted Western blotting with antibodies for the C and N termini of α-Catenin. Detection with both antibodies indicated that addition of cleaved Caspase-3 results in a major decrease in the level of full-length α-Catenin (FIG. 4C). Interestingly, the antibody raised against the N-termini of α-Catenin detected a novel band at a molecular weight of ~90 kDa and a ~85 kDa band barely detected in the control. These bands match to the remaining portion of α-Catenin post cleavage of either the C or N termini (FIG. 4C). Moreover, these two bands were also detected in extracts from EGFP$^{high}$ SGPZ cells, at much higher levels in cells treated with the caspase-3 activator PAC-1, correlating with decreased levels of full length α-Catenin (FIG. 4O).

Since 14-3-3 serves as the link between YAP and α-Catenin, the present inventors next examined whether cleavage of α-Catenin by Caspase-3 results in liberation of 14-3-3. Proteins isolated from HaCaT cells were co-immunoprecipitated (co-IPed) with an antibody against α-Catenin. Pull-down complexes were subjected to in vitro cleavage with cleaved Caspase-3 and the cleavage products were analyzed using antibodies against α-Catenin and 14-3-3. This data clearly shows that Caspase-3-mediated cleavage facilitates the release of 14-3-3 from α-Catenin (FIG. 4D).

Since Caspase-3 was found to cleave α-Catenin in vitro the present inventors next examined if an in vivo binding between α-Catenin and Caspase-3 can be detected. Skins of 8-week old mice were isolated and co-IP experiments were performed of endogenous proteins. α-Catenin was able to interact with and precipitated, the activated forms of Caspase-3 (FIG. 4E). As previously demonstrated, α-Catenin was also able to precipitate YAP (27), however YAP did not precipitate with Caspase-3 suggesting a specific interaction between α-Catenin and Caspase-3 (FIG. 4E).

Given that α-Catenin precipitated cleaved Caspase-3, the present inventors examined whether they co-localize. Utilizing K15$^+$ SGPZ cells the present inventors could detect speckles of co-localization between these two proteins (FIG. 4G, Extended data FIG. 7C).

The levels of α-Catenin are known to be a critical factor in the regulation of YAP (27). In low confluent cells, diminished levels of α-Catenin serve as a mechanotransduction mechanism that instructs the nuclear translocation of YAP and drives proliferation (27, 33). These data indicate that that Caspase-3 binds and cleaves α-Catenin. The present inventors therefore examined the levels of α-Catenin both in vitro and in vivo, by employing both Western blot analysis and immunofluorescence. In Casp3$^{-/-}$ SGs as well as in Caspase-3 inhibited mice and cells, the levels of α-Catenin were significantly increased (FIGS. 4H, 4I and 4J, FIG. 12D). Additionally, low confluent HaCaT cells treated with z-DEVD-fmk also displayed increased levels of α-Catenin (FIG. 4I). Importantly, activation of caspase-3 in vivo using the PAC-1 activator resulted in decreased levels of α-Catenin (FIG. 11D). These data suggest that the decrease of α-Catenin levels, as a result of caspase-3 activity, can trigger YAP activation.

Example 6

XIAP Serves as a Feedback Antagonist of the Caspase-3-YAP Module

XIAP serves as a feedback antagonist of the caspase-3-YAP module—An important family of endogenous caspase inhibitors are the inhibitor of apoptosis proteins (IAPs), which can bind to and inhibit caspases via their baculovirus inhibitory repeat (BR) domain (Vaux, D. L. & Silke, J. IAPs, RINGs and ubiquitylation. Nat. Rev. Mol. Cell. Biol. 6, 287-297 (2005)). The best-studied mammalian IAP is the X-linked inhibitor of apoptosis protein (XIAP), which is considered the most potent caspase inhibitor in vitro (Eckelman, B. P. & Salvesen, G. S. The human anti-apoptotic proteins cIAP1 and cIAP2 bind but do not inhibit caspases. J. Biol. Chem. 281, 3254-3260 (2006)). The present inventors have recently reported that XIAP is highly expressed in HFSCs as well as in the SG (Fuchs, Y., et al. Sept4/ARTS regulates stem cell apoptosis and skin regeneration. Science 341, 286-289 (2013)). Given that XIAP is expressed, but does not prevent the activation of either caspase-9 or caspase-3, the present inventors examined the possibility that its expression is required for averting the execution of a widespread apoptotic response. Indeed, in Drosophila, caspase activation is required for sperm differentiation, yet the IAP, dBruce, protects spermatids against excessive caspase activity and death (Arama, E., Agapite, J. & Steller, H. Caspase activity and a specific cytochrome C are required for sperm differentiation in Drosophila. Developmental cell 4, 687-697 (2003)). Nevertheless, an alternative scenario could be that upon XIAP deletion, caspase-3 becomes over-activated, resulting in increased proliferation and possibly enlarged SGs. Utilizing XIAP$^{-/-}$ mice, the present inventors found a significant increase in the number of Ki67$^+$ and cleaved caspase-3$^+$ cells in the SGPZ (FIGS. 29A-B). In accordance, the SGs of XIAP$^{-/-}$ mice were significantly larger (FIG. 29C). Importantly, XIAP does not protect SGPZ against apoptosis as no alteration in the number of TUNEL+ cells was detected in XIAP$^{-/-}$ mice (FIG. 29D).

In *Drosophila*, Yorkie (Yki) the homolog of YAP directly regulates the transcription of Death-associated inhibitor of apoptosis 1 (Diap1), which is the functional equivalent of XIAP [Fuchs, Y. & Steller, H. Programmed cell death in animal development and disease. Cell 147, 742-758 (2011); Zhang, L., et al. The TEAD/TEF family of transcription factor Scalloped mediates Hippo signaling in organ size control. Developmental cell 14, 377-387 (2008)]. Therefore, and without being bound by any theory, the present inventors hypothesized that in the SG, XIAP might be transcriptionally regulated by YAP to balance caspase-3 activity. The present inventors analyzed XIAP expression in mice treated with Verteporfin and found a decrease in XIAP levels (FIG. 29D). Moreover, XIAP protein levels were increased upon caspase-3 activation with PAC-1, but this effect was abolished when YAP was inhibited (FIG. 29D). An increase in XIAP levels was also detected in EGFP$^{high}$ SGPZ cells treated with PAC-1 (FIGS. 29E, 29F). To provide further evidence the present inventors extracted RNA from EGFP$^{high}$ SGPZ cells treated with Verteprofin and found that XIAP mRNA levels were 2-fold lower compared to control cells (FIG. 29G). Taken together, these results indicate that XIAP expression is regulated by the caspase-3-YAP module, generating a negative feedback loop, which prevents SG overgrowth.

Example 7

Inhibition of Caspase-3 Impairs Wound Repair

Inhibition of caspase-3 impairs wound repair—Since YAP is known to play a chief role in regeneration (34), the present inventors investigated whether in vivo inhibition of Caspase-3 affects the wound repair dynamic by modulating YAP activity. For this aim, 8-week old mice were injected with either Ivachtin or z-DEVD-fmk (SEQ ID NO: 71) for 2 days prior to wound infliction. Full thickness excision wounds (1.0 cm$^2$) were generated on the dorsalbacks and monitored for wound coverage. In control mice, three days post wound infliction (PWI) the wound size was reduced by 60% while in Ivachtin and z-DEVD-fnk (SEQ ID NO: 71) treated mice, it was reduced by only 10% and 20%, respectively (FIG. 5A and FIG. 5B). Impaired healing was seen at all time points of mice treated with inhibitors but appeared to be less efficient in Ivachtin treated animals (FIG. 5B).

The present inventors next investigated the underlying cause of the impaired healing in caspase-3 inhibited mice. Examining the levels of α-Catenin the present inventors found it to be expressed through out the epidermis but was decreased adjacent to the wound in the invading keratinocytes. This expression gradient/pattern was evident in both treated and control mice, however the levels of α-Catenin were drastically increased in Caspase-3 inhibited mice, and the present inventors could still detect relatively high levels of α-Catenin in the wound border (FIGS. 5C-F, FIG. 13A). In complement, p-YAP levels were strikingly high in the normal epidermis and wound border of the Caspase-3i treated animals (FIGS. 5C-F). Next, the present inventors monitored the level of proliferation in the invading keratinocytes adjacent to the wound. In accordance with the high levels of α-Catenin, the present inventors found significantly less the Ki67$^+$ cells in the wound border of Caspase-3 inhibited mice (FIG. 13B). Furthermore, in contrast to control animals, Caspase-3 inhibited mice displayed a dramatic reduction in the number of cells positive for nuclear YAP (FIGS. 5G-J, FIG. 13C).

Since wounds can stimulate de novo regeneration of HFs and SGs (35) the present inventors examined whether Caspase-3 inhibition affects this process. In control animals de novo pilosebaceous units spanning from the wound bed 20 and 30 days PWI were clearly visualized (FIGS. 5K-L, FIG. 13D). These regenerated HFs contained a HFSC niche positive for the CD34, K15 and Sox9 markers (FIGS. 5K-L). In contrast, this form of regeneration could not be detected in Caspase-3 inhibited mice (FIG. 13B).

Furthermore, as shown in FIGS. 19A-F, inhibition of caspase-3 by z-DEVD-fmk (SEQ ID NO: 71) or Ivachin inhibited wound repair as shown by the significant decrease in wound closure. Additionally, inhibition of caspase-3 and YAP did not result in an additive effect suggestive of their epistatic relationship (FIG. 19F). In contrast, when the mice were treated with PAC1 activator they healed significantly faster than control. This increased repair could be revered by YAP inhibition (VP) (FIG. 20B).

These findings reveal a novel non-canonical role of Caspase-3 as a key regulator of SG homeostasis, organ size and skin regeneration as well as the non-redundant role of Caspase-3 in these processes. Exploring the underlying mechanism, the present inventors find that alpha-catenin, known to sequester YAP in the cytoplasm, is cleaved by Caspase-3 thus facilitating the liberation and activation of YAP (FIGS. 16A-B).

These results are in line with the finding that skin carcinoma formation, known to be YAP/TAZ-dependent (30), is inhibited in Casp3$^{-/-}$ mice (36) as well as the report that in human tumors high levels of Caspase-3 activation is correlated with poor prognosis (37). Furthermore, it is becoming established that apoptotic cells can instruct compensatory proliferation in neighboring cells in a caspase-dependent manner (12, 15, 38, 39). In this process, caspase activation is not only responsible for cellular elimination but also regulates the secretion of mitogenic factors. Therefore, Caspase-3 activation could drive proliferation intrinsically by modulating YAP activity or by initiating the compensatory proliferation mechanism. In such a manner, Caspase-3 can govern both wound repair and tumor development, thus challenging the dogmatic approach in the way cancer is being treated. With these perspectives in mind these results suggest that targeting Caspase-3 might prove beneficial for tumor therapy.

Example 8

Caspase-3 Inhibitor(s) for Treating Cancer

Programmed cell death (PCD) serves as a fundamental mechanism for proper development and tissue homeostasis. One particular mode of PCD, called apoptosis, is responsible for eliminating undesired and potentially dangerous cells via the activation of caspases (Fuchs & Steller, 2011). Of this family, the cleavage and activation of Caspase-3 results in the destruction of a variety of substrates, which serves as the final step in the cell death program (Taylor, Cullen, & Martin, 2008). Current cancer therapies, including both chemotherapy and radiation, work by instructing tumor cell elimination supposedly via the activation of Caspase-3.

The findings described in hereinabove challenge the simplistic view of apoptosis as a tumor-suppressive or tumor-preventive mechanism and indicate that activation of caspase-3 might be considered as a double-edged sword. In support of this idea and in contrast to the straightforward expectation, caspase-3 has been found to promote genetic instability and carcinogenesis (Liu, X. et al. 2015, Caspase-3 promotes genetic instability and carcinogenesis. Mol. Cell 58: 284-96), instruct the secretion of tumor repopulating mitogens (Kurtova, A. V. et al. 2015, Blocking PGE-induced tumour repopulation abrogates bladder cancer chemoresistance. Nature 517(7533):209-13; Galluzzi, L., et al., 2012, Caspase-3 and prostaglandins signal for tumor regrowth in cancer therapy. Oncogene 31: 2805-8; Li, F. et al. 2010, Apoptotic cells activate the "phoenix rising" pathway to promote wound healing and tissue regeneration. Sci Signal 3, ra13) and regulate post-irradiation angiogenesis (Feng, X. et al. 2015, Caspase 3 in dying tumor cells mediates post-irradiation angiogenesis. Oncotarget 6: 32353-67). Furthermore, caspase3−/− and conditionally deleted YAP mice develop dramatically fewer skin carcinomas and in humans tumors high levels of caspase-3 activation is correlated with poor prognosis (Huang, Q. et al. 2011, Caspase 3-mediated stimulation of tumor cell repopulation during cancer radiotherapy. Nat. Med. 17: 860-6; Hu, Q. et al. 2014, Elevated cleaved caspase-3 is associated with shortened overall survival in several cancer types. Int. J. Clin. Exp. Pathol. 7: 5057-70). Hence, caspase-3 might contribute during different stages of carcinogenesis as well as initiation, promotion or response to tumor therapy; serving as a novel target with the potential to transform the field of skin cancer therapy.

In contrast to the straightforward expectation, the data uncovered by the present inventors indicate an important non-apoptotic role of Caspase-3 as a key regulator of cell proliferation and organ size via the Yap signaling module. In light of these intriguing findings, the present inventors study the effect of both Caspase-3 activation and inhibition on Yap-dependent melanoma maintenance and progression.

Experimental Results

As described in Examples 1-3 above, the present inventors have uncovered an important non-apoptotic role of caspase-3 as a key regulator of proliferation, organ size and regeneration. Caspase-3 is specifically activated in the proliferating cells of the sebaceous gland (SG) but in contrast to hair follicle stem and transient amplifying cells it does not instruct cellular elimination (FIGS. 1B-C, FIGS. 6A-C). Mice deficient for caspase-3 display significant reduction in sebocyte cell number and proliferation, resulting in a dramatic decrease in SG size (FIGS. 2B-I). Additionally, treating mice with different caspase-3 inhibitors (Ivachtin and z-DEVD-fmk (SEQ IS NO: 71)) resulted in a significant decrease in cellular proliferation (FIGS. 2J-K). In caspase3−/− mice, YAP, a known oncogene and vital transcription factor of the Hippo pathway, was found to reside outside of the nucleus in an inactivated phosphorylated state (FIGS. 3A-D). Furthermore, chemical inhibition of caspase-3 inhibited keratinocyte proliferation and impaired wound healing and skin.

Examination of the effect of caspase 3 activation on melanoma tumors in vivo—Mice injected with the murine melanoma cell line B16F10 formed melanoma in vivo (FIG. 21A), and following treatment with the pro-apoptotic agent, ABT-199 the tumors were increased in volume and weight (FIGS. 21B-C). The resected tumors stained for activated cleaved Caspase-3 (red) show higher expression (FIG. 21D) and higher proliferation (Ki67$^+$ cells; FIGS. 21E-F) in ABT-199-treated animals.

Examination of the effect of caspase-3 inhibition on melanoma formation in vivo—For this aim human melanoma cells were stably infected with GFP. Cells were then injected into to recipient mice and the effect of administrating caspase-3 inhibitors was monitored. Administration of both inhibitors resulted in a significant decrease in tumor development with z-DEVD-fmk (SEQ ID NO: 71) resulting in a stronger effect (FIGS. 15A, 15B).

The proliferation dynamics was further studied in extracted tumors using the Ki67 proliferative marker. In accordance with the in vitro data, administration of caspase-3 inhibitors dramatically impaired cell proliferation and significantly less GFP$^+$ melanoma cells were detected in the extracted tumors (FIG. 15C). In addition, administration of a caspase-3 activator (ABT-199) resulted in a two-fold increased tumor mass and massive tumor formation (FIG. 15D). Conducting in vivo imaging the present inventors found that upon caspase-3 activation the tumors dramatically expanded (FIG. 15E).

These data point to an intriguing future avenue of research in connection to cancer treatment and suggest that targeting caspase-3 might prove beneficial for tumor therapy. In order to examine this hypothesis, the present inventors first investigated the effect of caspase-3 inhibition on the proliferation rate of melanoma cells. Treating two different melanoma cell lines (501A and 624-38-) with z-DEVD-fmk (SEQ ID NO: 71) inhibitors resulted in a dramatic decrease in cell proliferation and number (FIGS. 14A-C). Similar results were also obtained when examining 4 additional cell types (HaCaT keratinocytes, Hek293E3, K15 SG progenitors and hair follicle stem cells) (FIGS. 10A-F).

In addition, as shown in FIGS. 22A-F inhibition of caspase 3 with a specific, reversible Caspase-3 inhibitor (Ivachtin), attenuates cancer cell proliferation and leads to increased cell death in vivo (FIGS. 22A-C) and in vitro (FIGS. 22D-F) as is evident by the decrease in tumor weight (FIG. 22C), reduced expression of the proliferative marker Ki67 (FIGS. 22D-E) and enhanced cell death by TUNEL assay (FIG. 22D (right panels, and FIG. 22F).

Furthermore, FIGS. 23A-F show that inhibition of caspase 3 attenuates cancer cell proliferation in vitro (FIGS. 23A-C) and leads to increased cell death in vitro (FIGS. 23D-F). Thus, the growth of B16F10 melanoma cells is hindered in the continuous presence of a specific irreversible Caspase-3 inhibitor, Z-DEVD-fmk (SEQ ID NO: 71) or Ivachtin.

Further experiments performed by the present inventors show that caspase-3 regulates melanoma maintenance via the Yap signaling pathway. Thus, as shown in FIGS. 24A-E, treatment of B16F10 melanoma cells with Z-DEVD-fmk (SEQ ID NO: 71) or Ivachtin revealed significant increases in phosphorylated YAP-positive cells (pYAP+) as compared to cells treated with DMSO (FIGS. 24A-C). In addition, B16F10 melanoma cells treated with Ivachtin present increased expression of α-Catenin (FIGS. 24D-E), known to inhibit YAP.

In addition, subsequent in vivo experiments showed that treatment with the caspase-3 inhibitor, Ivachtin, diminishes YAP signaling as is evident by the significant decreases in YAP positive cells (FIGS. 25A-B).

Thus, mice which were injected with highly malignant B16F10 melanoma cells supplemented with the pro-apoptotic chemical agent, ABT-199, or the Caspase-3 inhibitor, Ivachtin, do not respond as expected to these treatments. Surprisingly, tumors treated with ABT-199 showed a dramatic increase in size and high levels of proliferation (FIGS. 21A-F). In contrast, administration of Ivachtin significantly affected tumor development in vivo, resulting in smaller tumors that exhibited attenuated proliferation (FIGS. 25A-B). In support, the administration of Caspase-3 inhibitors to various human and mice melanoma cell lines dramatically hindered cell growth.

Inhibition of caspase-3 sensitizes the drug-resistant human melanoma cells to treatment with commercially available chemotherapy—Importantly, the present inventors found that the inhibition of Caspase-3 was sufficient to significantly sensitize drug-resistant human melanoma cells to treatment with the commercially available chemotherapeutic drug Vemurafenib (marketed as Zelboraf).

Thus, as shown in FIGS. 26A-F, 27A-D and 28, caspase-3 inhibition (by Z-DEVD fmk, SEQ ID NO: 71) coupled with a chemical BRAF inhibitor (Vemurafenib, marked as "Vem") attenuates proliferation of resistant melanoma cells (both A-375 and LU-1205 melanoma cells) in vitro and leads to increased cell death in a Yap-dependent fashion.

Taken together, the data presented here reveals a critical non-canonical role of Caspase-3 in melanoma progression and suggests that the activation of Caspase-3 for tumor therapy may serve as a double edged sword.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Additional References are Cited in Text

1. Fuchs, Y. & Steller, H. Programmed cell death in animal development and disease. *Cell* 147, 742-758 (2011).
2. Miura, M. Active participation of cell death in development and organismal homeostasis. *Dev Growth Differ* 53, 125-136 (2011).
3. Meier, P., Finch, A. & Evan, G. Apoptosis in development. *Nature* 407, 796-801 (2000).
4. Suzanne, M. & Steller, H. Shaping organisms with apoptosis. *Cell Death Differ* 20, 669-675 (2013).
5. Yamaguchi, Y. & Miura, M. Programmed cell death in neurodevelopment. *Dev Cell* 32, 478-490 (2015).
6. Ellis, H. M. & Horvitz, H. R. Genetic control of programmed cell death in the nematode *C. elegans*. *Cell* 44, 817-829 (1986).
7. Hengartner, M. O. The biochemistry of apoptosis. *Nature* 407, 770-776 (2000).
8. Thornberry, N. A. & Lazebnik, Y. Caspases: enemies within. *Science* 281, 1312-1316 (1998).
9. Nagata, S. Apoptosis by death factor. *Cell* 88, 355-365 (1997).
10. Bhola, P. D. & Letai, A. Mitochondria-Judges and Executioners of Cell Death Sentences. *Mol Cell* 61, 695-704 (2016).
11. Taylor, R. C., Cullen, S. P. & Martin, S. J. Apoptosis: controlled demolition at the cellular level. *Nat Rev Mol Cell Biol* 9, 231-241 (2008).
12. Bergmann, A. & Steller, H. Apoptosis, stem cells, and tissue regeneration. *Sci Signal* 3, re8 (2010).
13. Abraham, M. C. & Shaham, S. Death without caspases, caspases without death. *Trends Cell Biol* 14, 184-193 (2004).
14. Kuranaga, E. & Miura, M. Nonapoptotic functions of caspases: caspases as regulatory molecules for immunity and cell-fate determination. *Trends Cell Biol* 17, 135-144 (2007).
15. Fuchs, Y. & Steller, H. Live to die another way: modes of programmed cell death and the signals emanating from dying cells. *Nat Rev Mol Cell Biol* 16, 329-344 (2015).
16. Feinstein-Rotkopf, Y. & Arama, E. Can't live without them, can live with them: roles of caspases during vital cellular processes. *Apoptosis* 14, 980-995 (2009).
17. Yi, C. H. & Yuan, J. The Jekyll and Hyde functions of caspases. *Dev Cell* 16, 21-34 (2009).
18. Watt, F. M. Mammalian skin cell biology: at the interface between laboratory and clinic. *Science* 346, 937-940 (2014).
19. Fuchs, E. Scratching the surface of skin development. *Nature* 445, 834-842 (2007).
20. Woo, W. M. & Oro, A. E. SnapShot: hair follicle stem cells. *Cell* 146, 334-334 e332 (2011.
21. Niemann, C. & Horsley, V. Development and homeostasis of the sebaceous gland. *Semin Cell Dev Biol* 23, 928-936 (2012).
22. Nicholson, D. W. et al. Identification and inhibition of the ICE/CED-3 protease necessary for mammalian apoptosis. *Nature* 376, 37-43 (1995).
23. Morris, R. J. et al. Capturing and profiling adult hair follicle stem cells. *Nat Biotechnol* 22, 411-417 (2004).
24. Zanconato, F., Cordenonsi, M. & Piccolo, S. YAP/TAZ at the Roots of Cancer. *Cancer Cell* 29, 783-803 (2016).
25. Yu, F. X., Zhao, B. & Guan, K. L. Hippo Pathway in Organ Size Control, Tissue Homeostasis, and Cancer. *Cell* 163, 811-828 (2015).
26. Oren, M. & Aylon, Y. The Hippo signaling pathway and cancer (Springer Science & Business Media: New York, 2013).
27. Schlegelmilch, K. et al. Yap1 acts downstream of alpha-catenin to control epidermal proliferation. *Cell* 144, 782-795 (2011).
28. Silvis, M. R. et al. alpha-catenin is a tumor suppressor that controls cell accumulation by regulating the localization and activity of the transcriptional coactivator Yap1. *Sci Signal* 4, ra33 (2011).
29. Li, P. et al. alphaE-catenin inhibits a Src-YAP1 oncogenic module that couples tyrosine kinases and the effector of Hippo signaling pathway. *Genes Dev* 30, 798-811 (2016).

30. Zanconato, F. et al. Genome-wide association between YAP/TAZ/TEAD and AP-1 at enhancers drives oncogenic growth. *Nat Cell Biol* 17, 1218-1227 (2015).
31. Godwin, A. R. & Capecchi, M. R. Hoxc13 mutant mice lack external hair. *Genes Dev* 12, 11-20 (1998).
32. Ordonez-Moran, P., Dafflon, C., Imajo, M., Nishida, E. & Huelsken, J. HOXA5 Counteracts Stem Cell Traits by Inhibiting Wnt Signaling in Colorectal Cancer. *Cancer Cell* 28, 815-829 (2015).
33. Dupont, S. et al. Role of YAP/TAZ in mechanotransduction. *Nature* 474, 179-183 (2011).
34. Johnson, R. & Halder, G. The two faces of Hippo: targeting the Hippo pathway for regenerative medicine and cancer treatment. *Nat Rev Drug Discov* 13, 63-79 (2014).
35. Ito, M. et al. Wnt-dependent de novo hair follicle regeneration in adult mouse skin after wounding. *Nature* 447, 316-320 (2007).
36. Liu, X. et al. Caspase-3 promotes genetic instability and carcinogenesis. *Mol Cell* 58, 284-296 (2015).
37. Huang, Q. et al. Caspase 3-mediated stimulation of tumor cell repopulation during cancer radiotherapy. *Nat Med* 17, 860-866 (2011).
38. Morata, G., Shlevkov, E. & Perez-Garijo, A. Mitogenic signaling from apoptotic cells in Drosophila. *Dev Growth Differ* 53, 168-176 (2011).
39. Perez-Garijo, A. & Steller, H. Spreading the word: non-autonomous effects of apoptosis during development, regeneration and disease. *Development* 142, 3253-3262 (2015).
40. Putt, K. S., et al. Small-molecule activation of procaspase-3 to caspase-3 as a personalized anticancer strategy. *Nat. Chem. Biol.* 2, 543-550 (2006).
41. Souers, A. J., et al. ABT-199, a potent and selective BCL-2 inhibitor, achieves antitumor activity while sparing platelets. *Nat. Med.* 19, 202-208 (2013).
42. Liu-Chittenden, Y., et al. Genetic and pharmacological disruption of the TEAD-YAP complex suppresses the oncogenic activity of YAP. *Genes Dev.* 26, 1300-1305 (2012).

---

What is claimed is:

1. A method of treating a skin wound in a subject, comprising topically administering to a wounded skin area of the subject an effective amount of a wound healing caspase-3 activator, wherein said effective amount of said caspase-3 activator is capable of increasing activity of Yes associated protein 1 (YAP) above a predetermined level as compared to a wounded area of a subject non-treated by said caspase-3 activator.

2. The method of claim 1, wherein said activity of said YAP is characterized by coactivation of the transcription of the TEAD (TEA domain) complex.

3. The method of claim 1, wherein said caspase-3 activator is selected from the group consisting of PAC-1, and ABT-199.

* * * * *